(12) United States Patent
Mete et al.

(10) Patent No.: US 11,945,811 B2
(45) Date of Patent: Apr. 2, 2024

(54) POTASSIUM CHANNEL INHIBITORS

(71) Applicant: ACESION PHARMA APS, Copenhagen N (DK)

(72) Inventors: Antonio Mete, Leicestershire (DK); Ulrik Sørensen, Copenhagen N (DK)

(73) Assignee: ACESION PHARMA APS, Copenhagen N (DK)

( * ) Notice: Subject to any disclaimer, the term of this patent is extended or adjusted under 35 U.S.C. 154(b) by 0 days.

(21) Appl. No.: 18/239,348

(22) Filed: Aug. 29, 2023

(65) Prior Publication Data

US 2023/0406845 A1 Dec. 21, 2023

Related U.S. Application Data

(63) Continuation of application No. PCT/EP2022/056955, filed on Mar. 17, 2022.

(30) Foreign Application Priority Data

Mar. 22, 2021 (EP) .................................. 21164078.4

(51) Int. Cl.
| | |
|---|---|
| *C07D 413/12* | (2006.01) |
| *C07D 401/12* | (2006.01) |
| *C07D 403/06* | (2006.01) |
| *C07D 403/12* | (2006.01) |
| *C07D 413/06* | (2006.01) |
| *C07D 417/06* | (2006.01) |

(52) U.S. Cl.
CPC ......... *C07D 413/06* (2013.01); *C07D 403/06* (2013.01); *C07D 403/12* (2013.01); *C07D 413/12* (2013.01); *C07D 417/06* (2013.01)

(58) Field of Classification Search
CPC .. C07D 235/30; C07D 413/12; C07D 401/12; C07D 403/12
See application file for complete search history.

(56) References Cited

FOREIGN PATENT DOCUMENTS

WO 2006013210 A2 2/2006

OTHER PUBLICATIONS

Heijman et al. Cardiovascular Research, 2016, vol. 109, pp. 467-479.*
International Search Report, dated Jun. 27, 2022, in corresponding International Application No. PCT/EP2022/056955, 3 pages.

* cited by examiner

*Primary Examiner* — Samira J Jean-Louis
(74) *Attorney, Agent, or Firm* — Maier & Maier, PLLC

(57) ABSTRACT

A compound of the general formula (I), and the pharmaceutical composition including a compound of formula (I) and optionally a pharmaceutically acceptable additive. Also, the treatment of a cardiac disease, disorder or condition in a mammal, which includes the administration to the mammal a therapeutically effective amount of at least one compound of formula (I), or the pharmaceutically acceptable salt thereof.

20 Claims, No Drawings

POTASSIUM CHANNEL INHIBITORS

FIELD

The present invention relates to novel compounds, the use of said compounds as medicament and for the manufacture of a medicament for the treatment of a cardiac disease, disorder or condition in mammals. The invention also relates to pharmaceutical compositions comprising said novel compounds.

BACKGROUND

The heart is a muscle, which pumps the blood in the circulation by contracting 1-3 times per second. The heartbeat is caused by simultaneous contraction of the individual cardiac muscle cells (cardiac myocytes). The synchronization of the cellular contraction is governed by the electrical cardiac impulse (the cardiac action potential), which is generated in the pacemaker cells of the sine node and spreads rapidly over the heart through a specific conduction system.

Disturbances in the generation of the impulse and the conduction of impulse may occur either as a consequence of a disease, a drug treatment, or electrolyte imbalances. Such disturbances in the impulse are called arrhythmia or dysrythmia and they may lead to unease, emboli, syncope or sudden death. In its simplest form, an arrhythmia covers everything different from a normal cardiac sinus rhythm. Disturbances can cover anything from simple palpitations to devastating ventricular fibrillation including bradycardia and tachycardia.

At a molecular level a group of proteins called ion channels underlie the electrical events in the heart since they are able to conduct electrical currents across the cell membrane. Different types of ion channels are thus instrumental in the generation and conduction of the cardiac action potential, in the regulation of the heart rate by the autonomic nervous system, and in the contractile process in the individual heart cells. The different types of ion channels are therefore evident targets for anti-arrhythmic cardiac drugs, and many anti-arrhythmic drugs on the market do exert their effect by interacting with ion channels.

Anti-arrhythmic drugs are usually divided into four main classes according to the so-called Singh Vaughan Williams classification: Class I compounds all inhibit the cardiac voltage-dependent sodium channel. Some Class I compounds do have additional effects influencing the cardiac action potential being the basis for a further subdivision into three subclasses:

Class IA compounds are sodium channel inhibitors such as Quinidine, Procainamide or Disopyramid, which prolong the action potential;

Class IB compounds are sodium channel inhibitors such as Lidocaine, Mexiletine, Tocainide or Phenytoine, which shorten the action potential; and Class IC compounds are sodium channel inhibitors such as Flecainide, Moricizine or Propafenone, which do not change the action potential duration.

Class I compounds interact with the sodium channel during its open or inactivated state and are dissociated from the channels during its closed state (during diastole). The rate of dissociation determines whether they show a frequency-dependent channel inhibition. Some of the class I compounds also inhibit subtypes of potassium or calcium permeable channels in addition to their sodium channel inhibiting effect.

Class II compounds are β-adrenoceptor inhibitors and include drugs like Atenolol, Metoprolol, Timolol or Propranolol. β-adrenoceptor inhibitors can be selective for cardiac β1-receptors or have affinity for β1- as well as β2-receptors. Some of the compounds also have an intrinsic β-stimulating effect.

Class III compounds are potassium channel inhibitors such as Amiodarone, Dronedarone, Sotalol, Ibutilide and Dofetilide, which prolong the action potential.

Class IV compounds are inhibitors of L-type calcium channels such as Verapamil. Small-conductance calcium-activated potassium (SK) channels belongs to the family of $Ca^{2+}$-activated $K^+$ channels. Three SK channel subtypes have been cloned: SK1, SK2 and SK3 (corresponding to KCNN1-3 using the genomic nomenclature). The activity of these channels is determined by the concentration of free intracellular calcium ($[Ca^{2+}]i$) via calmodulin that is constitutively bound to the channels. SK channels are tightly regulated by $[Ca^{2+}]i$ in the physiological range being closed at $[Ca^{2+}]i$ up to around 0.1 µM but fully activated at a $[Ca^{2+}]i$ of 1 µM. Being selective for potassium, open or active SK channels have a hyperpolarizing influence on the membrane potential of the cell. SK channels are widely expressed in the central nervous system (CNS) and in peripheral tissue, including the heart.

The hyperpolarizing action of active SK channels plays an important role in the control of firing pattern and excitability of excitable cells. SK channel inhibitors such as apamin and N-methyl bicuculline, have been demonstrated to increase excitability, whereas the SK channel opener 1-EBIO is able to reduce electrical activity. In non-excitable cells, where the amount of $Ca^{2+}$ influx via voltage-independent pathways is highly sensitive to the membrane potential, an activation of SK channels will increase the driving force, whereas an inhibitor of SK channels will have a depolarizing effect, and thus diminish the driving force for calcium.

An SK channel inhibitor is a pharmaceutical agent that impairs the conduction of potassium ions ($K^+$) through $Ca^{2+}$-activated small conductance $K^+$ channels. The impairment can be obtained by any reduction in current resulting from e.g. a direct inhibition of ion conduction to a prevention of $Ca^{2+}$ binding, that is an obligate request for channel activation, or a reduction in calcium sensitivity.

A review of SK channels and SK channel modulators may be found in Wulff H et al.: "Modulators of Small- and Intermediate-Conductance Calcium-Activated Potassium Channels and their Therapeutic Indications", Current Medicinal Chemistry 2007 14 1437-1457; and in Liegeois J-F et al.: "Modulation of small conductance calcium-activated potassium (SK) channels: a new challenge in medicinal chemistry", Current Medicinal Chemistry 2003 10 625-647.

Based on the important role of SK channels in linking $[Ca^{2+}]i$ and membrane potential, SK channels are interesting targets for developing novel therapeutic agents, and the potential of inhibitors of SK channels for use in anti-arrhythmic treatment has been established, see e.g. Nattel S; J. Physiol. 2009 587 1385-1386 (doi: 10.1113/jphysiol.2009.170621); Xiao-Yan Qi et al, Circulation 2014 28 430-440 (doi: 10.1161/CIRCULATIONAHA.113.003019) and Diness et al; Circ. Arrhythm. Electrophysiol. 2017 10 1-13 (doi: 10.1161/CIRCEP.117.005125).

WO 2006/013210 describes certain 2-amino benzimidazole derivatives and their use as modulators of small-conductance calcium-activated potassium channels.

SUMMARY

The exemplified compounds of the present invention are inhibitors or negative modulators of the small-conductance calcium activated potassium (SK) channel (in particular (SK3)) and have an IC50 value of below 30 μM as demonstrated in the Automated patch clamping system described herein and are considered potent drug candidates. A certain selection of these compounds has a strongly improved IC50 value of below 1 μM. Some of these compounds also have physicochemical properties suitable for a drug substance and important for making pharmaceutical formulations and may have beneficial properties with respect to pharmacological selectivity profile, in vivo absorption/bioavailability, toxicity and safety profile, and manufacturability. Further, some of these compounds have pharmacokinetic properties making them suitable for use as pharmaceutical drugs.

In a broad aspect the present invention relates to a compound of formula (I)

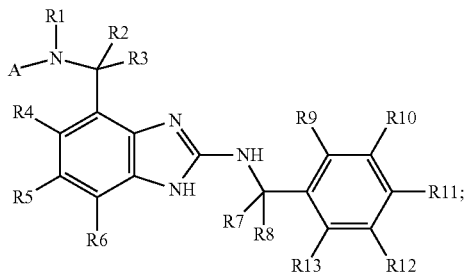

Wherein

A is a 5 or 6-membered aromatic heterocycle comprising at least one nitrogen atom and optionally 1 sulphur atom and optionally 1 oxygen atom, optionally substituted with at least one group selected from halogen, $C_{1-6}$ alkyl, $C_{1-6}$ alkyl substituted with at least one halogen, $C_{1-6}$ alkoxy, $C_{1-6}$ alkoxy substituted with at least one halogen, $C_{1-6}$ alkylthio, and cyano;

R1 is selected from hydrogen and $C_{1-6}$ alkyl;

or A and R1 taken together with the nitrogen atom to which they are linked form a 5-6 membered aromatic or non-aromatic heterocycle containing 1-2 nitrogen atoms, and optionally 1 oxygen atom, and optionally 1 sulphur atom, optionally substituted with a group selected from halogen, $C_{1-6}$ alkyl, $C_{1-6}$ alkyl substituted with a halogen, $C_{1-6}$ alkoxy, $C_{1-6}$ alkoxy substituted with a halogen, $C_{1-6}$ alkylthio, =NH, =O, —OH and cyano;

R2-R3 are independently a group selected from hydrogen and $C_{1-6}$ alkyl;

or R2 and R3 taken together with the carbon atom to which they are linked form a $C_{3-4}$ cycloalkyl;

R4-R6 are independently a group selected from hydrogen, halogen, and $C_{1-4}$ alkyl;

R7-R8 are independently a group selected from hydrogen, $C_{1-4}$ alkyl, $C_{1-4}$ alkyl substituted with one OH, $C_{1-4}$ alkyl substituted with one $OC_{1-3}$ alkyl, $C_{1-4}$ alkyl substituted with at least one halogen, or R7 and R8 taken together with the carbon atom to which they are linked form a $C_{3-4}$ cycloalkyl;

R9-R13 are independently a group selected from hydrogen, halogen, $C_{1-6}$ alkyl substituted with at least one halogen, $C_{1-6}$ alkoxy, $C_{1-6}$ alkoxy substituted with at least one halogen, $C_{1-6}$ alkylthio, and cyano; or a pharmaceutically acceptable salt thereof.

In an embodiment A is 5-membered aromatic heterocycle containing 1-3 nitrogen atoms and optionally 1 oxygen atom, optionally substituted with at least one group selected from halogen, $C_{1-6}$ alkyl, $C_{1-6}$ alkyl substituted with at least one halogen, $C_{1-6}$ alkoxy, $C_{1-6}$ alkoxy substituted with at least one halogen, $C_{1-6}$ alkylthio, and cyano.

In another embodiment A is 6-membered aromatic heterocycle containing 1-3 nitrogen atoms, optionally substituted with at least one group selected from halogen, $C_{1-6}$ alkyl, $C_{1-6}$ alkyl substituted with at least one halogen, $C_{1-6}$ alkoxy, $C_{1-6}$ alkoxy substituted with at least one halogen, $C_{1-6}$ alkylthio, and cyano.

In a further embodiment A is selected from an imidazolyl, a pyrazolyl, an oxazolyl, an isoxazolyl, an oxadiazolyl, and a pyrimidinyl, optionally substituted with at least one group selected from halogen, $C_{1-6}$ alkyl, $C_{1-6}$ alkyl substituted with at least one halogen, $C_{1-6}$ alkoxy, $C_{1-6}$ alkoxy substituted with at least one halogen, $C_{1-6}$ alkylthio, and cyano.

In a particular embodiment of the A-N bond in the compound of formula I, the A includes a carbon atom to which the N atom is connected. Thus, the situation when A includes a nitrogen, an oxygen or a sulphur attached to the N is disclaimed.

Furthermore, when a halogen is a substituent to the A ring it is attached to a carbon atom of the A ring. In particular, a halogen substituent is not attached to a nitrogen atom in the A ring.

In a still further embodiment R1 is selected from hydrogen (H) and methyl, typically H.

In a further embodiment A and R1 taken together with the nitrogen atom to which they are linked form a 5 membered aromatic or non-aromatic heterocycle containing 1-2 nitrogen atoms, optionally 1 oxygen atom, and optionally 1 sulphur atom, optionally substituted with a group selected from halogen, $C_{1-6}$ alkyl, $C_{1-6}$ alkyl substituted with a halogen, $C_{1-6}$ alkoxy, $C_{1-6}$ alkoxy substituted with a halogen, $C_{1-6}$ alkylthio, =NH, OH, =O and cyano.

In a further embodiment A and R1 taken together with the nitrogen atom to which they are linked form a 5 membered non-aromatic heterocycle containing 1 nitrogen atom and 1 oxygen atom, optionally substituted with a group selected from halogen, $C_{1-6}$ alkyl, $C_{1-6}$ alkyl substituted with a halogen, $C_{1-6}$ alkoxy, $C_{1-6}$ alkoxy substituted with a halogen, $C_{1-6}$ alkylthio, =NH, —OH, =O and cyano. Typically, the 5 membered non-aromatic heterocycle is substituted with one, two or three groups selected from methyl and =NH, such as a 2,3-dihydro-1,3-oxazol-2-imine optionally substituted with one or two methyl groups.

In a further embodiment R2-R3 are independently a group selected from H and $C_{1-3}$ alkyl, typically R2-R3 are both H. in a further embodiment R2 is H and R3 is $C_{1-3}$ alkyl, such as methyl.

In a still further embodiment R2 and R3 taken together with the carbon atom to which they are linked form a cyclopropyl.

In a further embodiment R4-R6 are independently a group selected from H, F, Cl, methyl, such as R4-R6 are all H.

In a still further embodiment R7 is a group selected from H and $C_{1-3}$ alkyl. Typically, R7 is H. In another embodiment R7 is methyl.

In a further embodiment R8 is a group selected from $C_{1-4}$ alkyl, $C_{1-4}$ alkyl substituted with one OH, and $C_{1-4}$ alkyl substituted with one $OC_{1-3}$ alkyl. In one embodiment R8 is $CH_2OH$.

In a further embodiment R7 and R8 taken together with the carbon atom to which they are linked form a cyclopropyl.

In a still further embodiment R9-R13 are independently a group selected from H, halogen, $C_{1-6}$ alkyl substituted with at least one halogen, and $C_{1-6}$ alkoxy substituted with at least one halogen.

In a further embodiment R9, R12 and R13 are all H, and R10-R11 are independently a group selected from H, halogen, $C_{1-6}$ alkyl substituted with at least one halogen, and $C_{1-6}$ alkoxy substituted with at least one halogen; provided that R10 and R11 are not both H.

In still further embodiments the compound of formula (I) is selected from any one of the exemplified compounds of examples 1-30b; or a pharmaceutically acceptable salt thereof.

In further embodiments the compound of formula (I) is selected from any one of the exemplified compounds of examples 1-49b; or a pharmaceutically acceptable salt thereof.

In a further aspect the present invention relates to a compound of formula (I) as defined above for use as a medicine.

In a still further aspect the present invention relates to a pharmaceutical composition comprising a compound of formula (I) as defined above and optionally a pharmaceutically acceptable additive, such as carrier or excipient.

In a further aspect the present invention relates to a compound of formula (I) as defined above for use in a method for treating a cardiac disease, disorder or condition in a mammal, such as a human. In an embodiment a cardiac disease, disorder or condition is selected from the cardiac disease, disorder or condition wherein the disease, disorder or condition is associated with an abnormal rhythm of the heart or variant and exercise induced angina. In another embodiment the cardiac disease, disorder or condition is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, and an abnormal rhythm arising after cardiac surgery or a cardiac ablation procedure.

According to a further aspect of the specification there is provided a pharmaceutical composition, which comprises a compound of Formula (I), or a pharmaceutically acceptable salt thereof, as defined herein, in association with a pharmaceutically acceptable excipient.

According to a further aspect of the specification there is provided a pharmaceutical composition, which comprises a compound of Formula (I), or a pharmaceutically acceptable salt thereof, as defined herein, for use in the treatment of cardiac disease, disorder or condition in a mammal, such as a human. In an embodiment a cardiac disease, disorder or condition is selected from the cardiac disease, disorder or condition wherein the disease, disorder or condition is associated with an abnormal rhythm of the heart or variant and exercise induced angina. In another embodiment the cardiac disease, disorder or condition is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, and an abnormal rhythm arising after cardiac surgery or a cardiac ablation procedure.

According to a further aspect of the specification, there is provided a compound of Formula (I), or a pharmaceutically acceptable salt thereof, as defined herein, for use as a medicament.

According to a further aspect of the specification, there is provided a compound of Formula (I), or a pharmaceutically acceptable salt thereof, as defined herein, for use in therapy.

According to a further aspect of the specification, there is provided a compound of Formula (I), or a pharmaceutically acceptable salt thereof, as defined herein, for use in a method of treatment of the human or animal body by therapy.

According to a further aspect of the specification, there is provided a compound of Formula (I), or a pharmaceutically acceptable salt thereof, as defined herein, for use in the prevention or treatment of mammals, such as humans.

According to a further aspect of the specification there is provided the use of a compound of Formula (I), or a pharmaceutically acceptable salt thereof, as defined herein, for the manufacture of a medicament for the prevention or treatment of mammals, such as humans.

According to a further aspect of the specification there is provided a method for the prevention or treatment of cardiac disease, disorder or condition in a mammal, such as a human. In an embodiment a cardiac disease, disorder or condition is selected from the cardiac disease, disorder or condition wherein the disease, disorder or condition is associated with an abnormal rhythm of the heart or variant and exercise induced angina. In another embodiment the cardiac disease, disorder or condition is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, and an abnormal rhythm arising after cardiac surgery or a cardiac ablation procedure, in a mammal such as humans, in need of such treatment, which comprises administering to said animal an effective amount of a compound of Formula (I), or a pharmaceutically acceptable salt thereof, as defined herein.

In a further aspect the present invention relates to a method for treatment of a cardiac disease, disorder or condition in a mammal, such as a human, wherein a therapeutically effective amount of at least one compound of formula (I) as defined above is administered to a mammal in need of said treatment. In an embodiment the cardiac disease, disorder or condition in a mammal is selected from the group consisting of cardiac arrhythmia, atrial arrhythmia, ventricular arrhythmia, atrial fibrillation, ventricular fibrillation, tachyarrhythmia, atrial tachyarrhythmia, ventricular tachyarrhythmia, bradyarrhythmias, and an abnormal rhythm arising after cardiac surgery or a cardiac ablation procedure, In a still further aspect the present invention relates to a process for preparing a compound of formula (I) or a pharmaceutically acceptable salt or solvate thereof, as well as the intermediates, comprising the steps described in connection with reaction schemes 1-9.

DETAILED DESCRIPTION

In a broad aspect the present invention relates to a compound of formula (I)

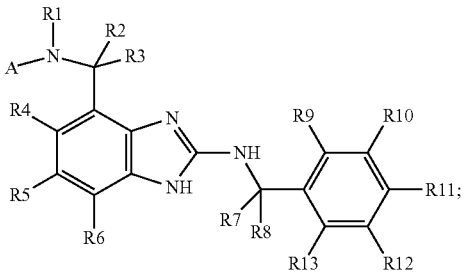

Wherein A and R1-R13 are as defined above; or
a pharmaceutically acceptable salt thereof.

In certain embodiments whenever $C_{1-6}$ alkyl or $C_{1-6}$ alkoxy is substituted with at least one halogen, it is preferred that such $C_{1-6}$ alkyl or $C_{1-6}$ alkoxy is substituted with 1 to 3 halogens, such as 1 to 3 F atoms, preferred are $CF_3$ and $OCF_3$.

In a further embodiment A is selected from any one of pyrrolyl, imidazolyl, pyrazolyl, oxazolyl, isoxazolyl, thiazolyl, isothiazolyl, triazolyl, furazanyl, oxadiazolyl, thiadiazolyl, tetrazolyl, pyrimidinyl, pyridinyl, diazinyl, pyridazinyl, triazinyl, and tetrazinyl.

In a still further embodiment A is selected from any one of pyrrolyl, imidazolyl, pyrazolyl, oxazolyl, isoxazolyl, thiazolyl, isothiazolyl, triazolyl, furazanyl, oxadiazolyl, thiadiazolyl, tetrazolyl, pyrimidinyl, pyridinyl, diazinyl, pyridazinyl, triazinyl, and tetrazinyl substituted with a group selected from $C_{1-6}$ alkyl.

In an embodiment A is 5-membered aromatic heterocycle containing 1-2 nitrogen atoms and optionally 1 oxygen atom, such as imidazolyl, a pyrazolyl, an oxazolyl, an isoxazolyl, or an oxadiazolyl.

In a further embodiment A is 5-membered aromatic heterocycle containing 1-2 nitrogen atoms and optionally 1 oxygen atom, selected from imidazolyl, a pyrazolyl, an oxazolyl, an isoxazolyl, and an oxadiazolyl substituted with 1 or 2 groups selected from $C_{1-6}$ alkyl, such as methyl.

In another embodiment A is 6-membered aromatic heterocycle containing 1-2 nitrogen atoms, such as pyrimidine.

In a further embodiment A is selected from an imidazolyl, a pyrazolyl, an oxazolyl, an isoxazolyl, an oxadiazolyl, and a pyrimidinyl, substituted with at least one group selected from $C_{1-6}$ alkyl.

In one embodiment R1 is H. In another embodiment R1 is methyl.

In a further embodiment A and R1 taken together with the nitrogen atom to which they are linked form a 5 membered aromatic heterocycle containing 1-2 nitrogen atom and 1 oxygen atom, optionally substituted with a group selected from halogen, $C_{1-6}$ alkyl, $C_{1-6}$ alkyl substituted with a halogen, $C_{1-6}$ alkoxy, $C_{1-6}$ alkoxy substituted with a halogen, $C_{1-6}$ alkylthio, =NH, —OH, =O and cyano.

In a further embodiment A and R1 taken together with the nitrogen atom to which they are linked form a 5 membered aromatic heterocycle containing 2 nitrogen atoms substituted with a group selected from =O, such as 2,3-dihydro-1H-imidazol-2-one.

In a further embodiment A and R1 taken together with the nitrogen atom to which they are linked form a 5 membered aromatic heterocycle containing 1 nitrogen atom and 1 oxygen atom substituted with a group selected from =NH, such as 2-imino-2,3-dihydro-1,3-oxazol-3-yl.

In a further embodiment A and R1 taken together with the nitrogen atom to which they are linked form a 5 membered aromatic heterocycle containing 1 nitrogen atom and 1 sulphur atom substituted with a group selected from =NH, such as 2-imino-2,3-dihydro-1,3-thiazol-3-yl.

In a further embodiment A and R1 taken together with the nitrogen atom to which they are linked form a 5 membered non-aromatic heterocycle containing 1 nitrogen atom and 1 oxygen atom, optionally substituted with a group selected from halogen, $C_{1-6}$ alkyl, $C_{1-6}$ alkyl substituted with a halogen, $C_{1-6}$ alkoxy, $C_{1-6}$ alkoxy substituted with a halogen, $C_{1-6}$ alkylthio, =NH, —OH; =O and cyano. Typically, the 5 membered non-aromatic heterocycle is substituted with one or more, such as 1-3, selected from methyl and =NH, such as a 2,3-dihydro-1,3-oxazol-2-imine optionally substituted with one or two methyl groups.

In a further embodiment A and R1 taken together with the nitrogen atom to which they are linked form a 5 membered non-aromatic heterocycle containing 1-2 nitrogen atom and 1 oxygen atom, optionally substituted with a group selected from halogen, $C_{1-6}$ alkyl, $C_{1-6}$ alkyl substituted with a halogen, $C_{1-6}$ alkoxy, $C_{1-6}$ alkoxy substituted with a halogen, $C_{1-6}$ alkylthio, =NH, —OH, =O and cyano. Typically, the 5 membered non-aromatic heterocycle is substituted with one or more, such as 1-3, methyl and =NH.

In a further embodiment A and R1 taken together with the nitrogen atom to which they are linked form a 5 membered non-aromatic heterocycle containing 2 nitrogen atoms substituted with =O and optionally with one methyl, such as imidazolidin-2-one or methylimidazolidin-2-one.

In a further embodiment A and R1 taken together with the nitrogen atom to which they are linked form a 5 membered non-aromatic heterocycle containing 1 nitrogen atom and one sulphur atom substituted with =O, such as 1,3-thiazolidin-2-one.

In a further embodiment A and R1 taken together with the nitrogen atom to which they are linked form a 5 membered non-aromatic heterocycle containing 1 nitrogen atom substituted with =O, such as pyrrolidin-2-one.

In a further embodiment A and R1 taken together with the nitrogen atom to which they are linked form a 6 membered aromatic heterocycle containing 1-2 nitrogen atoms, optionally substituted with a group selected from halogen, $C_{1-6}$ alkyl, $C_{1-6}$ alkyl substituted with a halogen, $C_{1-6}$ alkoxy, $C_{1-6}$ alkoxy substituted with a halogen, $C_{1-6}$ alkylthio, =NH, —OH, =O and cyano.

In a further embodiment A and R1 taken together with the nitrogen atom to which they are linked form a 6 membered non-aromatic heterocycle containing 1-2 nitrogen atoms, optionally substituted with a group selected from halogen, $C_{1-6}$ alkyl, $C_{1-6}$ alkyl substituted with a halogen, $C_{1-6}$ alkoxy, $C_{1-6}$ alkoxy substituted with a halogen, $C_{1-6}$ alkylthio, =NH, —OH, =O and cyano; such as 3,4-dihydropyrimidin-4-imine.

In a further embodiment R2 is selected from H and $C_{1-3}$ alkyl, such as H.

In a still further embodiment R3 is selected from H and $C_{1-3}$ alkyl, typically R3 is H. In one embodiment R3 is methyl.

In a further embodiment R2 and R3 taken together with the carbon atom to which they are linked form a cyclopropyl. In another embodiment R2 and R3 taken together with the carbon atom to which they are linked form a cyclobutyl.

In a still further embodiment R4 is selected from H, F, Cl, methyl, such as H.

In a further embodiment R5 is selected from H, F, Cl, methyl, such as H.

In a still further embodiment R6 is selected from H, F, Cl, methyl, such as H.

In a further embodiment R7 is H. In another embodiment R7 is a $C_{1-3}$ alkyl, such as methyl or ethyl.

In a further embodiment R8 is a $C_{1-4}$ alkyl, such as methyl.

In a still further embodiment R8 is a $C_{1-4}$ alkyl substituted with one OH, such as $CH_2OH$ or $CH_2CH_2OH$.

In a further embodiment R8 is a $C_{1-4}$ alkyl substituted with one $OC_{1-3}$ alkyl, such as $C_{1-3}$ alkyl substituted with at least one methoxy or ethoxy, typically $CH_2OCH_3$ or $CH_2CH_2OCH_3$.

In a further embodiment R7 and R8 taken together with the carbon atom to which they are linked form a cyclopropyl. In another embodiment R7 and R8 taken together with the carbon atom to which they are linked form a cyclobutyl.

In a still further embodiment R9 is a H. In another embodiment R9 is a, halogen, such as F or Cl. In a further embodiment R9 is a $C_{1-6}$ alkyl substituted with at least one halogen, such as $CF_3$. In another embodiment R9 is a $C_{1-6}$ alkoxy substituted with at least one halogen, such as $OCF_3$.

In a still further embodiment R10 is a halogen, such as F or Cl. In a further embodiment R10 is H. In a further embodiment R10 is a $C_{1-6}$ alkyl substituted with at least one halogen, such as $CF_3$. In another embodiment R10 is a $C_{1-6}$ alkoxy substituted with at least one halogen, such as $OCF_3$.

In a still further embodiment R11 is a H. In another embodiment R11 is a, halogen, such as F or Cl. In a further embodiment R11 is a $C_{1-6}$ alkyl substituted with at least one halogen, such as $CF_3$. In another embodiment R11 is a $C_{1-6}$ alkoxy substituted with at least one halogen, such as $OCF_3$.

In a still further embodiment R12 is a H. In another embodiment R12 is a, halogen, such as F or Cl. In a further embodiment R12 is a $C_{1-6}$ alkyl substituted with at least one halogen, such as $CF_3$. In another embodiment R12 is a $C_{1-6}$ alkoxy substituted with at least one halogen, such as $OCF_3$.

In a still further embodiment R13 is a H. In another embodiment R13 is a, halogen, such as F or Cl. In a further embodiment R13 is a $C_{1-6}$ alkyl substituted with at least one halogen, such as $CF_3$. In another embodiment R13 is a $C_{1-6}$ alkoxy substituted with at least one halogen, such as $OCF_3$.

In a further embodiment R9, R12 and R13 are all H, and R10 is a group selected from halogen, $C_{1-6}$ alkyl substituted with at least one halogen, and $C_{1-6}$ alkoxy substituted with at least one halogen, and R11 is a group selected from H, halogen, $C_{1-6}$ alkyl substituted with at least one halogen, and $C_{1-6}$ alkoxy substituted with at least one halogen.

In a further embodiment R9, R12 and R13 are all H, and R10 is a group selected from F, Cl, $CF_3$, and $OCF_3$, and R11 is a group selected from H, F, Cl, $CF_3$, and $OCF_3$.

In a further embodiment each of R9, R10, R11 and R12 is a group selected from H and halogen and R13 is H. Preferably, each of R9, R10, R11 and R12 is a group selected from H, Cl and F and R13 is H, provided that at least two of R9-R12 is a halogen, such as a halogen selected from F and Cl.

Each of the compounds as described in the experimental part constitutes an embodiment of the present invention in any form, such as a salt or free base, and may be subject to a claim to such compound, or a salt thereof.

In a still further embodiment the compound of formula (I) is selected from a trifluoroacetic acid salt of any one of the compounds of examples 1-30b.

In a further embodiment the compound of formula (I) is selected from a trifluoroacetic acid salt of any one of the compounds of examples 1-49b.

In a still further embodiment the compound of formula (I) is selected from a trifluoroacetic acid salt of any one of the compounds of examples 31-49b.

Cardiac Diseases

In the context of this invention a cardiac disease, disorder or condition is any cardiac disease, disorder or condition, including, but not limited to, an abnormal rhythm of the heart or variant and exercise induced angina.

In a more specific embodiment the cardiac disease, disorder or condition is any disease, disorder or condition associated with an abnormal rhythm of the heart or variant and exercise induced angina.

In a more specific embodiment the cardiac disease, disorder or condition is any disease, disorder or condition associated with an abnormal rhythm of the heart.

In a more specific embodiment the cardiac disease, disorder or condition associated with an abnormal rhythm of the heart is selected from cardiac arrhythmia, atrial arrhythmia, ventricular arrhythmia, atrial fibrillation, ventricular fibrillation, tachyarrhythmia, atrial tachyarrhythmia, ventricular tachyarrhythmia, and bradyarrhythmias.

In another embodiment a cardiac disease, disorder or condition of the invention is an abnormal rhythm caused by myocardial ischaemia, myocardial infarction, cardiac hypertrophy, or cardiomyopathy.

In another embodiment a cardiac disease, disorder or condition of the invention is an abnormal rhythm arising after cardiac surgery or a cardiac ablation procedure.

In a further specific embodiment, the cardiac disease, disorder or condition associated with an abnormal rhythm of the heart is a cardiac arrhythmia caused by a genetic disease.

In a still further preferred embodiment the cardiac disease, disorder or condition associated with an abnormal rhythm of the heart is cardiac arrhythmia.

In a preferred embodiment the cardiac disease, disorder or condition associated with an abnormal rhythm of the heart is atrial fibrillation.

In a particular embodiment the compound of formula (I) of the present invention is useful for treatment of atrial fibrillation by acute cardioversion to normal sinus rhythm.

In another particular embodiment the compound of formula (I) of the present invention is useful for treatment of atrial fibrillation by maintaining normal sinus rhythm and avoiding or reducing the occurrence of new episodes of atrial fibrillation.

Pharmacological Treatment of Atrial Fibrillation

In the context of this invention, and as understood by a person skilled in the art, treatment of atrial fibrillation is acute cardioversion or maintenance of sinus rhythm or both. Acute conversion is defined as application of compound that has the ability to convert atrial fibrillation to a normal cardiac sinus rhythm. Normal sinus rhythm is defined as regular stable heart beating at frequencies between 40 and 100 beats at rest in adults with normal regular p-wave on a standard 12-lead electrocardiogram. Maintenance of sinus rhythm is defined as the ability for a compound to preserve a normal stable sinus rhythm over time with no relapse to atrial fibrillation or the ability of a compound to significantly reduced the incidence of relapse from atrial fibrillation to normal sinus rhythm compared to non-treated controls.

Description of General Process

Schemes 1-9 summarises some of the synthetic approaches that can be used to prepare compounds of general formula (I).

Scheme 1

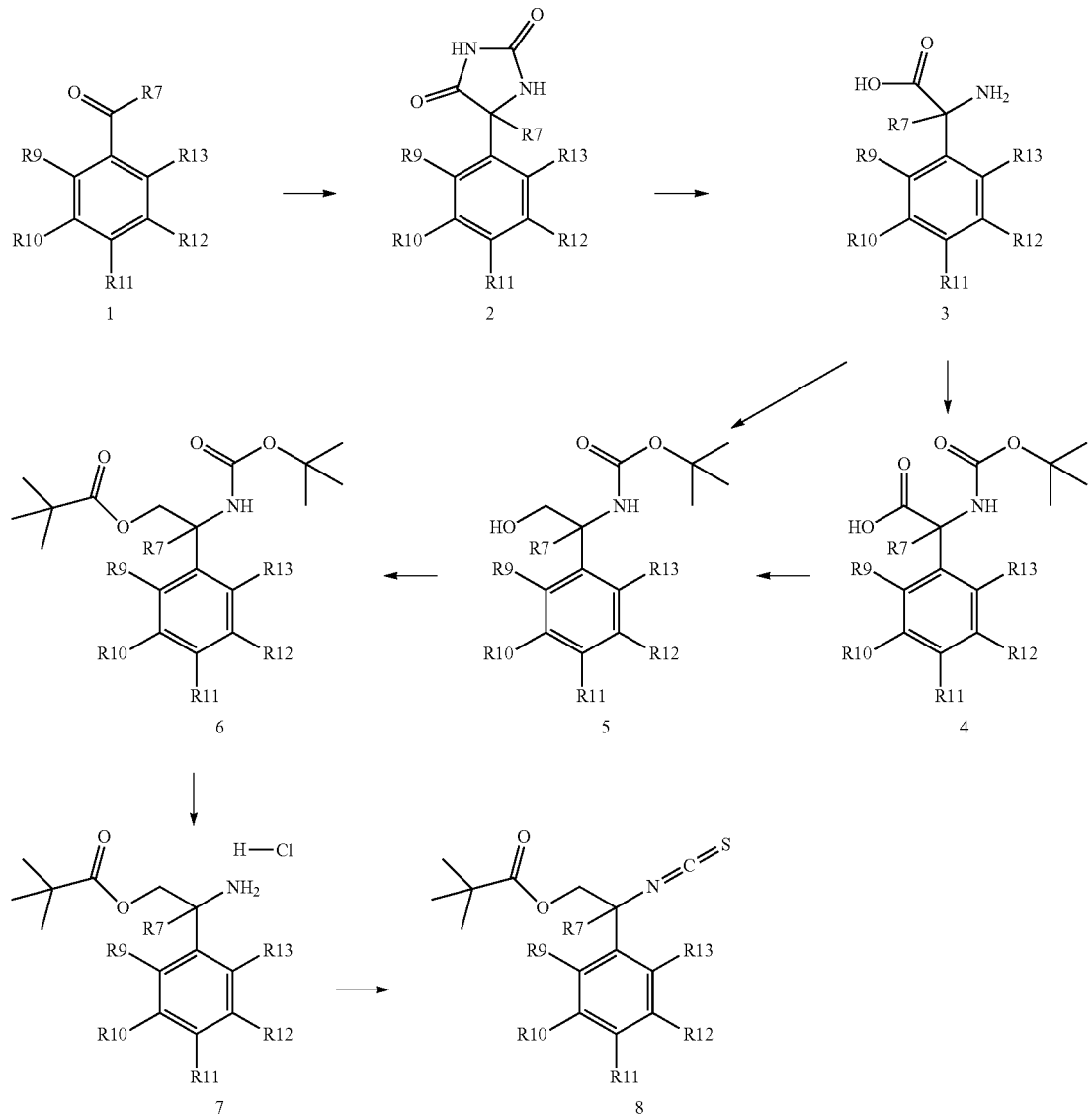

Scheme 1: A large number of ketones and aldehydes (1) are commercially available or can be readily prepared by many routes described in the literature. The ketones and aldehydes (1) can be converted to the hydantoin derivatives (2) by a wide range of methods, such as reaction of (1) with potassium cyanide under the influence of ammonium salts (e.g. ammonium carbonate) upon heating (50° C. to 100° C.) in solvents such as water and alcohols (e.g. ethanol). The hydantoin derivatives (2) can be converted to the amino acid derivatives (3) by hydrolysis under the influence of a strong base (e.g. sodium hydroxide) and heat in water (100° C.). There are many other well-established methods for the preparation of amino acids described in the literature. Many amino acid derivatives are also readily available commercially. Amino acids (3) can be protected as the N-(tert-butoxy)carbonyl derivatives (4) by treatment with di-tert-butyl dicarbonate and a base (e.g. sodium bicarbonate) in a suitable solvent (e.g. tetrahydrofuran/water) at 0° C. to ambient temperature. Intermediates (4) can be reduced to the alcohol derivatives (5) by a variety of methods, including by hydride reducing agents (e.g. sodium borohydride or lithium aluminium hydride). This can be achieved by direct reduction of the acid group (e.g. with lithium aluminium hydride (in a solvent such as tetrahydrofuran) at ambient temperature or by first activation of the acid group in (4) by converting it to a mixed anhydride (e.g. with isobutyl chloroformate and triethylamine in tetrahydrofuran) at 0° C., followed by reduction with sodium borohydride (e.g. in water) at 0° C. to ambient temperature. The alcohol derivative (5) may require protection such as converting it to an ester (e.g. 2,2-dimethylpropanoate ester) by reacting with 2,2-dimethylpropanoyl chloride and a base (such as triethylamine) in a solvent (such as dichloromethane) at 0° C. to ambient temperature. Intermediate (6) can be deprotected to the amine derivative (7) by treatment with an acid (e.g. hydrochloric acid or trifluoroacetic acid) in a suitable solvent (e.g. dioxane or dichloromethane) at 0° C. to ambient temperature. The intermediates (7) can be converted to the isothiocyanate derivatives (8) by reaction with thiophosgene in a suitable solvent (e.g. dichloromethane) under the influence of a base (e.g. sodium hydrogen carbonate) at 0° C. to ambient temperature.

esters (10) can be reduced to the alcohol derivatives (11) by a variety of methods, including by hydride reducing agents (e.g. lithium aluminium hydride) in a suitable solvent (e.g. tetrahydrofuran) at 0° C. The alcohol derivative (12) may

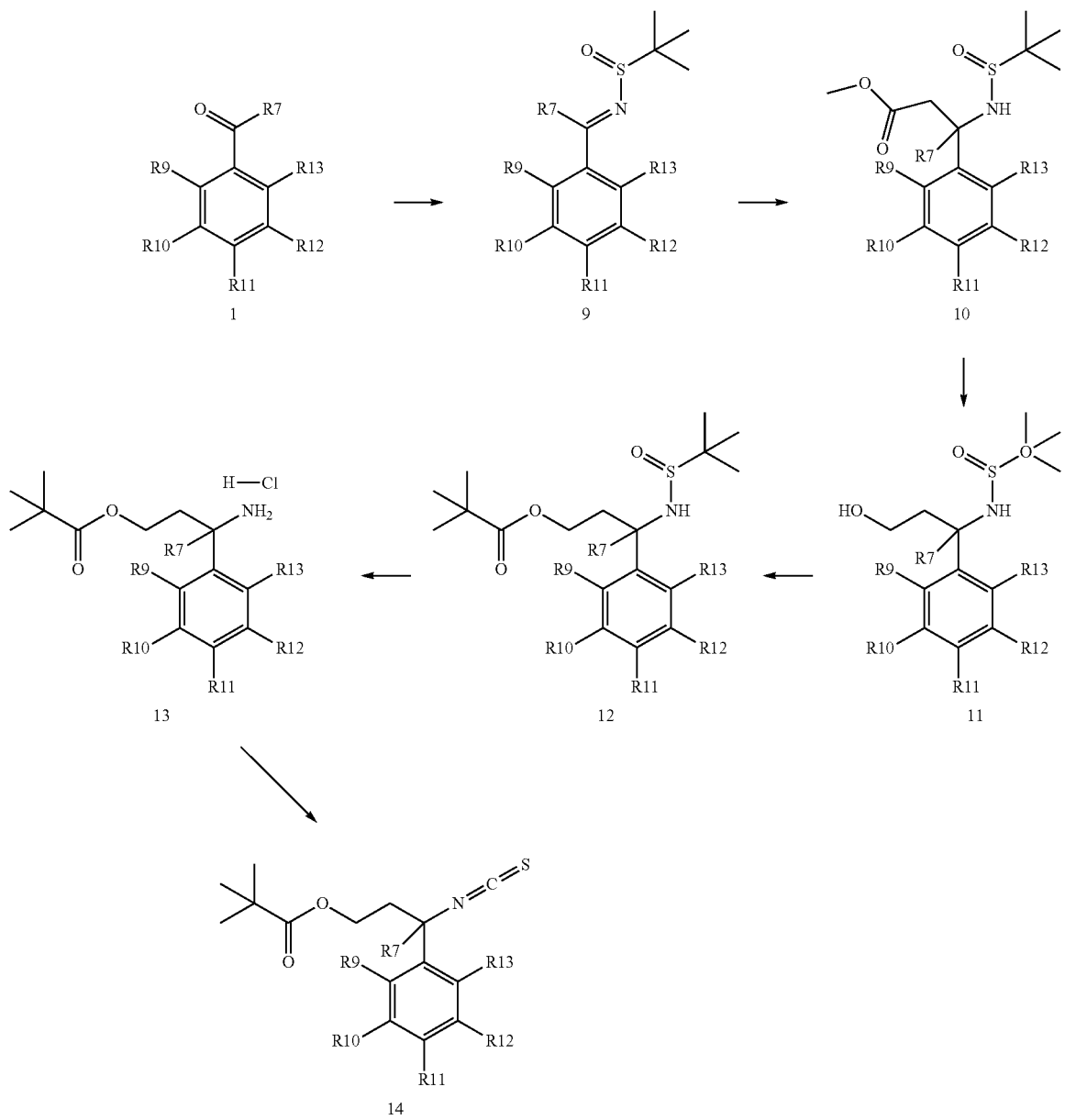

Scheme 2: The ketones and aldehydes (1) can be converted to the sulfinamide derivatives (9) by reaction of (1) with 2-methylpropane-2-sulfinamide under the influence of a Lewis acid (e.g. titanium (IV) ethoxide) and heating at 70° C. in a suitable solvent (e.g. tetrahydrofuran). The sulfinamide derivatives (9) can be converted to the β-amino acid esters (10) by reaction with methyl 2-bromoacetate under the influence of zinc and copper (I) iodide at 0-5° C. in a solvent (e.g. tetrahydrofuran). There are many other well-established methods for the preparation of β-amino acids described in the literature. Some β-amino acid derivatives are also readily available commercially. The β-amino acid require protection such as converting it to an ester (e.g. 2,2-dimethylpropanoate ester) by reacting with 2,2-dimethylpropanoyl chloride and a base (such as triethylamine) in a solvent (e.g. dichloromethane) at 0° C. Intermediate (12) can be deprotected to the free derivative (13) by treatment with an acid (e.g. hydrochloric acid or trifluoroacetic acid) in a suitable solvent (e.g. dioxane or dichloromethane) 0° C. The intermediates (13) can be converted to the isothiocyanate derivatives (14) by reaction with thiophosgene in a suitable solvent (e.g. dichloromethane) under the influence of a base (e.g. sodium hydrogen carbonate) at ambient temperature.

Scheme 3

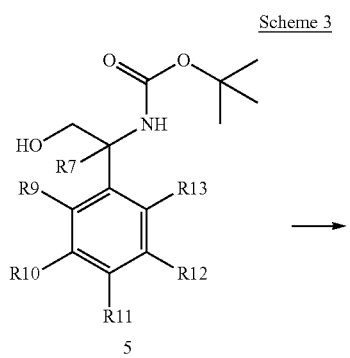

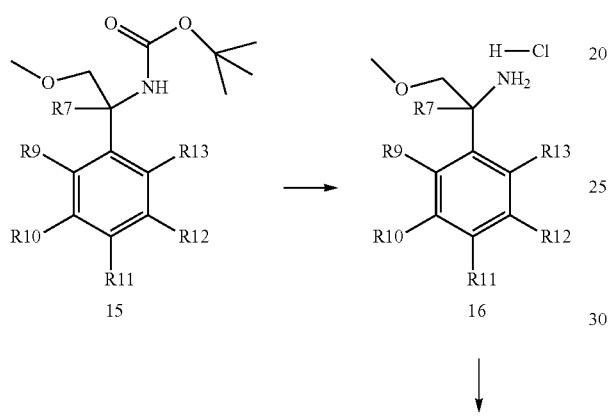

Scheme 4 (Where R7 and R8 together form a small ring or are H or alkyl groups)

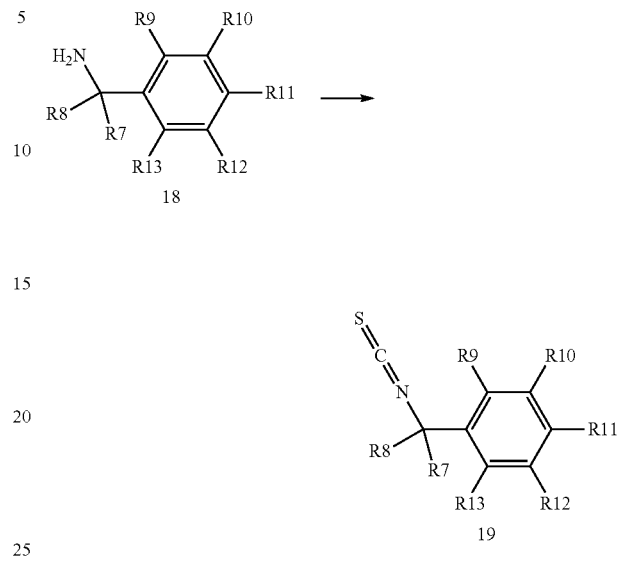

Scheme 4: There are a wide range of intermediates (18) that are readily available commercially or can be prepared by methods described in the literature. The intermediates (18) can be converted to the isothiocyanate derivatives (19) by reaction with thiophosgene in a suitable solvent (e.g. dichloromethane) under the influence of a base (e.g. sodium hydrogen carbonate) at ambient temperature.

Scheme 5

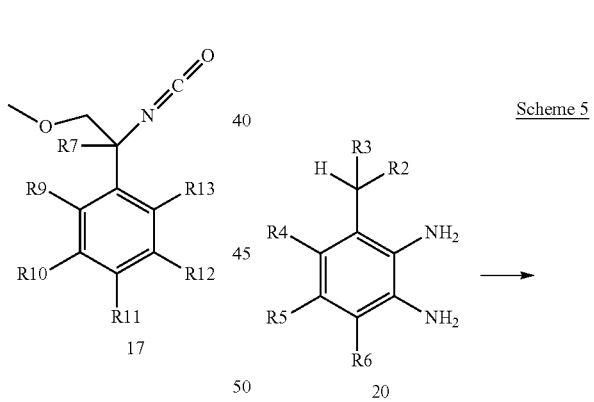

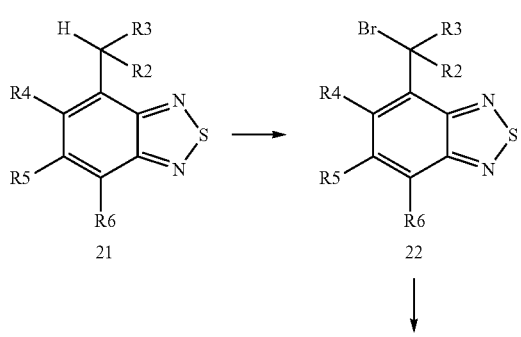

Scheme 3: The alcohol derivatives (5) can be alkylated on the alcohol oxygen atom by reacting with methyl iodide under the influence of a metal oxide (e.g. silver oxide) in a solvent (e.g. acetonitrile) at ambient temperature and converted to intermediates (15). Intermediate (15) can be deprotected to the amine derivative (16) by treatment with an acid (e.g. hydrochloric acid or trifluoroacetic acid) in a suitable solvent (e.g. dioxane or dichloromethane) at 0° C. to ambient temperature. The intermediates (16) can be converted to the isothiocyanate derivatives (17) by reaction with thiophosgene in a suitable solvent (e.g. dichloromethane) under the influence of a base (e.g. sodium hydrogen carbonate) at 0° C. to ambient temperature.

-continued

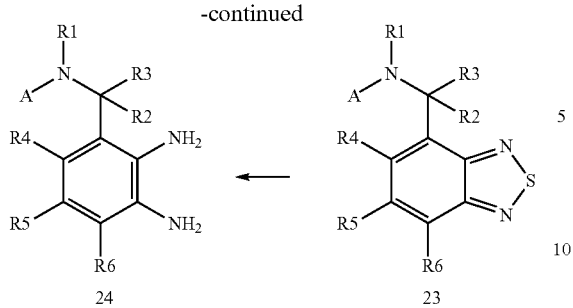

Scheme 5: There are a wide range of benzene-1,2-diamine intermediates (20) that are readily available commercially or can be prepared by methods described in the literature. The intermediates (20) can be converted to the 2,1,3-benzothiadiazole derivatives (21) by reaction with thionyl chloride in pyridine (at temperatures between 0° C. to 45° C.). The intermediates (21) can be converted to the benzyl bromide derivatives (22) by reaction with N-bromosuccinimide in a solvent (e.g. chloroform) under the influence of radical initiators (e.g. benzoyl peroxide) upon heating at reflux temperature. Intermediates (22) can react with a wide range of amino-heterocycles upon heating at 60° C. in a solvent (e.g. acetonitrile) to afford intermediates (23). The intermediates (23) can be converted to benzene-1,2-diamine derivatives (24) by desulphurisation with hydrogen gas under the influence of metal catalysts (e.g. Raney nickel) in a suitable solvent (e.g. methanol) at ambient temperature.

Scheme 6

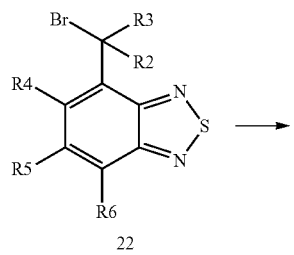

-continued

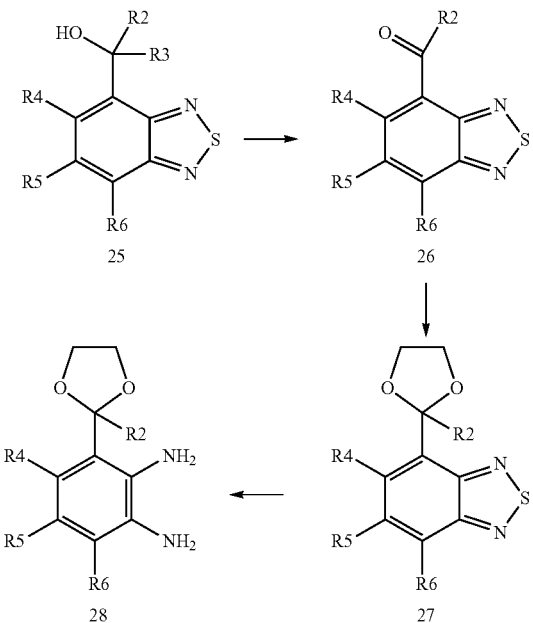

Scheme 6: The intermediates (22) can be converted to the alcohol derivatives (25) by reaction with metal carbonate salts (e.g. potassium carbonate) in suitable solvents (e.g. dioxane/water) at reflux temperature. The alcohol derivatives (25) can be oxidized to aldehydes or ketone derivatives (26) with oxidizing agents (e.g. Dess-Martin Periodinane) is a solvent (e.g. dichloromethane) at ambient temperature. The intermediates (26) can be protected as the 1,3-dioxolan-2-yl derivatives (27) by reaction with 1,2-ethanediol under the influence tetra-butylammonium tribromide in a solvent (e.g. dichloromethane) at ambient temperature.

The intermediates (27) can be converted to benzene-1,2-diamine derivatives (28) by desulphurisation with hydrogen gas under the influence of metal catalysts (e.g. Raney nickel) in a suitable solvent (e.g. methanol) at ambient temperature.

Scheme 7

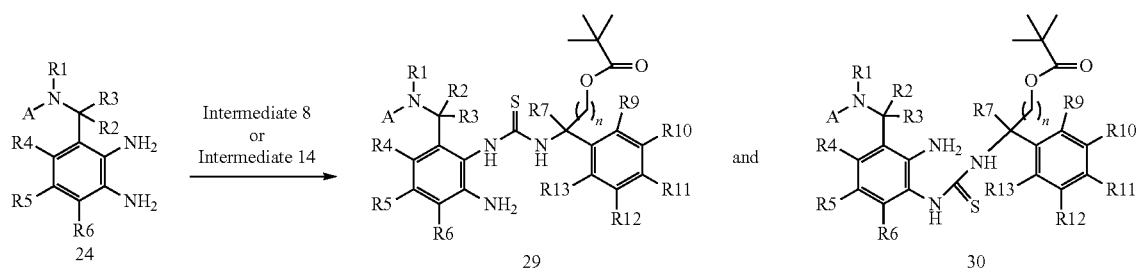

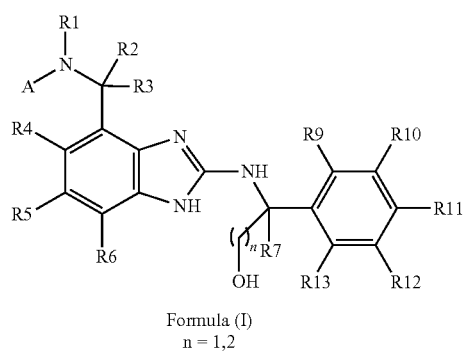

Formula (I)
n = 1,2

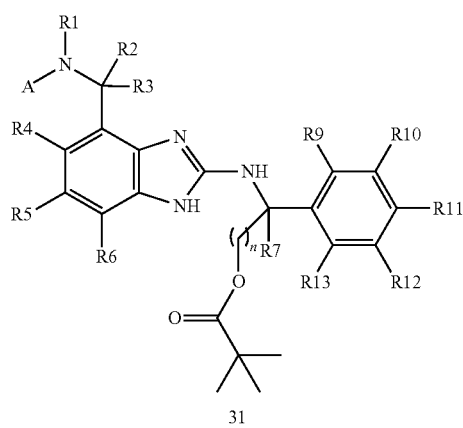

31

Scheme 7, Route 1 to Examples of Formula (I): The benzene-1,2-diamine derivatives (24) can react with the isothiocyanates (8) or (14) in a suitable solvent (e.g. dichloromethane) at ambient temperature to afford a mixture of the thiourea products (29) and (30). A wide range of other benzene-1,2-diamine derivatives are available commercially or can be readily prepared by well-established methods described in the literature (e.g. by nitration and subsequent reduction of commercial substituted benzene starting materials). The thiourea derivatives (29) and (30) can be converted to 2-aminobenzimidazole derivatives (31) by a ring forming reaction that occurs under the influence of iodoacetic acid at ambient temperature in a suitable solvent (such as methanol or acetonitrile). The cyclisation of (29) and (30) to afford (31) can also occur under the influence of mercury salts (e.g. mercuric oxide) with heating in a suitable solvent (e.g. acetonitrile). The 2-aminobenzimidazole ester derivatives (31) can be converted to compounds of Formula (I) by deprotection of the ester under the influence of a base (e.g. sodium hydroxide) in a suitable solvent (e.g. methanol) at ambient temperature. The 2-aminobenzimidazole derivatives Formula (I) can be a racemic mixture, which can be separated into the two enantiomers A and B by a range of methods, including chromatography using a chiral stationary phase. This can be normal-phase or reverse phase chromatography, which uses suitable solvent mixtures as eluent (e.g. chloroform, dichloromethane, ethanol, ethyl acetate, methanol, ethanol) sometimes with additives (e.g. ammonia, triethylamine, trifluoroacetic acid, acetic acid).

Scheme 8

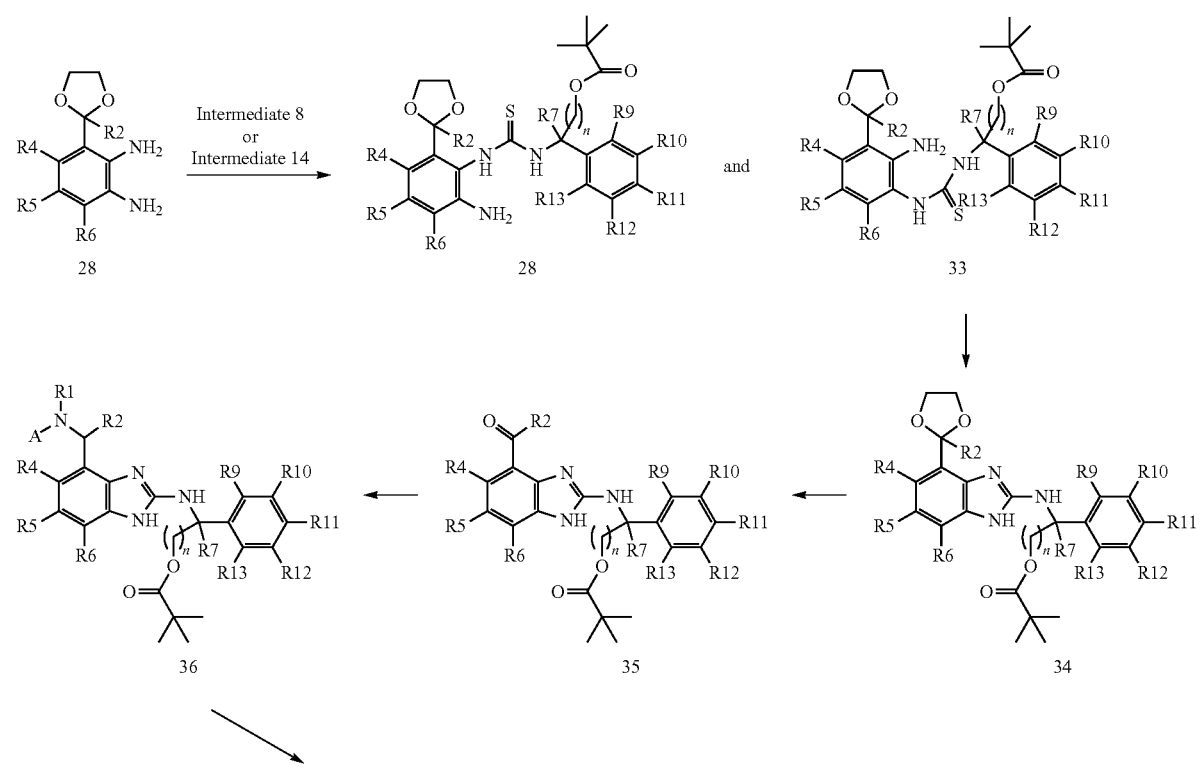

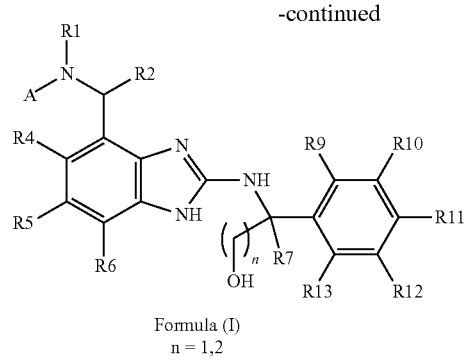

Formula (I)
n = 1,2

Enantiomer A and Enantiomer B
are seperated by chiral SFC

Scheme 8, Route 2 to Examples of Formula (I): The benzene-1,2-diamine derivatives (28) can react with the isothiocyanates (8) or (14) in a suitable solvent (e.g. dichloromethane) at ambient temperature to afford a mixture of the thiourea products (32) and (33). A wide range of other benzene-1,2-diamine derivatives are available commercially or can be readily prepared by well-established methods described in the literature (e.g. by nitration and subsequent reduction of commercial substituted benzene starting materials). The thiourea derivatives (32) and (33) can be converted to 2-aminobenzimidazole derivatives (34) by a ring forming reaction that occurs under the influence of iodoacetic acid at ambient temperature in a suitable solvent (such as methanol or acetonitrile). Intermediates (34) can be deprotected to the ketone and aldehyde derivatives (35) by reaction with an acid (e.g. p-toluenesulphonic acid) in a suitable solvent (e.g. acetone) at ambient temperature. The derivatives (35) can react with a wide range of aminoheterocycles in tetrahydrofuran under the influence of a dehydrating agent (e.g. titanium(IV)isopropoxide) at reflux, followed by reaction with a reducing agent (e.g. sodium cyanoborohydride) in tetrahydrofuran at ambient temperature to afford intermediates (36). The 2-aminobenzimidazole ester derivatives (36) can be converted to compounds of Formula (I) by deprotection of the ester under the influence of a base (e.g. sodium hydroxide) in a suitable solvent (e.g. methanol) at ambient temperature. The 2-aminobenzimidazole derivatives Formula (I) can be a racemic mixture, which can be separated into the two enantiomers A and B by a range of methods, including chromatography using a chiral stationary phase. This can be normal-phase or reverse phase chromatography, which uses suitable solvent mixtures as eluent (e.g. chloroform, dichloromethane, ethanol, ethyl acetate, methanol, ethanol) sometimes with additives (e.g. ammonia, triethylamine, trifluoroacetic acid, acetic acid).

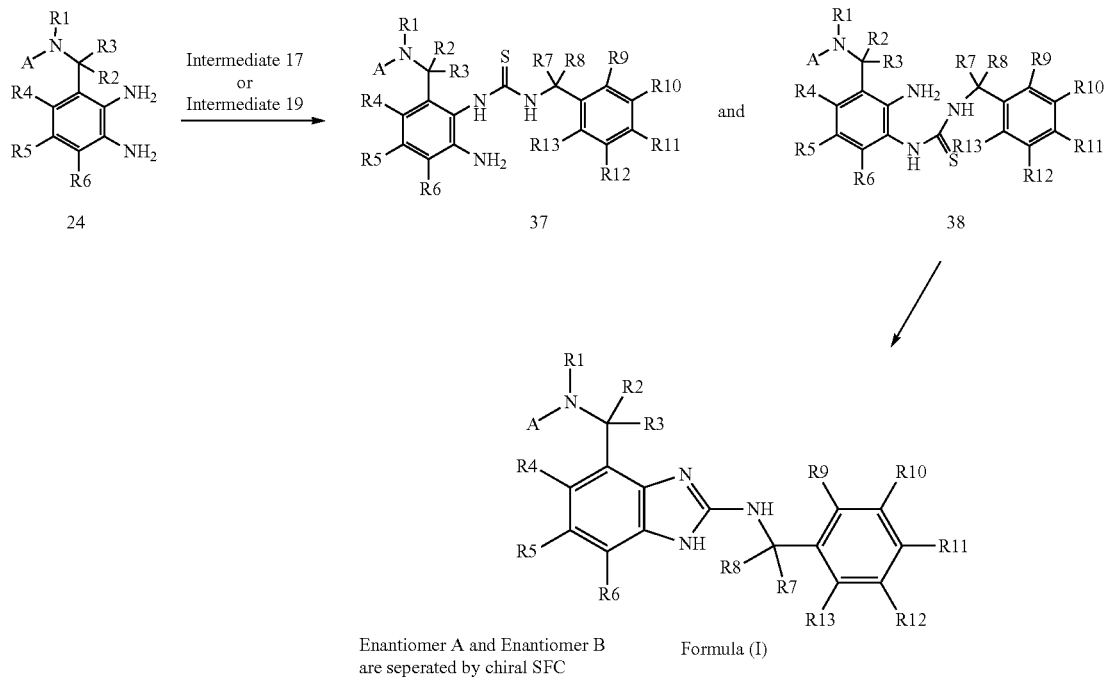

Scheme 9

Enantiomer A and Enantiomer B
are seperated by chiral SFC

Formula (I)

Scheme 9, Route 3 to Examples of Formula (I): The benzene-1,2-diamine derivatives (24) can react with the isothiocyanates (17) or (19) at ambient temperature in a suitable solvent (e.g. dichloromethane) to afford a mixture of the thiourea products (37) and (38). The thiourea derivatives (37) and (38) can be converted to 2-aminobenzimidazole derivatives Formula (I) by a ring forming reaction that occurs under the influence of iodoacetic acid at ambient temperature in a suitable solvent (such as methanol or acetonitrile). The cyclisation of (37) and (38) to afford derivatives Formula (I) can also occur under the influence of mercury salts (e.g. mercuric oxide) with heating in a suitable solvent (e.g. acetonitrile). The 2-aminobenzimidazole derivatives Formula (I) can be a racemic mixture, which can be separated into the two enantiomers A and B by a range of methods, including chromatography using a chiral stationary phase. This can be normal-phase or reverse phase chromatography, which uses suitable solvent mixtures as eluent (e.g. chloroform, dichloromethane, ethanol, ethyl acetate, methanol, ethanol) sometimes with additives (e.g. ammonia, triethylamine, trifluoroacetic acid, acetic acid).

The skilled person will understand that it may be necessary to adjust or change the order of steps in the processes described above, and such change of order is encompassed by the aspects of the process as described above in the reaction schemes and accompanying description of the process steps.

Furthermore, the skilled person will understand that the processes described above and hereinafter the functional groups of intermediate compounds may need to be protected by protecting group.

Functional groups that it is desirable to protect include hydroxy, amino and carboxylic acid. Suitable protecting groups for hydroxy include optionally substituted and/or unsaturated alkyl groups (e.g. methyl, allyl, benzyl or tert-butyl), trialkyl silyl or diarylalkylsilyl groups (e.g., t-butyldimethylsilyl, t-butyldiphenylsilyl or trimethylsilyl), AcO(acetoxy), TBS(t-butyldimethylsilyl), TMS(trimethylsilyl), PMB (p-methoxybenzyl), and tetrahydropyranyl. Suitable protecting groups for carboxylic acid include (C1-C6)-alkyl or benzyl esters. Suitable protecting groups for amino include t-butyloxycarbonyl, benzyloxycarbonyl, 2-(trimethylsilyl)-ethoxy-methyl or 2-trimethylsilylethoxy-carbonyl (Teoc). Suitable protecting groups for S include S—C(=N)NH$_2$, TIPS.

The protection and deprotection of functional groups may take place before or after any reaction in the above mentioned processes.

Furthermore the skilled person will appreciate that, in order to obtain compounds of the invention in an alternative, and on some occasions, more convenient, manner, the individual process steps mentioned hereinbefore may be performed in different order, and/or the individual reactions may be performed at a different stage in the overall route (i.e. substituents may be added to and/or chemical transformations performed upon, different intermediates to those mentioned hereinbefore in conjunction with a particular reaction). This may negate, or render necessary, the need for protecting groups.

The compounds of formula (I) have at least one asymmetric center, and may have further asymmetric centres and it is intended that any optical isomers (i.e. enantiomers or diastereomers), in the form of separated, pure or partially purified optical isomers and any mixtures thereof including racemic mixtures, i.e. a mixture of stereoisomers, are included within the scope of the invention. In particular, the carbon atom of formula (I) wherein the 4 valence bonds are linked to R7, R8, NH, phenyl and is an asymmetric centre giving rise to two optical isomers, an R form and an S form. In one embodiment, the compounds of the present invention have the S form. In another embodiment, the compounds of the present invention have the R form. In a further embodiment, the compounds of the present invention are a racemic mixture.

In this context it is understood that when specifying the enantiomeric form, then the compound is in enantiomeric excess, e.g. essentially in a pure, mono-enantiomeric form. Accordingly, one embodiment of the invention relates to a compound of the invention having an enantiomeric excess of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography of an optically active matrix. The compounds of the present invention may also be resolved by the formation of diastereomeric derivatives.

Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, the compound of the general formula I of the present invention has a benzimidazole structure which exists in tautomeric forms, and as used herein all tautomers are comprised by the compound of formula I although only one is shown.

Tautomers of formula (I) are:

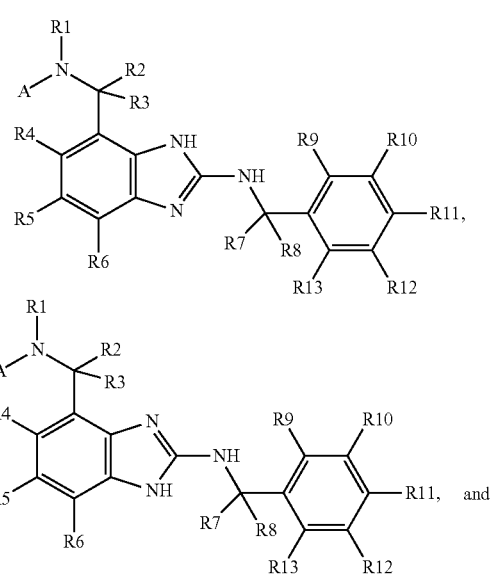

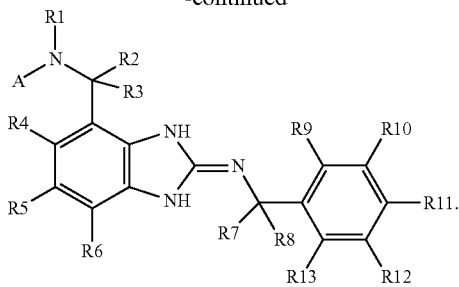

The benzimidazole tautomers of formula I above means that the hydrogen switches back and forth from one nitrogen to the other and that the double bond consequently switches back and forth between the nitrogen and carbon attachment point to the NH-group. Further, when a structure is presented with a benzimidazole either as part of a general structure or as individual specified compounds it is to be understood as the benzimidazole covers all tautomers, thus although only one tautomer is shown it includes all.

Whenever a "compound of formula (I)" is used herein it means the compound of formula (I) in any form incl the free form or as a salt thereof, such as a pharmaceutically acceptable salt thereof, unless otherwise indicated herein or clearly contradicted by context.

Whenever substituents are disclosed as R1-R13 it means that each and every consecutive possibility is disclosed, for instance R2-R4 means R2, R3 and R4, and e.g. R9-R13 means R9, R10, R11, R12 and R13. In a still further embodiment the compound I is on free form. In one embodiment the free form is an anhydrate. In another embodiment the free form is a solvate, such as a hydrate.

In a further embodiment the compound is a crystalline form. The skilled person may carry out tests in order to find polymorphs, and such polymorphs are intended to be encompassed by the term "crystalline form" as used herein.

When the compounds and pharmaceutical compositions herein disclosed are used for the above treatment, a therapeutically effective amount of at least one compound is administered to a mammal in need of said treatment.

The term "free form" as used herein means a compound of formula (I) which is a free base or free acid, as the case may be, and which is not in any salt form.

The term "$C_{1-x}$ alkyl" as used herein means an alkyl group containing 1 to x carbon atoms, e.g. $C_{1-3}$, $C_{1-4}$, $C_{1-5}$ or $C_{1-6}$, such as methyl, ethyl, propyl, butyl, pentyl or hexyl, and also includes branched $C_{3-6}$ alkyl, such as isopropyl, isobutyl, tert-butyl, isopentyl, 3-methylbutyl, 2,2-dimethylpropyl, n-hexyl, 2-methylpentyl, 2,2-dimethylbutyl, 2,3-dimethylbutyl. When $C_{1-x}$ alkyl, such as $C_{1-6}$ alkyl, is substituted with a group, such as halogen, such as a F, it means that such F, e.g. 3 F are attached to one carbon ($CF_3$) or two carbons ($CF_2$—CF) or even three carbons (CF—CF—CF).

The term "$C_{1-x}$ alkylene" as used herein means an alkylene group containing 1 to x carbon atoms, e.g. $C_{1-3}$, $C_{1-4}$, $C_{1-5}$ or $C_{1-6}$, such as methylene, ethylene, propylene, butylene, pentylene or hexylene, and also includes branched $C_{3-6}$ alkylene, such as isopropylene, isobutylene, tert-butylene, isopentylene, 3-methylbutylene, 2,2-dimethylpropylene, n-hexylene, 2-methylpentylene, 2,2-dimethylbutylene, 2,3-dimethylbutylene.

The term "$C_{1-x}$ alkoxy" or "O—$C_{1-x}$ alkyl" (used interchangeable) as used herein means one oxygen atom covalently linked to an alkyl group containing 1 to x carbon atoms, e.g. $C_{1-5}$ or $C_{1-6}$, such as methoxy, ethoxy, n-propoxy, iso-propoxy, n-butyloxy, n-pentyloxy, or n-hexyloxy.

The term "$C_{1-x}$ alkylthio" or "S—$C_{1-x}$ alkyl" (used interchangeable) as used herein means one sulphur atom covalently linked to an alkyl group containing 1 to x carbon atoms, e.g. $C_{1-5}$ or $C_{1-6}$, such as methylthio, ethylthio, n-propylthio.

The term "$C_{3-4}$ cycloalkyl" as used herein means a cyclic alkyl group containing 3-4 carbon atoms, such as cyclopropyl or cyclobutyl.

The term "CN" as used herein means a cyano or nitril (C and N linked by triple bond).

The term "$C_{1-6}$ alkyl substituted with at least one halogen" as used herein means one or more halogen atoms as defined herein linked to one or more carbon atoms of the $C_{1-6}$ alkyl as defined herein, such as $CHFCF_3$ or $CF_3$.

The term "$C_{1-6}$ alkoxy substituted with at least one halogen" as used herein means one or more halogen atoms as defined herein linked to one or more carbon atoms of the $C_{1-6}$ alkoxy as defined herein, such as $OCH_2CHF_2$ or $OCF_3$.

The term "$C_{1-4}$alkyl substituted with one OH" as used herein means one OH group linked via the oxygen to one carbon atoms of the $C_{1-4}$alkyl as defined herein, such as $CH_2OH$, $CH_2CH_2OH$, or $CHOHCH_3$.

The term "$C_{1-4}$ alkyl substituted with one $OC_{1-3}$ alkyl" as used herein means one $OC_{1-3}$ alkyl group linked via the oxygen to one carbon atoms of the $C_{1-4}$ alkyl as defined herein, such as $CH_2OCH_3$, or $CH_2CH_2OCH_3$.

The term "halogen" as used herein means an atom selected from Chloro (Cl), Flouro (F), Iodo (I) and Bromo (Br). Whenever a halogen is disclosed in any one of the embodiments herein it is preferably a F or a Cl.

The term "a 5 or 6-membered aromatic heterocycle comprising at least one nitrogen atom and optionally 1 oxygen atom and optionally 1 sulphur atom" as used herein means a chemically stable mono aromatic ring system containing at least one nitrogen, and preferably from 1 to 3 N, and no more than 5 carbon atoms, 1 oxygen atom may be included and/or 1 sulphur atom, such as including but not limited to pyrrolyl, imidazolyl, pyrazolyl, oxazolyl, isoxazolyl, thiazolyl, isothiazolyl, triazolyl, furazanyl, oxadiazolyl, thiadiazolyl, tetrazolyl, pyrimidinyl, pyridinyl, diazinyl, pyridazinyl, triazinyl, and tetrazinyl.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment may either be performed in an acute or in a chronic way. The patient to be treated is preferably a mammal; in particular a human being, but it may also include animals, such as dogs, cats, cows, sheep and pigs.

The term "a pharmaceutically acceptable salt" as used herein is used to specify that the salt is suitable for use in the human or animal body. An example list of pharmaceutically acceptable salts can be found in the Handbook of Pharmaceutical Salts: Properties, Selection and Use, P. H. Stahl and C. G. Wermuth, editors, Weinheim/Zurich:Wiley-VCH/VHCA, 2002. A pharmaceutically acceptable salt of a compound of Formula (I) includes such salts that may be formed within the human or animal body after administration of said compound to said human or animal body.

The term "a therapeutically effective amount" of a compound of formula (I) of the present invention as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

In a still further aspect the present invention relates to a pharmaceutical composition comprising the compound of formula (I) and optionally a pharmaceutically acceptable additive, such as a carrier or an excipient. Typically, the present invention relates to a pharmaceutical composition comprising the compound of formula (I) and a pharmaceutically acceptable additive, such as a carrier or an excipient.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (1) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In some embodiments, the pharmaceutical compositions comprise from 1 to 99 weight % of said at least one pharmaceutically acceptable adjuvant, diluent, excipient and/or carrier and from 1 to 99 weight % of a compound as herein disclosed. The combined amount of the active ingredient and of the pharmaceutically acceptable adjuvant, diluent, excipient and/or carrier may not constitute more than 100% by weight of the composition, particularly the pharmaceutical composition.

In some embodiments, only one compound as herein disclosed is used for the purposes discussed above.

In some embodiments, two or more of the compound as herein disclosed are used in combination for the purposes discussed above.

The composition, particularly pharmaceutical composition comprising a compound set forth herein may be adapted for oral, intravenous, topical, intraperitoneal, nasal, buccal, sublingual, or subcutaneous administration, or for administration via the respiratory tract in the form of, for example, an aerosol or an air-suspended fine powder. Therefore, the pharmaceutical composition may be in the form of, for example, tablets, capsules, powders, nanoparticles, crystals, amorphous substances, solutions, transdermal patches or suppositories.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

Experimental Procedures
Automated Patch Clamping

Automated whole cell patch-clamp recordings were performed using a QPatch 16 HT system and single-hole Qplates (Sophion, Denmark) on HEK-293 cells stably expressing the human SK3 channel (hK$_{Ca}$2.3). Cells were cultured and prepared for experiments using normal cell culturing procedures. A total of 4-5 million cells were used per experiment. The Qpatch automatically generates giga sealing, whole-cell formation, compound application and recording of current. hK$_{Ca}$2.3 currents were recorded in symmetrical K$^+$ solutions. The intracellular/pipette solution contained 154 mM KCl, 10 mM HEPES and 10 mM EGTA. CaCl$_2$ is added to give calculated free concentrations of Ca$^{2+}$ of 0.4 μM and MgCl$_2$ is added to give a free concentration of 1 mM. In order to maintain a total [K$^+$] of 156 mM (corresponding to the concentration in the extracellular ringer) a fixed amount of KOH (15 mM) is added, thereafter pH is adjusted with HCl to pH=7.2. Expected osmolarity: 275 mOsm. Sucrose was added to a final osmolarity around 295 mosm. The extracellular solution consisted of (in mM): CaCl$_2$ 0.1, MgCl$_2$ 3, KCl 150, HEPES 10 and glucose 10, pH=7.4 adjusted with KOH. Osmolarity between 285-295 mosm. The cells were held at 0 mV and hK$_{Ca}$2.3 currents were elicited by a linear voltage ramp from −80 mV to +80 mV (200 ms in duration) applied every 5th second.

The compound application protocol consisted of 12 recording periods lasting 200 s: 1) Baseline recordings in extracellular solution; 2) Application of the positive control N-methyl bicuculline (100 μM), which is characterized by full efficacy, fast on- and off-rate; 3-4) Wash-out; 5-10) Increasing concentrations of test compound to establish an IC50 value; 11-12) Wash-out; 13) positive control with compound NS8593 (N-[(1R)-1,2,3,4-tetrahydro-1-naphthalenyl]-1H-benzimidazol-2-amine) (1 μM) or with N-methyl bicuculline (100 μM). Data were sampled at 10 kHz, 4th order Bessel filter, cut-off frequency 3 kHz. Currents were compensated for run-down. Potency was quantified as the concentration needed to inhibit half of the SK channel activity and reported as an IC50 value.

All effects of compounds of the present invention as tested were normalized to the observed inhibitory effect of N-methyl bicuculline. Currents were measured at −80 mV.

Results

The examples described are potent inhibitors of the SK3 channel and have shown the following IC$_{50}$ in the Automated patch clamping assay described above:

Examples: 1, 3b, 6, 8b, 10, 11, 12b, 14, 15, 16, 17, 18b, 19b, 21, 22, 24a, 25, 26, 27b, 28, 31, 33, 34, 35, 36, 37, 38, 39b, 40a, 40b, 41b, 42a, 42b, 43a, 43b, 44a, 44b, 45b, 46a, 46b, 47b, 48a, 48b, 49a, 49b all have an IC$_{50}$ below 30 μM.

Examples: 2, 3, 3a, 4, 5, 7, 8, 8a, 9, 12, 12a, 13, 13a, 13b, 18, 18a, 19, 19a, 20, 23, 23a, 23b, 24, 24b, 27, 27a, 29, 30, 30a, 30b, 32, 32a, 32b, 39a, 41a, 45a, 47a all have an IC$_{50}$ below 1 μm.

Materials and Methods

Commercial reagents were used without further purification unless otherwise stated. Analytical TLC was performed on silica gel 60-F$_{254}$ (Merck) with detection by fluorescence and by immersion in a KMnO$_4$ solution [KMnO$_4$ solution recipe: Dissolve 1.5 g KMnO$_4$, 10 g K$_2$CO$_3$, and 1.25 mL 10% NaOH in 200 mL of water] followed by charring. Purification of compound was carried out by column chromatography on silica gel (60-120 mesh, Swambe Chemicals, India). NMR spectra such as $^1$H, $^{13}$C and 2D COSY were recorded with Bruker AV 400 MHz spectrometer (400 MHz for $^1$H, 100 MHz for $^{13}$C) at ambient temperature by using deuterated DMSO-d$_6$, CDCl$_3$, CD$_3$CO$_2$D (AcOH-d4) or CD$_3$OD as a solvent for NMR. Chemical shifts are reported in δ parts per million (ppm). ESI-MS was recorded on Agilent LC1200 series MS single quadrupole 6130 mass spectrometer.

Abbreviations Used in Experimental Section:
   BOP=(Benzotriazol-1-yloxy)tris(dimethylamino)phosphonium hexafluorophosphate
   PyBOP=(Benzotriazol-1-yloxy)tripyrrolidinophosphonium hexafluorophosphate
   EDC·HCl=N-(3-Dimethylaminopropyl)-N'-ethylcarbodiimide hydrochloride
   HBTU=N,N,N',N'-Tetramethyl-O-(1H-benzotriazol-1-yl)uronium hexafluorophosphate.
   DCM=Dichloromethane; DMF=N,N-Dimethylformamide; TEA=Triethylamine
   TFA=Trifluoroacetic acid; Boc-anhydride=Di-tert-butyl dicarbonate; THF=Tetrahydrofuran; t-BuOH=2-Methylpropan-2-ol; DEA=Diethylamine; DIEA Ethylbis(propan-2-yl)amine; IPA=Propan-2-ol; Pd/C=Palladium on Carbon; RT=Ambient Temperature; MeOH=Methanol.

Grace Flash Chromatography System:
   The Grace REVELERIS® Prep Purification System was used to perform sample purification by flash chromatography, using Flash Cartridges pre-packed with silica:
   Columns Used:
   Hi-Purit Flash Columns Silica (Normal Phase);
   12 g, 60 A, max pressure 350 psi (24 bar),
   24 g, 60 A, max pressure 350 psi (24 bar),
   40 g, 60 A, max pressure 350 psi (24 bar),
   80 g, 60 A, max pressure 350 psi (24 bar).
   Solvents: Hexane, EtOAc, CHCl$_3$ and MeOH.

Example 1

N-[1-(3-chlorophenyl)cyclopropyl]-4-[(2-imino-2,3-dihydro-1,3-oxazol-3-yl)methyl]-1H-1,3-benzodiazol-2-amine

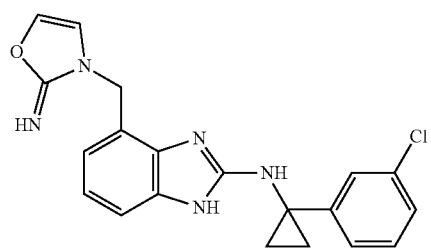 [SMILES: N=c1occn1Cc1cccc2[nH]c(NC3(c4cccc(Cl)c4)CC3)nc12]

Example 1, Step 1: Preparation of 1-chloro-3-(1-isothiocyanatocyclopropyl) benzene

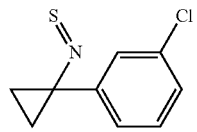 [SMILES: S=NC1(c2cccc(Cl)c2)CC1]

To an ice cooled solution of 1-(3-chlorophenyl)cyclopropanamine (commercially available) (1.00 g, 5.97 mmol) in dichloromethane (50 mL) was added 10% sodium bicarbonate solution (50 mL) followed by thiophosgene (1.14 mL, d=1.50 g/cm³, 14.90 mmol) and the whole mixture was stirred at ambient temperature for 30 min. The organic layer was separated, washed with brine (15 mL), dried over sodium sulphate, filtered and concentrated to afford 1-chloro-3-(1-isothiocyanato cyclopropyl) benzene (1.00 g) as a light yellow liquid, which was used in the next step without further purification.

$^1$H NMR (400 MHz, DMSO-d$_6$) δ 7.44 (s, 1H), 7.39 (d, J=8.00 Hz, 1H), 7.34 (t, J=7.20 Hz, 1H), 7.31 (d, J=7.60 Hz, 1H), 1.67 (t, J=4.80 Hz, 2H), 1.51 (t, J=6.00 Hz, 2H).

Example 1, Step 2: Preparation of 4-methyl-2,1,3-benzothiadiazole

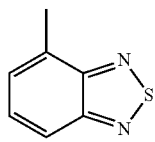

To a solution of 3-methylbenzene-1,2-diamine (commercially available) (330.0 g, 2700.0 mmol) in dry pyridine (1800 mL) was added thionyl chloride (500.0 mL, d=1.64 g/cm³, 6750.00 mmol) dropwise over a period of 60 min at 0° C., during this addition the internal temperature was kept below 45° C. and the reaction mixture was stirred at ambient temperature for 3 h. The reaction mixture was quenched with conc. hydrochloric acid (1300 mL) by dropwise addition until the pH of the reaction adjusted to between pH2-pH3, during this stage internal temperature was kept below 65° C. The reaction mixture was diluted with water (1500 mL) and ethyl acetate (2000 mL) and stirred for 2 h. Then it was filtered through a celite bed and the organic layer was separated and the aqueous layer was extracted further with ethyl acetate (3×1500 mL). The combined organic layer was washed with brine solution (300 mL), dried over sodium sulphate, filtered and concentrated to afford 4-methyl-2,1,3-benzothiadiazole (380.0 g) as a brown liquid, which was used in the next step without further purification.

$^1$H NMR (400 MHz, DMSO-d$_6$) δ 7.90 (d, J=8.80 Hz, 1H), 7.61 (t, J=8.80 Hz, 1H), 7.51 (d, J=6.80 Hz, 1H), 2.69 (s, 3H);

MS: m/z 151.2 (M+1).

Example 1, Step 3: Preparation of 4-(bromomethyl)-2,1,3-benzothiadiazole

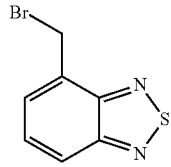

To a stirred solution of 4-methyl-2,1,3-benzothiadiazole (from Example 1, Step 2) (100.0 g, 666.0 mmol) under a nitrogen atmosphere in dry chloroform (1200 mL) was added benzoyl peroxide (3.23 g, 13.30 mmol) followed by N-bromosuccinimide (118.0 g, 666.0 mmol) and the reaction mixture was refluxed for 28 h. The reaction mixture was cooled and the succinimide solidified and it was removed by filtration. The filtrate was concentrated to afford a crude mass (170.0 g) as a brown semi solid which was taken in methanol (1000 mL) and stirred for 30 min. The solid was filtered, dried under high-vacuum to afford 4-(bromomethyl)-2,1,3-benzothiadiazole (110.0 g) as a yellow solid, which was used in the next step without further purification.

$^1$H NMR (400 MHz, DMSO-d$_6$) δ 8.09 (d, J=8.60 Hz, 1H), 7.87 (d, J=8.80 Hz, 1H), 7.71 (t, J=8.40 Hz, 1H), 5.13 (s, 2H).

Example 1, Step 4: Preparation of 3-[(2,1,3-benzothiadiazol-4-yl)methyl]-2,3-dihydro-1,3-oxazol-2-imine hydrobromide

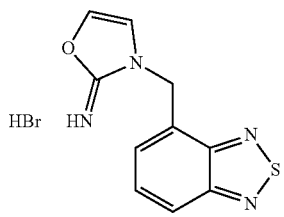 [SMILES: Br ; N=c1occn1Cc1cccc2nsnc12]

To a solution of 4-(bromomethyl)-2,1,3-benzothiadiazole (Example 1, Step 3) (30.00 g, 131.00 mmol) in acetonitrile (300 mL) was added oxazol-2-amine (22.00 g, 262.00 mmol) and the mixture was stirred at 60° C. for 16 h. The solid that formed in the reaction mixture was filtered and dried to afford a crude mass (33.00 g) as an off-white solid. This was dissolved in a mixture of acetonitrile:water (1:1; 60 mL) and the solvent volume was reduced to around 40 mL at 40° C., and it was kept at ambient temperature overnight. The obtained crystals were filtered and dried under high vacuum at 40° C. to afford 3-[(2,1,3-benzothiadiazol-4-yl) methyl]-2,3-dihydro-1,3-oxazol-2-imine hydrobromide (21.00 g) as an off-white solid.

$^1$H NMR (400 MHz, DMSO-d$_6$) δ 9.86 (bs, 2H), 8.13 (d, J=8.40 Hz, 1H), 7.93 (d, J=2.00 Hz, 1H), 7.77 (t, J=9.20 Hz, 1H), 7.69 (d, J=9.20 Hz, 1H), 7.60 (d, J=2.40 Hz, 1H), 5.62 (s, 2H);

MS: m/z 233.2 [(M+1)-HBr].

Example 1, Step 5: Preparation of 3-[(2-imino-2,3-dihydro-1,3-oxazol-3-yl)methyl]benzene-1,2-diamine

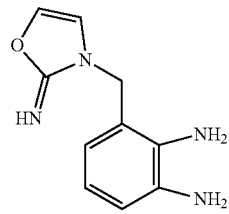 [SMILES: N=c1occn1Cc1cccc(N)c1N]

To a de-gassed solution of 3-[(2,1,3-benzothiadiazol-4-yl)methyl]-2,3-dihydro-1,3-oxazol-2-imine hydrobromide (from Example 1, Step 4) (12.00 g, 38.34 mmol) in dry methanol (1200 mL) was added Raney nickel (36.00 g, 300% w/w, pre-washed five times with dry methanol) and the resultant reaction mixture was stirred under a hydrogen atmosphere at bladder pressure (Approx. 1.5 kg/cm$^2$) at ambient temperature for 24 h. The reaction mixture was filtered through a celite bed and the bed was washed with methanol (1000 mL). The combined filtrates were concentrated to afford 3-[(2-imino-2,3-dihydro-1,3-oxazol-3-yl)methyl]benzene-1,2-diamine (10.00 g) as a grey gum, which was used in the next step without further purification.
MS: m/z 205.2 (M+1).

Example 1, Step 6: Preparation of 1-{2-amino-3-[(2-imino-2,3-dihydro-1,3-oxazol-3-yl)methyl]phenyl}-3-[1-(3-chlorophenyl)cyclopropyl]thiourea and 1-{2-amino-6-[(2-imino-2,3-dihydro-1,3-oxazol-3-yl)methyl]phenyl}-3-[1-(3-chlorophenyl)cyclopropyl]thiourea (Mixture of Regioisomers)

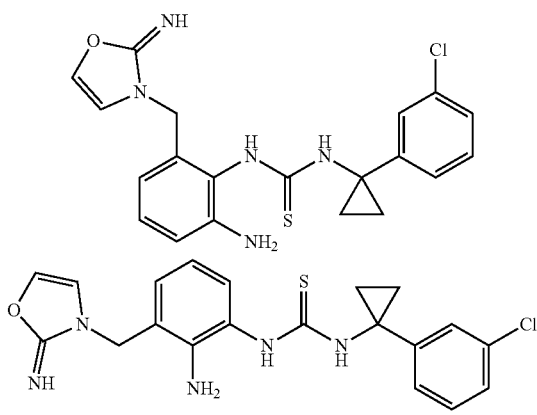

To a solution of 3-[(2-imino-2,3-dihydro-1,3-oxazol-3-yl)methyl]benzene-1,2-diamine (from Example 1, Step 5) (0.192 g, 0.954 mmol) in a mixture of solvents dichloromethane:methanol (4:1; 10 mL) was added 1-chloro-3-(1-isothiocyanatocyclopropyl) benzene (from Example 1, Step 1) (0.200 g, 0.954 mmol) and the mixture was stirred at ambient temperature for 16 h. The reaction mixture was concentrated at 30° C. in a water bath to afford 1-{2-amino-3-[(2-imino-2,3-dihydro-1,3-oxazol-3-yl)methyl]phenyl}-3-[1-(3-chlorophenyl)cyclopropyl]thiourea and 1{2-amino-6-[(2-imino-2,3-dihydro-1,3-oxazol-3-yl)methyl]phenyl}-3-[1-(3-chlorophenyl)cyclopropyl]thiourea (as a mixture of non-separable regioisomers) (0.395 g) as a yellow gum, which was used in the next step without further purification.
MS: m/z 414.1 (M+1).

Example 1: N-[1-(3-chlorophenyl)cyclopropyl]-4-[(2-imino-2,3-dihydro-1,3-oxazol-3-yl)methyl]-1H-1,3-benzodiazol-2-amine

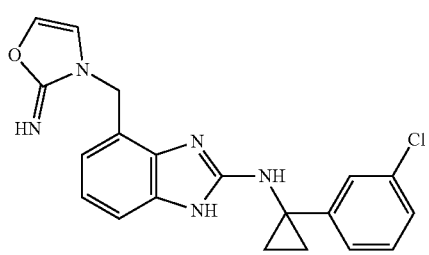 [SMILES: N=c1occn1Cc1cccc2[nH]c(NC3(c4cccc(Cl)c4)CC3)nc12]

To a solution of 1-{2-amino-3-[(2-imino-2,3-dihydro-1,3-oxazol-3-yl)methyl]phenyl}-3-[1-(3-chlorophenyl)cyclopropyl]thiourea and 1{2-amino-6-[(2-imino-2,3-dihydro-1,3-oxazol-3-yl)methyl]phenyl}-3-[1-(3-chlorophenyl)cyclopropyl]thiourea (as a mixture of non-separable regioisomers) (from Example 1, Step 6) (0.390 g, 0.660 mmol) in methanol (30 mL) was added iodoacetic acid (0.274 g, 1.45 mmol) and the mixture was stirred at 65° C. for 1 h. The reaction mixture was concentrated to remove the solvent methanol at 30° C. to afford a crude mass (0.320 g) as a brown gum, which was purified by preparative HPLC using a TFA method to afford N-[1-(3-chlorophenyl)cyclopropyl]-4-[(2-imino-2,3-dihydro-1,3-oxazol-3-yl)methyl]-1H-1,3-benzodiazol-2-amine, isolated as the trifluoroacetate salt (0.275 g) as a yellow solid.
$^1$H NMR (400 MHz, AcOH-d$_4$) δ 7.58 (s, 1H), 7.53 (d, J=7.60 Hz, 1H), 7.36 (d, J=8.00 Hz, 2H), 7.31 (d, J=7.20 Hz, 3H), 7.25 (t, J=6.00 Hz, 2H), 5.44 (s, 2H), 1.67 (t, J=4.80 Hz, 2H), 1.51 (t, J=6.00 Hz, 2H);
MS: m/z 380.2 (M+1).

Example 2: Preparation of N-[2-(3-chlorophenyl)propan-2-yl]-4-[(2-imino-2,3-dihydro-1,3-oxazol-3-yl)methyl]-1H-1,3-benzodiazol-2-amine

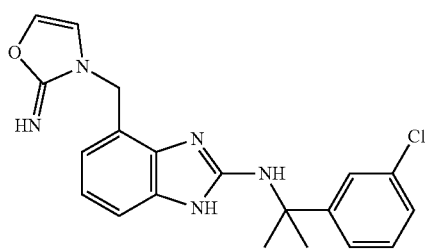 [SMILES: CC(C)(Nc1nc2c(Cn3ccoc3=N)cccc2[nH]1)c1cccc(Cl)c1]

Example 2, Step 1: Preparation of 1-chloro-3-(2-isothiocyanatopropan-2-yl)benzene

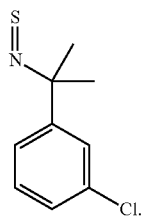

To an ice cooled solution of 2-(3-chlorophenyl)propan-2-amine (commercially available) (1.00 g, 5.89 mmol) in dichloromethane (40 mL) was added 10% sodium bicarbonate solution (40 mL) followed by thiophosgene (0.452 mL, d=1.50 g/cm$^3$, 5.89 mmol) and the mixture was stirred at ambient temperature for 30 min. The organic layer was separated, washed with brine (25 mL), dried over sodium sulphate, filtered and concentrated to afford 1-chloro-3-(2-isothiocyanatopropan-2-yl)benzene (0.800 g) as a light yellow liquid, which was used in the next step without further purification.

$^1$H NMR (400 MHz, DMSO-d$_6$) δ 7.54 (d, J=8.40 Hz, 1H), 7.45 (t, J=8.00 Hz, 1H), 7.43 (s, 1H), 7.41 (dd, J=2.00, 5.20 Hz, 1H), 1.77 (s, 6H).

Example 2, Step 2: Preparation of 3-{2-amino-3-[(2-imino-2,3-dihydro-1,3-oxazol-3-yl)methyl]phenyl}-1-[2-(3-chlorophenyl)propan-2-yl]thiourea and 3-{2-amino-6-[(2-imino-2,3-dihydro-1,3-oxazol-3-yl)methyl]phenyl}-1-[2-(3-chlorophenyl)propan-2-yl]thiourea (Mixture of Regioisomers)

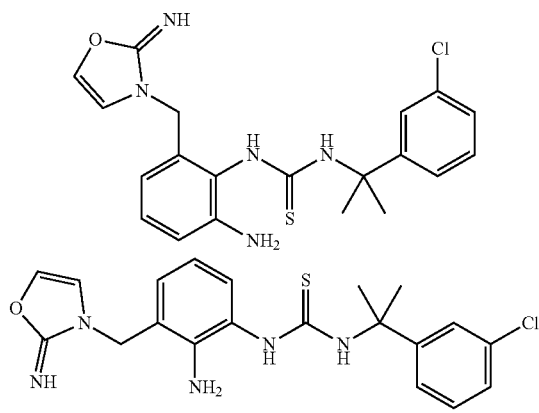

To a solution of 3-[(2-imino-2,3-dihydro-1,3-oxazol-3-yl)methyl]benzene-1,2-diamine (from Example 1, Step 5) (0.289 g, 1.42 mmol) in dichloromethane (6 mL) was added 1-chloro-3-(2-isothiocyanatopropan-2-yl) benzene (from Example 2, Step 1) (0.300 g, 1.42 mmol) and the mixture was stirred at ambient temperature for 48 h. The reaction mixture was concentrated at 30° C. in a water bath to afford 3-{2-amino-3-[(2-imino-2,3-dihydro-1,3-oxazol-3-yl) methyl]phenyl}-1-[2-(3-chlorophenyl)propan-2-yl]thiourea and 3-{2-amino-6-[(2-imino-2,3-dihydro-3-oxazol-3-yl) methyl]phenyl}-1-[2-(3-chlorophenyl)propan-2-yl]thiourea (as a mixture of non-separable regioisomers) (0.500 g) as a yellow gum, which was used in the next step without further purification.

MS: m/z 416.1 (M+1).

Example 2: Preparation of N-[2-(3-chlorophenyl)propan-2-yl]-4-[(2-imino-2,3-dihydro-1,3-oxazol-3-yl)methyl]-1H-1,3-benzodiazol-2-amine

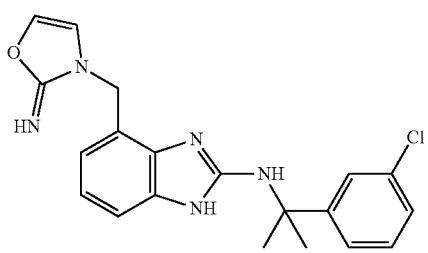 [SMILES: CC(C)(Nc1nc2c(Cn3ccoc3=N)cccc2[nH]1)c1cccc(Cl)c1]

To a solution of 3-{2-amino-3-[(2-imino-2,3-dihydro-1,3-oxazol-3-yl)methyl]phenyl}-1-[2-(3-chlorophenyl)propan-2-yl]thiourea and 3-{2-amino-6-[(2-imino-2,3-dihydro-1,3-oxazol-3-yl)methyl]phenyl}-1-[2-(3-chlorophenyl)propan-2-yl]thiourea (as a mixture of non-separable regioisomers) (from Example 2, Step 2) (0.200 g, 0.481 mmol) in methanol (20 mL) was added iodoacetic acid (0.089 g, 0.481 mmol) and the mixture was stirred at 65° C. for 1 h. The reaction mixture was concentrated to remove the solvent methanol at 30° C. to afford a crude mass (0.240 g) as a brown gum, which was purified by preparative HPLC using a TFA method to afford N-[2-(3-chlorophenyl)propan-2-yl]-4-[(2-imino-2,3-dihydro-1,3-oxazol-3-yl)methyl]-1H-1,3-benzodiazol-2-amine, isolated as the trifluoroacetate salt, (0.040 g) as a brown gum.

$^1$H NMR (400 MHz, AcOH-d$_4$) δ 7.58 (d, J=7.12 Hz, 2H), 7.50 (d, J=7.44 Hz, 1H), 7.40 (d, J=7.92 Hz, 1H), 7.37 (d, J=7.68 Hz, 1H), 7.33 (d, J=7.96 Hz, 1H), 7.30 (t, J=7.56 Hz, 1H), 7.26 (d, J=7.04 Hz, 2H), 5.40 (s, 2H), 1.87 (s, 6H);

MS: m/z 381.2 (M+1).

Example 3: Preparation of 2-(3-chlorophenyl)-2-({4-[(2-imino-2,3-dihydro-1,3-oxazol-3-yl)methyl]-1H-1,3-benzodiazol-2-yl}amino)propan-1-ol

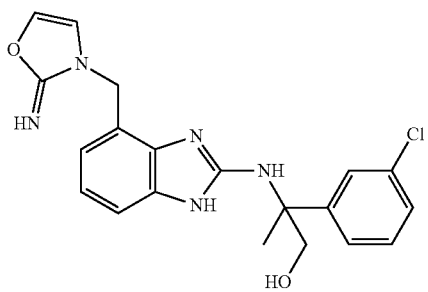 [SMILES: CC(CO)(Nc1nc2c(Cn3ccoc3=N)cccc2[nH]1)c1cccc(Cl)c1]

Example 3, Step 1: Preparation of 5-(3-chlorophenyl)-5-methylimidazolidine-2,4-dione

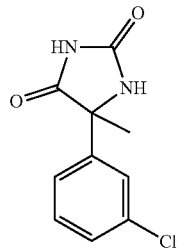

To a stirred solution of 1-(3-chlorophenyl) ethan-1-one (commercially available) (120.00 g, 776.00 mmol) in a mixture of solvents ethanol/water (1:1; 2400 mL) was added ammonium carbonate (448.00 g, 4660.00 mmol) followed by potassium cyanide (45.60 g, 931.00 mmol) and the mixture was stirred at 60° C. for 16 h. The reaction mixture was poured into ice-cold water (1500 mL) and it was stirred for 30 min. The solid that formed was filtered off and dried to afford 5-(3-chlorophenyl)-5-methylimidazolidine-2,4-dione (160.00 g) as an off-white solid, which was used in the next step without further purification.

$^1$H NMR (400 MHz, DMSO-$d_6$) δ 10.87 (bs, 1H), 8.63 (s, 1H), 7.50 (d, J=1.60 Hz, 1H), 7.47 (d, J=4.80 Hz, 1H), 7.45 (t, J=2.40 Hz, 1H), 7.42 (dd, J=2.40 Hz, 1H), 1.65 (s, 3H);

MS: m/z 225.2 (M+1).

Example 3, Step 2: Preparation of 2-amino-2-(3-chlorophenyl) propanoic acid

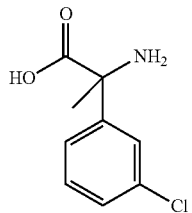

5-(3-chlorophenyl)-5-methylimidazolidine-2,4-dione (from Example 3, Step 1) (160.00 g, 712.00 mmol) was taken up into 10% aqueous sodium hydroxide solution (1200 mL) and the mixture was stirred at 110° C. for 72 h. The reaction mixture was neutralized (adjusted pH=7) with 6.0 N HCl (500 mL), and the solid that formed was filtered and dried to afford 2-amino-2-(3-chlorophenyl) propanoic acid (205.00 g) as a white solid, which was used in the next step without further purification.

$^1$H NMR (400 MHz, DMSO-$d_6$: $D_2O$) δ 7.56 (s, 1H), 7.46 (d, J=7.60 Hz, 1H), 7.37 (t, J=7.60 Hz, 1H), 7.35 (d, J=7.60 Hz, 1H), 1.65 (s, 3H);

MS: m/z 200.1 (M+1).

Example 3, Step 3: Preparation of 2-((tert-butoxycarbonyl) amino)-2-(3-chlorophenyl) propanoic acid

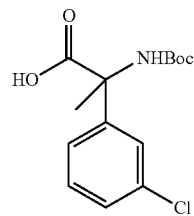

To a suspension of 2-amino-2-(3-chlorophenyl) propanoic acid (from Example 3, Step 2) (286.00 g, 1430.00 mmol) in a mixture of solvents tetrahydrofuran:water (1:1; 5000 mL) was added sodium bicarbonate (842.00 g, 10000.0 mmol) followed by di-tert-butyl dicarbonate (658.00 mL, d: 0.950 g/cm$^3$, 2870.00 mmol) and the mixture was stirred at ambient temperature for 15 days. The reaction mixture was diluted with water (2000 mL) and extracted with ethyl acetate (4×5000 mL). The combined organic layer was dried over sodium sulphate, filtered and concentrated to afford 2-((tert-butoxycarbonyl) amino)-2-(3-chlorophenyl) propanoic acid (410.00 g) as a colourless gum, which was used in the next step without further purification.

$^1$H NMR (400 MHz, DMSO-$d_6$) δ 7.23 (dd, J=6.40 Hz, 2H), 7.16 (t, J=6.40 Hz, 2H), 1.70 (s, 3H), 1.34 (s, 9H);

MS: m/z 200.1 [(M+1)-Boc].

Example 3, Step 4: Preparation of tert-butyl N-[2-(3-chlorophenyl)-1-hydroxypropan-2-yl]carbamate

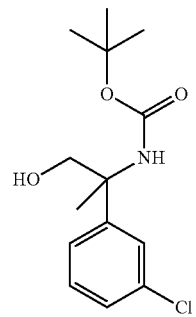 [SMILES: CC(C)(C)OC(=O)NC(C)(CO)c1cccc(Cl)c1]

To a solution of 2-((tert-butoxycarbonyl) amino)-2-(3-chlorophenyl) propanoic acid (from Example 3, Step 3) (250.00 g, 834.00 mmol) in dry tetrahydrofuran (2000 mL) was added triethylamine (349.0 mL, d=0.726 g/cm$^3$, 2500.0 mmol) followed by isobutyl chloroformate (130.0 mL, d=1.053 g/cm$^3$, 1080.0 mmol) at 0° C. and stirred at the same temperature for 4 h. The solid that formed was filtered off at 0° C. and the residue was washed with tetrahydrofuran (400 mL). The combined filtrate was added to a cooled mixture of sodium borohydride (221.00 g, 5840.00 mmol) in water (500 mL). The reaction mixture was slowly warmed to ambient temperature and stirred for 48 h. The reaction mixture was quenched with ice cold water (1000 mL) and extracted with ethyl acetate (4×5000 mL), the combined organic layer was washed with brine (300 mL), dried over sodium sulphate, filtered and concentrated to afford (250.00 g) of a yellowish liquid. This was purified by gravity column chromatography using 60-120 silica gel and the product was eluted with 30-35% ethyl acetate in petroleum ether to afford tert-butyl N-[2-(3-chlorophenyl)-1-hydroxypropan-2-yl]carbamate (95.00 g) as a colourless liquid.

$^1$H NMR (400 MHz, DMSO-$d_6$: $D_2O$) δ 7.34 (s, 1H), 7.32 (d, J=7.60 Hz, 1H), 7.28 (t, J=7.40 Hz, 1H), 7.25 (d, J=7.20 Hz, 1H), 3.57 (d, J=6.40 Hz, 2H), 1.52 (s, 3H), 1.34 (s, 9H); MS: m/z 186.1 [(M+1)-Boc].

Example 3, Step 5: Preparation of 2-{[(tert-butoxy)carbonyl]amino}-2-(3-chlorophenyl)propyl 2,2-dimethylpropanoate

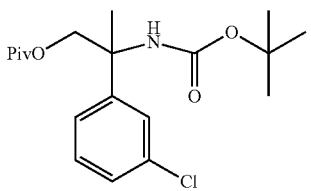

To a solution of tert-butyl (2-(3-chlorophenyl)-1-hydroxypropan-2-yl)carbamate (from Example 3, Step 4) (170.00 g, 595.00 mmol) in dry dichloromethane (1500 mL) under a nitrogen atmosphere was added triethylamine (250.00 mL, d=0.726 g/cm$^3$, 1780.00 mmol) followed by pivaloyl chloride (145.50 mL, d=0.985 g/cm$^3$, 1190.00 mmol) at 0° C. dropwise and the reaction mixture was stirred at ambient temperature for 48 h. The reaction mixture was quenched with ice cold water (1000 mL) and extracted with dichloromethane (4×2500 mL). The combined organic layer was dried over sodium sulphate, filtered and concentrated to afford a brown liquid (200.00 g), which was purified by chromatography on a Chromatography on a Grace instrument using 330.0 g pre-packed flash cartridge with 60-120 silica gel and the product eluted at 20% ethyl acetate in hexane to afford 2-{[(tert-butoxy)carbonyl]amino}-2-(3-chlorophenyl)propyl 2,2-dimethylpropanoate (218.00 g) as a yellowish liquid.

$^1$H NMR (400 MHz, DMSO-$d_6$: $D_2O$) δ 7.35 (d, J=8.00 Hz, 1H), 7.32 (s, 1H), 7.30 (d, J=7.20 Hz, 1H), 7.28 (t, J=6.80 Hz, 1H), 4.30 (d, J=10.40 Hz, 1H), 4.21 (d, J=10.80 Hz, 1H), 1.50 (s, 3H), 1.31 (s, 9H), 1.10 (s, 9H); MS: m/z 270.2 [(M+1)-Boc].

Example 3, Step 6: Preparation of 2-amino-2-(3-chlorophenyl)propyl 2,2-dimethylpropanoate hydrochloride

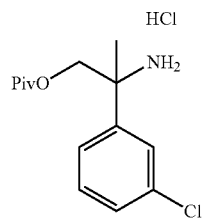

To a solution of 2-{[(tert-butoxy)carbonyl]amino}-2-(3-chlorophenyl)propyl 2,2-dimethylpropanoate (from Example 3, Step 5) (218.00 g, 589.00 mmol) in dry dichloromethane (1200 mL) under a nitrogen atmosphere was added 4M HCl in dioxane solution (442.00 mL, 1770.00 mmol) dropwise at 0° C. and the reaction mixture was stirred at ambient temperature for 16 h. The reaction mixture was concentrated on high vacuum to afford 2-amino-2-(3-chlorophenyl)propyl 2,2-dimethylpropanoate hydrochloride (180.00 g) as a yellowish gum, which was used in the next step without further purification.

$^1$H NMR (400 MHz, DMSO-$d_6$: $D_2O$) δ 7.64 (s, 1H), 7.51-7.47 (m, 3H), 4.44 (d, J=11.60 Hz, 1H), 4.26 (d, J=11.60 Hz, 1H), 1.69 (s, 3H), 1.04 (s, 9H); MS: m/z 270.1 [(M+1)-HCl].

Example 3, Step 7: Preparation of 2-(3-chlorophenyl)-2-isothiocyanatopropyl 2,2-dimethylpropanoate

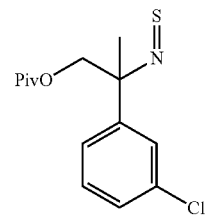

To a solution of 2-amino-2-(3-chlorophenyl)propyl 2,2-dimethylpropanoate hydrochloride (from Example 3, Step 6) (90.00 g, 294.00 mmol) in dry dichloromethane (900 mL) was added 10% aqueous sodium bicarbonate solution (900 mL) at 0° C. After 30 min, thiophosgene (33.80 mL, d=1.5 g/cm$^3$, 441.00 mmol) was added and allowed to stir at the same temperature for 1 h. The reaction mixture was extracted with dichloromethane (3×2000 mL) and the combined organic layer was dried over anhydrous sodium sulphate, filtered, and concentrated to afford a yellow liquid (95.00 g), which was purified by gravity column chromatography over 60-120 mesh silica gel using 3-5% ethyl acetate in hexane as eluent to afford 2-(3-chlorophenyl)-2-isothiocyanatopropyl 2,2-dimethylpropanoate (75.00 g) as a yellow liquid.

$^1$H NMR (400 MHz, DMSO-$d_6$) δ 7.55 (s, 1H), 7.55-7.45 (m, 3H), 4.45 (dd, J=11.20 Hz, 2H), 1.79 (s, 3H), 1.11 (s, 9H).

Example 3, Step 8: Preparation of 2-[({2-amino-3-[(2-imino-2,3-dihydro-1,3-oxazol-3-yl)methyl]phenyl}carbamothioyl)amino]-2-(3-chlorophenyl)propyl 2,2-dimethylpropanoate and 2-[({2-amino-6-[(2-imino-2,3-dihydro-1,3-oxazol-3-yl)methyl]phenyl}carbamothioyl)amino]-2-(3-chlorophenyl)propyl 2,2-dimethylpropanoate (Mixture of Regioisomers)

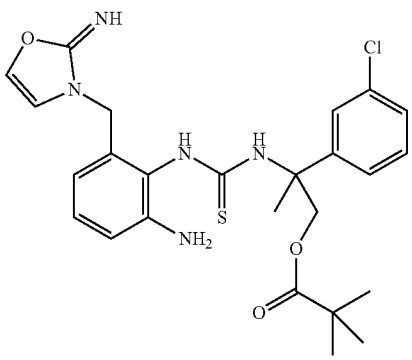

-continued

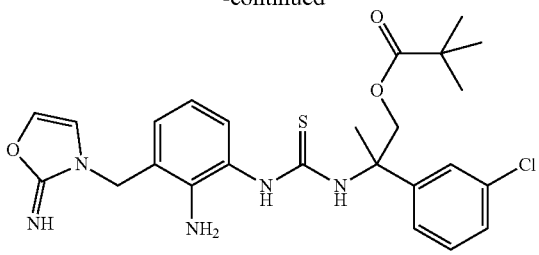

To a solution of 3-[(2-imino-2,3-dihydro-1,3-oxazol-3-yl)methyl]benzene-1,2-diamine (from Example 1, step 5) (4 g, 13.70 mmol) in a mixture of solvents dichloromethane:methanol (1:1; 70 mL) was added [2-(3-chlorophenyl)-2-isothiocyanato-propyl] 2,2-dimethylpropanoate (from Example 3, Step 7) (3.56 g, 11.40 mmol) and stirred at room temperature for 20 h. The reaction mixture was concentrated at 30° C. in a water bath to 2-[({2-amino-3-[(2-imino-2,3-dihydro-1,3-oxazol-3-yl)methyl]phenyl}carbamothioyl)amino]-2-(3-chlorophenyl)propyl 2,2-dimethylpropanoate and 2-[({2-amino-6-[(2-imino-2,3-dihydro-1,3-oxazol-3-yl)methyl]phenyl}carbamothioyl)amino]-2-(3-chlorophenyl)propyl 2,2-dimethylpropanoate (as a mixture of non-separable regioisomers) (7.00 g) as a yellow gum, which was used in the next step without purification.

MS: m/z 516.2/517.4 (M+1).

Example 3, Step 9: Preparation of 2-(3-chlorophenyl)-2-({4-[(2-imino-2,3-dihydro-1,3-oxazol-3-yl)methyl]-1H-1,3-benzodiazol-2-yl}amino)propyl 2,2-dimethylpropanoate

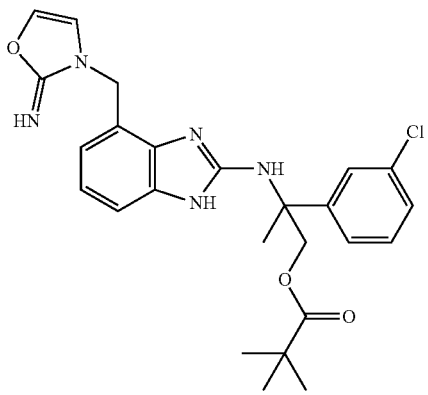 [SMILES: CC(C)(C)C(=O)OCC(C)(Nc1nc2c(Cn3ccoc3=N)cccc2[nH]1)c1cccc(Cl)c1]

To a solution of 2-[({2-amino-3-[(2-imino-2,3-dihydro-1,3-oxazol-3-yl)methyl]phenyl}carbamothioyl)amino]-2-(3-chlorophenyl)propyl 2,2-dimethylpropanoate and 2-[({2-amino-6-[(2-imino-2,3-dihydro-1,3-oxazol-3-yl)methyl]phenyl}carbamothioyl)amino]-2-(3-chlorophenyl)propyl 2,2-dimethylpropanoate (as a mixture of non-separable regioisomers) (Example 3, Step 8) (7.00 g, 13.60 mmol) in methanol (40 mL) was added iodoacetic acid (3.78 g, 20.30 mmol) and the mixture was refluxed for 1 h. The reaction mixture was concentrated to remove the solvent methanol at 30° C. to afford a reddish gum (6.50 g), which was purified by preparative HPLC (TFA/Acetonitrile) to afford 2-(3-chlorophenyl)-2-({4-[(2-imino-2,3-dihydro-1,3-oxazol-3-yl)methyl]-1H-1,3-benzodiazol-2-yl}amino)propyl 2,2-dimethylpropanoate, isolated as the trifluoroacetate salt, (0.800 g) as a yellow gum.

$^1$H NMR (400 MHz, AcOH-$d_4$) δ 7.59 (s, 2H), 7.52-7.50 (m, 1H), 7.44-7.38 (m, 2H), 7.34 (d, J=8.00 Hz, 1H), 7.26 (t, J=8.00 Hz, 1H), 7.22 (d, J=1.60 Hz, 1H), 7.17 (d, J=7.60 Hz, 1H), 5.40 (s, 2H), 4.55 (d, J=11.60 Hz, 1H), 4.46 (d, J=11.60 Hz, 1H), 1.96 (s, 3H), 1.18 (s, 9H);

MS: m/z 482.4/484.1 (M+1).

The above product was resolved into its two enantiomers by Chiral SFC using the method: Column: YMC Cellulose—SB; Mobile Phase: 0.5% isopropyl amine in isopropyl alcohol; co-solvent 30% $CO_2$; Flow rate: 3 mL/min, pressure: 100 bar; Temperature: 35° C.

Example 3-9a: 2-(3-chlorophenyl)-2-({4-[(2-imino-2,3-dihydro-1,3-oxazol-3-yl)methyl]-1H-1,3-benzodiazol-2-yl}amino)propyl 2,2-dimethylpropanoate (Enantiomer A)

The first enantiomer to elute off the column was Enantiomer A:

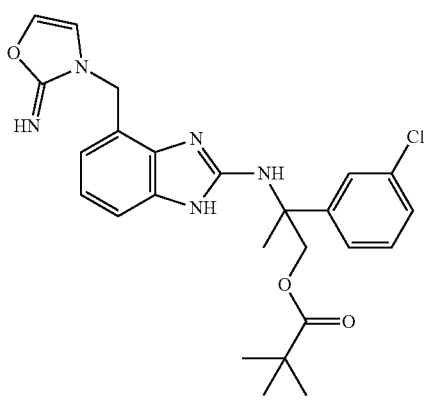 [SMILES: CC(C)(C)C(=O)OCC(C)(Nc1nc2c(Cn3ccoc3=N)cccc2[nH]1)c1cccc(Cl)c1]

$^1$H NMR (400 MHz, AcOH-$d_4$) δ 7.59 (s, 2H), 7.52-7.50 (m, 1H), 7.44-7.38 (m, 2H), 7.34 (d, J=8.00 Hz, 1H), 7.26 (t, J=8.00 Hz, 1H), 7.22 (d, J=1.60 Hz, 1H), 7.17 (d, J=7.60 Hz, 1H), 5.40 (s, 2H), 4.55 (d, J=11.60 Hz, 1H), 4.46 (d, J=11.60 Hz, 1H), 1.96 (s, 3H), 1.18 (s, 9H);

MS: m/z 482.4/484.1 (M+1).

Example 3-9b: 2-(3-chlorophenyl)-2-({4-[(2-imino-2,3-dihydro-1,3-oxazol-3-yl)methyl]-1H-1,3-benzodiazol-2-yl}amino)propyl 2,2-dimethylpropanoate (Enantiomer B)

The second enantiomer to elute off the column was Enantiomer B.

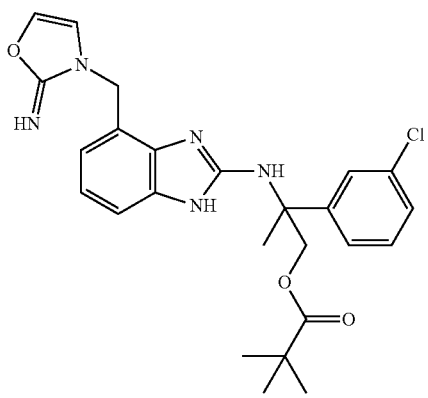 [SMILES: CC(C)(C)C(=O)OCC(C)(Nc1nc2c(Cn3ccoc3=N)cccc2[nH]1)c1cccc(Cl)c1]

¹H NMR (400 MHz, AcOH-d₄) δ 7.59 (s, 2H), 7.52-7.50 (m, 1H), 7.44-7.38 (m, 2H), 7.34 (d, J=8.00 Hz, 1H), 7.26 (t, J=8.00 Hz, 1H), 7.22 (d, J=1.60 Hz, 1H), 7.17 (d, J=7.60 Hz, 1H), 5.40 (s, 2H), 4.55 (d, J=11.60 Hz, 1H), 4.46 (d, J=11.60 Hz, 1H), 1.96 (s, 3H), 1.18 (s, 9H);

MS: m/z 482.4/484.1 (M+1).

Example 3: Preparation of 2-(3-chlorophenyl)-2-({4-[(2-imino-2,3-dihydro-1,3-oxazol-3-yl)methyl]-1H-1,3-benzodiazol-2-yl}amino)propan-1-ol

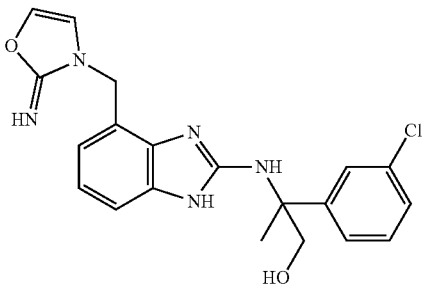 [SMILES: CC(CO)(Nc1nc2c(Cn3ccoc3=N)cccc2[nH]1)c1cccc(Cl)c1]

To a solution of 2-(3-chlorophenyl)-2-({4-[(2-imino-2,3-dihydro-1,3-oxazol-3-yl)methyl]-1H-1,3-benzodiazol-2-yl}amino)propyl 2,2-dimethylpropanoate; trifluoroacetic acid (Example 3, Step 9) (0.090 g, 0.151 mmol) in methanol (10 mL) was added 0.5 M sodium hydroxide in methanol (0.900 mL, 0.453 mmol) dropwise and the mixture was stirred at ambient temperature for 1 h. The reaction mixture was quenched with 1.5 N hydrochloride solution (1 mL) and concentrated under reduced pressure at 30° C. to afford (0.070 g) as a brown gum, it was purified by preparative HPLC using 0.1% TFA in acetonitrile:water to afford 2-(3-chlorophenyl)-2-({4-[(2-imino-2,3-dihydro-1,3-oxazol-3-yl)methyl]-1H-1,3-benzodiazol-2-yl}amino)propan-1-ol, isolated as the trifluoroacetate salt, (0.040 g) as a brown gum.

¹H NMR (400 MHz, AcOH-d₄) δ 7.57 (d, J=2.88 Hz, 2H), 7.50-7.48 (m, 1H), 7.41-7.35 (m, 3H), 7.31-7.24 (m, 2H), 7.20 (d, J=1.48 Hz, 1H), 5.40 (d, J=5.64 Hz, 2H), 4.36 (d, J=12.04 Hz, 1H), 4.08 (d, J=11.96 Hz, 1H), 1.76 (s, 3H);

MS: m/z 398.1 (M+1).

Example 3a: Preparation of (−)-2-(3-chlorophenyl)-2-({4-[(2-imino-2,3-dihydro-1,3-oxazol-3-yl)methyl]-1H-1,3-benzodiazol-2-yl}amino)propan-1-ol

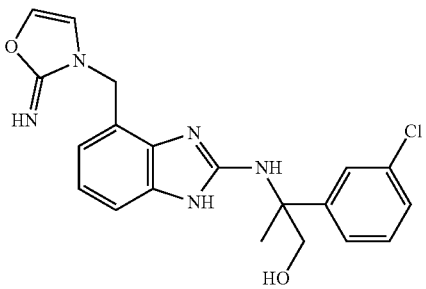 [SMILES: CC(CO)(Nc1nc2c(Cn3ccoc3=N)cccc2[nH]1)c1cccc(Cl)c1]

To a solution of 2-(3-chlorophenyl)-2-({4-[(2-imino-2,3-dihydro-1,3-oxazol-3-yl)methyl]-1H-1,3-benzodiazol-2-yl}amino)propyl 2,2-dimethylpropanoate (Example 3-9a, Enantiomer A) (0.180 g, 0.302 mmol) in methanol (20 mL) was added 0.5 M sodium hydroxide in methanol (2.42 mL, 1.21 mmol) dropwise and the mixture was stirred at ambient temperature for 1 h. The reaction mixture was quenched with 1.5 N hydrochloride solution (2 mL) and concentrated under reduced pressure at 30° C. to afford a brown gum (0.15 g), which was purified by preparative HPLC using 0.1% TFA in acetonitrile:water to afford (−)-2-(3-chlorophenyl)-2-({4-[(2-imino-2,3-dihydro-1,3-oxazol-3-yl)methyl]-1H-1,3-benzodiazol-2-yl}amino)propan-1-ol, isolated as the trifluoroacetate salt, (0.065 g) as a brown gum.

¹H NMR (400 MHz, AcOH-d₄) δ 7.57 (d, J=2.88 Hz, 2H), 7.50-7.48 (m, 1H), 7.41-7.35 (m, 3H), 7.31-7.24 (m, 2H), 7.20 (d, J=1.48 Hz, 1H), 5.40 (d, J=5.64 Hz, 2H), 4.36 (d, J=12.04 Hz, 1H), 4.08 (d, J=11.96 Hz, 1H), 1.76 (s, 3H);

MS: m/z 398.1 (M+1);

SOR: [α]$_D^{22.9}$ (−) 9.12, (MeOH, c=0.5).

Example 3b: Preparation of (+)-2-(3-chlorophenyl)-2-({4-[(2-imino-2,3-dihydro-1,3-oxazol-3-yl)methyl]-1H-1,3-benzodiazol-2-yl}amino)propan-1-ol

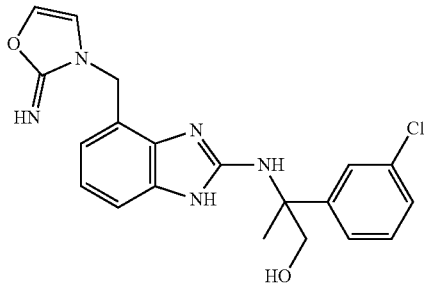 [SMILES: CC(CO)(Nc1nc2c(Cn3ccoc3=N)cccc2[nH]1)c1cccc(Cl)c1]

To a solution of 2-(3-chlorophenyl)-2-({4-[(2-imino-2,3-dihydro-1,3-oxazol-3-yl)methyl]-1H-1,3-benzodiazol-2-yl}amino)propyl 2,2-dimethylpropanoate (Example 3-9b, Enantiomer B) (0.170 g, 0.285 mmol) in methanol (20 mL) was added 0.5 N sodium hydroxide in methanol (2.28 mL, 1.14 mmol) dropwise and the mixture was stirred at ambient temperature for 1 h. The reaction mixture was quenched with 1.5 N hydrochloride solution (2 mL) and concentrated under reduced pressure at 30° C. to afford a brown gum (0.15 g), which was purified by preparative HPLC using 0.1% TFA in acetonitrile:water to afford (+)-2-(3-chlorophenyl)-2-({4-[(2-imino-2,3-dihydro-1,3-oxazol-3-yl)methyl]-1H-1,3-benzodiazol-2-yl}amino)propan-1-ol, isolated as the trifluoroacetate salt, (0.060 g) as a brown gum.

¹H NMR (400 MHz, AcOH-d₄) δ 7.58-7.57 (m, 2H), 7.50-7.47 (m, 1H), 7.41-7.36 (m, 3H), 7.32-7.26 (m, 2H), 7.21 (d, J=1.60 Hz, 1H), 5.40 (d, J=4.56 Hz, 2H), 4.36 (d, J=12.08 Hz, 1H), 4.08 (d, J=12.08 Hz, 1H), 1.77 (s, 3H);

MS: m/z 398.1 (M+1);

SOR: [α]$_D^{22.9}$ (+) 9.20, (MeOH, c=0.5).

Example 4: Preparation of 4-[(2-imino-2,3-dihydro-1,3-oxazol-3-yl)methyl]-N-{1-[3-(trifluoromethyl)phenyl]ethyl}-1H-1,3-benzodiazol-2-amine

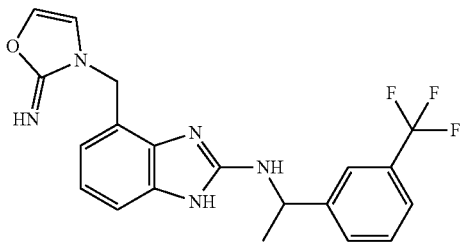

Example 4, Step 1: Preparation of 1-(1-isothiocyanatoethyl)-3-(trifluoromethyl)benzene

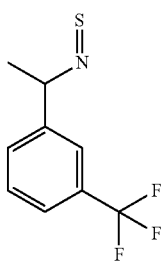

To an ice cooled solution of 1-[3-(trifluoromethyl)phenyl]ethanamine (commercially available) (10.0 g, 52.86 mmol) in dichloromethane (200 mL) was added 10% sodium bicarbonate solution (200 mL) followed by thiophosgene (10.10 mL, d=1.50 g/cm$^3$, 132.15 mmol) and whole mixture was stirred at ambient temperature for 30 min. The organic layer was separated, washed with brine (80 mL), dried over sodium sulphate, filtered and concentrated to afford a yellow gum (11.00 g) This was purified by Chromatography on a Grace instrument using 60.0 g pre-packed flash cartridge filled with normal phase silica gel 60 Å, 40-63 μm and the product was eluted at 8-12% ethyl acetate in hexane to afford 1-(1-isothiocyanatoethyl)-3-(trifluoromethyl)benzene (12.00 g) as a light yellow liquid.

$^1$H NMR (400 MHz, DMSO-d$_6$) δ 7.65-7.77 (m, 4H), 5.41 (q, J=5.40 Hz, 1H), 1.65 (d, J=8.80 Hz, 3H).

Example 4, Step 2: Preparation of 3-{2-amino-3-[(2-imino-2,3-dihydro-1,3-oxazol-3-yl)methyl]phenyl}-1-{1-[3-(trifluoromethyl)phenyl]ethyl}thiourea and 3-{2-amino-6-[(2-imino-2,3-dihydro-1,3-oxazol-3-yl)methyl]phenyl}-1-{1-[3-(trifluoromethyl)phenyl]ethyl}thiourea (Mixture of Regioisomers)

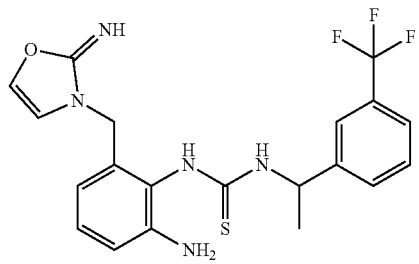

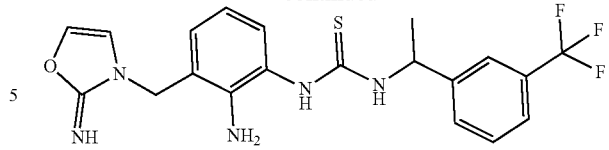

To a solution of 1-(1-isothiocyanatoethyl)-3-(trifluoromethyl)benzene (from Example 4, Step 1) (0.414 g, 1.791 mmol) in a mixture of solvents dichloromethane:methanol (4:2; 6 mL) was added 3-[(2-imino-2,3-dihydro-1,3-oxazol-3-yl)methyl]benzene-1,2-diamine (from Example 1, Step 5) (0.350 g, 1.710 mmol) and the mixture was stirred at ambient temperature for 16 h. The reaction mixture was concentrated to afford 3-{2-amino-3-[(2-imino-2,3-dihydro-1,3-oxazol-3-yl)methyl]phenyl}-1-{1-[3-(trifluoromethyl)phenyl]ethyl}thiourea and 3-{2-amino-6-[(2-imino-2,3-dihydro-1,3-oxazol-3-yl)methyl]phenyl}-1-{1-[3-(trifluoromethyl)phenyl]ethyl}thiourea (as mixture of non-separable regioisomers) (0.750 g) as a brown gum, which was used in the next step without purification.

MS: m/z 436.1 (M+1)

Example 4: Preparation of 4-[(2-imino-2,3-dihydro-1,3-oxazol-3-yl)methyl]-N-{1-[3-(trifluoromethyl)phenyl]ethyl}-1H-1,3-benzodiazol-2-amine

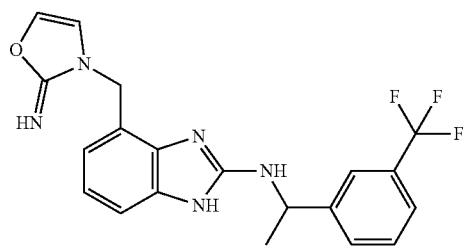 [SMILES: CC(Nc1nc2c(Cn3ccoc3=N)cccc2[nH]1)c1cccc(C(F)(F)F)c1]

To a solution of 3-{2-amino-3-[(2-imino-2,3-dihydro-1,3-oxazol-3-yl)methyl]phenyl}-1-{1-[3-(trifluoromethyl)phenyl]ethyl}thiourea and 3-{2-amino-6-[(2-imino-2,3-dihydro-1,3-oxazol-3-yl)methyl]phenyl}-1-{1-[3-(trifluoromethyl)phenyl]ethyl}thiourea (as a mixture of non-separable regioisomers) (from Example 4, Step 2) (0.450 g, 1.03 mmol) in methanol (8 mL) was added iodoacetic acid (0.288 g, 1.55 mmol) and the mixture was stirred at 65° C. for 1.5 h. The reaction mixture was concentrated at 25° C. to afford a yellow gum (0.500 g). This was purified by preparative HPLC using the TFA method to afford 4-[(2-imino-2,3-dihydro-1,3-oxazol-3-yl)methyl]-N-{1-[3-(trifluoromethyl)phenyl]ethyl}-1H-1,3-benzodiazol-2-amine, isolated as the trifluoroacetate salt, (0.300 g) as an off-white solid.

$^1$H NMR (400 MHz, AcOH-d$_4$) δ 7.78 (t, J=1.00 Hz, 2H), 7.63-7.53 (m, 4H), 7.32 (t, J=7.92 Hz, 1H), 7.18 (t, J=1.44 Hz, 2H), 5.42 (d, J=4.60 Hz, 2H), 5.21 (d, J=7.64 Hz, 1H), 1.73 (d, J=7.72 Hz, 3H);

MS: m/z 402.1 (M+1).

Example 5: Preparation of 2-(3-chlorophenyl)-2-({4-[(2-imino-4-methyl-2,3-dihydro-1,3-oxazol-3-yl)methyl]-1H-1,3-benzodiazol-2-yl}amino)propan-1-ol

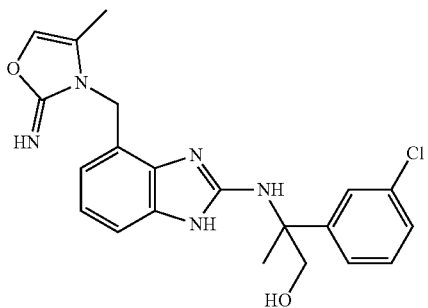 [SMILES: Cc1coc(=N)n1Cc1cccc2[nH]c(NC(C)(CO)c3cccc(Cl)c3)nc12]

Example 5, Step 1: 3-[(2,1,3-benzothiadiazol-4-yl)methyl]-4-methyl-2,3-dihydro-1,3-oxazol-2-imine hydrobromide

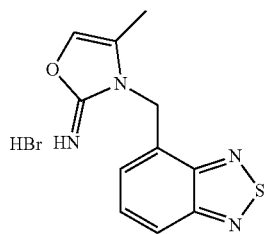 [SMILES: Br ; Cc1coc(=N)n1Cc1cccc2nsnc12]

To a solution of 4-(bromomethyl)-2,1,3-benzothiadiazole (Example 1, Step 3) (20.00 g, 87.30 mmol) in N, N-dimethyl formamide (100 mL) was added 4-methyloxazol-2-amine (10.30 g, 105.00 mmol) and the mixture was stirred at ambient temperature for 16 h. The reaction mixture was concentrated to afford a yellow gum (22.00 g). This was purified by Chromatography on a Grace instrument using 120.00 g pre-packed flash cartridge filled with normal phase silica gel 60 Å, 40-63 μm and the product was eluted at 25-30% ethyl acetate in hexane to afford 3-[(2,1,3-benzothiadiazol-4-yl)methyl]-4-methyl-2,3-dihydro-1,3-oxazol-2-imine hydrobromide (15.20 g) as a yellow solid.

$^1$H NMR (400 MHz, DMSO-$d_6$) δ 9.74 (bs, 2H), 8.13 (dd, J=3.60, 8.20 Hz, 1H), 7.95 (s, 1H), 7.76 (dd, J=2.00, 6.60 Hz, 1H), 7.68 (t, J=6.00 Hz, 1H), 5.63 (s, 2H), 1.86 (s, 3H); MS: m/z 247.1 [(M+1)-HBr].

Example 5, Step 2: Preparation of 3-[(2-imino-4-methyl-2,3-dihydro-1,3-oxazol-3-yl)methyl]benzene-1,2-diamine

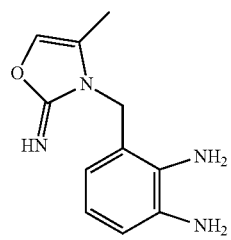 [SMILES: Cc1coc(=N)n1Cc1cccc(N)c1N]

To a de-gassed solution of 3-[(2,1,3-benzothiadiazol-4-yl)methyl]-4-methyl-2,3-dihydro-1,3-oxazol-2-imine hydrobromide (from Example 5, Step 1) (1.00 g, 3.08 mmol) in dry methanol (100 mL) was added Raney nickel (3.00 g, 300% w/w, pre-washed five times with dry methanol) and the resultant reaction mixture was stirred under a hydrogen atmosphere at bladder pressure (Approx. 1.5 kg/cm$^2$) at ambient temperature for 16 h. The reaction mixture was filtered through a celite bed and the bed was washed with methanol (750 mL). The combined filtrates were concentrated to afford of 3-[(2-imino-4-methyl-2,3-dihydro-1,3-oxazol-3-yl)methyl]benzene-1,2-diamine (0.650 g) as a black gum, which was used in the next step without further purification.

MS: m/z 219.2 (M+1).

Example 5, Step 3: Preparation of 2-[({2-amino-3-[(2-imino-4-methyl-2,3-dihydro-1,3-oxazol-3-yl)methyl]phenyl}carbamothioyl)amino]-2-(3-chlorophenyl)propyl 2,2-dimethylpropanoate and 2-[({2-amino-6-[(2-imino-4-methyl-2,3-dihydro-1,3-oxazol-3-yl)methyl]phenyl}carbamothioyl)amino]-2-(3-chlorophenyl)propyl 2,2-dimethylpropanoate (Mixture of Regioisomers)

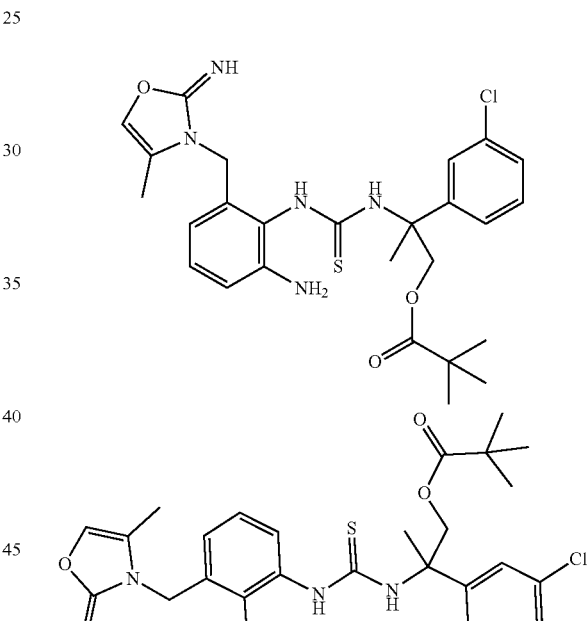

To a solution of 3-[(2-imino-4-methyl-2,3-dihydro-1,3-oxazol-3-yl)methyl]benzene-1,2-diamine (from Example 5, Step 2) (0.210 g, 0.962 mmol) in a mixture of solvents dichloromethane:methanol (4:1; 6 mL) was added [2-(3-chlorophenyl)-2-isothiocyanato-propyl] 2,2-dimethylpropanoate (from Example 3, Step 7) (0.300 g, 0.962 mmol) and the mixture was stirred at ambient temperature for 48 h. The reaction mixture was concentrated at 30° C. in a water bath to afford 2-[({2-amino-3-[(2-imino-4-methyl-2,3-dihydro-1,3-oxazol-3-yl)methyl]phenyl}carbamothioyl)amino]-2-(3-chlorophenyl)propyl 2,2-dimethylpropanoate and 2-[({2-amino-6-[(2-imino-4-methyl-2,3-dihydro-1,3-oxazol-3-yl)methyl]phenyl}carbamothioyl)amino]-2-(3-chlorophenyl)propyl 2,2-dimethylpropanoate (as a mixture of non-separable regioisomers) (0.510 g) as a brown gum, which was used in the next step without further purification.

MS: m/z 531.1 (M+1).

Example 5, Step 4: Preparation of 2-(3-chlorophenyl)-2-({4-[(2-imino-4-methyl-2,3-dihydro-1,3-oxazol-3-yl)methyl]-1H-1,3-benzodiazol-2-yl}amino)propyl 2,2-dimethylpropanoate

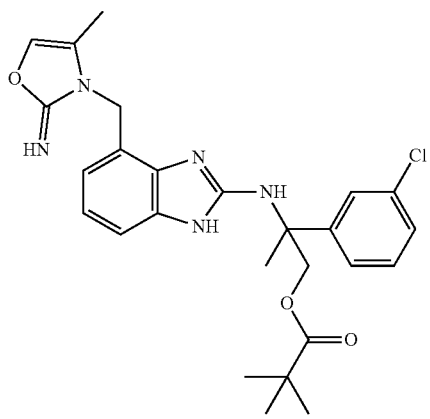 [SMILES: Cc1coc(=N)n1Cc1cccc2[nH]c(NC(C)(COC(=O)C(C)(C)C)c3cccc(Cl)c3)nc12]

To a solution of 2-[({2-amino-3-[(2-imino-4-methyl-2,3-dihydro-1,3-oxazol-3-yl)methyl]phenyl}carbamothioyl)amino]-2-(3-chlorophenyl)propyl 2,2-dimethylpropanoate and 2-[({2-amino-6-[(2-imino-4-methyl-2,3-dihydro-1,3-oxazol-3-yl)methyl]phenyl}carbamothioyl)amino]-2-(3-chlorophenyl)propyl 2,2-dimethylpropanoate (from Example 5, Step 3) (0.300 g, 0.566 mmol) in methanol (15 mL) was added iodoacetic acid (0.126 g, 0.679 mmol) and the mixture was stirred at 65° C. for 1 h. The reaction mixture was concentrated on high vacuum and the residue was diluted with aqueous 10% sodium bicarbonate solution (25 mL), and it was extracted with a mixture of solvents dichloromethane/methanol (9:1)(3×75 mL). The combined organic layer was dried over sodium sulphate, filtered and concentrated to afford a brown gum (0.280 g), which was purified by preparative HPLC using the TFA method to afford 2-(3-chlorophenyl)-2-({4-[(2-imino-4-methyl-2,3-dihydro-1,3-oxazol-3-yl)methyl]-1H-1,3-benzodiazol-2-yl}amino)propyl 2,2-dimethylpropanoate, isolated as the trifluoroacetate salt, (0.090 g) as a brown gum.

MS: m/z 497.2 (M+1).

Example 5: Preparation of 2-(3-chlorophenyl)-2-({4-[(2-imino-4-methyl-2,3-dihydro-1,3-oxazol-3-yl)methyl]-1H-1,3-benzodiazol-2-yl}amino)propan-1-ol

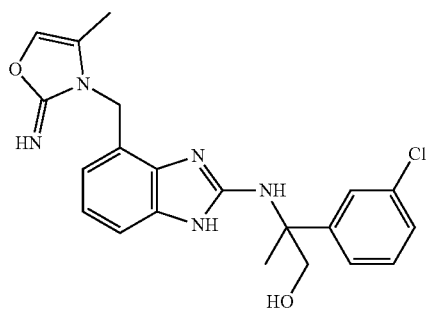 [SMILES: Cc1coc(=N)n1Cc1cccc2[nH]c(NC(C)(CO)c3cccc(Cl)c3)nc12]

To a solution of 2-(3-chlorophenyl)-2-({4-[(2-imino-4-methyl-2,3-dihydro-1,3-oxazol-3-yl)methyl]-1H-1,3-benzodiazol-2-yl}amino)propyl 2,2-dimethylpropanoate; trifluoroacetic acid (from Example 5, Step 4) (0.090 g, 0.147 mmol) in methanol (3 mL) was added a solution of 1.5 M sodium hydroxide in methanol (0.400 mL, 0.590 mmol) and the mixture was stirred at ambient temperature for 2 h. The reaction mixture was quenched with 1.5N hydrochloric acid (2 mL) and the resultant reaction mixture was concentrated under high vacuum to afford a brown gum (0.100 g). This was purified by preparative HPLC using a TFA method to afford 2-(3-chlorophenyl)-2-({4-[(2-imino-4-methyl-2,3-dihydro-1,3-oxazol-3-yl)methyl]-1H-1,3-benzodiazol-2-yl}amino)propan-1-ol, isolated as the trifluoroacetate salt, (0.020 g) as a brown solid.

$^1$H NMR (400 MHz, AcOH-d$_4$) δ 7.59 (s, 1H), 7.50 (d, J=6.76 Hz, 1H), 7.44 (s, 1H), 7.40 (t, J=7.32 Hz, 1H), 7.35 (d, J=8.00 Hz, 2H), 7.24 (t, J=7.96 Hz, 1H), 6.86 (d, J=7.68 Hz, 1H), 5.46 (s, 2H), 4.36 (d, J=12.08 Hz, 1H), 4.09 (d, J=12.12 Hz, 1H), 2.09 (s, 3H), 1.77 (s, 3H);

MS: m/z 412.2 (M+1).

Example 6: Preparation of N-[2-(3-chlorophenyl)-1-methoxypropan-2-yl]-4-[(2-imino-2,3-dihydro-1,3-oxazol-3-yl)methyl]-1H-1,3-benzodiazol-2-amine

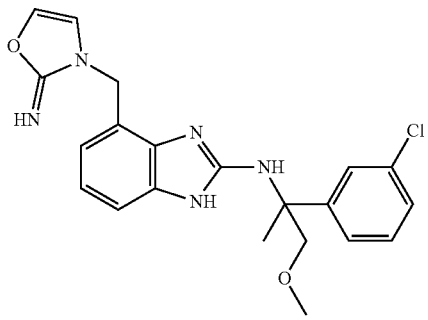 [SMILES: COCC(C)(Nc1nc2c(Cn3ccoc3=N)cccc2[nH]1)c1cccc(Cl)c1]

Example 6, Step 1: Preparation of tert-butyl (2-(3-chlorophenyl)-1-methoxypropan-2-yl)carbamate

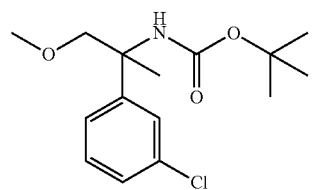 [SMILES: COCC(C)(NC(=O)OC(C)(C)C)c1cccc(Cl)c1]

To a solution of tert-butyl (2-(3-chlorophenyl)-1-hydroxypropan-2-yl)carbamate (from Example 3, Step 4) (6.00 g, 21.00 mmol) under a nitrogen atmosphere in acetonitrile (150 mL) was added silver oxide (24.30 g, 105.00 mmol) followed by iodomethane (12.00 mL, d=2.28 g/cm$^3$, 0.189 mmol) and resultant mixture was stirred at ambient temperature for 48 h. The reaction mixture was filtered through a celite bed and the bed was washed with ethyl acetate (3×500 mL) and the combined filtrates were concentrated on vacuum to afford a brown gum (6.00 g). This was purified by chromatography on a Grace instrument using 80.00 g pre-packed flash cartridge filled with normal phase silica gel 60 Å, 40-63 μm and the product was eluted at 18% ethyl acetate in petroleum ether to afford tert-butyl (2-(3-chlorophenyl)-1-methoxypropan-2-yl)carbamate (4.50 g) as yellow gum.

$^1$H NMR (400 MHz, DMSO-$d_6$: $D_2O$) δ 7.35 (s, 1H), 7.32 (d, J=7.96 Hz, 2H), 7.27 (t, J=6.76 Hz, 1H), 3.47 (s, 2H), 3.22 (s, 3H), 1.53 (s, 3H), 1.19 (s, 9H);

MS: m/z 200.1 [(M+1)-Boc].

Example 6, Step 2: Preparation of 2-(3-chlorophenyl)-1-methoxypropan-2-amine hydrochloride

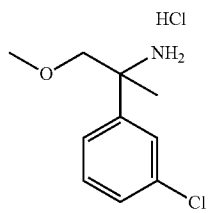

To a solution of tert-butyl (2-(3-chlorophenyl)-1-methoxypropan-2-yl)carbamate (from Example 6, Step 1) (4.50 g, 15.00 mmol) in dry dichloromethane (50 mL) under a nitrogen atmosphere was added 4M HCl in dioxane solution (11.25 mL, 45.00 mmol) dropwise at 0° C. and the reaction mixture was stirred at ambient temperature for 16 h. The reaction mixture was concentrated on high vacuum to afford 2-(3-chlorophenyl)-1-methoxypropan-2-amine hydrochloride (3.50 g) as a yellowish gum, which was used in the next step without further purification.

$^1$H NMR (400 MHz, DMSO-$d_6$: $D_2O$) δ 7.50 (s, 1H), 7.46 (t, J=7.60 Hz, 1H), 7.43-7.39 (m, 2H), 3.67 (d, J=10.40 Hz, 1H), 3.56 (d, J=10.40 Hz, 1H), 3.27 (s, 3H), 1.54 (s, 3H);

MS: m/z 200.1 [(M+1)-HCl].

Example 6, Step 3: Preparation of 1-chloro-3-(2-isothiocyanato-1-methoxypropan-2-yl)benzene

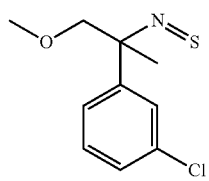

To an ice cooled solution of 2-(3-chlorophenyl)-1-methoxypropan-2-amine hydrochloride (from Example 6, Step 2) (3.00 g, 12.70 mmol) in dichloromethane (50 mL) was added 10% sodium bicarbonate solution (50 mL) followed by thiophosgene (1.20 mL, d=1.50 g/cm³, 15.20 mmol) and whole mixture was stirred at ambient temperature for 30 min. The organic layer was separated, washed with brine (25 mL), dried over sodium sulphate, filtered and concentrated to afford 1-chloro-3-(2-isothiocyanato-1-methoxypropan-2-yl)benzene (2.10 g) as a light yellow liquid, which was used in the next step without further purification.

$^1$H NMR (400 MHz, DMSO-$d_6$) δ 7.46 (s, 1H), 7.45 (t, J=7.20 Hz, 1H), 7.41 (dd, J=2.40, 9.80 Hz, 2H), 3.68 (q, J=10.40 Hz, 2H), 3.33 (s, 3H), 1.58 (s, 3H).

Example 6, Step 4: Preparation of 3-{2-amino-3-[(2-imino-2,3-dihydro-1,3-oxazol-3-yl)methyl]phenyl}-1-[2-(3-chlorophenyl)-1-methoxypropan-2-yl]thiourea and 3-{2-amino-6-[(2-imino-2,3-dihydro-1,3-oxazol-3-yl)methyl]phenyl}-1-[2-(3-chlorophenyl)-1-methoxypropan-2-yl]thiourea (Mixture of Regioisomers)

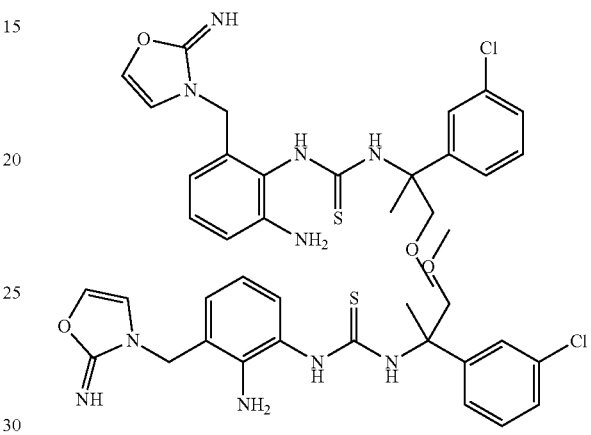

To a solution of 3-[(2-imino-2,3-dihydro-1,3-oxazol-3-yl)methyl]benzene-1,2-diamine (from Example 1, Step 5) (0.400 g, 1.96 mmol) in dichloromethane:methanol (4:2; 6 mL) was added 1-chloro-3-(2-isothiocyanato-1-methoxypropan-2-yl)benzene (from Example 6, Step 3) (0.470 g, 1.96 mmol) and the mixture was stirred at ambient temperature for 96 h. The reaction mixture was concentrated at 25° C. under high vacuum to afford 3-{2-amino-3-[(2-imino-2,3-dihydro-1,3-oxazol-3-yl)methyl]phenyl}-1-[2-(3-chlorophenyl)-1-methoxypropan-2-yl]thiourea and 3-{2-amino-6-[(2-imino-2,3-dihydro-1,3-oxazol-3-yl)methyl]phenyl}-1-[2-(3-chlorophenyl)-1-methoxypropan-2-yl]thiourea (as a mixture of non-separable regioisomers) (0.850 g) as a brown gum which was used in the next step without further purification.

MS: m/z 446.2 (M+1).

Example 6: Preparation of N-[2-(3-chlorophenyl)-1-methoxypropan-2-yl]-4-[(2-imino-2,3-dihydro-1,3-oxazol-3-yl)methyl]-1H-1,3-benzodiazol-2-amine

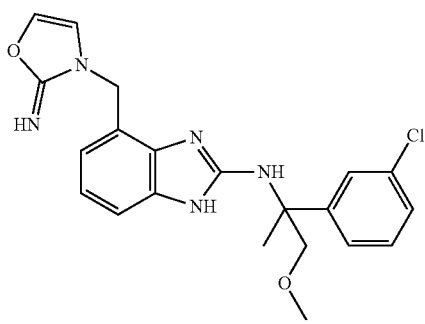 [SMILES: COCC(C)(Nc1nc2c(Cn3ccoc3=N)cccc2[nH]1)c1cccc(Cl)c1]

To a solution of 3-{2-amino-3-[(2-imino-2,3-dihydro-1,3-oxazol-3-yl)methyl]phenyl}-1-[2-(3-chlorophenyl)-1-methoxypropan-2-yl]thiourea and 3-{2-amino-6-[(2-imino-2,3-dihydro-1,3-oxazol-3-yl)methyl]phenyl}-1-[2-(3-chlorophenyl)-1-methoxypropan-2-yl]thiourea (as a mixture of non-separable regioisomers) (0.400 g, 0.896 mmol) in methanol (5 mL) was added iodoacetic acid (0.250 g, 1.34 mmol) and the mixture was stirred at 60° C. for 1 h. The reaction mixture was concentrated to afford a dark brown gum (0.450 g), which was purified by preparative HPLC purification using a TFA method to afford N-[2-(3-chlorophenyl)-1-methoxypropan-2-yl]-4-[(2-imino-2,3-dihydro-1,3-oxazol-3-yl)methyl]-1H-1,3-benzodiazol-2-amine, isolated as the trifluoroacetate salt, (0.060 g) as a brown gum.

$^1$H NMR (400 MHz, AcOH-d$_4$) δ 7.58 (d, J=1.00 Hz, 1H), 7.54 (s, 1H), 7.46-7.44 (m, 1H), 7.39-7.37 (m, 3H), 7.29 (d, J=4.60 Hz, 2H), 7.24 (d, J=7.64 Hz, 1H), 5.42 (d, J=7.72 Hz, 2H), 4.03 (d, J=10.40 Hz, 1H), 3.79 (d, J=10.0 Hz, 1H), 3.49 (s, 3H), 1.81 (s, 3H);

MS: m/z 412.2 (M+1).

Example 7: Preparation of 4-[(2-imino-2,3-dihydro-1,3-oxazol-3-yl)methyl]-N-{2-[3-(trifluoromethyl)phenyl]propan-2-yl}-1H-1,3-benzodiazol-2-amine

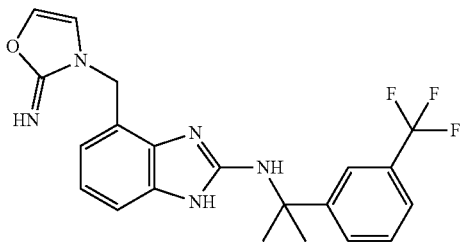 [SMILES: CC(C)(Nc1nc2c(Cn3ccoc3=N)cccc2[nH]1)c1cccc(C(F)(F)F)c1]

Starting with commercially available 2-[3-(trifluoromethyl)phenyl]propan-2-amine, the titled compound was made by the method described for Example 2 and isolated as the trifluoroacetate salt.

$^1$H NMR (400 MHz, AcOH-d$_4$) δ 7.86 (s, 1H), 7.84 (d, J=8.40 Hz, 1H), 7.67 (dd, J=7.60 Hz, 2H), 7.60 (dd, J=1.60, 8.20 Hz, 1H), 7.33 (t, J=7.60 Hz, 1H), 7.27 (dd, J=1.60, 8.80 Hz, 3H), 5.40 (s, 2H), 1.92 (s, 6H);

MS: m/z 416.1 (M+1).

Example 8: Preparation of 2-(3-chloro-4-fluorophenyl)-2-({4-[(2-imino-2,3-dihydro-1,3-oxazol-3-yl)methyl]-1H-1,3-benzodiazol-2-yl}amino)propan-1-ol

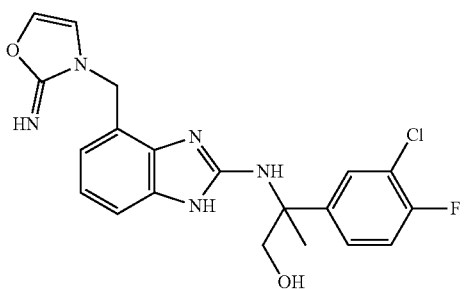 [SMILES: CC(CO)(Nc1nc2c(Cn3ccoc3=N)cccc2[nH]1)c1ccc(F)c(Cl)c1]

Example 8, Step 1: Preparation of 5-(3-chloro-4-fluorophenyl)-5-methylimidazolidine-2,4-dione

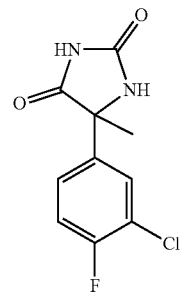 [SMILES: CC1(c2ccc(F)c(Cl)c2)NC(=O)NC1=O]

To a stirred solution of 1-(3-chloro-4-fluorophenyl)ethan-1-one (commercially available) (45.00 g, 261.00 mmol) in a mixture of solvents ethanol/water (1:1; 1200 mL) was added ammonium carbonate (125.00 g, 1300.00 mmol) followed by potassium cyanide (20.40 g, 313.00 mmol) and the mixture was stirred at 65° C. for 18 h. The reaction mixture was poured into ice-cold water (1500 mL) and it was stirred for 30 min. The solid that formed was filtered off and dried to afford 5-(3-chloro-4-fluorophenyl)-5-methylimidazolidine-2,4-dione (55.00 g) as an off-white solid, which was used in the next step without further purification.

$^1$H NMR (400 MHz, DMSO-d$_6$) δ 10.89 (bs, 1H), 8.65 (s, 1H), 7.65 (d, J=6.80 Hz, 1H), 7.52 (s, 1H,), 7.50 (d, J=6.80 Hz, 1H), 1.65 (s, 3H);

MS: m/z 243.0 (M+1).

Example 8, Step 2: Preparation of 2-amino-2-(3-chloro-4-fluorophenyl) propanoic acid

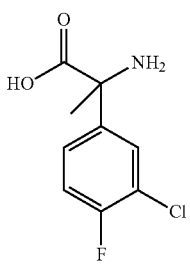

5-(3-chloro-4-fluorophenyl)-5-methylimidazolidine-2,4-dione (from Example 8, Step 1) (55.00 g, 227.00 mmol) was dissolved in 10% aqueous sodium hydroxide solution (600 mL) and the mixture was stirred at 110° C. for 120 h. The reaction mixture was neutralized (adjusted pH=7) with 6.0 N HCl (500 mL) and the solid that formed was filtered, washed with petroleum ether (2×150 mL) and dried to afford 2-amino-2-(3-chloro-4-fluorophenyl) propanoic acid (49.00 g) as a white solid, which was used in the next step without further purification.

$^1$H NMR (400 MHz, DMSO-d$_6$) δ 8.06 (bs, 2H), 7.69 (d, J=6.80 Hz, 1H), 7.48 (s, 1H), 7.37 (d, J=7.38 Hz, 1H), 1.61 (s, 3H);

MS: m/z 218.1 (M+1).

Example 8, Step 3: Preparation of 2-((tert-butoxycarbonyl) amino)-2-(3-chloro-4-fluorophenyl)propanoic acid

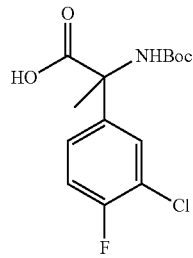

To a suspension of 2-amino-2-(3-chloro-4-fluorophenyl) propanoic acid (from Example 8, Step 2) (75.00 g, 345.00 mmol) in a mixture of solvents tetrahydrofuran:water (1:1; 1500 mL) was added sodium bicarbonate (29.00 g, 345.00 mmol) followed by di-tert-butyl dicarbonate (158.00 mL, d: 0.950 g/cm³, 689.00 mmol) and the mixture was stirred at ambient temperature for 72 h. The reaction mixture was diluted with water (750 mL) and extracted with ethyl acetate (4×1500 mL). The combined organic layer was dried over sodium sulphate, filtered and concentrated to afford 2-((tert-butoxycarbonyl) amino)-2-(3-chloro-4-fluorophenyl) propanoic acid (100.00 g) as a colourless gum, which was used in the next step without further purification.

$^1$H NMR (400 MHz, DMSO-$d_6$) δ 7.36 (d, J=7.80 Hz, 1H), 7.25 (d, J=7.60 Hz, 1H), 7.23 (s, 1H), 7.12 (s, 1H), 1.71 (s, 3H), 1.33 (s, 9H);

MS: m/z 316.0 (M−1).

Example 8, Step 4: Preparation of tert-butyl N-[2-(3-chloro-4-fluorophenyl)-1-hydroxypropan-2-yl] carbamate

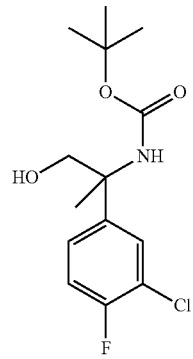 [SMILES: CC(C)(C)OC(=O)NC(C)(CO)c1ccc(F)c(Cl)c1]

To a solution of 2-((tert-butoxycarbonyl) amino)-2-(3-chloro-4-fluorophenyl) propanoic acid (from Example 8, Step 3) (70.00 g, 220.00 mmol) in dry tetrahydrofuran (500 mL) was added triethylamine (92.10 mL, d=0.726 g/cm³, 661.00 mmol) followed by isobutyl chloroformate (34.25 mL, d=1.053 g/cm³, 263.00 mmol) at 0° C. and stirred at same temperature for 4 h. The solid that formed was filtered off at 0° C. and the residue was washed with tetrahydrofuran (100 mL). The combined filtrate was added to a cooled mixture of sodium borohydride (58.30 g, 1540.00 mmol) in water (75 mL). The reaction mixture was slowly warmed to ambient temperature and stirred for 30 h. The reaction mixture was quenched with ice cold water (500 mL) and extracted with ethyl acetate (4×2000 mL) and the combined organic layer was washed with brine (75 mL), dried over sodium sulphate, filtered and concentrated to afford a yellowish liquid (70.00 g). This was purified by gravity column chromatography using 60-120 silica gel and the product was eluted with 25-30% ethyl acetate in petroleum ether to afford tert-butyl (2-(3-chloro-4-fluorophenyl)-1-hydroxy propan-2-yl)carbamate (32.50 g) as a colourless liquid.

$^1$H NMR (400 MHz, DMSO-$d_6$) δ 7.43 (d, J=6.80 Hz, 1H), 7.34 (d, J=8.40 Hz, 1H), 7.30 (s, 1H), 6.85 (bs, 1H), 4.56 (t, J=5.20 Hz, 1H), 3.45 (d, J=6.00 Hz, 2H), 1.55 (s, 3H), 1.26 (s, 9H);

MS: m/z 304.0 (M+1).

Example 8, Step 5: Preparation of 2-{[(tert-butoxy)carbonyl]amino}-2-(3-chloro-4-fluorophenyl)propyl 2,2-dimethylpropanoate

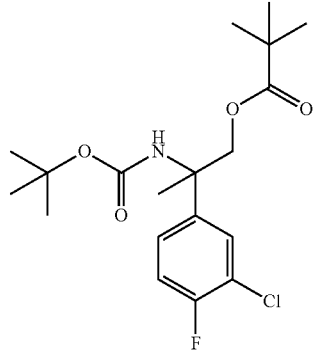 [SMILES: CC(C)(C)OC(=O)NC(C)(COC(=O)C(C)(C)C)c1ccc(F)c(Cl)c1]

To a solution of tert-butyl N-[1-(3-chloro-4-fluoro-phenyl)-2-hydroxy-1-methyl-ethyl]carbamate (from Example 8, Step 4) (55.0 g, 181.00 mmol) in dry dichloromethane was added triethylamine (75.50 mL, 543.00 mmol) followed by 2,2-dimethylpropanoyl chloride (33.40 mL, 272.00 mmol) at 0° C. and the reaction mixture was stirred at ambient temperature for 16 h. The reaction mixture was diluted with water (500 mL) and the aqueous layer was extracted with dichloromethane (4×1000 mL). The combined organic layer was washed with brine (200 mL), dried over sodium sulphate, filtered and concentrated to afford crude mass (70.50 g) as a yellow liquid, which was purified by gravity column chromatography over 601-20 silica gel and the product was eluted with 30% ethyl acetate in petroleum ether to afford 2-{[(tert-butoxy)carbonyl]amino}-2-(3-chloro-4-fluorophenyl)propyl 2,2-dimethylpropanoate (40.20 g) as a yellow oil.

$^1$H NMR (400 MHz, DMSO-$d_6$) δ 7.47 (dd, J=1.60, 7.00 Hz, 1H), 7.36-7.32 (m, 2H), 4.32-4.23 (m, 2H), 1.55 (s, 3H), 1.18 (s, 9H), 1.17 (s, 9H);

MS: m/z 288.2 [(M+1)-Boc].

Example 8, Step 6: Preparation of 2-amino-2-(3-chloro-4-fluorophenyl)propyl 2,2-dimethylpropanoate hydrochloride

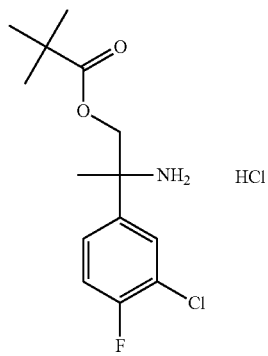 [SMILES: CC(C)(C)C(=O)OCC(C)(N)c1ccc(F)c(Cl)c1 ; Cl]

To a stirred solution of 2-{[(tert-butoxy)carbonyl]amino}-2-(3-chloro-4-fluorophenyl)propyl 2,2-dimethylpropanoate (from Example 8, Step 5) (40.0 g, 103.00 mmol) in dichloromethane (300 mL) was added 4M HCl in dioxane (103.00 mL, 413.00 mmol) at 0° C. and the reaction mixture was stirred at ambient temperature for 16 h. The reaction mixture was concentrated to afford 2-amino-2-(3-chloro-4-fluorophenyl)propyl 2,2-dimethylpropanoate hydrochloride (32.30 g) as a brown gum, which was used in the next step without further purification.

$^1$H NMR (400 MHz, DMSO-$d_6$) δ 7.87 (d, J=8.80 Hz, 1H), 7.63-7.60 (m, 1H), 7.55-7.49 (m, 1H), 4.44 (d, J=15.60 Hz, 1H), 4.29 (d, J=15.20 Hz, 1H), 1.70 (s, 3H), 1.11 (s, 9H); MS: m/z 288.2 [(M+1)-HCl].

Example 8, Step 7: Preparation of [2-(3-chloro-4-fluoro-phenyl)-2-isothiocyanato-propyl] 2,2-dimethyl propanoate

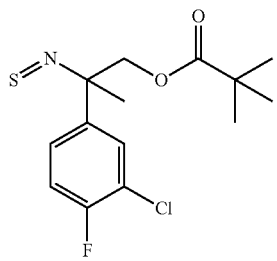 [SMILES: CC(C)(C)C(=O)OCC(C)(N=S)c1ccc(F)c(Cl)c1]

To a stirred solution of 2-amino-2-(3-chloro-4-fluorophenyl)propyl 2,2-di methylpropanoate hydrochloride (from Example 8, Step 6) (30.0 g, 92.50 mmol) in dichloromethane (300 mL) was added 10% aqueous sodium bicarbonate solution (300 mL) followed by thiophosgene (14.2 mL, 185.00 mmol) at 0° C. and stirred at the same temperature for 1 h. The reaction mixture was diluted with water (100 mL), extracted with dichloromethane (3×1000 mL) and the combined organic layer was dried over sodium sulphate, filtered and concentrated to a yellow liquid (33.5 g). This was purified by gravity column chromatography over 60-120 silica gel and the product was eluted with 10% ethyl acetate in petroleum ether to afford [2-(3-chloro-4-fluorophenyl)-2-isothiocyanato-propyl] 2,2-dimethylpropanoate (18.20 g) as a yellow oil.

$^1$H NMR (400 MHz, DMSO-$d_6$) δ 7.73 (dd, J=2.00, 7.00 Hz, 1H), 7.54-7.50 (m, 2H), 4.44 (dd, J=11.20, 17.20 Hz, 2H), 1.80 (s, 3H), 1.11 (s, 9H);

Example 8, Step 8: Preparation of 2-[({2-amino-3-[(2-imino-2,3-dihydro-1,3-oxazol-3-yl)methyl]phenyl}carbamothioyl)amino]-2-(3-chloro-4-fluorophenyl)propyl 2,2-dimethylpropanoate and 2-[({2-amino-6-[(2-imino-2,3-dihydro-1,3-oxazol-3-yl)methyl]phenyl}carbamothioyl)amino]-2-(3-chloro-4-fluorophenyl)propyl 2,2-dimethylpropanoate (Mixture of Regioisomers)

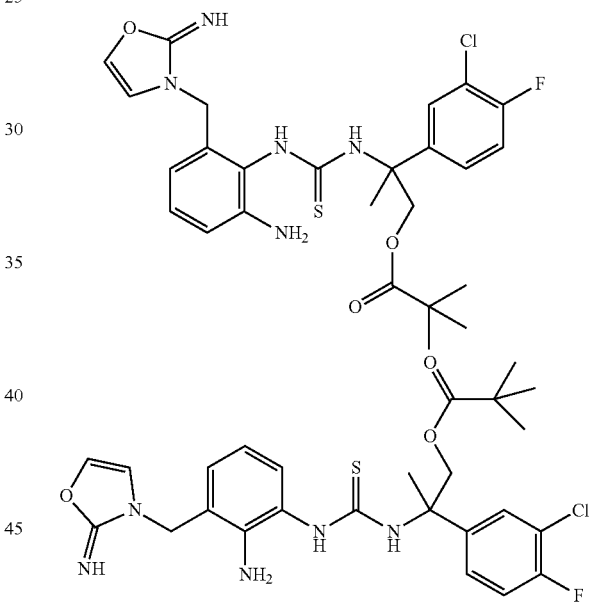

To a solution of 3-[(2-imino-2,3-dihydro-1,3-oxazol-3-yl)methyl]benzene-1,2-diamine (from Example 1, step 5) (1.70 g, 8.32 mmol) in a mixture of solvents dichloromethane:methanol (1:1; 40 mL) was added [2-(3-chloro-4-fluorophenyl)-2-isothiocyanato-propyl] 2,2-dimethylpropanoate (from Example 8, Step 7) (1.50 g, 3.18 mmol) and stirred at ambient temperature for 20 h. The reaction mixture was concentrated at 30° C. in a water bath to afford 2-[({2-amino-3-[(2-imino-2,3-dihydro-1,3-oxazol-3-yl)methyl]phenyl}carbamothioyl)-amino]-2-(3-chloro-4-fluorophenyl)propyl 2,2-dimethylpropanoate and 2-[({2-amino-6-[(2-imino-2,3-dihydro-1,3-oxazol-3-yl)methyl]phenyl}carbamothioyl)amino]-2-(3-chloro-4-fluorophenyl)propyl 2,2-dimethylpropanoate (as a mixture of non-separable regioisomers) (3.20 g) as a yellowish gum, which was used in the next step without purification.

MS: m/z 534.2/536.2 (M+1).

Example 8, Step 9: Preparation of 2-(3-chloro-4-fluorophenyl)-2-({4-[(2-imino-2,3-dihydro-1,3-oxazol-3-yl)methyl]-1H-1,3-benzodiazol-2-yl}amino)propyl 2,2-dimethylpropanoate

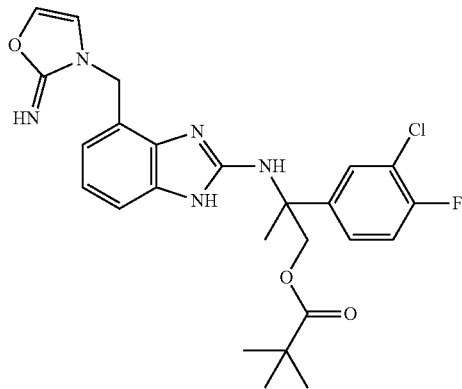 [SMILES: CC(C)(C)C(=O)OCC(C)(Nc1nc2c(Cn3ccoc3=N)cccc2[nH]1)c1ccc(F)c(Cl)c1]

To a solution of 2-[({2-amino-3-[(2-imino-2,3-dihydro-1,3-oxazol-3-yl)methyl]phenyl}carbamothioyl)amino]-2-(3-chloro-4-fluorophenyl)propyl 2,2-dimethylpropanoate and 2-[({2-amino-6-[(2-imino-2,3-dihydro-1,3-oxazol-3-yl)methyl]phenyl}carbamothioyl)amino]-2-(3-chloro-4-fluorophenyl)propyl 2,2-dimethylpropanoate (as a mixture of non-separable regioisomers) (Example 8, Step 8) (3.20 g, 5.99 mmol) in methanol (25 mL) was added iodoacetic acid (1.67 g, 8.99 mmol) and the mixture was refluxed for 1 h. The reaction mixture was concentrated to remove the solvent methanol to afford a reddish gum (3 g), which was purified by preparative HPLC (TFA:Acetonitrile) to afford 2-(3-chloro-4-fluorophenyl)-2-({4-[(2-imino-2,3-dihydro-1,3-oxazol-3-yl)methyl]-1H-1,3-benzodiazol-2-yl}amino)propyl 2,2-dimethylpropanoate, isolated as the trifluoroacetate salt, (0.800 g) as a yellow gum.

$^1$H NMR (400 MHz, AcOH-d$_4$) δ 7.70 (dd, J=6.84, 2.36 Hz, 1H), 7.59 (d, J=1.68 Hz, 1H), 7.56-7.53 (m, 1H), 7.37 (dd, J=7.22, 1.88 Hz, 1H), 7.33-7.26 (m, 3H), 7.24 (d, J=1.64 Hz, 1H), 5.40 (s, 2H), 4.54 (d, J=11.64 Hz, 1H), 4.46 (d, J=11.60 Hz, 1H), 1.99 (s, 3H), 1.19 (s, 9H);

MS: m/z 500.1/502.1 [(M+1)-TFA].

Example 8: Preparation of 2-(3-chloro-4-fluorophenyl)-2-({4-[(2-imino-2,3-dihydro-1,3-oxazol-3-yl)methyl]-1H-1,3-benzodiazol-2-yl}amino)propan-1-ol

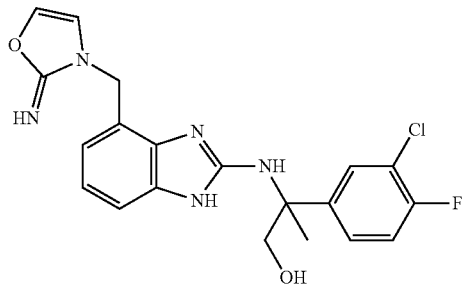 [SMILES: CC(CO)(Nc1nc2c(Cn3ccoc3=N)cccc2[nH]1)c1ccc(F)c(Cl)c1]

To a solution of 2-(3-chloro-4-fluorophenyl)-2-({4-[(2-imino-2,3-dihydro-1,3-oxazol-3-yl)methyl]-1H-1,3-benzodiazol-2-yl}amino)propyl 2,2-dimethylpropanoate; trifluoroacetic acid (Example 8, Step 9) (0.780 g, 1.27 mmol) in methanol (80 mL) was added 0.5 N sodium hydroxide in methanol (10.20 mL, 5.08 mmol) dropwise and the mixture was stirred at ambient temperature for 1 h. The reaction mixture was quenched with 1.5 N hydrochloride solution (4 mL) and concentrated under reduced pressure at 30° C. to afford a brown gum (0.7 g), which was purified by preparative HPLC using 0.1% TFA in acetonitrile:water to afford 2-(3-chloro-4-fluorophenyl)-2-({4-[(2-imino-2,3-dihydro-1,3-oxazol-3-yl)methyl]-1H-1,3-benzodiazol-2-yl}amino)propan-1-ol, isolated as the trifluoroacetate salt, (0.180 g) as a brown gum.

$^1$H NMR (400 MHz, AcOH-d$_4$) δ 7.67 (dd, J=6.80, 2.36 Hz, 1H), 7.57 (s, 1H), 7.53-7.49 (m, 1H), 7.40 (d, J=7.48 Hz, 1H), 7.31-7.22 (m, 3H), 7.21 (d, J=1.52 Hz, 1H), 5.37 (dd, J=21.86, 7.16 Hz, 2H), 4.32 (d, J=12.08 Hz, 1H), 4.07 (d, J=12.08 Hz, 1H), 1.77 (s, 3H);

MS: m/z 416.1/418.1 (M+1).

The above product was separated into its two enantiomers by Chiral SFC using the method: Column: Chiralcel OZ-H, Mobile Phase: 0.5% isopropyl amine in methanol co-solvent 30% CO$_2$; Flow rate: 3 mL/min, pressure: 100 bar; Temperature: 35° C. to obtain the two enantiomers.

Example 8a: (−)-2-(3-chloro-4-fluorophenyl)-2-({4-[(2-imino-2,3-dihydro-1,3-oxazol-3-yl)methyl]-1H-1,3-benzodiazol-2-yl}amino)propan-1-ol The (−) enantiomer was the first compound to elute off the column, isolated as the trifluoroacetate salt.

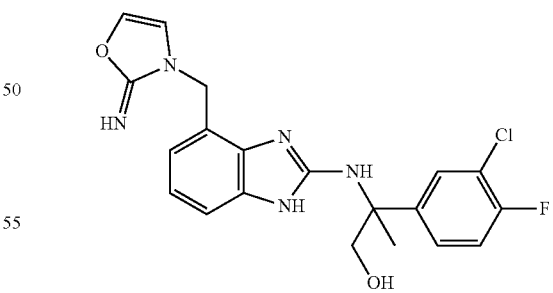

$^1$H NMR (400 MHz, AcOH-d$_4$) δ 7.67 (dd, J=6.80, 2.36 Hz, 1H), 7.57 (s, 1H), 7.53-7.49 (m, 1H), 7.40 (d, J=7.48 Hz, 1H), 7.31-7.22 (m, 3H), 7.21 (d, J=1.52 Hz, 1H), 5.37 (dd, J=21.86, 7.16 Hz, 2H), 4.32 (d, J=12.08 Hz, 1H), 4.07 (d, J=12.08 Hz, 1H), 1.77 (s, 3H);

MS: m/z 416.1/418.1 (M+1);

SOR: [α]$_D^{24.2}$ (−) 7.80, (MeOH, c=1.0).

Example 8b: (+)-2-(3-chloro-4-fluorophenyl)-2-({4-[(2-imino-2,3-dihydro-1,3-oxazol-3-yl)methyl]-1H-1,3-benzodiazol-2-yl}amino)propan-1-ol The (+) enantiomer was the second compound to elute off the column, isolated as the trifluoroacetate salt.

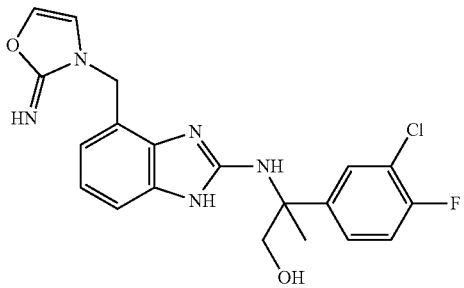 [SMILES: CC(CO)(Nc1nc2c(Cn3ccoc3=N)cccc2[nH]1)c1ccc(F)c(Cl)c1]

$^1$H NMR (400 MHz, AcOH-d$_4$) δ 7.67 (dd, J=6.80, 2.36 Hz, 1H), 7.57 (s, 1H), 7.53-7.49 (m, 1H), 7.40 (d, J=7.48 Hz, 1H), 7.31-7.22 (m, 3H), 7.21 (d, J=1.52 Hz, 1H), 5.37 (dd, J=21.86, 7.16 Hz, 2H), 4.32 (d, J=12.08 Hz, 1H), 4.07 (d, J=12.08 Hz, 1H), 1.77 (s, 3H);

MS: m/z 416.1/418.1 (M+1).

Example 9: Preparation of 2-(3-chloro-4-fluorophenyl)-2-[(4-{[(1,2-oxazol-3-yl)amino]methyl}-1H-1,3-benzodiazol-2-yl)amino]propan-1-ol

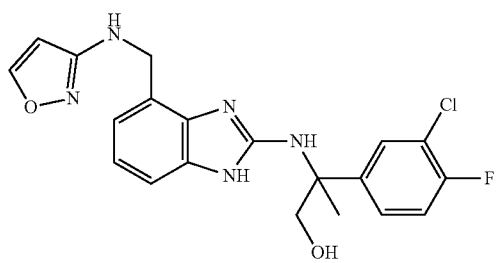 [SMILES: CC(CO)(Nc1nc2c(CNc3ccon3)cccc2[nH]1)c1ccc(F)c(Cl)c1]

Example 9, Step 1: Preparation of 2,1,3-benzothiadiazol-4-ylmethanol

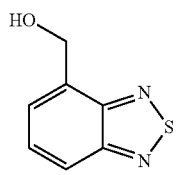

To a stirred solution of 4-(bromomethyl)-2,1,3-benzothiadiazole (from Example 1, Step 3) (60.00 g, 183.00 mmol) in a 1:1 mixture of dioxane/water (300 mL) was added potassium carbonate (177.0 g, 1280.0 mmol) and it was refluxed for 48 h. The reaction mixture was quenched with water (100 mL) and extracted with ethyl acetate (3×750 mL). The combined organic layer was washed with brine solution (75 mL), dried over sodium sulphate, filtered and concentrated to afford a dark-brown liquid (31.0 g). This was purified by chromatography on a Grace instrument using 220.0 g pre-packed flash cartridge filled with normal phase silica gel 60 Å, 40-63 μm and the product eluted with 30-40% ethyl acetate in hexane to afford 2,1,3-benzothiadiazol-4-ylmethanol (20.0 g) as a yellow solid.

$^1$H NMR (400 MHz, DMSO-d$_6$) δ 7.95 (d, J=8.40 Hz, 1H), 7.72 (t, J=10.00 Hz, 2H), 5.52 (t, J=4.80 Hz, 1H), 5.02 (d, J=4.00 Hz, 2H);

Example 9, Step 2: Preparation of 2,1,3-benzothiadiazole-4-carbaldehyde

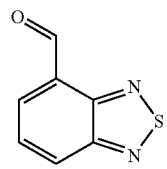 [SMILES: O=Cc1cccc2nsnc12]

To a stirred solution of 2,1,3-benzothiadiazol-4-ylmethanol (from Example 9, Step 1) (10.00 g, 60.20 mmol) in dichloromethane (150 mL) was added Dess-Martin Periodinane (30.60 g, 72.20 mmol) and the mixture was stirred at ambient temperature for 1 h. The reaction mixture was quenched with 10% aqueous sodium bicarbonate solution (100 mL) and extracted with dichloromethane (3×500 mL). The combined organic layer was washed with brine solution (50 mL), dried over sodium sulphate, filtered and concentrated to afford a yellow gum (10.00 g). This was purified by chromatography on an Isolera instrument using 120.0 g pre-packed flash cartridge filled with normal phase silica gel 60 Å, 40-63 μm and the product eluted with 30-40% ethyl acetate in hexane to afford 2,1,3-benzothiadiazole-4-carbaldehyde (8.20 g) as a pale yellow solid.

$^1$H NMR (400 MHz, DMSO-d$_6$) δ 10.62 (s, 1H), 8.47 (dd, J=0.80, 8.80 Hz, 1H), 8.30 (dd, J=0.80, 6.80 Hz, 1H), 7.95 (t, J=6.80 Hz, 1H);

MS: m/z 165.0 (M+1).

Example 9, Step 3: Preparation of 4-(1,3-dioxolan-2-yl)-2,1,3-benzothiadiazole

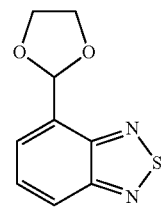 [SMILES: c1cc(C2OCCO2)c2nsnc2c1]

To a stirred solution of 2,1,3-benzothiadiazole-4-carbaldehyde (from Example 9, Step 2) (5.00 g, 30.50 mmol) in dichloromethane (100 mL) was added 1,2-ethanediol (6.80 mL, d=1.11 g/cm$^3$, 122.0 mmol) followed by tetra-butylammonium tribromide (1.47 g, 30.5 mmol) and the reaction mixture was stirred at ambient temperature for 16 h. The reaction mixture was cooled to 0° C., diluted with ethyl acetate (500 mL) and solid sodium bicarbonate (3.00 g) was added and stirred for 30 min. The mixture was filtered and concentrated to afford a yellow gum (6.50 g), which was purified by gravity column chromatography over 60-120 neutral silica gel and the product was eluted with 10-12% ethyl acetate in hexane to afford 4-(1,3-dioxolan-2-yl)-2,1,3-benzothiadiazole (4.80 g) as a colourless gum.

$^1$H NMR (400 MHz, DMSO-$d_6$) δ 8.14 (dd, J=1.20, 8.80 Hz, 1H), 7.81 (d, J=6.00 Hz, 1H), 7.75 (t, J=6.80 Hz, 1H), 6.44 (s, 1H), 4.17 (t, J=2.00 Hz, 2H), 4.07 (t, J=2.00 Hz, 2H);

MS: m/z 209.1 (M+1).

Example 9, Step 4: Preparation of 3-(1,3-dioxolan-2-yl)benzene-1,2-diamine

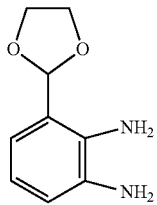 [SMILES: Nc1cccc(C2OCCO2)c1N]

To a de-gassed solution of 4-(1,3-dioxolan-2-yl)-2,1,3-benzothiadiazole (from Example 9, Step 3) (1.50 g, 7.20 mmol) in dry methanol (75 mL) was added Raney nickel (4.50 g, 300% w/w, pre-washed five times with dry methanol) and the resultant reaction mixture was stirred under a hydrogen atmosphere at bladder pressure (Approx. 1.5 kg/cm$^2$) at ambient temperature for 48 h. The reaction mixture was filtered through a celite bed and the bed was washed with methanol (500 mL). The combined filtrates were concentrated to afford 3-(1,3-dioxolan-2-yl)benzene-1,2-diamine (1.10 g) as a brown gum, which was used in the next step without further purification.

$^1$H NMR (400 MHz, CD$_3$OD) δ 6.77 (dd, J=2.80, 8.20 Hz, 2H), 6.61 (t, J=7.60 Hz, 1H), 5.75 (s, 1H), 4.13 (t, J=3.20 Hz, 2H), 4.04 (t, J=1.60 Hz, 2H);

MS: m/z 181.2 (M+1).

Example 9, Step 5: Preparation of 2-({[2-amino-3-(1,3-dioxolan-2-yl)phenyl]carbamothioyl}amino)-2-(3-chloro-4-fluorophenyl)propyl 2,2-dimethylpropanoate and 2-({[2-amino-6-(1,3-dioxolan-2-yl)phenyl]carbamothioyl}amino)-2-(3-chloro-4-fluorophenyl)propyl 2,2-dimethylpropanoate (Mixture of Regioisomers)

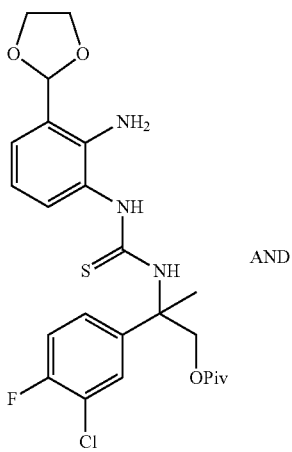

AND

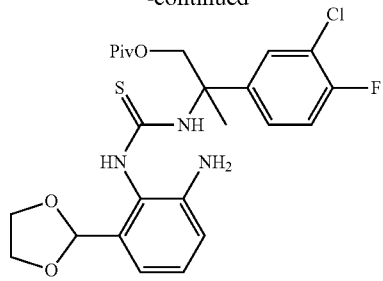

To a solution of [2-(3-chloro-4-fluoro-phenyl)-2-isothiocyanato-propyl] 2,2-dimethylpropanoate (from Example 8, Step 7) (1.50 g, 4.55 mmol) in a mixture of solvents acetonitrile/dichloromethane/methanol (3:1:1; 50 mL) was added 3-(1,3-dioxolan-2-yl)benzene-1,2-diamine (from Example 9, Step 4) (0.820 g, 4.55 mmol) and the mixture was stirred at ambient temperature for 48 h. The reaction mixture was evaporated under vacuum at 20° C. to afford a brown gum (2.40 g). This was purified by chromatography on a Grace instrument using 60.0 g pre-packed flash cartridge filled with normal phase silica gel 60 Å, 40-63 μm and the product eluted with 3% methanol in chloroform to afford 2-({[2-amino-3-(1,3-dioxolan-2-yl)phenyl]carbamothioyl}amino)-2-(3-chloro-4-fluorophenyl)propyl 2,2-dimethylpropanoate and 2-({[2-amino-6-(1,3-dioxolan-2-yl)phenyl]carbamothioyl}amino)-2-(3-chloro-4-fluorophenyl)propyl 2,2-dimethylpropanoate (as a mixture of non-separable regioisomers) (1.80 g) as a brown solid.

MS: m/z 511.2 (M+1).

Example 9, Step 6: Preparation of 2-(3-chloro-4-fluorophenyl)-2-{[4-(1,3-dioxolan-2-yl)-1H-1,3-benzodiazol-2-yl]amino}propyl 2,2-dimethylpropanoate

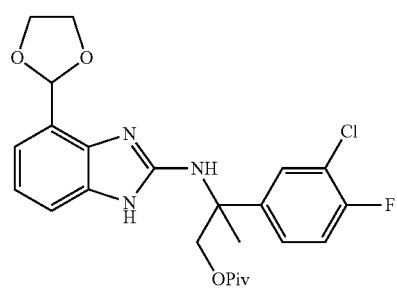

To a solution of 2-({[2-amino-3-(1,3-dioxolan-2-yl)phenyl]carbamothioyl}amino)-2-(3-chloro-4-fluorophenyl)propyl 2,2-dimethylpropanoate and 2-({[2-amino-6-(1,3-dioxolan-2-yl)phenyl]carbamothioyl}amino)-2-(3-chloro-4-fluorophenyl)propyl 2,2-dimethylpropanoate (as a mixture of non-separable regioisomers) (from Example 9, Step 5) (0.620 g, 1.22 mmol) in methanol (20 mL) was added iodoacetic acid (0.294 g, 1.58 mmol) and the mixture was stirred at ambient temperature for 3 h. The reaction mixture was concentrated under vacuum at 25° C. and diluted with 10% aqueous sodium bicarbonate solution (75 mL) and then extracted with ethyl acetate (3×150 mL). The combined obtained organic layers were dried over sodium sulphate, filtered and concentrated to afford 2-(3-chloro-4-fluorophenyl)-2-{[4-(1,3-dioxolan-2-yl)-1H-1,3-benzodiazol-2-yl]

amino}propyl 2,2-dimethylpropanoate (0.550 g) as a brown solid, which was used in the next step without further purification.

MS: m/z 476.1 (M+1).

Example 9, Step 7: Preparation of 2-(3-chloro-4-fluorophenyl)-2-[(4-formyl-1H-1,3-benzodiazol-2-yl)amino]propyl 2,2-dimethylpropanoate

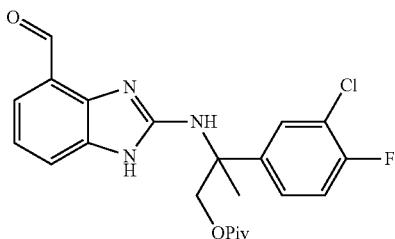

To a solution of 2-(3-chloro-4-fluorophenyl)-2-{[4-(1,3-dioxolan-2-yl)-1H-1,3-benzodiazol-2-yl]amino}propyl 2,2-dimethylpropanoate (from Example 9, Step 5) (0.550 g, 0.573 mmol) in acetone (30 mL) was added p-toluenesulphonic acid monohydrate (0.164 g, 0.860 mmol) and the mixture was stirred at ambient temperature for 16 h. The reaction mixture was concentrated under vacuum at 25° C. and it was diluted with 10% aqueous sodium bicarbonate solution (30 mL). It was extracted with ethyl acetate (3×75 mL), the combined obtained organic layer was dried over sodium sulphate, filtered and concentrated to afford a brown solid (0.500 g). It was purified by chromatography on a Grace instrument using 24.0 g pre-packed flash cartridge filled with normal phase silica gel 60 Å, 40-63 μm and the product eluted with 21% ethyl acetate in hexane to afford 2-(3-chloro-4-fluorophenyl)-2-[(4-formyl-1H-1,3-benzodiazol-2-yl)amino]propyl 2,2-dimethylpropanoate (0.120 g) as a yellow solid.

$^1$H NMR (400 MHz, DMSO-d$_6$) δ 11.34 (s, 1H), 10.04 (s, 1H), 7.65 (dd, J=2.00, 7.00 Hz, 1H), 7.49 (dd, J=3.20, 7.20 Hz, 2H), 7.46 (dd, J=3.60, 7.40 Hz, 1H), 7.38 (t, J=9.20 Hz, 1H), 7.11 (t, J=8.00 Hz, 1H), 6.97 (s, 1H), 4.48 (dd, J=2.40, 8.40 Hz, 2H), 1.86 (s, 3H), 1.06 (s, 9H);

MS: m/z 432.1 (M+1).

Example 9: Preparation of 2-(3-chloro-4-fluorophenyl)-2-[(4-{[(1,2-oxazol-3-yl)amino]methyl}-1H-1,3-benzodiazol-2-yl)amino]propan-1-ol

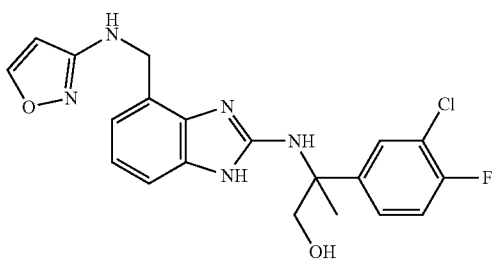 [SMILES: CC(CO)(Nc1nc2c(CNc3ccon3)cccc2[nH]1)c1ccc(F)c(Cl)c1]

To a solution of [2-(3-chloro-4-fluoro-phenyl)-2-[(4-formyl-1H-benzimidazol-2-yl) amino] propyl] 2, 2-dimethylpropanoate (0.18 g, 0.41 mmol) (from Example 9, Step 7) and isoxazol-3-amine (0.042 g, 0.50 mmol) in dry tetrahydrofuran (20 mL) was added titanium(IV) isopropoxide (0.35 g, 1.25 mmol) at 0° C. and the reaction mixture was refluxed for 16 h. The reaction mixture was cooled and sodium cyano borohydride (0.26 g, 4.17 mmol) was added and allowed to stir at ambient temperature for 16 h. It was filtered through a celite bed, washed with tetrahydrofuran (10 mL) and concentrated to afford a yellow gum (0.350 g). This was purified by preparative HPLC to afford 2-(3-chloro-4-fluorophenyl)-2-[(4-{[(1,2-oxazol-3-yl)amino]methyl}-1H-1,3-benzodiazol-2-yl)amino]propan-1-ol, isolated as the trifluoroacetate salt, (0.103 g) as a colourless gum.

$^1$H NMR (400 MHz, AcOH-d$_4$) δ 8.20 (d, J=1.60 Hz, 1H), 7.68 (dd, J=2.40, 6.80 Hz, 1H), 7.55-7.51 (m, 1H), 7.32 (t, J=2.40 Hz, 1H), 7.31-7.24 (m, 3H), 6.03 (d, J=2.00 Hz, 1H), 4.59 (s, 2H), 4.17 (d, J=11.60 Hz, 1H), 4.02 (d, J=12.00 Hz, 1H), 1.87 (s, 3H);

MS: m/z 416.0 [(M+1)-TFA].

Example 10: Preparation of N-[2-(3-chlorophenyl)-1-methoxypropan-2-yl]-4-[(2-imino-4-methyl-2,3-dihydro-1,3-oxazol-3-yl)methyl]-1H-1,3-benzodiazol-2-amine

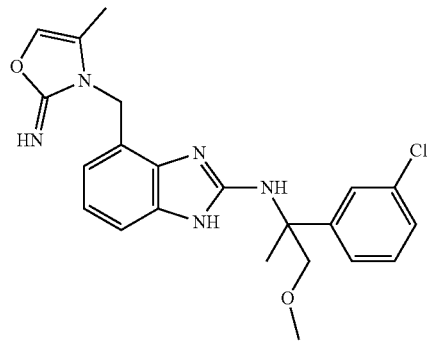 [SMILES: COCC(C)(Nc1nc2c(Cn3c(C)coc3=N)cccc2[nH]1)c1cccc(Cl)c1]

Example 10, Step 1: 3-{2-amino-3-[(2-imino-4-methyl-2,3-dihydro-1,3-oxazol-3-yl)methyl]phenyl}-1-[2-(3-chlorophenyl)-1-methoxypropan-2-yl]thiourea and 3-{2-amino-6-[(2-imino-4-methyl-2,3-dihydro-1,3-oxazol-3-yl)methyl]phenyl}-1-[2-(3-chlorophenyl)-1-methoxypropan-2-yl]thiourea (Mixture of Regioisomers)

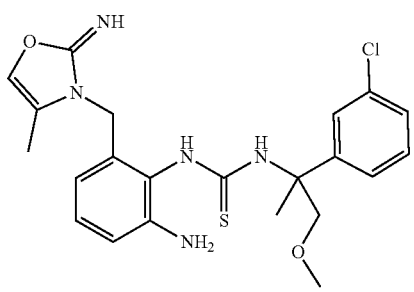

-continued

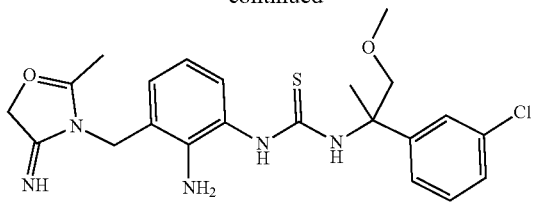

To a solution 3-[(2-imino-4-methyl-2,3-dihydro-1,3-oxazol-3-yl)methyl]benzene-1,2-diamine (from Example 5, Step 2) (0.271 g, 1.24 mmol) in a mixture of solvents dichloromethane:methanol (4:1; 8 mL) was added 1-chloro-3-(2-isothiocyanato-1-methoxypropan-2-yl)benzene (from Example 6, Step 3) (0.300 g, 1.24 mmol) and the mixture was stirred at ambient temperature for 48 h. The reaction mixture was concentrated at 30° C. in a water bath to afford 3-{2-amino-3-[(2-imino-4-methyl-2,3-dihydro-1,3-oxazol-3-yl)methyl]phenyl}-1-[2-(3-chlorophenyl)-1-methoxypropan-2-yl]thiourea and 3-{2-amino-6-[(2-imino-4-methyl-2,3-dihydro-1,3-oxazol-3-yl)methyl]phenyl}-1-[2-(3-chlorophenyl)-1-methoxypropan-2-yl]thiourea (as a mixture of non-separable regioisomers) (0.300 g) as a brown gum, which was used in the next step without further purification.

MS: m/z 461.1 (M+1).

Example 10: N-[2-(3-chlorophenyl)-1-methoxypropan-2-yl]-4-[(2-imino-4-methyl-2,3-dihydro-1,3-oxazol-3-yl)methyl]-1H-1,3-benzodiazol-2-amine

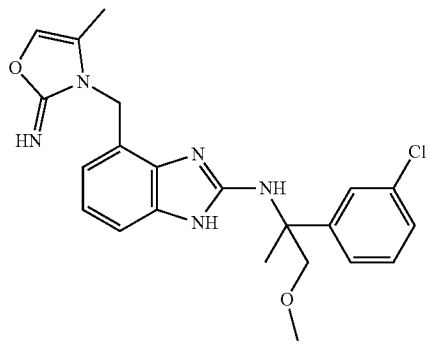 [SMILES: COCC(C)(Nc1nc2c(Cn3c(C)coc3=N)cccc2[nH]1)c1cccc(Cl)c1]

To a solution of 3-{2-amino-3-[(2-imino-4-methyl-2,3-dihydro-1,3-oxazol-3-yl)methyl]phenyl}-1-[2-(3-chlorophenyl)-1-methoxypropan-2-yl]thiourea and 3-{2-amino-6-[(2-imino-4-methyl-2,3-dihydro-1,3-oxazol-3-yl)methyl]phenyl}-1-[2-(3-chlorophenyl)-1-methoxypropan-2-yl]thiourea (as a mixture of non-separable regioisomers) (from Example 10, Step 4) (0.300 g, 0.652 mmol) in methanol (15 mL) was added iodoacetic acid (0.121 g, 0.652 mmol) and the mixture was stirred at 65° C. for 1 h. The reaction mixture was concentrated on high vacuum and the residue was diluted with aqueous 10% sodium bicarbonate solution (20 mL), it was extracted with a mixture of solvents dichloromethane/methanol (9:1) (2×100 mL). The combined organic layer was dried over sodium sulphate, filtered and concentrated to afford crude mass (0.360 g) as a brown gum, which was purified by preparative HPLC in TFA method to afford N-[2-(3-chlorophenyl)-1-methoxypropan-2-yl]-4-[(2-imino-4-methyl-2,3-dihydro-1,3-oxazol-3-yl)methyl]-1H-1,3-benzodiazol-2-amine, isolated as the trifluoroacetate salt, (0.050 g) as a brown solid.

$^1$H NMR (400 MHz, AcOH-d$_4$) δ 7.55 (s, 1H), 7.47 (dd, J=2.00, 6.60 Hz, 2H), 7.38 (t, J=8.80 Hz, 1H), 7.33 (d, J=8.40 Hz, 2H), 7.24 (t, J=8.00 Hz, 1H), 6.86 (d, J=7.60 Hz, 1H), 5.46 (s, 2H), 4.05 (d, J=10.40 Hz, 1H), 3.80 (d, J=10.00 Hz, 1H), 3.49 (s, 3H), 2.11 (s, 3H), 1.82 (s, 3H);

MS: m/z 426.1 [(M+1).

Example 11: Preparation of 2-(3-chloro-4-fluorophenyl)-2-[(4-{[(pyrimidin-4-yl)amino]methyl}-1H-1,3-benzodiazol-2-yl)amino]propan-1-ol

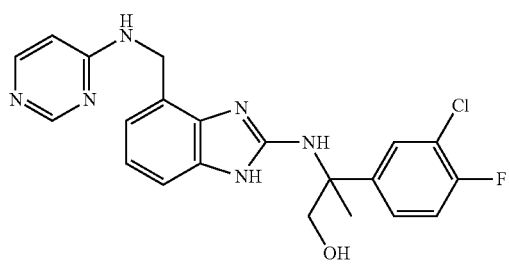 [SMILES: CC(CO)(Nc1nc2c(CNc3ccncn3)cccc2[nH]1)c1ccc(F)c(Cl)c1]

Starting with commercially available pyrimidine-4-amine the titled product was prepared by the method described for Example 16 and was isolated as the trifluoroacetate salt.

$^1$H NMR (400 MHz, AcOH-d$_4$) δ 8.94 (d, J=1.20 Hz, 1H), 8.22-8.19 (m, 1H), 7.68-7.65 (m, 1H), 7.52-7.49 (m, 1H), 7.41-7.36 (m, 2H), 7.32-7.22 (m, 2H), 7.01 (d, J=7.72 Hz, 1H), 5.65 (t, J=5.20 Hz, 2H), 4.31 (d, J=12.0 Hz, 1H), 4.06 (d, J=11.92 Hz, 1H), 1.76 (s, 3H);

MS: m/z 427.1 (M+1).

Example 12: Preparation of 2-(3-chloro-4-fluorophenyl)-2-[(4-{[(5-methyl-1,2-oxazol-3-yl)amino]methyl}-1H-1,3-benzodiazol-2-yl)amino]propan-1-ol

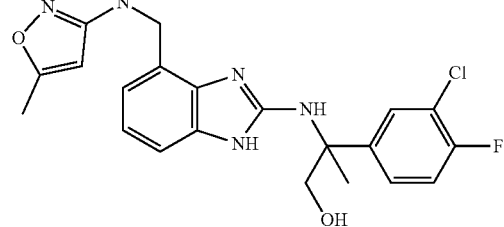

To a solution of 2-(3-chloro-4-fluorophenyl)-2-[(4-formyl-1H-1,3-benzodiazol-2-yl)amino]propyl 2,2-dimethylpropanoate (from Example 9, Step 7) (0.800 g, 1.85 mmol) in dry tetrahydrofuran (30 mL) was added 3-methylisoxazol-5-amine (0.218 g, 2.22 mmol) followed by titanium isopropoxide (10.80 mL, d=0.937 kg/cm$^3$, 37.00 mmol) and the mixture was heated at 72° C. for 48 h. To this reaction mixture dry methanol (20 mL) was added followed by sodium cyanoborohydride (0.582 g, 9.26 mmol) added at 0° C. and it was stirred at ambient temperature for 24 h. The reaction mixture was concentrated and the residue was quenched with ice cold water (50 mL), diluted with a mixture of solvents dichloromethane/methanol (9:1; 200 mL) and filtered through a celite bed. The bi-phasic filtrate was separated and the aqueous layer was further extracted with dichloromethane (2×200 mL). The combined organic layers were dried over sodium sulphate, filtered and concentrated to afford a brown gum (1.10 g). This was purified by preparative HPLC using a TFA method to afford 2-(3-chloro-4-fluorophenyl)-2-[(4-{[(5-methyl-1,2-oxazol-3-yl)amino]methyl}-1H-1,3-benzodiazol-2-yl)amino]propan-1-ol, isolated as the trifluoroacetate salt, (0.360 g) as an off-white solid.

$^1$H NMR (400 MHz, AcOH-d$_4$) δ 7.68 (dd, J=2.40, 7.00 Hz, 1H), 7.53-7.50 (m, 1H), 7.30 (t, J=8.40 Hz, 1H), 7.24 (d, J=8.00 Hz, 2H), 7.21 (t, J=7.60 Hz, 1H), 5.60 (s, 1H), 4.52 (s, 2H), 4.25 (d, J=12.00 Hz, 1H), 4.04 (d, J=12.00 Hz, 1H), 2.29 (s, 3H), 1.78 (s, 3H);

MS: m/z 430.0 (M+1).

The above product was resolved into its two enantiomers by Chiral SFC using the method:

Column: Chiral Pak OX-H; Flow rate: 3.0 mL/min; Co-Solvent: 40%; Co-solvent Name: 0.5% isopropyl amine in isopropyl alcohol; injected Volume: 15.0 μL; outlet pressure: 100 bar; Temperature: 35° C. to obtain the two enantiomers 12a and 12b.

Example 12a: (−)-2-(3-chloro-4-fluorophenyl)-2-((4-(((5-methylisoxazol-3-yl)amino)methyl)-1H-benzo[d]imidazol-2-yl)amino)propan-1-ol The (−) enantiomer was the first compound to elute off the column, isolated as the trifluoroacetate salt.

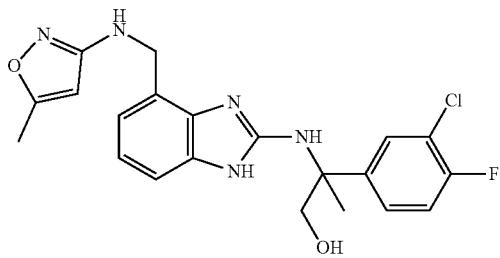 [SMILES: Cc1cc(NCc2cccc3[nH]c(NC(C)(CO)c4ccc(F)c(Cl)c4)nc23)no1]

$^1$H NMR (400 MHz, AcOH-d$_4$) δ 7.67 (dd, J=2.40, 6.80 Hz, 1H), 7.52-7.49 (m, 1H), 7.30 (t, J=7.40 Hz, 1H), 7.23 (t, J=8.80 Hz, 1H), 7.19 (d, J=7.80 Hz, 2H), 5.63 (s, 1H), 4.51 (s, 2H), 4.25 (d, J=12.00 Hz, 1H), 4.04 (d, J=12.00 Hz, 1H), 2.29 (s, 3H), 1.77 (s, 3H);

MS: m/z 430.0 (M+1);

$[α]_D^{22.7}$ (−) 2.64 (MeOH, c=1.0).

Example 12b: (+)-2-(3-chloro-4-fluorophenyl)-2-((4-(((5-methylisoxazol-3-yl)amino)methyl)-1H-benzo[d]imidazol-2-yl)amino)propan-1-ol The (+) enantiomer was the second compound to elute off the trifluoroacetate salt.

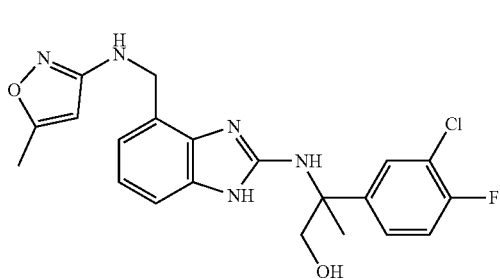

$^1$H NMR (400 MHz, AcOH-d$_4$) δ 7.67 (dd, J=2.00, 7.00 Hz, 1H), 7.52 (dd, J=2.80, 7.40 Hz, 1H), 7.30 (t, J=4.40 Hz, 1H), 7.23 (t, J=9.20 Hz, 1H), 7.20 (d, J=4.80 Hz, 2H), 5.63 (s, 1H), 4.51 (s, 2H), 4.25 (d, J=12.00 Hz, 1H), 4.04 (d, J=12.00 Hz, 1H), 2.29 (s, 3H), 1.77 (s, 3H);

MS: m/z 430.0 (M+1);

$[α]_D^{22.6}$ (+) 2.92 (MeOH, c=1.0).

Example 13: Preparation of 2-(3-chloro-4-fluorophenyl)-2-({4-[(2-imino-4-methyl-2,3-dihydro-1,3-oxazol-3-yl)methyl]-1H-1,3-benzodiazol-2-yl}amino)propan-1-ol

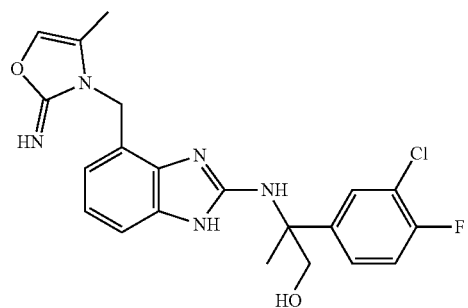 [SMILES: Cc1coc(=N)n1Cc1cccc2[nH]c(NC(C)(CO)c3ccc(F)c(Cl)c3)nc12]

Starting with 3-[(2-imino-4-methyl-2,3-dihydro-1,3-oxazol-3-yl)methyl]benzene-1,2-diamine (from Example 5, Step 2) and [2-(3-chloro-4-fluoro-phenyl)-2-isothiocyanatopropyl] 2,2-dimethylpropanoate (from Example 8, Step 7) the titled compound was prepared using the method described for Steps 8, 9 and 10 in Example 8 and was isolated as the trifluoroacetate salt.

$^1$H NMR (400 MHz, AcOH-d$_4$) δ 7.68 (dd, J=6.80, 2.40 Hz, 1H), 7.52-7.52 (m, 1H), 7.45 (d, J=1.60 Hz, 1H), 7.36 (d, J=8.00 Hz, 1H), 7.28-7.24 (m, 2H), 6.87 (d, J=7.60 Hz, 1H), 5.46 (s, 2H), 4.33 (d, J=12.40 Hz, 1H), 4.08 (d, J=12.00 Hz, 1H), 2.10 (s, 3H), 1.79 (s, 3H);

MS: m/z 430.2/431.2 (M+1).

The above product was resolved into its two enantiomers by Chiral SFC using the method: Column: Lux C4, Mobile Phase: 0.5% isopropyl amine in methanol co-solvent 40% CO$_2$; Flow rate: 3 ml/min, pressure: 100 bar; Temperature: 35° C. to obtain the two enantiomers 13a and 13b.

Example 13a: (−)-2-(3-chloro-4-fluorophenyl)-2-({4-[(2-imino-4-methyl-2,3-dihydro-1,3-oxazol-3-yl)methyl]-1H-1,3-benzodiazol-2-yl}amino)propan-1-ol The (−) enantiomer was the first compound to elute off the column, isolated as the trifluoroacetate salt.

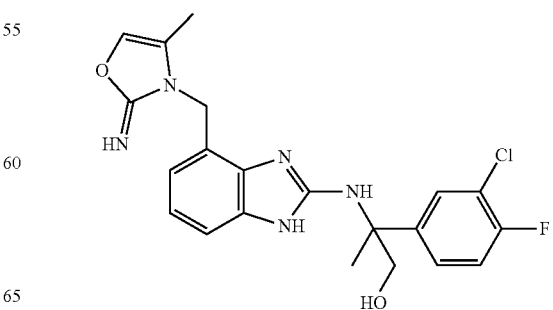

¹H NMR (400 MHz, AcOH-d₄) δ 7.68 (dd, J=6.80, 2.40 Hz, 1H), 7.52-7.52 (m, 1H), 7.45 (d, J=1.60 Hz, 1H), 7.36 (d, J=8.00 Hz, 1H), 7.28-7.24 (m, 2H), 6.87 (d, J=7.60 Hz, 1H), 5.46 (s, 2H), 4.33 (d, J=12.40 Hz, 1H), 4.08 (d, J=12.00 Hz, 1H), 2.10 (s, 3H), 1.79 (s, 3H);

MS: m/z 430.2/431.2 (M+1);

SOR: $[\alpha]_D^{23.0}$ (−) 7.60, (MeOH, c=0.5).

Example 13b: (+)-2-(3-chloro-4-fluorophenyl)-2-({4-[(2-imino-4-methyl-2,3-dihydro-1,3-oxazol-3-yl)methyl]-1H-1,3-benzodiazol-2-yl}amino)propan-1-ol The (+) enantiomer was the second to elute-off the column, isolated as the trifluoroacetate salt.

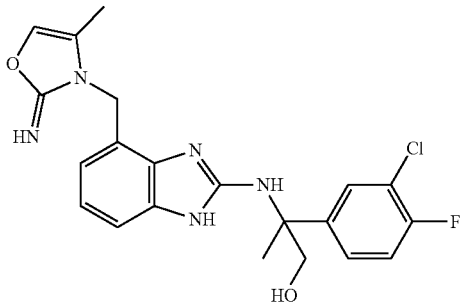 [SMILES: Cc1coc(=N)n1Cc1cccc2[nH]c(NC(C)(CO)c3ccc(F)c(Cl)c3)nc12]

¹H NMR (400 MHz, AcOH-d₄) δ 7.68 (dd, J=6.80, 2.40 Hz, 1H), 7.52-7.52 (m, 1H), 7.45 (d, J=1.60 Hz, 1H), 7.36 (d, J=8.00 Hz, 1H), 7.28-7.24 (m, 2H), 6.87 (d, J=7.60 Hz, 1H), 5.46 (s, 2H), 4.33 (d, J=12.40 Hz, 1H), 4.08 (d, J=12.00 Hz, 1H), 2.10 (s, 3H), 1.79 (s, 3H);

MS: m/z 430.2/431.2 (M+1);

SOR: $[\alpha]_D^{23.5}$ (+) 8.40, (MeOH, c=0.5).

Example 14: Preparation of N-[2-(3-chloro-4-fluorophenyl)-1-methoxypropan-2-yl]-4-[(2-imino-2,3-dihydro-1,3-oxazol-3-yl)methyl]-1H-1,3-benzodiazol-2-amine

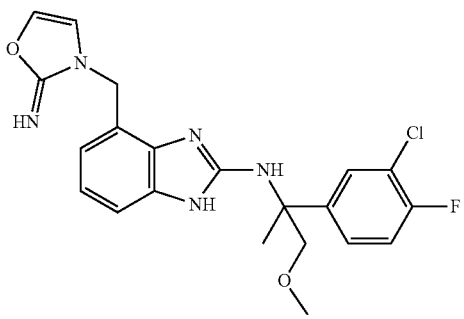 [SMILES: COCC(C)(Nc1nc2c(Cn3ccoc3=N)cccc2[nH]1)c1ccc(F)c(Cl)c1]

Using tert-butyl (2-(3-chloro-4-fluorophenyl)-1-hydroxypropan-2-yl)carbamate (from Example 8, Step 4) and 3-[(2-imino-2,3-dihydro-1,3-oxazol-3-yl)methyl]benzene-1,2-diamine (from Example 1, Step 5) the titled compound was made by the method described for Example 6 and isolated as the trifluoroacetate salt.

¹H NMR (400 MHz, AcOH-d₄) δ 7.64 (dd, J=2.36, 6.84 Hz, 1H), 7.59 (s, 1H), 7.51-7.48 (m, 1H), 7.39 (dd, J=2.48, 6.54 Hz, 1H), 7.31 (t, J=7.64 Hz, 1H), 7.24 (d, J=8.52 Hz, 3H), 5.41 (s, 2H), 3.99 (d, J=10.12 Hz, 1H), 3.78 (d, J=10.12 Hz, 1H), 3.49 (s, 3H), 1.83 (s, 3H);

MS: m/z 430.1 n (M+1).

Example 15: Preparation of 2-(3-chloro-4-fluorophenyl)-2-[(4-{[(5-methyl-1,2,4-oxadiazol-3-yl)amino]methyl}-1H-1,3-benzodiazol-2-yl)amino]propan-1-ol

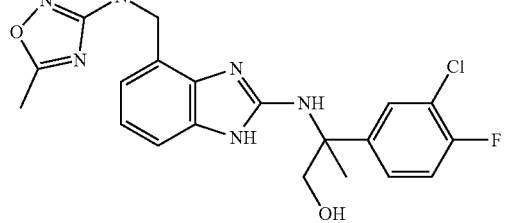

To a solution of 2-(3-chloro-4-fluorophenyl)-2-[(4-formyl-1H-1,3-benzodiazol-2-yl)amino]propyl 2,2-dimethylpropanoate (from Example 9, Step 7) (0.120 g, 0.278 mmol) in dry tetrahydrofuran (5 mL) was added 5-methyl-1,2,4-oxadiazol-3-amine (0.033 g, 0.333 mmol) followed by titanium isopropoxide (1.23 mL, d=0.937 kg/cm³, 4.17 mmol) and the mixture was heated at 72° C. for 48 h. To this reaction mixture dry methanol (5 mL) was added followed by sodium cyanoborohydride (0.087 g, 1.39 mmol), added at 0° C. and it was stirred at ambient temperature for 24 h. The reaction mixture was concentrated and the residue was quenched with ice cold water (25 mL), diluted with a mixture of solvents dichloromethane/methanol (9:1; 50 mL) and it was filtered through a celite bed. The bi-phasic filtrate was separated and the aqueous layer was further extracted with dichloromethane (2×50 mL). The combined organic layers were dried over sodium sulphate, filtered and concentrated to afford a brown gum (0.100 g). This was purified by preparative HPLC using a TFA method to afford 2-(3-chloro-4-fluorophenyl)-2-[(4-{[(5-methyl-1,2,4-oxadiazol-3-yl)amino]methyl}-1H-1,3-benzodiazol-2-yl)amino]propan-1-ol, isolated as the trifluoroacetate salt, (0.070 g) as a pale brown gum.

¹H NMR (400 MHz, AcOH-d₄) δ 7.69 (dd, J=2.00, 7.00 Hz, 1H), 7.53 (d, J=7.60 Hz, 1H), 7.30 (d, J=7.60 Hz, 1H), 7.25 (t, J=6.40 Hz, 1H), 7.22 (s, 1H), 7.20 (d, J=7.60 Hz, 1H), 4.55 (s, 2H), 4.27 (d, J=12.00 Hz, 1H), 4.06 (d, J=12.00 Hz, 1H), 2.49 (s, 3H), 1.79 (s, 3H);

MS: m/z 431.1 (M+1).

Example 16: Preparation of 2-(3-chloro-4-fluorophenyl)-2-((4-(((5-methyl-1, 3, 4-oxadiazol-2-yl)amino) methyl)-1H-benzo[d]imidazol-2-yl) amino)propan-1-ol

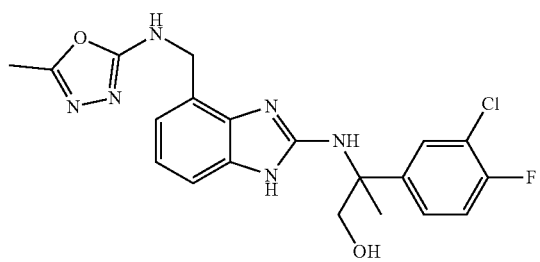 [SMILES: Cc1nnc(NCc2cccc3[nH]c(NC(C)(CO)c4ccc(F)c(Cl)c4)nc23)o1]

Example 16, Step 1: Preparation of N-[(2,1,3-benzothiadiazol-4-yl)methyl]-5-methyl-1,3,4-oxadiazol-2-amine hydrobromide

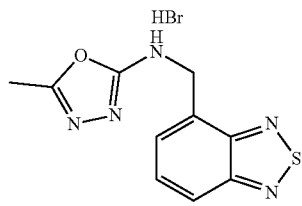 [SMILES: Br ; Cc1nnc(NCc2cccc3nsnc23)o1]

To a stirred solution of 4-(bromomethyl)-2,1,3-benzothiadiazole (from Example 1, Step 3) (4.00 g, 17.4 mmol) under a nitrogen atmosphere in dry acetonitrile (20 mL) was added 5-methyl-1,3,4-oxadiazol-2-amine (1.98 g, 20.00 mmol) and the resultant reaction mixture stirred at 70° C. for 16 h. The solid that formed in the reaction mixture was filtered, washed with hexane (2×100 mL) and dried under high vacuum to afford N-[(2,1,3-benzothiadiazol-4-yl) methyl]-5-methyl-1,3,4-oxadiazol-2-amine hydrobromide (1.80 g) as an off-white solid, which was used in the next step without further purification.

$^1$H NMR (400 MHz, DMSO-$d_6$: $D_2O$) δ 8.14 (t, J=8.40 Hz, 1H), 7.77 (d, J=6.80 Hz, 2H), 5.65 (s, 2H), 2.39 (s, 3H);

MS: m/z 248.2 (M+1).

Example 16, Step 2: Preparation of 3-(((5-methyl-1,3,4-oxadiazol-2-yl)amino) methyl)benzene-1,2-diamine

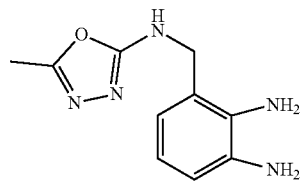 [SMILES: Cc1nnc(NCc2cccc(N)c2N)o1]

To a de-gassed solution of N-[(2,1,3-benzothiadiazol-4-yl)methyl]-5-methyl-1,3,4-oxadiazol-2-amine hydrobromide (from Example 16, Step 1) (1.50 g, 4.60 mmol) in dry methanol (100 mL) was added Raney nickel (3.00 g, 200% w/w, pre-washed five times with dry methanol) and the resultant reaction mixture was stirred under a hydrogen atmosphere at bladder pressure (Approx. 1.5 kg/cm$^2$) at ambient temperature for 16 h. The reaction mixture was filtered through a celite bed and the bed was washed with methanol (1000 mL). The combined filtrates were concentrated to afford 3-(((5-methyl-1, 3, 4-oxadiazol-2-yl) amino) methyl) benzene-1, 2-diamine (1.00 g) as a light brown solid, which was used in the next step without further purification.

$^1$H NMR (400 MHz, DMSO-$d_6$: $D_2O$) δ 6.87 (t, J=7.60 Hz, 1H), 6.70 (d, J=8.00 Hz, 1H), 6.45 (d, J=7.20 Hz, 1H), 4.58 (s, 2H), 1.97 (s, 3H);

MS: m/z 220.2 (M+1).

Example 16, Step 3: Preparation of 2-{[(2-amino-3-{[(5-methyl-1,3,4-oxadiazol-2-yl)amino] methyl}phenyl)carbamothioyl]amino}-2-(3-chloro-4-fluorophenyl)-propyl 2,2-dimethylpropanoate and 2-{[(2-amino-6-{[(5-methyl-1,3,4-oxadiazol-2-yl)amino]methyl}phenyl)carbamothioyl]amino}-2-(3-chloro-4-fluorophenyl)-propyl 2,2-dimethylpropanoate (Mixture of Regioisomers)

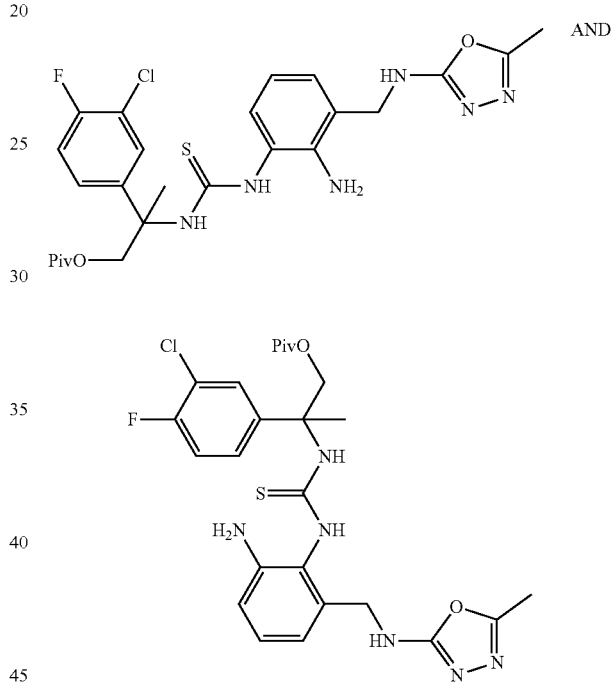

To a solution 3-(((5-methyl-1, 3, 4-oxadiazol-2-yl) amino) methyl) benzene-1, 2-diamine (from Example 16, Step 2) (0.250 g, 11.40 mmol) in a mixture of solvents dichloromethane:methanol (4:1:12 mL) was added [2-(3-chloro-4-fluoro-phenyl)-2-isothiocyanato-propyl] 2,2-dimethyl propanoate (from Example 8, Step 7) (0.376 g, 11.40 mmol) and the mixture was stirred at ambient temperature for 16 h. The reaction mixture was concentrated at 30° C. in a water bath to afford 2-{[(2-amino-3-{[(5-methyl-1,3,4-oxadiazol-2-yl)amino]methyl}phenyl)carbamothioyl] amino}-2-(3-chloro-4-fluorophenyl)propyl 2,2-dimethylpropanoate and 2-{[(2-amino-6-{[(5-methyl-1,3,4-oxadiazol-2-yl)amino]methyl}phenyl)carbamothioyl] amino}-2-(3-chloro-4-fluorophenyl)propyl 2,2-dimethylpropanoate (as a mixture of non-separable regioisomers) (0.650 g) as a yellow gummy material, which was used in the next step without further purification.

MS: m/z 550.1 (M+1).

Example 16, Step 4: Preparation of 2-(3-chloro-4-fluorophenyl)-2-[(4-{[(5-methyl-1,3,4-oxadiazol-2-yl)amino]methyl}-1H-1,3-benzodiazol-2-yl)amino]propyl 2,2-dimethylpropanoate

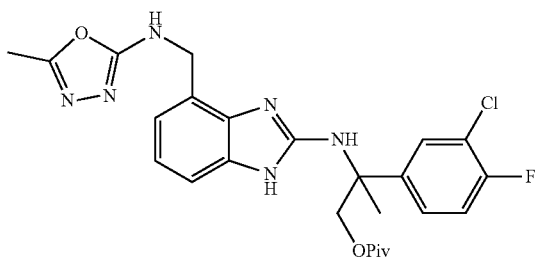

To a solution of 2-{[(2-amino-3-{[(5-methyl-1,3,4-oxadiazol-2-yl)amino]methyl}phenyl)carbamothioyl]amino}-2-(3-chloro-4-fluorophenyl)propyl 2,2-dimethylpropanoate and 2-{[(2-amino-6-{[(5-methyl-1,3,4-oxadiazol-2-yl)amino]methyl}phenyl)carbamothioyl]amino}-2-(3-chloro-4-fluorophenyl)propyl 2,2-dimethylpropanoate (as a mixture of non-separable regioisomers) (from Example 16, Step 3) (0.650 g, 1.18 mmol) in methanol (40 mL) was added iodoacetic acid (0.447 g, 2.36 mmol) and the mixture was stirred at 65° C. for 1 h. The reaction mixture was concentrated to remove the solvent methanol, and the residue was purified by chromatography on a Grace instrument using 24.00 g pre-packed flash cartridge filled with normal phase silica gel 60 Å, 40-63 μm and the product eluted at 40-45% ethyl acetate in hexane to afford 2-(3-chloro-4-fluorophenyl)-2-[(4-{[(5-methyl-1,3,4-oxadiazol-2-yl)amino]methyl}-1H-1,3-benzodiazol-2-yl)amino]propyl 2,2-dimethylpropanoate (0.120 g) as a white gum.

$^1$H NMR (400 MHz, DMSO-d$_6$) δ 10.24 (s, 1H), 9.38 (s, 1H), 7.64 (d, J=5.20 Hz, 1H), 7.46 (d, J=4.80 Hz, 1H), 7.39 (t, J=8.80 Hz, 1H), 7.19 (s, 1H), 7.03 (d, J=8.00 Hz, 2H), 6.81 (d, J=6.00 Hz, 1H), 4.80 (s, 2H), 4.40 (d, J=10.80 Hz, 1H), 4.50 (d, J=11.20 Hz, 1H), 2.00 (s, 3H), 1.92 (s, 3H), 1.06 (s, 9H);

MS: m/z 515.1 (M+1).

Example 16: Preparation of 2-(3-chloro-4-fluorophenyl)-2-((4-(((5-methyl-1, 3, 4-oxadiazol-2-yl)amino) methyl)-1H-benzo[d]imidazol-2-yl) amino) propan-1-ol

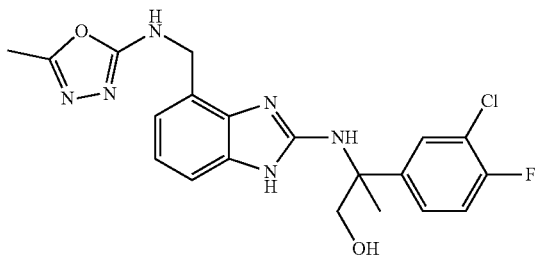 [SMILES: Cc1nnc(NCc2cccc3[nH]c(NC(C)(CO)c4ccc(F)c(Cl)c4)nc23)o1]

To a solution of 2-(3-chloro-4-fluorophenyl)-2-[(4-{[(5-methyl-1,3,4-oxadiazol-2-yl)amino]methyl}-1H-1,3-benzodiazol-2-yl)amino]propyl 2,2-dimethylpropanoate (from Example 16, Step 4) (0.120 g, 0.228 mmol) in methanol (10 mL) was added sodium hydroxide pellets (0.038 g, 0.912 mmol) and the mixture was stirred at ambient temperature for 1 h. The reaction mixture was quenched with 1.5N hydrochloric acid (2 mL) and the resultant reaction mixture was concentrated under high vacuum to afford a brown gum (0.100 g). This was purified by preparative HPLC to afford 2-(3-chloro-4-fluorophenyl)-2-((4-(((5-methyl-1, 3, 4-oxadiazol-2-yl) amino) methyl)-1H-benzo[d]imidazol-2-yl) amino) propan-1-ol (0.060 g) as an off-white solid.

$^1$H NMR (400 MHz, AcOH-d$_4$) δ 7.61 (s, 1H), 7.41 (d, J=10.40 Hz, 2H), 7.41 (d, J=10.40 Hz, 2H), 7.25 (t, J=8.80 Hz, 1H), 5.00 (d, J=8.80 Hz, 2H), 4.94 (d, J=9.20 Hz, 2H), 2.21 (s, 3H), 1.89 (s, 3H);

MS: m/z 431.2 (M+1).

Example 17: Preparation of 2-(3-chloro-4-fluorophenyl)-2-[(4-{[(3-methyl-1,2,4-oxadiazol-5-yl)amino]methyl}-1H-1,3-benzodiazol-2-yl)amino]propan-1-ol

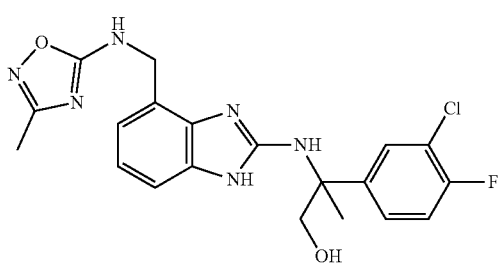 [SMILES: Cc1noc(NCc2cccc3[nH]c(NC(C)(CO)c4ccc(F)c(Cl)c4)nc23)n1]

Using the commercially available 3-methyl-1,2,4-oxadiazol-5-amine the titled compound was made by the method described for Example 8 and was isolated as the trifluoroacetate salt, as a white solid.

$^1$H NMR (400 MHz, AcOH-d$_4$) δ 7.75 (dd, J=2.40, 6.80 Hz, 1H), 7.59-7.56 (m, 1H), 7.39 (d, J=8.00 Hz, 1H), 7.28 (t, J=7.60 Hz, 1H), 7.26 (d, J=10.40 Hz, 1H), 7.22 (t, J=7.60 Hz, 1H), 4.69 (q, J=15.32 Hz, 2H), 4.25 (d, J=11.60 Hz, 1H), 4.06 (d, J=12.00 Hz, 1H), 2.74 (s, 3H), 1.85 (s, 3H);

MS: m/z 431.1 (M+1).

Example 18: Preparation of 2-({4-[(2-imino-2,3-dihydro-1,3-oxazol-3-yl)methyl]-1H-1,3-benzodiazol-2-yl}amino)-2-[3-(trifluoromethyl)phenyl]propan-1-ol

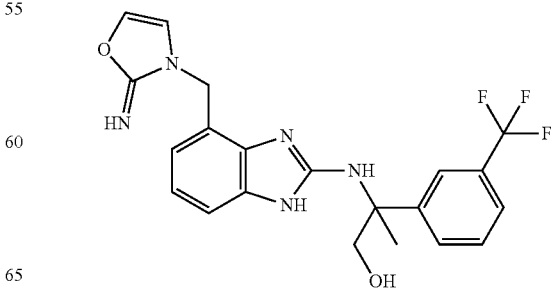

Example 18, Step 1: Preparation of 5-methyl-5-(3-(trifluoromethyl) phenyl) imidazolidine-2, 4-dione

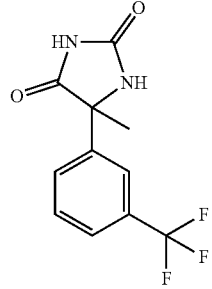 [SMILES: CC1(c2cccc(C(F)(F)F)c2)NC(=O)NC1=O]

To a stirred solution of 3-trifluoromethyl acetophenone (commercially available) (45.00 g, 239.00 mmol) in a mixture of solvents ethanol/water (1:1; 1000 mL) was added ammonium carbonate (115.00 g, 1200.00 mmol) followed by potassium cyanide (18.70 g, 287.00 mmol) and the mixture was stirred at 60° C. for 16 h. The reaction mixture was poured into ice-cold water (1500 mL) and stirred for 30 min. The solid that formed was filtered off and dried to afford 5-methyl-5-(3-(trifluoromethyl) phenyl) imidazolidine-2, 4-dione (61.00 g) as an off-white solid, which was used in the next step without further purification.

(400 MHz, DMSO-$d_6$: $D_2O$) δ 7.78 (d, J=7.70 Hz, 1H), 7.72 (d, J=8.90 Hz, 2H), 7.65 (t, J=7.70 Hz, 1H), 1.69 (s, 3H);

MS: m/z 259.0 (M+1).

Example 18, Step 2: Preparation of 2-amino-2-(3-(trifluoromethyl) phenyl) propanoic acid

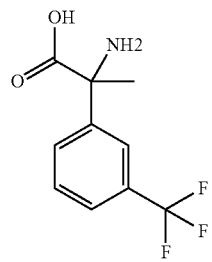 [SMILES: CC(N)(C(=O)O)c1cccc(C(F)(F)F)c1]

5-methyl-5-(3-(trifluoromethyl) phenyl) imidazolidine-2, 4-dione (from Example 18, Step 1) (110.0 g, 426.0 mmol) was taken up into 10% aqueous sodium hydroxide solution (600 mL) and the mixture was refluxed for 48 h. The reaction mixture was neutralized (adjusted pH=7) with 6.0 N HCl (250 mL) and the solid formed was filtered and dried to afford 2-amino-2-(3-(trifluoromethyl) phenyl) propanoic acid (100.0 g) as a white solid, which was used in the next step without further purification.

$^1$H NMR (400 MHz, DMSO-$d_6$: $D_2O$) δ 7.85 (s, 1H), 7.79 (d, J=8.00 Hz, 1H), 7.65 (d, J=7.60 Hz, 1H), 7.60 (t, J=7.60 Hz, 1H), 1.68 (s, 3H);

MS: m/z 234.1 (M+1).

Example 18, Step 3: Preparation of 2-((tert-butoxycarbonyl) amino)-2-(3-(trifluoromethyl) phenyl) propanoic acid

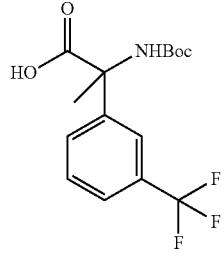 [SMILES: CC(C)(C)OC(=O)NC(C)(C(=O)O)c1cccc(C(F)(F)F)c1]

To a suspension of 2-amino-2-(3, 4-dichlorophenyl) propanoic acid (from Example 18, Step 2) (100.00 g, 429.00 mmol) in a mixture of solvents tetrahydrofuran:water (1:1; 1400 mL) was added sodium bicarbonate (216.00 g, 2570.00 mmol) followed by di-tert-butyl dicarbonate (148.00 mL, d=0.95 g/cm$^3$, 643.00 mmol) and the mixture was stirred at ambient temperature for 72 h. The reaction mixture was diluted with water (1000 mL) and extracted with ethyl acetate (4×2000 mL). The combined organic layer was dried over sodium sulphate, filtered and concentrated to afford 2-((tert-butoxycarbonyl) amino)-2-(3-(trifluoromethyl) phenyl) propanoic acid (140.00 g) as a yellowish gum, which was used in the next step without further purification.

$^1$H NMR (400 MHz, DMSO-$d_6$: $D_2O$) δ 7.64 (s, 1H), 7.57 (s, 1H), 7.47 (d, J=4.40 Hz, 2H), 1.47 (s, 3H), 1.35 (s, 9H);

MS: m/z 234.1 [(M+1)-Boc].

Example 18, Step 4: Preparation of tert-butyl N-{1-hydroxy-2-[3-(trifluoromethyl)phenyl]propan-2-yl}carbamate

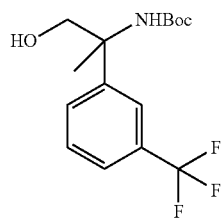 [SMILES: CC(C)(C)OC(=O)NC(C)(CO)c1cccc(C(F)(F)F)c1]

To a solution of 2-((tert-butoxycarbonyl) amino)-2-(3-(trifluoromethyl) phenyl) propanoic acid (from Example 18, Step 3) (140.0 g, 378.0 mmol) in dry tetrahydrofuran (1000 mL) was added triethylamine (158.00 mL, d=0.726 g/cm$^3$, 1130.00 mmol) followed by isobutyl chloroformate (68.8 mL, d=1.053 g/cm$^3$, 529.00 mmol) at 0° C. and stirred at same temperature for 4 h. The solid that formed was filtered off at 0° C. and the residue was washed with dry tetrahydrofuran (400 mL). The combined filtrate was added to a cooled mixture of sodium borohydride (85.8 g, 2270.00 mmol) in water (200 mL). The reaction mixture was slowly warmed to ambient temperature and stirred for 30 h. The reaction mixture was quenched with ice cold water (1000 mL) and extracted with ethyl acetate (4×2000 mL). The combined organic layer was washed with brine (250 mL), dried over sodium sulphate, filtered and concentrated to afford a yellowish liquid (200 g). This was purified by chromatography on a Grace instrument using 330 g pre-packed flash column with 60-120 silica gel and the product was eluted at 30-35% ethyl acetate in petroleum ether to afford tert-butyl N-{1-hydroxy-2-[3-(trifluoromethyl)phenyl]propan-2-yl}carbamate (63.0 g) as a colorless liquid.

$^1$H NMR (400 MHz, DMSO-d$_6$) δ 7.61 (t, J=6.80 Hz, 2H), 7.57 (s, 1H), 7.53 (t, J=7.20 Hz, 1H), 6.92 (bs, 1H), 4.98 (t, J=5.20 Hz, 1H), 3.50 (d, J=6.00 Hz, 2H), 1.59 (s, 3H), 1.35 (s, 9H);

MS: m/z 221.2 [(M+1)-Boc].

Example 18, Step 5: Preparation of 2-{[(tert-butoxy)carbonyl]amino}-2-[3-(trifluoromethyl)phenyl]propyl 2,2-dimethylpropanoate

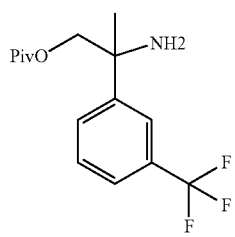

To a solution of tert-butyl N-{1-hydroxy-2-[3-(trifluoromethyl)phenyl]propan-2-yl}carbamate (from Example 18, Step 4) (63.0 g, 197.0 mmol) in dry dichloromethane (800 mL) under a nitrogen atmosphere was added triethyl amine (96.2 mL, d=0.726 g/cm$^3$, 691.0 mmol) followed by pivaloyl chloride (36.4 mL, d=0.985 g/cm$^3$, 296.0 mmol) at 0° C. dropwise and the reaction mixture was stirred at ambient temperature for 36 h. The reaction mixture was quenched with ice cold water (500 mL) and extracted with dichloromethane (4×1000 mL). The combined organic layer was dried over sodium sulphate, filtered and concentrated to afford crude as a brown liquid (110.0 g). This was purified by chromatography on a Grace instrument using 330 g pre-packed 60-120 silica gel and the product eluted at 20% ethyl acetate in hexane to afford 2-{[(tert-butoxy)carbonyl]amino}-2-[3-(trifluoromethyl)phenyl]propyl 2,2-dimethylpropanoate (70.00 g) as a yellowish liquid.

$^1$H NMR (400 MHz, DMSO-d$_6$: D$_2$O) δ 7.61 (d, J=6.80 Hz, 2H), 7.55 (t, J=7.60 Hz, 1H), 7.51 (s, 1H), 4.26 (q, J=10.40 Hz, 2H), 1.52 (s, 3H), 1.35 (s, 9H), 1.05 (s, 9H);

MS: m/z 304.1 [(M+1)-Boc].

Example 18, Step 6: Preparation of 2-amino-2-[3-(trifluoromethyl)phenyl]propyl 2,2-dimethylpropanoate hydrochloride

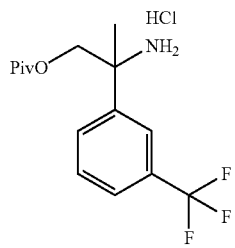

To a solution of 2-{[(tert-butoxy)carbonyl]amino}-2-[3-(trifluoromethyl)-phenyl]propyl 2,2-dimethylpropanoate (from Example 18, Step 5) (70.0 g, 174.0 mmol) in dry dichloromethane (700 mL) under a nitrogen atmosphere was added 4M HCl in dioxane solution (127.0 mL, 521.0 mmol) dropwise at 0° C. The reaction mixture was stirred at ambient temperature for 16 h. The reaction mixture was concentrated on high vacuum to afford 2-amino-2-[3-(trifluoromethyl)phenyl]propyl 2,2-dimethylpropanoate hydrochloride (60.0 g) as a yellowish gum, which was used in the next step without further purification.

$^1$H NMR (400 MHz, DMSO-d$_6$: D$_2$O) δ 7.88 (s, 1H), 7.84 (d, J=8.00 Hz, 1H), 7.79 (d, J=7.60 Hz, 1H), 7.71 (t, J=7.60 Hz, 1H), 4.49 (d, J=12.00 Hz, 1H), 4.27 (d, J=12.00 Hz, 1H), 1.72 (s, 3H), 1.01 (s, 9H);

MS: m/z 304.1 [(M+1)-HCl].

Example 18, Step 7: Preparation of 2-isothiocyanato-2-[3-(trifluoromethyl)-phenyl]propyl 2,2-dimethylpropanoate

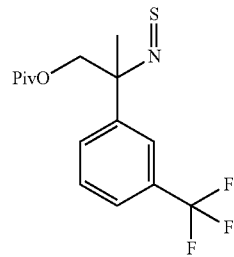

To a solution of 2-amino-2-[3-(trifluoromethyl)phenyl]propyl 2,2-dimethylpropanoate hydrochloride (from Example 18, Step 6) (40.0 g, 118.0 mmol) in dry dichloromethane (500 mL) was added 10% aq. sodium bicarbonate solution (500 mL) at 0° C. After 15 min, thiophosgene (14.40 mL, d=1.5 g/cm$^3$, 188.0 mmol) was added and allowed to stir at same temperature for 1 h. The reaction mixture was extracted with dichloromethane (3×1000 mL) and the combined organic layer was dried over anhydrous sodium sulphate, filtered and concentrated to a yellow liquid (75.0 g). This was purified by gravity column chromatography over 60-120 mesh silica gel using 5% ethyl acetate in hexane as eluent to afford 2-isothiocyanato-2-[3-(trifluoromethyl)phenyl]propyl 2,2-dimethylpropanoate (44.0 g) as a yellow liquid.

$^1$H NMR (400 MHz, DMSO-d$_6$) δ 7.85 (s, 1H), 7.81 (d, J=7.20 Hz, 1H), 7.76 (d, J=7.60 Hz, 1H), 7.69 (t, J=8.40 Hz, 1H), 4.51 (q, J=15.20 Hz, 2H), 1.83 (s, 3H), 1.35 (s, 9H);

MS: m/z 344.0 (M−1).

Example 18, Step 8: Preparation of 2-[({2-amino-3-[(2-imino-2,3-dihydro-1,3-oxazol-3-yl)methyl]phenyl}carbamothioyl)amino]-2-[3-(trifluoromethyl)phenyl]propyl 2,2-dimethylpropanoate and 2-[({2-amino-6-[(2-imino-2,3-dihydro-1,3-oxazol-3-yl)methyl]phenyl}carbamothioyl)amino]-2-[3(trifluoromethyl)phenyl]propyl 2,2-dimethylpropanoate (Mixture of Regioisomers)

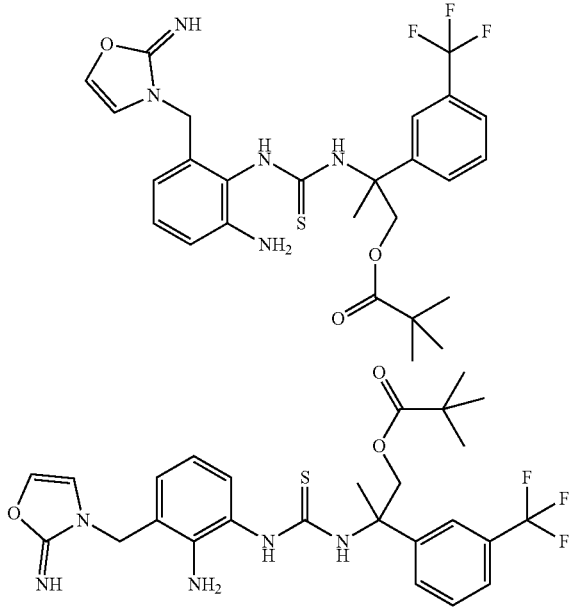

To a solution of 3-[(2-imino-2,3-dihydro-1,3-oxazol-3-yl)methyl]benzene-1,2-diamine (Example 1, step 5) (1.80 g, 5.29 mmol) in a mixture of solvents dichloromethane:methanol (1:1; 50 mL) was added [2-isothiocyanato-2-[3-(trifluoromethyl) phenyl]propyl]2,2-dimethylpropanoate (from Example 18, Step 7) (1.50 g, 4.34 mmol) and it was stirred at ambient temperature for 20 h. The reaction mixture was concentrated at 30° C. to afford 2-[({2-amino-3-[(2-imino-2,3-dihydro-1,3-oxazol-3-yl)methyl]phenyl}carbamothioyl)amino]-2-[3-(trifluoromethyl)-phenyl]propyl 2,2-dimethylpropanoate and 2-[({2-amino-6-[(2-imino-2,3-dihydro-1,3-oxazol-3-yl)methyl]phenyl}carbamothioyl)amino]-2-[3(trifluoromethyl)-phenyl]propyl 2,2-dimethylpropanoate (as a mixture of non-separable regioisomers) (2.90 g) as a brown gum, which was used in the next step without purification.

MS: m/z 550.2 (M+1).

Example 18, Step 9: Preparation of 2-({4-[(2-imino-2,3-dihydro-1,3-oxazol-3-yl)methyl]-1H-1,3-benzodiazol-2-yl}amino)-2-[3-(trifluoromethyl)phenyl]propyl 2,2-dimethylpropanoate

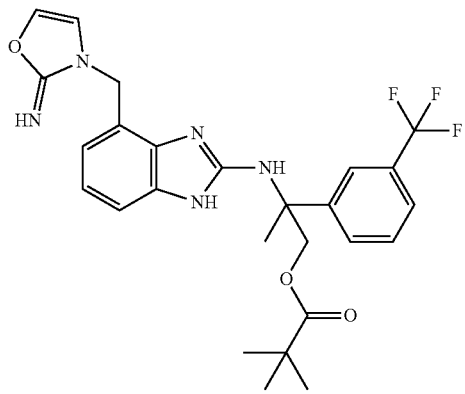 [SMILES: CC(C)(C)C(=O)OCC(C)(Nc1nc2c(Cn3ccoc3=N)cccc2[nH]1)c1cccc(C(F)(F)F)c1]

To a solution of 2-[({2-amino-3-[(2-imino-2,3-dihydro-1,3-oxazol-3-yl)methyl]phenyl}carbamothioyl)amino]-2-[3-(trifluoromethyl)phenyl]propyl 2,2-dimethylpropanoate and 2-[({2-amino-6-[(2-imino-2,3-dihydro-1,3-oxazol-3-yl)methyl]phenyl}carbamothioyl)amino]-2-[3(trifluoromethyl)phenyl]propyl 2,2-dimethylpropanoate (as a mixture of non-separable regioisomers) (Example 18, Step 8) (2.90 g, 5.28 mmol) in methanol (20 mL) was added iodoacetic acid (1.47 g, 7.91 mmol) and the mixture was refluxed for 1.5 h. The reaction mixture was concentrated at 30° C. to afford a brown gum (3.3 g), which was purified by preparative HPLC (TFA:acetonitrile) to afford 2-({4-[(2-imino-2,3-dihydro-1,3-oxazol-3-yl)methyl]-1H-1,3-benzodiazol-2-yl}amino)-2-[3-(trifluoromethyl)phenyl]propyl 2,2-dimethylpropanoate, isolated as the trifluoroacetate salt, (0.390 g) as a brown gum.

$^1$H NMR (400 MHz, AcOH-$d_4$) δ 7.87 (s, 1H), 7.86 (s, 1H), 7.72 (d, J=7.76 Hz, 1H), 7.64 (t, J=7.92 Hz, 1H), 7.60 (d, J=1.48 Hz, 1H), 7.33-7.16 (m, 4H), 5.41 (s, 2H), 4.55 (q, J=11.64 Hz, 2H), 2.03 (s, 3H), 1.17 (s, 9H);

MS: m/z 516.2 (M+1).

The above product was resolved into its two enantiomers by Chiral SFC using the method: Chiralcel OX-H, Mobile Phase: 0.5% isopropyl amine in isopropyl alcohol; co-solvent 40% CO$_2$; Flow rate: 3 mL/min, pressure: 100 bar; Temperature: 35° C. to obtain the two enantiomers 18-9a and 18-9b.

Example 18-9a: 2-({4-[(2-imino-2,3-dihydro-1,3-oxazol-3-yl)methyl]-1H-1,3-benzodiazol-2-yl}amino)-2-[3-(trifluoromethyl)phenyl]propyl 2,2-dimethylpropanoate (Enantiomer A)

The first compound to elute off the column was Enantiomer A, isolated as the trifluoroacetate salt.

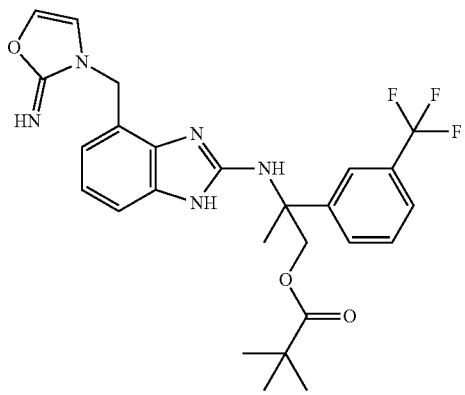 [SMILES: CC(C)(C)C(=O)OCC(C)(Nc1nc2c(Cn3ccoc3=N)cccc2[nH]1)c1cccc(C(F)(F)F)c1]

$^1$H NMR (400 MHz, AcOH-$d_4$) δ 7.87 (s, 1H), 7.86 (s, 1H), 7.72 (d, J=7.76 Hz, 1H), 7.64 (t, J=7.92 Hz, 1H), 7.60 (d, J=1.48 Hz, 1H), 7.33-7.16 (m, 414), 5.41 (s, 2H), 4.55 (q, J=11.64 Hz, 2H), 2.03 (s, 3H), 1.17 (s, 9H);

MS: m/z 516.2 (M+1).

Example 18-9b: 2-({4-[(2-imino-2,3-dihydro-1,3-oxazol-3-yl)methyl]-1H-1,3-benzodiazol-2-yl}amino)-2-[3-(trifluoromethyl)phenyl]propyl 2,2-dimethylpropanoate (Enantiomer B)

The second compound to elute off the column was Enantiomer B, isolated as the trifluoroacetate salt,

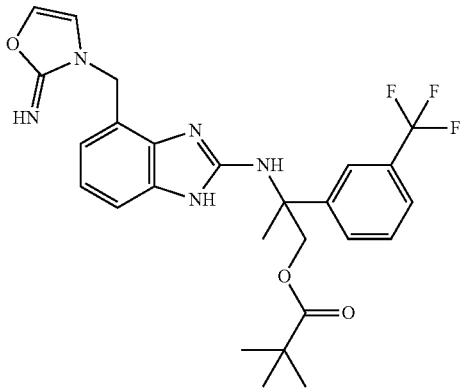 [SMILES: CC(C)(C)C(=O)OCC(C)(Nc1nc2c(Cn3ccoc3=N)cccc2[nH]1)c1cccc(C(F)(F)F)c1]

$^1$HNMR (400 MHz, AcOH-d$_4$) δ 7.87 (s, 1H), 7.86 (s, 1H), 7.72 (d, J=7.76 Hz, 1H), 7.64 (t, J=7.92 Hz, 1H), 7.60 (d, J=1.48 Hz, 1H), 7.33-7.16 (m, 4H), 5.41 (s, 2H), 4.55 (q, J=11.64 Hz, 2H), 2.03 (s, 3H), 1.17 (s, 9H);
MS: m/z 516.2 (M+1).

Example 18: Preparation of 2-({4-[(2-imino-2,3-dihydro-1,3-oxazol-3-yl)methyl]-1H-1,3-benzodiazol-2-yl}amino)-2-[3-(trifluoromethyl)phenyl]propan-1-ol

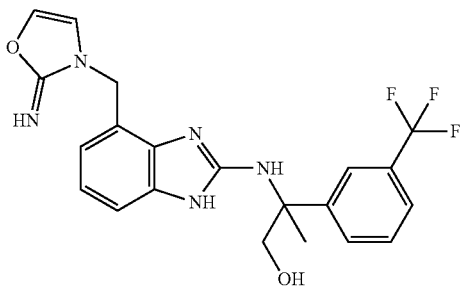 [SMILES: CC(CO)(Nc1nc2c(Cn3ccoc3=N)cccc2[nH]1)c1cccc(C(F)(F)F)c1]

To a solution of 2-({4-[(2-imino-2,3-dihydro-1,3-oxazol-3-yl)methyl]-1H-1,3-benzodiazol-2-yl}amino)-2-[3-(trifluoromethyl)phenyl]propyl 2,2-dimethylpropanoate; trifluoroacetic acid (Example 18, Step 9) (0.100 g, 0.159 mmol) in methanol (20 mL) was added 0.5 N sodium hydroxide in methanol (1.00 mL, 0.500 mmol) dropwise and stirred at ambient temperature for 2 h. The reaction mixture was quenched with 1.5 N hydrochloride solution (1 mL) and concentrated under reduced pressure at 30° C. to afford a brown gum (0.080 g). This was purified by preparative HPLC using 0.1% TFA in acetonitrile:water to afford 2-({4-[(2-imino-2,3-dihydro-1,3-oxazol-3-yl)methyl]-1H-1,3-benzodiazol-2-yl}amino)-2-[3-(trifluoromethyl)-phenyl]propan-1-ol, isolated as the trifluoroacetate salt, (0.030 g) as a brown gum.
$^1$H NMR (400 MHz, AcOH-d$_4$) δ 7.84 (t, J=7.84 Hz, 2H), 7.69 (d, J=7.80 Hz, 1H), 7.62-7.56 (m, 2H), 7.39 (d, J=7.24 Hz, 1H), 7.31-7.26 (m, 2H), 7.21 (s, 1H), 5.40 (d, J=4.20 Hz, 2H), 4.42 (d, J=12.00 Hz, 1H), 4.13 (d, J=12.16 Hz, 1H), 1.81 (s, 3H);
MS: m/z 432.1 (M+1).

Example 18a: Preparation of (−)-2-({4-[(2-imino-2,3-dihydro-1,3-oxazol-3-yl)methyl]-1H-1,3-benzodiazol-2-yl}amino)-2-[3-(trifluoromethyl)-phenyl]propan-1-ol

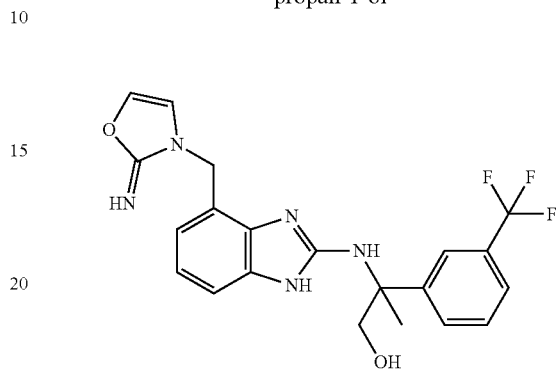

To a solution of 2-({4-[(2-imino-2,3-dihydro-1,3-oxazol-3-yl)methyl]-1H-1,3-benzodiazol-2-yl}amino)-2-[3-(trifluoromethyl)phenyl]propyl 2,2-dimethylpropanoate; trifluoroacetic acid (Example 18, Enantiomer A) (0.13 g, 0.0206 mmol) in methanol (20 mL) was added 0.5 N sodium hydroxide in methanol (1.65 mL, 0.826 mmol) dropwise and stirred at ambient temperature for 2 h. The reaction mixture was quenched with 1.5 N hydrochloride solution (2 mL) and concentrated under reduced pressure at 30° C. to afford a brown gum (0.11 g). This was purified by preparative HPLC using 0.1% TFA in acetonitrile:water to afford (−)-2-({4-[(2-imino-2,3-dihydro-1,3-oxazol-3-yl)methyl]-1H-1,3-benzodiazol-2-yl}amino)-2-[3-(trifluoromethyl)phenyl]propan-1-ol, isolated as the trifluoroacetate salt, (0.080 g) as a colorless gum.
$^1$H NMR (400 MHz, AcOH-d$_4$) δ 7.84 (t, J=8.00 Hz, 2H), 7.68 (d, J=7.68 Hz, 1H), 7.62-7.56 (m, 2H), 7.39 (dd, J=7.36, 1.60 Hz, 1H), 7.31-7.26 (m, 2H), 7.20 (d, J=1.64 Hz, 1H), 5.40 (q, J=15.80 Hz, 2H), 4.42 (d, J=12.04 Hz, 1H), 4.13 (d, J=12.12 Hz, 1H), 1.81 (s, 3H);
MS: m/z 432.1 (M+1);
SOR: [α]$_D^{24.8}$ (−) 8.00, (MeOH, c=0.5)).

Example 18b: Preparation of (+)-2-({4-[(2-imino-2,3-dihydro-1,3-oxazol-3-yl)methyl]-1H-1,3-benzodiazol-2-yl}amino)-2-[3-(trifluoromethyl)-phenyl]propan-1-ol

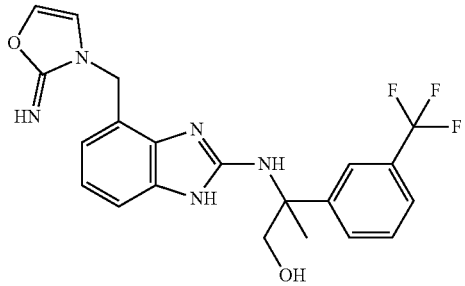 [SMILES: CC(CO)(Nc1nc2c(Cn3ccoc3=N)cccc2[nH]1)c1cccc(C(F)(F)F)c1]

To a solution of 2-({4-[(2-imino-2,3-dihydro-1,3-oxazol-3-yl)methyl]-1H-1,3-benzodiazol-2-yl}amino)-2-[3-(trifluoromethyl)phenyl]propyl 2,2-dimethylpropanoate; trifluoroacetic acid (Example 18, Enantiomer B) (0.130 g, 0.0206 mmol) in methanol (20 mL) was added 0.5 N sodium hydroxide in methanol (1.65 mL, 0.826 mmol) dropwise and stirred at ambient temperature for 2 h. The reaction mixture was quenched with 1.5 N hydrochloride solution (2 mL) and concentrated under reduced pressure at 30° C. to afford a brown gum (0.11 g), which was purified by preparative HPLC using 0.1% TFA in acetonitrile:water to afford (+)-2-({4-[(2-imino-2,3-dihydro-1,3-oxazol-3-yl)methyl]-1H-1,3-benzodiazol-2-yl}amino)-2-[3-(trifluoromethyl)phenyl]propan-1-ol, isolated as the trifluoroacetate salt, (0.075 g) as a colorless gum.

$^1$H NMR (400 MHz, AcOH-d$_4$) δ 7.84 (t, J=8.00 Hz, 2H), 7.68 (d, J=7.68 Hz, 1H), 7.62-7.56 (m, 2H), 7.39 (dd, J=7.36, 1.60 Hz, 1H), 7.31-7.26 (m, 2H), 7.20 (d, J=1.64 Hz, 1H), 5.40 (q, J=15.80 Hz, 2H), 4.42 (d, J=12.04 Hz, 1H), 4.13 (d, J=12.12 Hz, 1H), 1.81 (s, 3H);

MS: m/z 432.1 (M+1);

SOR: [α]$_D^{25.0}$ (+) 6.80, (MeOH, c=0.5).

Example 19: Preparation of 2-(3,4-dichlorophenyl)-2-({4-[(2-imino-2,3-dihydro-1,3-oxazol-3-yl)methyl]-1H-1,3-benzodiazol-2-yl}amino)propan-1-ol

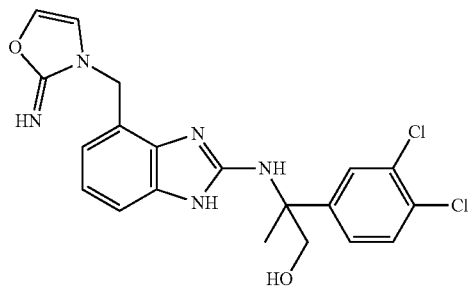 [SMILES: CC(CO)(Nc1nc2c(Cn3ccoc3=N)cccc2[nH]1)c1ccc(Cl)c(Cl)c1]

Example 19, Step 1: Preparation of 5-(3,4-dichlorophenyl)-5-methylimidazolidine-2,4-dione

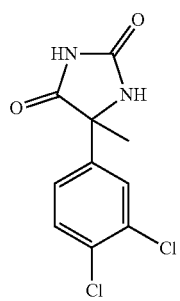 [SMILES: CC1(c2ccc(Cl)c(Cl)c2)NC(=O)NC1=O]

To a stirred solution of 1-(3,4-dichlorophenyl)ethan-1-one (commercially available) (45.0 g, 238.0 mmol) in a mixture of solvents ethanol/water (1:1; 1000 mL) was added ammonium carbonate (114.0 g, 1190.0 mmol) followed by potassium cyanide (18.60 g, 286.0 mmol) and the mixture was stirred at 65° C. for 16 h. The reaction mixture was poured into ice-cold water (1500 mL) and it was stirred for 30 min. The solid that formed was filtered off and dried to afford 5-(3, 4-dichlorophenyl)-5-methylimidazolidine-2, 4-dione (55.0 g) as an off-white solid, which was used in the next step without further purification.

$^1$H NMR (400 MHz, DMSO-d$_6$) δ 10.91 (bs, 1H), 8.68 (s, 1H), 7.70 (s, 1H), 7.68 (d, J=6.40 Hz, 1H), 7.49 (d, J=8.40 Hz, 1H), 1.65 (s, 3H);

MS: m/z 260.1 (M+1).

Example 19, Step 2: Preparation of 2-amino-2-(3, 4-dichlorophenyl) propanoic acid

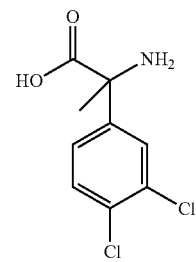 [SMILES: CC(C)(C)OC(=O)NC(C)(C(=O)O)c1ccc(Cl)c(Cl)c1]

A solution of 5-(3, 4-dichlorophenyl)-5-methylimidazolidine-2, 4-dione (from Example 19, Step 1) (50.0 g, 193.0 mmol) in 10% aqueous sodium hydroxide solution (400 mL) was refluxed for 48 h. The reaction mixture was neutralized (adjusted pH=7) with 6.0 N HCl (150 mL), and the solid that formed was filtered and dried to afford 2-amino-2-(3, 4-dichloro phenyl) propanoic acid (43.0 g) as a white solid, which was used in the next step without further purification.

$^1$H NMR (400 MHz, DMSO-d$_6$) δ 8.77 (bs, 2H), 7.80 (s, 1H), 7.70 (d, J=8.40 Hz, 1H), 7.52 (dd, J=2.00, 8.40 Hz, 1H), 1.76 (s, 3H);

MS: m/z 235.1 (M+1).

Example 19, Step 3: Preparation of 2-((tert-butoxycarbonyl) amino)-2-(3, 4-dichlorophenyl) propanoic acid

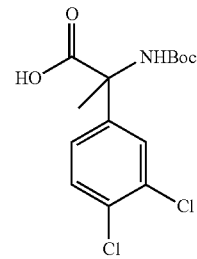

To a suspension of 2-amino-2-(3, 4-dichlorophenyl) propanoic acid (from Example 19, Step 2) (100.0 g, 429.0 mmol) in a mixture of solvents tetrahydrofuran:water (1:1; 900 mL) was added sodium bicarbonate (15.40 g, 184.0 mmol) followed by di-tert-butyl dicarbonate (84.4 mL, d=0.95 g/cm$^3$, 367.0 mmol) and the mixture was stirred at ambient temperature for 4 days. The reaction mixture was diluted with water (1000 mL) and extracted with ethyl acetate (4×2000 mL). The combined organic layer was dried over sodium sulphate, filtered and concentrated to afford 2-((tert-butoxycarbonyl)amino)-2-(3, 4-dichlorophenyl)propanoic acid (140.0 g) as a yellowish gum, which was used in the next step without further purification.

$^1$H NMR (400 MHz, DMSO-$d_6$: $D_2O$) δ 7.45 (d, J=8.40 Hz, 1H), 7.39 (s, 1H), 7.25 (dd, J=2.00, 8.40 Hz, 1H), 1.68 (s, 3H), 1.33 (s, 9H);

MS: m/z 235.1 [(M+1)-Boc].

Example 19, Step 4: Preparation of tert-butyl N-[2-(3,4-dichlorophenyl)-1-hydroxypropan-2-yl]carbamate

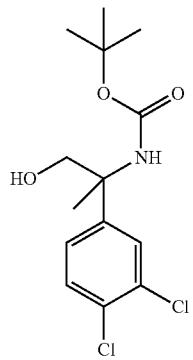 [SMILES: CC(C)(C)OC(=O)NC(C)(CO)c1ccc(Cl)c(Cl)c1]

To a solution of 2-((tert-butoxycarbonyl) amino)-2-(3, 4-dichlorophenyl) propanoic acid (from Example 19, Step 3) (45.0 g, 135.0 mmol) in dry tetrahydrofuran (650 mL) was added triethylamine (56.3 mL, d=0.726 g/cm³, 404.0 mmol) followed by isobutyl chloroformate (19.40 mL, d=1.053 g/cm³, 162.0 mmol) at 0° C. and stirred at the same temperature for 4 h. The solid that formed was filtered off at 0° C. and the residue was washed with dry tetrahydrofuran (200 mL). The combined filtrate was added to a cooled mixture of sodium borohydride (50.9 g, 1350.0 mmol) in water (200 mL). The reaction mixture was slowly warmed to ambient temperature and stirred for 72 h. The reaction mixture was quenched with ice cold water (1000 mL) and extracted with ethyl acetate (4×1500 mL), the combined organic layer was washed with brine (150 mL), dried over sodium sulphate, filtered and concentrated to afford a yellowish liquid (45.0 g). This was purified by chromatography on a Grace instrument using 200 g prepacked flash column with 60-120 silica gel and the product was eluted at 30-35% ethyl acetate in petroleum ether to afford tert-butyl N-[2-(3, 4-dichlorophenyl)-1-hydroxypropan-2-yl]carbamate (28.0 g) as an off-white solid.

$^1$H NMR (400 MHz, DMSO-$d_6$: $D_2O$) δ 7.51 (d, J=8.40 Hz, 1H), 7.43 (s, 1H), 7.26 (dd, J=2.00, 8.40 Hz, 1H), 3.46 (d, J=10.80 Hz, 2H), 1.50 (s, 3H), 1.31 (s, 9H);

MS: m/z 319.2 (M−1).

Example 19, Step 5: Preparation of 2-{[(tert-butoxy)carbonyl]amino}-2-(3,4-dichlorophenyl)propyl 2,2-dimethylpropanoate

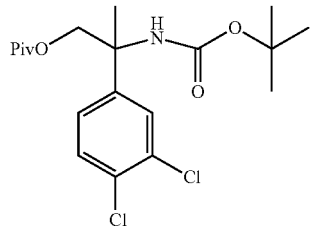

To a solution of tert-butyl N-[2-(3,4-dichlorophenyl)-1-hydroxypropan-2-yl]carbamate (from Example 19, Step 4) (28.0 g, 87.4 mmol) in dry dichloromethane (200 mL) under a nitrogen atmosphere was added triethyl amine (36.50 mL, d=0.726 g/cm³, 262.00 mmol) followed by pivaloyl chloride (21.50 mL, d=0.985 g/cm³, 175.0 mmol) at 0° C. dropwise and the whole reaction mixture was stirred at ambient temperature for 36 h. The reaction mixture was quenched with ice cold water (150 mL) and extracted with dichloromethane (4×500 mL). The combined organic layer was dried over sodium sulphate, filtered and concentrated to afford crude a brown liquid (36.0 g). This was purified by chromatography on a Grace instrument using 220 g prepacked 60-120 silica gel and the product was eluted with 20% ethyl acetate in hexane to afford 2-{[(tert-butoxy)carbonyl]amino}-2-(3,4-dichlorophenyl)propyl 2,2-dimethylpropanoate (30.0 g) as a colourless gum.

$^1$H NMR (400 MHz, DMSO-$d_6$: $D_2O$) δ 7.58 (d, J=8.44 Hz, 1H), 7.50 (s, 1H), 7.32 (dd, J=1.76, 8.42 Hz, 1H), 4.26 (q, J=10.44 Hz, 2H), 1.55 (s, 3H), 1.22 (s, 9H), 1.11 (s, 9H);

MS: m/z 305.2 [(M+1)-Boc].

Example 19, Step 6: Preparation of 2-amino-2-(3,4-dichlorophenyl)propyl 2,2-dimethylpropanoate hydrochloride

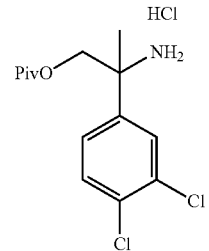

To a solution of 2-{[(tert-butoxy)carbonyl]amino}-2-(3, 4-dichlorophenyl)propyl 2,2-dimethylpropanoate (from Example 19, Step 5) (30.0 g, 74.20 mmol) in dry dichloromethane (300 mL) under a nitrogen atmosphere was added 4M HCl in dioxane solution (70.0 mL, 223.0 mmol) dropwise at 0° C. and the reaction mixture was stirred at ambient temperature for 16 h. The reaction mixture was concentrated on high vacuum to afford 2-amino-2-(3,4-dichlorophenyl) propyl 2,2-dimethylpropanoate hydrochloride (23.0 g) as a yellowish gum, which was used in the next step without further purification.

¹H NMR (400 MHz, DMSO-d₆: D₂O) δ 7.85 (s, 1H), 7.75 (dd, J=2.88, 8.52 Hz, 1H), 7.53 (dd, J=2.24, 5.72 Hz, 1H), 4.43 (d, J=11.76 Hz, 1H), 4.25 (d, J=11.72 Hz, 1H), 1.68 (s, 3H), 1.11 (s, 9H);

MS: m/z 305.1 [(M+1)-HCl].

Example 19, Step 7: Preparation of 2-(3,4-dichlorophenyl)-2-isocyanatopropyl 2,2-dimethylpropanoate

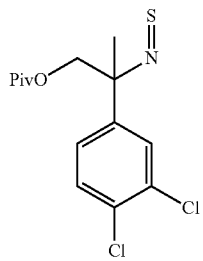

To a solution of 2-amino-2-(3,4-dichlorophenyl)propyl 2,2-dimethylpropanoate hydrochloride (from Example 19, Step 6) (25.0 g, 73.40 mmol) in dry dichloromethane (200 mL) was added 10% aq. sodium bicarbonate solution (200 mL) at 0° C. After 15 min, thiophosgene (7.40 mL, d=1.5 g/cm³, 95.40 mmol) was added and allowed to stir at same temperature for 1 h. The reaction mixture was extracted with dichloromethane (3×750 mL) and the combined organic layer was dried over anhydrous sodium sulphate, filtered and concentrated to afford a yellow liquid (26.0 g). This was purified by gravity column chromatography over 60-120 mesh silica gel using 25% ethyl acetate in hexane as eluent to afford 2-(3,4-dichlorophenyl)-2-isocyanatopropyl 2,2-dimethylpropanoate (15.0 g) as a yellow liquid.

¹H NMR (400 MHz, DMSO-d₆) δ 7.76 (s, 1H), 7.73 (d, J=8.40 Hz, 1H), 7.51 (dd, J=2.40, 8.40 Hz, 1H), 4.45 (q, J=11.60 Hz, 2H), 1.79 (s, 3H), 1.12 (s, 9H).

Example 19, Step 8: Preparation of 2-[({2-amino-3-[(2-imino-2,3-dihydro-1,3-oxazol-3-yl)methyl]phenyl}carbamothioyl)amino]-2-(3,4-dichlorophenyl)propyl 2,2-dimethylpropanoate and 2-[({2-amino-6-[(2-imino-2,3-dihydro-1,3-oxazol-3-yl)methyl]phenyl}carbamothioyl)amino]-2-(3,4-dichlorophenyl)propyl 2,2-dimethylpropanoate (Mixture of Regioisomers)

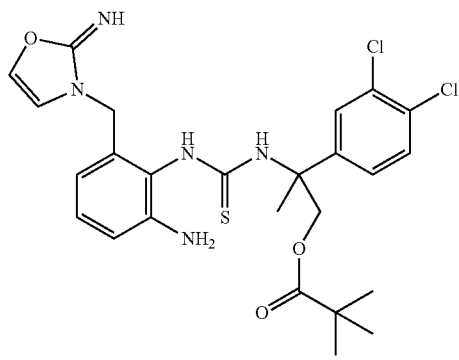

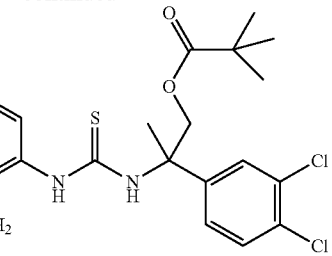

To a solution of 3-[(2-imino-2,3-dihydro-1,3-oxazol-3-yl)methyl]benzene-1,2-diamine (from Example 1, Step 5) (1.50 g, 7.34 mmol) in a mixture of solvents dichloromethane:methanol (1:1; 50 mL) was added 2-(3,4-dichlorophenyl)-2-isocyanatopropyl 2,2-dimethylpropanoate (from Example 19, Step 7) (1.53 g, 4.41 mmol) and the mixture was stirred at ambient temperature for 48 h. The reaction mixture was concentrated to afford 2-[({2-amino-3-[(2-imino-2,3-dihydro-1,3-oxazol-3-yl)methyl]phenyl}carbamothioyl)amino]-2-(3,4-dichlorophenyl)propyl 2,2-dimethylpropanoate and 2-[({2-amino-6-[(2-imino-2,3-dihydro-1,3-oxazol-3-yl)methyl]phenyl}carbamothioyl)amino]-2-(3,4-dichlorophenyl)propyl 2,2-dimethylpropanoate (as a mixture of non-separable regioisomers) (4.00 g) as a yellow gum, which was used in the next step without further purification.

MS: m/z 551.1 (M+1).

Example 19, Step 9: Preparation of 2-(3,4-dichlorophenyl)-2-({4-[(2-imino-2,3-dihydro-1,3-oxazol-3-yl)methyl]-1H-1,3-benzodiazol-2-yl}amino)propyl 2,2-dimethylpropanoate

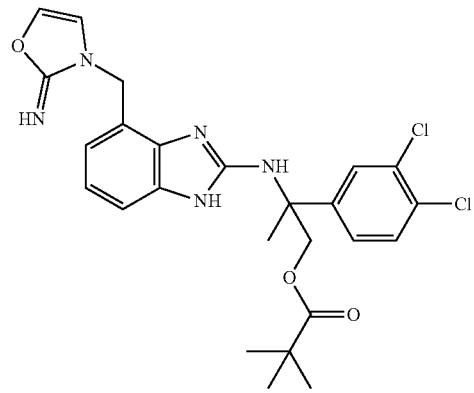 [SMILES: CC(C)(C)C(=O)OCC(C)(Nc1nc2c(Cn3ccoc3=N)cccc2[nH]1)c1ccc(Cl)c(Cl)c1]

To a solution of 2-[({2-amino-3-[(2-imino-2,3-dihydro-1,3-oxazol-3-yl)methyl]phenyl}carbamothioyl)amino]-2-(3,4-dichlorophenyl)propyl 2,2-dimethylpropanoate and 2-[({2-amino-6-[(2-imino-2,3-dihydro-1,3-oxazol-3-yl)methyl]phenyl}carbamothioyl)amino]-2-(3,4-dichlorophenyl)propyl 2,2-dimethylpropanoate (as a mixture of non-separable regioisomers) (from Example 19, Step 8) (4.00 g, 7.27 mmol) in methanol (100 mL) was added iodoacetic acid (1.35 g, 7.27 mmol) and the mixture was stirred at 65° C. for 1 h. The reaction mixture was concentrated to remove the solvent methanol and the residue was dissolved in 10% aqueous sodium bicarbonate solution (100 mL) and extracted with ethyl acetate (3×200 mL). The combined organic extracts were dried over sodium sulphate, filtered and concentrated to afford a brown gum (4.00 g). It was purified by preparative HPLC to afford 2-(3,4-dichlorophenyl)-2-({4-[(2-imino-2,3-dihydro-1,3-oxazol-3-yl)methyl]-1H-1,3-benzodiazol-2-yl}amino)propyl 2,2-dimethylpropanoate (0.900 g) as a brown gum.

$^{1}$H NMR (400 MHz, DMSO-d$_{6}$: D$_{2}$O) δ 7.69 (s, 1H), 7.62 (d, J=8.40 Hz, 2H), 7.44 (dd, J=2.00, 8.40 Hz, 1H), 7.29 (d, J=8.00 Hz, 1H), 7.14 (s, 1H), 7.05 (t, J=7.20 Hz, 1H), 7.03 (d, J=7.20 Hz, 1H), 5.11 (s, 2H), 4.45 (q, J=11.20 Hz, 2H), 1.82 (s, 3H), 1.05 (s, 9H);

MS: m/z 517.1 (M+1).

Example 19: Preparation of 2-(3,4-dichlorophenyl)-2-({4-[(2-imino-2,3-dihydro-1,3-oxazol-3-yl)methyl]-1H-1,3-benzodiazol-2-yl}amino)propan-1-ol

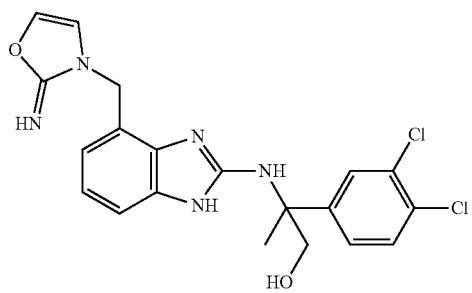 [SMILES: CC(CO)(Nc1nc2c(Cn3ccoc3=N)cccc2[nH]1)c1ccc(Cl)c(Cl)c1]

To a solution of 2-(3,4-dichlorophenyl)-2-({4-[(2-imino-2,3-dihydro-1,3-oxazol-3-yl)methyl]-1H-1,3-benzodiazol-2-yl}amino)propyl 2,2-dimethylpropanoate (from Example 19, Step 9) (0.750 g, 1.19 mmol) in methanol (50 mL) was added 0.5 M sodium hydroxide in methanol (5.95 mL, 2.97 mmol) dropwise and the mixture was stirred at ambient temperature for 30 min. The reaction mixture was quenched with 1.5 N aqueous HCl solution (10 mL) at 0° C. and then concentrated at 28° C. to afford a brown gum (0.520 g), which was purified by preparative HPLC to afford 2-(3,4-dichlorophenyl)-2-({4-[(2-imino-2,3-dihydro-1,3-oxazol-3-yl)methyl]-1H-1,3-benzodiazol-2-yl}amino)propan-1-ol (0.380 g) as a brown gum.

$^{1}$H NMR (400 MHz, AcOH-d$_{4}$) δ 7.72 (s, 1H), 7.57 (d, J=7.20 Hz, 1H), 7.53 (d, J=8.40 Hz, 1H), 7.48 (dd, J=2.40, 8.60 Hz, 1H), 7.41 (dd, J=1.20, 7.40 Hz, 1H), 7.31 (t, J=7.60 Hz, 1H), 7.27 (dd, J=1.60, 7.60 Hz, 1H), 7.21 (d, J=7.20 Hz, 1H), 5.40 (q, J=15.60 Hz, 2H), 4.33 (d, J=12.00 Hz, 1H), 4.08 (d, J=12.40 Hz, 1H), 1.78 (s, 3H);

MS: m/z 433.1 (M+1).

The above product was resolved into its two enantiomers by Chiral SFC using the method: Column: Chiral Pak OX-H; Flow rate: 5.0 mL/min; Co-Solvent: 50%; Co-solvent Name: 0.5% isopropyl amine in isopropyl alcohol; injected Volume: 7.0 μL; outlet pressure: 100 bar; Temperature: 35° C. to obtain the two enantiomers 19a and 19b.

Example 19a: (+2-(3,4-dichlorophenyl)-2-({4-[(2-imino-2,3-dihydro-1,3-oxazol-3-yl)methyl]-1H-1,3-benzodiazol-2-yl}amino)propan-1-ol The (−) enantiomer was the first compound to elute off the column.

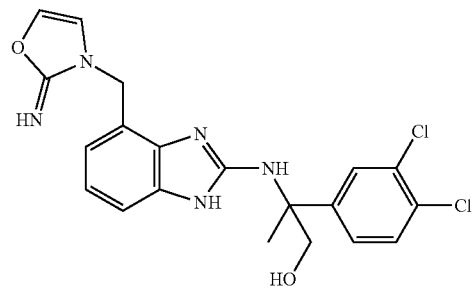 [SMILES: CC(CO)(Nc1nc2c(Cn3ccoc3=N)cccc2[nH]1)c1ccc(Cl)c(Cl)c1]

$^{1}$H NMR (400 MHz, AcOH-d$_{4}$) δ 7.72 (s, 1H), 7.57 (d, J=7.20 Hz, 1H), 7.53 (d, J=8.40 Hz, 1H), 7.48 (dd, J=2.40, 8.60 Hz, 1H), 7.41 (dd, J=1.20, 8.40 Hz, 1H), 7.30 (t, J=7.60 Hz, 1H), 7.27 (dd, J=2.40, 8.00 Hz, 1H), 7.22 (d, J=7.60 Hz, 1H), 5.40 (q, J=15.60 Hz, 2H), 4.33 (d, J=12.00 Hz, 1H), 4.08 (d, J=12.40 Hz, 1H), 1.77 (s, 3H);

MS: m/z 432.1 (M+1);

$[α]_{D}^{25.4}$ (−) 8.00 (MeOH, c=0.5).

Example 19b: (+)-2-(3,4-dichlorophenyl)-2-({4-[(2-imino-2,3-dihydro-1,3-oxazol-3-yl)methyl]-1H-1,3-benzodiazol-2-yl}amino)propan-1-ol The (+) enantiomer was the second compound to elute-off the column.

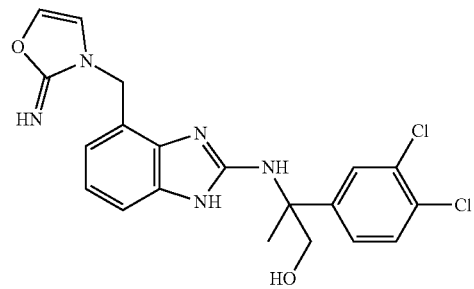 [SMILES: CC(CO)(Nc1nc2c(Cn3ccoc3=N)cccc2[nH]1)c1ccc(Cl)c(Cl)c1]

$^{1}$H NMR (400 MHz, AcOH-d$_{4}$) δ 7.72 (s, 1H), 7.57 (d, J=8.00 Hz, 1H), 7.53 (d, J=8.40 Hz, 1H), 7.48 (dd, J=2.00, 8.40 Hz, 1H), 7.40 (dd, J=1.20, 7.60 Hz, 1H), 7.30 (t, J=7.60 Hz, 1H), 7.26 (dd, J=1.60, 7.80 Hz, 1H), 7.22 (d, J=7.60 Hz, 1H), 5.40 (q, J=16.00 Hz, 2H), 4.33 (d, J=12.00 Hz, 1H), 4.08 (d, J=12.00 Hz, 1H), 1.77 (s, 3H);

MS: m/z 432.1 (M+1);

$[α]_{D}^{25.5}$ (+) 7.20 (MeOH, c=0.5).

Example 20: Preparation of 2-(3-chloro-4-fluoro-phenyl)-2-({4-[(2-imino-4,5-dimethyl-2,3-dihydro-1,3-oxazol-3-yl)methyl]-1H-1,3-benzodiazol-2-yl}amino)propan-1-ol

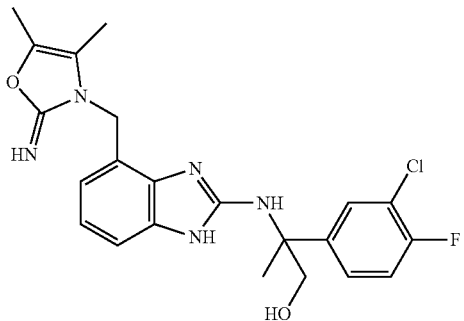 [SMILES: Cc1oc(=N)n(Cc2cccc3[nH]c(NC(C)(CO)c4ccc(F)c(Cl)c4)nc23)c1C]

Starting with commercially available 4,5-dimethyloxazol-2-amine, the titled compound was made by the method described for Example 8 and isolated as the trifluoroacetate salt.

$^1$H NMR (400 MHz, AcOH-$d_4$) δ 7.68 (dd, J=2.40, 6.80 Hz, 1H), 7.54-7.51 (m, 1H), 7.35 (d, J=8.00 Hz, 1H), 7.25 (dd, J=8.00, 16.00 Hz, 2H), 6.87 (d, J=8.00 Hz, 1H), 5.40 (s, 2H), 4.32 (d, J=12.00 Hz, 1H), 4.08 (d, J=12.40 Hz, 1H), 2.28 (d, J=0.80 Hz, 3H), 2.02 (d, J=1.20 Hz, 3H), 1.78 (s, 3H);

MS: m/z 444.1 (M+1).

Example 21: Preparation of 2-((4-(((1-methyl-1H-pyrazol-5-yl)amino)methyl)-1H-benzo[d]imidazol-2-yl)amino)-2-(3-(trifluoromethyl)phenyl) propan-1-ol

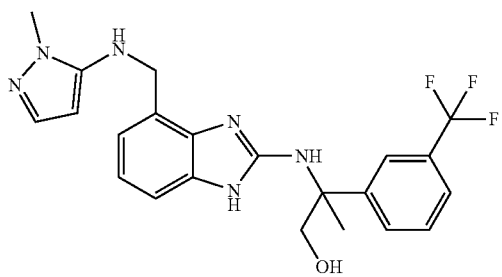 [SMILES: Cn1nccc1NCc1cccc2[nH]c(NC(C)(CO)c3cccc(C(F)(F)F)c3)nc12]

Starting with the commercially available 2-methylpyrazol-3-amine the titled compound was made by using the methods described for Example 16 and Example 18.

$^1$H NMR (400 MHz, AcOH-$d_4$) δ 7.85 (s, 1H), 7.81 (d, J=8.00 Hz, 1H), 7.66 (d, J=8.00 Hz, 1H), 7.58 (t, J=7.60 Hz, 1H), 7.44 (s, 1H), 7.36 (d, J=14.80 Hz, 1H), 7.26 (d, J=6.80 Hz, 2H), 7.20 (t, J=7.20 Hz, 1H), 4.54 (q, J=15.60 Hz, 2H), 4.42 (d, J=12.00 Hz, 1H), 4.13 (d, J=12.00 Hz, 1H), 3.70 (s, 3H), 1.82 (s, 3H);

MS: m/z 445.2 (M+1).

Example 22: Preparation of 2-((4-(((1-methyl-1H-imidazol-2-yl)amino)methyl)-1H-benzo[d]imidazol-2-yl)amino)-2-(3-(trifluoromethyl)phenyl)propan-1-ol

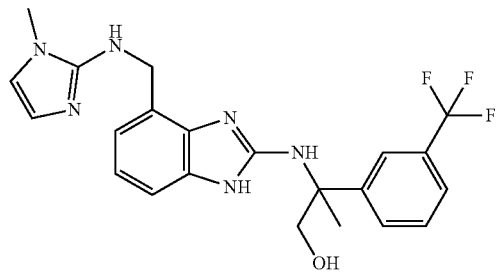 [SMILES: Cn1ccnc1NCc1cccc2[nH]c(NC(C)(CO)c3cccc(C(F)(F)F)c3)nc12]

Starting with commercially available 1-methyl imidazol-2-amine the titled compound was prepared by the methods described for Example 1 and Example 18.

$^1$H NMR (400 MHz, AcOH-$d_4$) δ 7.84 (s, 1H), 7.81 (d, J=8.00 Hz, 1H), 7.67 (d, J=7.60 Hz, 1H), 7.60 (t, J=7.60 Hz, 1H), 7.34 (d, J=8.00 Hz, 1H), 7.23 (t, J=8.00 Hz, 1H), 7.02 (d, J=7.60 Hz, 1H), 6.85 (d, J=2.80 Hz, 1H), 6.78 (d, J=2.40 Hz, 1H), 5.35 (d, J=7.60 Hz, 2H), 4.41 (d, J=12.40 Hz, 1H), 4.11 (d, J=12.00 Hz, 1H), 3.60 (s, 3H), 1.78 (s, 3H);

MS: m/z 445.2 (M+1).

Example 23: Preparation of 2-({4-[(2-imino-4-methyl-2,3-dihydro-1,3-oxazol-3-yl)methyl]-1H-1,3-benzodiazol-2-yl}amino)-2-[3-(trifluoromethyl)phenyl]-propan-1-ol

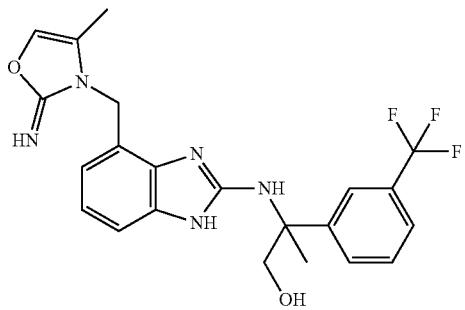 [SMILES: Cc1coc(=N)n1Cc1cccc2[nH]c(NC(C)(CO)c3cccc(C(F)(F)F)c3)nc12]

Example 23, Step 1: Preparation of 2-[({2-amino-3-[(2-imino-4-methyl-2,3-dihydro-1,3-oxazol-3-yl)methyl]phenyl}carbamothioyl)amino]-2-[3-(trifluoromethyl)phenyl]propyl 2,2-dimethylpropanoate and 2-[({2-amino-6-[(2-imino-4-methyl-2,3-dihydro-1,3-oxazol-3-yl)methyl]phenyl}carbamothioyl)amino]-2-[3-(trifluoromethyl)phenyl]propyl 2,2-dimethylpropanoate (Mixture of Regioisomers)

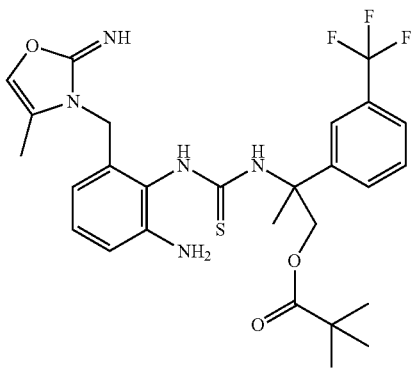

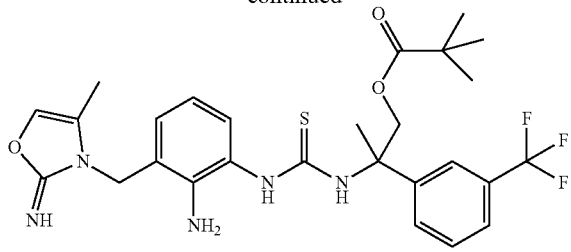

To a solution of 3-[(2-imino-4-methyl-2,3-dihydro-1,3-oxazol-3-yl)methyl]benzene-1,2-diamine (from Example 5, Step 2) (1.8 g, 8.25 mmol) in a mixture of solvents dichloromethane:methanol (1:1; 40 mL) was added [2-isothiocyanato-2-[3-(trifluoromethyl)phenyl]propyl]2,2-dimethylpropanoate (from Example 18, Step 7) (1.71 g, 4.95 mmol) and stirred at ambient temperature for 72 h. The reaction mixture was concentrated at 30° C. to afford 2-[({2-amino-3-[(2-imino-4-methyl-2,3-dihydro-1,3-oxazol-3-yl)methyl]phenyl}carbamothioyl)amino]-2-[3-(trifluoromethyl)phenyl]propyl 2,2-dimethylpropanoate and 2-[({2-amino-6-[(2-imino-4-methyl-2,3-dihydro-1,3-oxazol-3-yl)methyl]phenyl}carbamothioyl)amino]-2-[3-(trifluoromethyl)phenyl]propyl 2,2-dimethylpropanoate (as a mixture of non-separable regioisomers) (3.30 g) as a brown gum, which was used in the next step without purification.

MS: m/z 564.2.2 (M+1).

Example 23, Step 2: Preparation of 2-({4-[(2-imino-4-methyl-2,3-dihydro-1,3-oxazol-3-yl)methyl]-1H-1,3-benzodiazol-2-yl}amino)-2-[3-(trifluoromethyl)phenyl]propyl 2,2-dimethylpropanoate

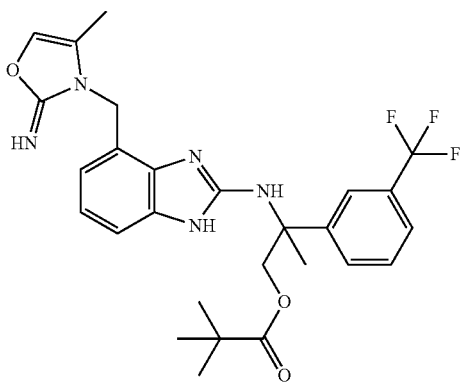 [SMILES: Cc1coc(=N)n1Cc1cccc2[nH]c(NC(C)(COC(=O)C(C)(C)C)c3cccc(C(F)(F)F)c3)nc12]

To a solution of 2-[({2-amino-3-[(2-imino-4-methyl-2,3-dihydro-1,3-oxazol-3-yl)methyl]phenyl}carbamothioyl)amino]-2-[3-(trifluoromethyl)phenyl]propyl 2,2-dimethylpropanoate and 2-[({2-amino-6-[(2-imino-4-methyl-2,3-dihydro-1,3-oxazol-3-yl)methyl]phenyl}carbamothioyl)amino]-2-[3-(trifluoromethyl)phenyl]propyl 2,2-dimethylpropanoate (as a mixture of non-separable regioisomers) (Example 23, Step 1) (3.30 g, 5.85 mmol) in methanol (40 mL) was added iodoacetic acid (1.63 g, 8.78 mmol) and the mixture was refluxed for 1.5 h. The reaction mixture was concentrated at 30° C. to afford a brown gum (3.3 g), which was purified by preparative HPLC (TFA: Acetonitrile) to afford 2-({4-[(2-imino-4-methyl-2,3-dihydro-1,3-oxazol-3-yl)methyl]-1H-1,3-benzodiazol-2-yl}amino)-2-[3-(trifluoromethyl)phenyl]propyl 2,2-dimethylpropanoate, isolated as the trifluoroacetate salt, (0.550 g) as a brown gum.

$^1$H NMR (400 MHz, AcOH-$d_4$) δ 7.88 (d, J=7.52 Hz, 2H), 7.73 (d, J=8.04 Hz, 1H), 7.65 (t, J=7.92 Hz, 1H), 7.47 (d, J=1.56 Hz, 1H), 7.30-7.23 (m, 2H), 6.86 (d, J=0.92 Hz, 1H), 5.48 (s, 2H), 4.55 (q, J=11.64 Hz, 2H), 2.13 (s, 3H), 2.05 (s, 3H), 1.19 (s, 9H);

MS: m/z 530.2 (M+1).

The above product was been resolved by Chiral SFC using the method: Chiralcel OX-H, Mobile Phase: 0.5% isopropyl amine in isopropyl alcohol; co-solvent 40% $CO_2$; Flow rate: 3 ml/min, pressure: 100 bar; Temperature: 35° C. to obtain the two enantiomers 23-2a and 23-2b.

Example 23-2a: 2-({4-[(2-imino-4-methyl-2,3-dihydro-1,3-oxazol-3-yl)methyl]-1H-1,3-benzodiazol-2-yl}amino)-2-[3-(trifluoromethyl)phenyl]propyl 2,2-dimethylpropanoate (Enantiomer A)

Enantiomer A was the first compound to elute off the column.

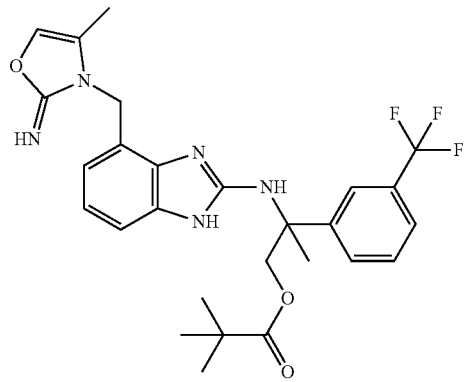 [SMILES: Cc1coc(=N)n1Cc1cccc2[nH]c(NC(C)(COC(=O)C(C)(C)C)c3cccc(C(F)(F)F)c3)nc12]

$^1$H NMR (400 MHz, AcOH-$d_4$) δ 7.88 (d, J=7.52 Hz, 2H), 7.73 (d, J=8.04 Hz, 1H), 7.65 (t, J=7.92 Hz, 1H), 7.47 (d, J=1.56 Hz, 1H), 7.30-7.23 (m, 2H), 6.86 (d, J=0.92 Hz, 1H), 5.48 (s, 2H), 4.55 (q, J=11.64 Hz, 2H), 2.13 (s, 3H), 2.05 (s, 3H), 1.19 (s, 9H);

MS: m/z 530.2 [(M+1).

Example 23-2b: 2-({4-[(2-imino-4-methyl-2,3-dihydro-1,3-oxazol-3-yl)methyl]-1H-1,3-benzodiazol-2-yl}amino)-2-[3-(trifluoromethyl)phenyl]propyl 2,2-dimethylpropanoate (Enantiomer B)

Enantiomer B was the second compound to elute off the column.

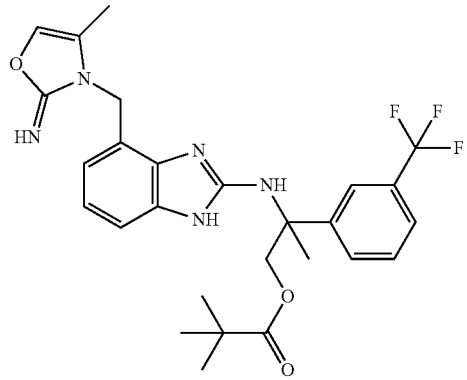 [SMILES: Cc1coc(=N)n1Cc1cccc2[nH]c(NC(C)(COC(=O)C(C)(C)C)c3cccc(C(F)(F)F)c3)nc12]

¹H NMR (400 MHz, AcOH-d₄) δ 7.88 (d, J=7.52 Hz, 2H), 7.73 (d, J=8.04 Hz, 1H), 7.65 (t, J=7.92 Hz, 1H), 7.47 (d, J=1.56 Hz, 1H), 7.30-7.23 (m, 2H), 6.86 (d, J=0.92 Hz, 1H), 5.48 (s, 2H), 4.55 (q, J=11.64 Hz, 2H), 2.13 (s, 3H), 2.05 (s, 3H), 1.19 (s, 9H);

MS: m/z 530.2 [(M+1).

Example 23: 2-({4-[(2-imino-4-methyl-2,3-dihydro-1,3-oxazol-3-yl)methyl]-1H-1,3-benzodiazol-2-yl}amino)-2-[3-(trifluoromethyl)phenyl]propan-1-ol

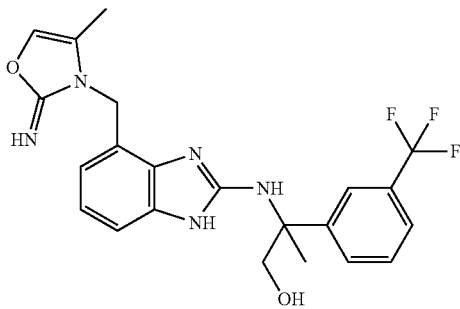 [SMILES: Cc1coc(=N)n1Cc1cccc2[nH]c(NC(C)(CO)c3cccc(C(F)(F)F)c3)nc12]

To a solution of 2-({4-[(2-imino-4-methyl-2,3-dihydro-1,3-oxazol-3-yl)methyl]-1H-1,3-benzodiazol-2-yl}amino)-2-[3-(trifluoromethyl)phenyl]propyl 2,2-dimethylpropanoate; trifluoroacetic acid (Example 23, Step 2) (0.050 g, 0.077 mmol) in methanol (10 mL) was added 0.5 N sodium hydroxide in methanol (0.600 ml, 0.311 mmol) dropwise and stirred at ambient temperature for 1.5 h. The reaction mixture was quenched with 1.5 N hydrochloride solution (1 mL) and concentrated under reduced pressure at 30° C. to afford a brown gum (0.04 g), which was purified by preparative HPLC using 0.1% TFA in acetonitrile:water to afford 2-({4-[(2-imino-4-methyl-2,3-dihydro-1,3-oxazol-3-yl)methyl]-1H-1,3-benzodiazol-2-yl}amino)-2-[3-(trifluoromethyl)phenyl]propan-1-ol, isolated as the trifluoroacetate salt, (0.028 g) as a brown gum.

¹H NMR (400 MHz, AcOH-d₄) δ 7.85 (t, J=8.00 Hz, 2H), 7.69 (d, J=7.84 Hz, 1H), 7.61 (t, J=7.64 Hz, 1H), 7.44 (d, J=1.52 Hz, 1H), 7.35 (d, J=7.88 Hz, 1H), 7.25 (t, J=8.00 Hz, 1H), 6.87 (d, J=7.60 Hz, 1H), 5.46 (s, 2H), 4.42 (d, J=12.08 Hz, 1H), 4.14 (d, J=12.12 Hz, 1H), 2.08 (s, 3H), 1.82 (s, 3H); MS: m/z 446.1[(M+1)-TFA].

Example 23a: Preparation of (−)-2-({4-[(2-imino-4-methyl-2,3-dihydro-1,3-oxazol-3-yl)methyl]-1H-1,3-benzodiazol-2-yl}amino)-2-[3-(trifluoromethyl)phenyl]propan-1-ol

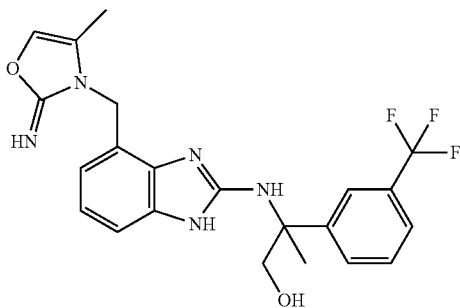 [SMILES: Cc1coc(=N)n1Cc1cccc2[nH]c(NC(C)(CO)c3cccc(C(F)(F)F)c3)nc12]

To a solution of 2-({4-[(2-imino-4-methyl-2,3-dihydro-1,3-oxazol-3-yl)methyl]-1H-1,3-benzodiazol-2-yl}amino)-2-[3-(trifluoromethyl)phenyl]propyl 2,2-dimethylpropanoate (Example 23-2a, Enantiomer A) (0.150 g, 0.233 mmol) in methanol (20 mL) was added 0.5 N sodium hydroxide in methanol (1.86 ml, 0.932 mmol) dropwise and stirred at ambient temperature for 1.5 h. The reaction mixture was quenched with 1.5 N hydrochloride solution (1 mL) and concentrated under reduced pressure at 30° C. to afford a brown gum (0.130 g), which was purified by preparative HPLC using 0.1% TFA in acetonitrile:water to afford (−)-2-({4-[(2-imino-4-methyl-2,3-dihydro-1,3-oxazol-3-yl)methyl]-1H-1,3-benzodiazol-2-yl}amino)-2-[3-(trifluoromethyl)phenyl]propan-1-ol, isolated as the trifluoroacetate salt, (0.060 g) as a colorless gum.

¹H NMR (400 MHz, AcOH-d₄ δ 7.84 (t, J=8.40 Hz, 2H), 7.68 (d, J=7.60 Hz, 1H), 7.60 (t, J=8.00 Hz, 1H), 7.43 (d, J=1.20 Hz, 1H), 7.34 (d, J=8.00 Hz, 1H), 7.24 (t, J=8.00 Hz, 1H), 6.86 (d, J=8.00 Hz, 1H), 5.45 (s, 2H), 4.42 (d, J=12.00 Hz, 1H), 4.13 (d, J=12.00 Hz, 1H), 2.07 (s, 3H), 1.81 (s, 3H);

MS: m/z 446.1[(M+1)];

SOR: $[\alpha]_D^{20.6}$ (−) 10.16, (MeOH, c=0.5).

Example 23b: Preparation of (+)-2-({4-[(2-imino-4-methyl-2,3-dihydro-1,3-oxazol-3-yl)methyl]-1H-1,3-benzodiazol-2-yl}amino)-2-[3-(trifluoromethyl)phenyl]propan-1-ol

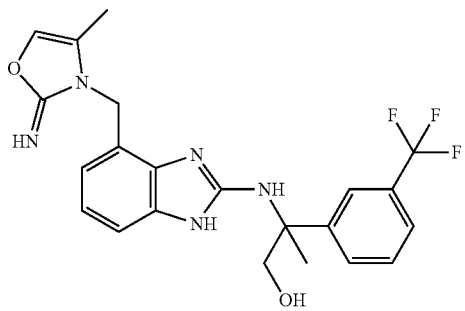 [SMILES: Cc1coc(=N)n1Cc1cccc2[nH]c(NC(C)(CO)c3cccc(C(F)(F)F)c3)nc12]

To a solution of 2-({4-[(2-imino-4-methyl-2,3-dihydro-1,3-oxazol-3-yl)methyl]-1H-1,3-benzodiazol-2-yl}amino)-2-[3-(trifluoromethyl)phenyl]propyl 2,2-dimethylpropanoate (Example 23-2b, Enantiomer B) (0.11 g, 0.171 mmol) in methanol (12 mL) was added 0.5 N sodium hydroxide in methanol (1.37 ml, 0.684 mmol) dropwise and stirred at ambient temperature for 1.5 h. The reaction mixture was quenched with 1.5 N hydrochloride solution (1 mL) and concentrated under reduced pressure at 30° C. to afford a brown gum (0.09 g), which was purified by preparative HPLC using 0.1% TFA in acetonitrile:water to afford (+)-2-({4-[(2-imino-4-methyl-2,3-dihydro-1,3-oxazol-3-yl)methyl]-1H-1,3-benzodiazol-2-yl}amino)-2-[3-(trifluoromethyl)phenyl]propan-1-ol, isolated as the trifluoroacetate salt, (0.030 g) as a colorless gum.

¹H NMR (400 MHz, AcOH-d₄ δ 7.84 (t, J=8.40 Hz, 2H), 7.68 (d, J=7.60 Hz, 1H), 7.60 (t, J=8.00 Hz, 1H), 7.43 (d, J=1.20 Hz, 1H), 7.34 (d, J=8.00 Hz, 1H), 7.24 (t, J=8.00 Hz,

1H), 6.86 (d, J=8.00 Hz, 1H), 5.45 (s, 2H), 4.42 (d, J=12.00 Hz, 1H), 4.13 (d, J=12.00 Hz, 1H), 2.07 (s, 3H), 1.81 (s, 3H);

MS: m/z 446.1 (M+1);

SOR: [α]$_D^{20.2}$ (+) 5.60, (MeOH, c=0.5).

Example 24: Preparation of 2-({4-[(2-imino-5-methyl-2,3-dihydro-1,3-oxazol-3-yl)methyl]-1H-1,3-benzodiazol-2-yl}amino)-2-[3-(trifluoromethyl)phenyl]propan-1-ol

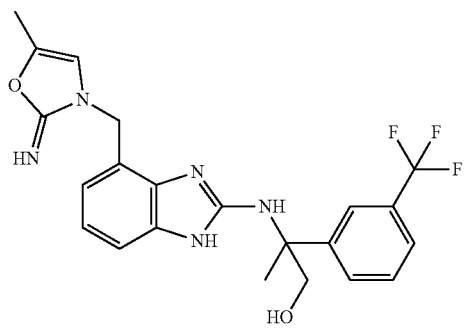 [SMILES: Cc1cn(Cc2cccc3[nH]c(NC(C)(CO)c4cccc(C(F)(F)F)c4)nc23)c(=N)o1]

Example 24, Step 1: Preparation of 3-[(2,1,3-benzothiadiazol-4-yl)methyl]-5-methyl-2,3-dihydro-1,3-oxazol-2-imine hydrobromide

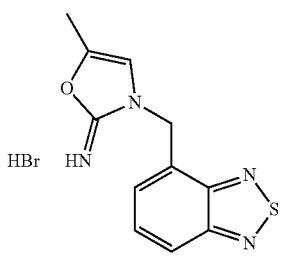 [SMILES: Br ; Cc1cn(Cc2cccc3nsnc23)c(=N)o1]

To a solution of 4-(bromomethyl)-2,1,3-benzothiadiazole (Example 1, Step 3) (2.00 g, 8.73 mmol) in acetonitrile (20 mL) was added 5-methyloxazol-2-amine (1.03 g, 10.50 mmol) and the mixture was stirred at ambient temperature for 60 h. The reaction mixture was concentrated to afford an off-white gum (2.10 g), which was purified by prep HPLC (H$_2$O:Acetonitrile) and the solution was concentrated at 40° C. to afford 3-[(2,1,3-benzothiadiazol-4-yl)methyl]-5-methyl-2,3-dihydro-1,3-oxazol-2-imine hydrobromide (1.60 g) as an off-white solid.

$^1$H-NMR (400 MHz, DMSO-d$_6$: D$_2$O) δ 8.12 (d, J=8.72 Hz, 1H), 7.76 (t, J=8.60 Hz, 1H), 7.67 (d, J=6.72 Hz, 1H), 7.12 (s, 1H), 5.50 (s, 2H), 2.18 (s, 3H);

MS: m/z 247.1 [(M+1)-HBr].

Example 24, Step 2: Preparation of 3-[(2-imino-5-methyl-2,3-dihydro-1,3-oxazol-3-yl)methyl]benzene-1,2-diamine

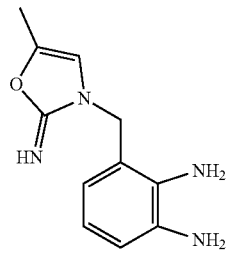 [SMILES: Cc1cn(Cc2cccc(N)c2N)c(=N)o1]

To a de-gassed solution of 3-[(2,1,3-benzothiadiazol-4-yl)methyl]-5-methyl-2,3-dihydro-1,3-oxazol-2-imine hydrobromide (from Example 24, Step 1) (1.90 g, 7.71 mmol) in dry methanol (190 mL) was added Raney nickel (5.70 g, 300% w/w, pre-washed five times with dry methanol) and the resultant reaction mixture was stirred under a hydrogen atmosphere at bladder pressure (Approx. 1.5 kg/cm$^2$) at ambient temperature for 24 h. The reaction mixture was filtered through a celite bed and the bed was washed with methanol (200 mL). The combined filtrates were concentrated at 15-20° C. to afford 3-[(2-imino-5-methyl-2,3-dihydro-1,3-oxazol-3-yl)methyl]benzene-1,2-diamine (1.50 g) as a grey gum, which was used in the next step without purification.

MS: m/z 219.2 (M+1).

Example 24, Step 3: Preparation of 2-[({2-amino-3-[(2-imino-5-methyl-2,3-dihydro-1,3-oxazol-3-yl)methyl]phenyl}carbamothioyl)amino]-2-[3-(trifluoromethyl)phenyl]propyl 2,2-dimethylpropanoate and 2-[({2-amino-6-[(2-imino-5-methyl-2,3-dihydro-1,3-oxazol-3-yl)methyl]phenyl}carbamothioyl)amino]-2-[3-(trifluoromethyl)phenyl]propyl 2,2-dimethylpropanoate (Mixture of Regioisomers)

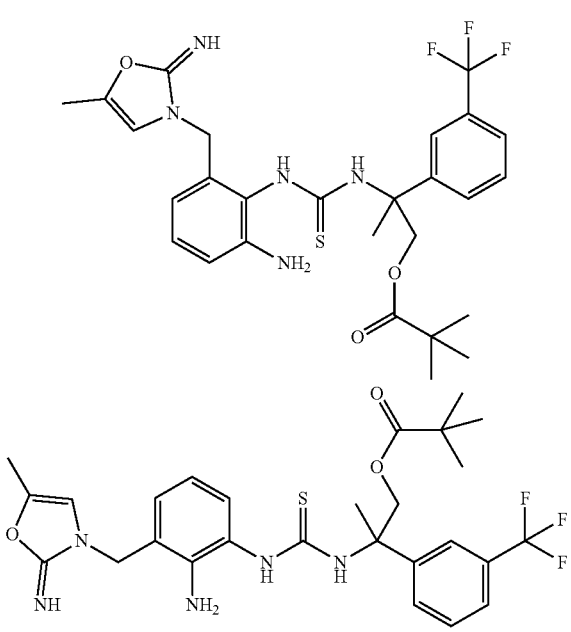

To a solution of 3-(((5-methyloxazol-2-yl)amino)methyl)benzene-1,2-diamine (Example 24, Step 2) (1.50 g, 6.87 mmol) in a mixture of solvents dichloromethane:methanol (1:1; 60 mL) was added [2-isothiocyanato-2-[3-(trifluoromethyl)phenyl]propyl] 2,2-dimethylpropanoate (from Example 18, Step 7) (1.90 g, 5.50 mmol) and stirred at ambient temperature for 72 h. The reaction mixture was concentrated at 30° C. to afford 2-[({2-amino-3-[(2-imino-5-methyl-2,3-dihydro-1,3-oxazol-3-yl)methyl]phenyl}carbamothioyl)amino]-2-[3-(trifluoromethyl)phenyl]propyl 2,2-dimethylpropanoate and 2-[({2-amino-6-[(2-imino-5-methyl-2,3-dihydro-1,3-oxazol-3-yl)methyl]phenyl}carbamothioyl)amino]-2-[3-(trifluoromethyl)phenyl]propyl 2,2-dimethylpropanoate (as a mixture of non-separable regioisomers) (3.40 g) as a brown gum, which was used in the next step without purification.

MS: m/z 564.2.2 (M+1).

Example 24, Step 4: Preparation of 2-({4-[(2-imino-5-methyl-2,3-dihydro-1,3-oxazol-3-yl)methyl]-1H-1,3-benzodiazol-2-yl}amino)-2-[3-(trifluoromethyl)phenyl]propyl 2,2-dimethylpropanoate

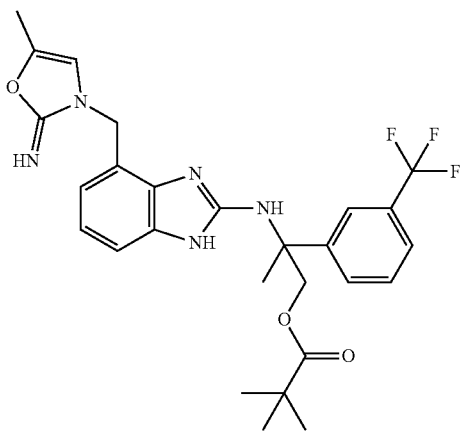 [SMILES: Cc1cn(Cc2cccc3[nH]c(NC(C)(COC(=O)C(C)(C)C)c4cccc(C(F)(F)F)c4)nc23)c(=N)o1]

To a solution of 2-[({2-amino-3-[(2-imino-5-methyl-2,3-dihydro-1,3-oxazol-3-yl)methyl]phenyl}carbamothioyl)amino]-2-[3-(trifluoromethyl)phenyl]propyl 2,2-dimethylpropanoate and 2-[({2-amino-6-[(2-imino-5-methyl-2,3-dihydro-1,3-oxazol-3-yl)methyl]phenyl}carbamothioyl)amino]-2-[3-(trifluoromethyl)phenyl]propyl 2,2-dimethylpropanoate (as a mixture of non separable regioisomers) (Example 24, Step 3) (3.40 g, 6.03 mmol) in methanol (30 mL) was added iodoacetic acid (1.68 g, 9.05 mmol) and the mixture was refluxed for 1.5 h. The reaction mixture was concentrated at 30° C. to afford a brown gum (3.80 g), which was purified by preparative HPLC (TFA: Acetonitrile) to afford 2-({4-[(2-imino-5-methyl-2,3-dihydro-1,3-oxazol-3-yl)methyl]-1H-1,3-benzodiazol-2-yl}amino)-2-[3-(trifluoromethyl)phenyl]propyl 2,2-dimethylpropanoate, isolated as the trifluoroacetate salt, (1.00 g) as a brown gum.

$^1$H NMR (400 MHz, DMSO-d$_6$: D$_2$O) δ 7.80-7.65 (m, 4H), 7.32 (d, J=10.40 Hz, 1H), 7.20 (d, J=10.00 Hz, 1H), 7.06 (d, J=10.40 Hz, 1H), 6.89 (s, 1H), 5.16 (s, 2H), 4.48 (s, 2H), 2.16 (s, 3H), 1.91 (s, 3H), 1.03 (s, 9H);

MS: m/z 530.2 [(M+1)-TFA].

The above product was resolved into its two enantiomers by Chiral SFC using the method: Chiralcel OX-H, Mobile Phase: 0.5% isopropyl amine in methanol; co-solvent 30% CO$_2$; Flow rate: 3 ml/min, pressure: 100 bar; Temperature: 35° C. to obtain the two enantiomers 24-4a and 24-4b.

Example 24-4a: 2-({4-[(2-imino-5-methyl-2,3-dihydro-1,3-oxazol-3-yl)methyl]-1H-1,3-benzodiazol-2-yl}amino)-2-[3-(trifluoromethyl)phenyl]propyl 2,2-dimethylpropanoate (Enantiomer A)

Enantiomer A was the first compound to elute off the column.

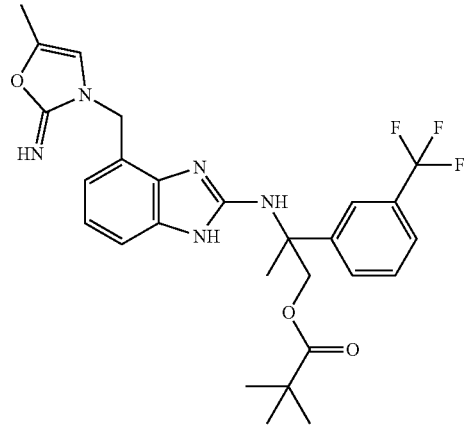 [SMILES: Cc1cn(Cc2cccc3[nH]c(NC(C)(COC(=O)C(C)(C)C)c4cccc(C(F)(F)F)c4)nc23)c(=N)o1]

$^1$H NMR (400 MHz, DMSO-d$_6$: D$_2$O) δ 7.80-7.65 (m, 4H), 7.32 (d, J=10.40 Hz, 1H), 7.20 (d, J=10.00 Hz, 1H), 7.06 (d, J=10.40 Hz, 1H), 6.89 (s, 1H), 5.16 (s, 2H), 4.48 (s, 2H), 2.16 (s, 3H), 1.91 (s, 3H), 1.03 (s, 9H);

MS: m/z 530.2 [(M+1).

Example 24-4b: 2-({4-[(2-imino-5-methyl-2,3-dihydro-1,3-oxazol-3-yl)methyl]-1H-1,3-benzodiazol-2-yl}amino)-2-[3-(trifluoromethyl)phenyl]propyl 2,2-dimethylpropanoate (Enantiomer B)

Enantiomer B was the second compound to elute off the column.

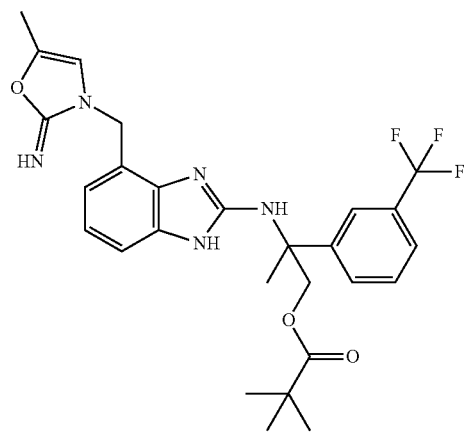 [SMILES: Cc1cn(Cc2cccc3[nH]c(NC(C)(COC(=O)C(C)(C)C)c4cccc(C(F)(F)F)c4)nc23)c(=N)o1]

$^1$H NMR (400 MHz, DMSO-d$_6$: D$_2$O) δ 7.80-7.65 (m, 4H), 7.32 (d, J=10.40 Hz, 1H), 7.20 (d, J=10.00 Hz, 1H), 7.06 (d, J=10.40 Hz, 1H), 6.89 (s, 1H), 5.16 (s, 2H), 4.48 (s, 2H), 2.16 (s, 3H), 1.91 (s, 3H), 1.03 (s, 9H);

MS: m/z 530.2 [(M+1).

Example 24: Preparation of 2-({4-[(2-imino-5-methyl-2,3-dihydro-1,3-oxazol-3-yl)methyl]-1H-1,3-benzodiazol-2-yl}amino)-2-[3-(trifluoromethyl)phenyl]propan-1-ol

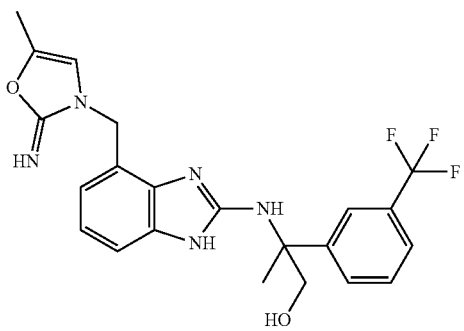 [SMILES: Cc1cn(Cc2cccc3[nH]c(NC(C)(CO)c4cccc(C(F)(F)F)c4)nc23)c(=N)o1]

To a solution of 2-({4-[(2-imino-5-methyl-2,3-dihydro-1,3-oxazol-3-yl)methyl]-1H-1,3-benzodiazol-2-yl}amino)-2-[3-(trifluoromethyl)phenyl]propyl 2,2-dimethylpropanoate; trifluoroacetic acid (Example 24, Step 4) (0.130 g, 0.202 mmol) in methanol (20 mL) was added 0.5 N sodium hydroxide in methanol (1.62 ml, 0.808 mmol) dropwise and stirred at ambient temperature for 1.5 h. The reaction mixture was quenched with 1.5 N hydrochloride solution (1 mL) and concentrated under reduced pressure at 30° C. to afford a brown gum (0.110 g). This was purified by preparative HPLC using 0.1% TFA in acetonitrile:water to afford 2-({4-[(2-imino-5-methyl-2,3-dihydro-1,3-oxazol-3-yl)methyl]-1H-1,3-benzodiazol-2-yl}amino)-2-[3-(trifluoromethyl)phenyl]propan-1-ol, isolated as the trifluoroacetate salt, (0.055 g) as a brown gum.

$^1$H NMR (400 MHz, AcOH-$d_4$) δ 7.83 (t, J=8.00 Hz, 2H), 7.67 (d, J=7.20 Hz, 1H), 7.59 (t, J=7.60 Hz, 1H), 7.37 (d, J=6.80 Hz, 1H), 7.30-7.26 (m, 2H), 6.81 (s, 1H), 5.32 (d, J=2.80 Hz, 2H), 4.41 (d, J=12.00 Hz, 1H), 4.12 (d, J=12.00 Hz, 1H), 2.24 (s, 3H), 1.80 (s, 3H);

MS: m/z 446.1[(M+1)].

Example 24a: Preparation of (+2-({4-[(2-imino-5-methyl-2,3-dihydro-1,3-oxazol-3-yl)methyl]-1H-1,3-benzodiazol-2-yl}amino)-2-[3-(trifluoromethyl)phenyl]propan-1-ol

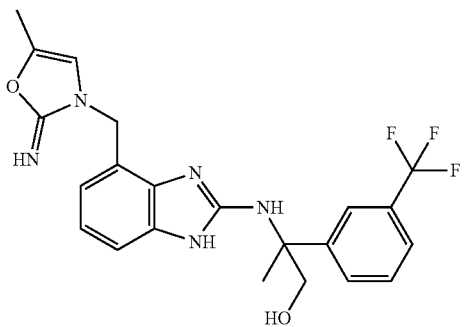 [SMILES: Cc1cn(Cc2cccc3[nH]c(NC(C)(CO)c4cccc(C(F)(F)F)c4)nc23)c(=N)o1]

To a solution of 2-({4-[(2-imino-5-methyl-2,3-dihydro-1,3-oxazol-3-yl)methyl]-1H-1,3-benzodiazol-2-yl}amino)-2-[3-(trifluoromethyl)phenyl]propyl 2,2-dimethylpropanoate (Example 24-4a, Enantiomer A) (0.350 g, 0.545 mmol) in methanol (40 mL) was added 0.5 N sodium hydroxide in methanol (4.36 ml, 2.18 mmol) dropwise and stirred at ambient temperature for 2 h. The reaction mixture was quenched with 1.5 N hydrochloride solution (3 mL) and concentrated under reduced pressure at 30° C. to afford a brown gum (0.300 g). This was purified by preparative HPLC using 0.1% TFA in acetonitrile:water to afford (−)-2-({4-[(2-imino-5-methyl-2,3-dihydro-1,3-oxazol-3-yl)methyl]-1H-1,3-benzodiazol-2-yl}amino)-2-[3-(trifluoromethyl)phenyl]propan-1-ol, isolated as the trifluoroacetate salt, (0.160 g) as a colorless gum.

$^1$H NMR (400 MHz, AcOH-$d_4$) δ 7.83 (t, J=8.00 Hz, 2H), 7.67 (d, J=7.20 Hz, 1H), 7.59 (t, J=7.60 Hz, 1H), 7.38 (dd, J=6.62, 2.36 Hz, 1H), 7.30-7.26 (m, 2H), 6.81 (s, 1H), 5.32 (d, J=2.80 Hz, 2H), 4.41 (d, J=12.00 Hz, 1H), 4.12 (d, J=12.00 Hz, 1H), 2.24 (s, 3H), 1.80 (s, 3H);

MS: m/z 446.1 (M+1);

SOR: $[α]_D^{20.5}$ (−) 6.80, (MeOH, c=0.5).

Example 24b: Preparation of (+)-2-({4-[(2-imino-5-methyl-2,3-dihydro-1,3-oxazol-3-yl)methyl]-1H-1,3-benzodiazol-2-yl}amino)-2-[3-(trifluoromethyl)phenyl]propan-1-ol

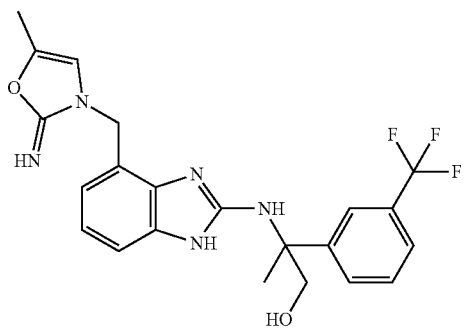 [SMILES: Cc1cn(Cc2cccc3[nH]c(NC(C)(CO)c4cccc(C(F)(F)F)c4)nc23)c(=N)o1]

To a solution of 2-({4-[(2-imino-5-methyl-2,3-dihydro-1,3-oxazol-3-yl)methyl]-1H-1,3-benzodiazol-2-yl}amino)-2-[3-(trifluoromethyl)phenyl]propyl 2,2-dimethylpropanoate (Example 24-4b, Enantiomer B) (0.170 g, 0.265 mmol) in methanol (20 mL) was added 0.5 N sodium hydroxide in methanol (2.12 ml, 0.106 mmol) dropwise and stirred at ambient temperature for 2 h. The reaction mixture was quenched with 1.5 N hydrochloride solution (2 mL) and concentrated under reduced pressure at 30° C. to afford a brown gum (0.150 g). This was purified by preparative HPLC using 0.1% TFA in acetonitrile:water to afford (+)-2-({4-[(2-imino-5-methyl-2,3-dihydro-1,3-oxazol-3-yl)methyl]-1H-1,3-benzodiazol-2-yl}amino)-2-[3-(trifluoromethyl)phenyl]propan-1-ol, isolated as the trifluoroacetate salt, (0.120 g) as a colorless gum.

$^1$H NMR (400 MHz, AcOH-$d_4$) δ 7.83 (t, J=8.00 Hz, 2H), 7.67 (d, J=7.20 Hz, 1H), 7.59 (t, J=7.60 Hz, 1H), 7.38 (dd, J=6.62, 2.36 Hz, 1H), 7.30-7.26 (m, 2H), 6.81 (s, 1H), 5.32 (d, J=2.80 Hz, 2H), 4.41 (d, J=12.00 Hz, 1H), 4.12 (d, J=12.00 Hz, 1H), 2.24 (s, 3H), 1.80 (s, 3H);

MS: m/z 446.1 (M+1);

SOR: $[α]_D^{20.9}$ (+) 7.20, (MeOH, c=0.5).

Example 25: Preparation of 2-({4-[(2-imino-2,3-dihydro-1,3-oxazol-3-yl)methyl]-1H-1,3-benzodiazol-2-yl}amino)-2-[3-(trifluoromethyl)phenyl]butan-1-ol

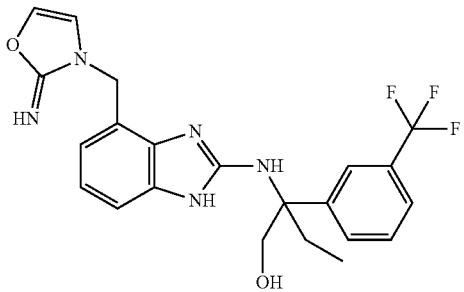 [SMILES: CCC(CO)(Nc1nc2c(Cn3ccoc3=N)cccc2[nH]1)c1cccc(C(F)(F)F)c1]

Example 25, Step 1: Preparation of 5-ethyl-5-(3-(trifluoromethyl) phenyl) imidazolidine-2, 4-dione

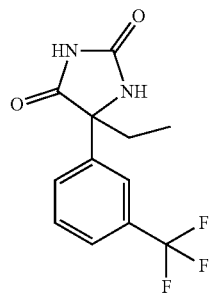 [SMILES: CCC1(c2cccc(C(F)(F)F)c2)NC(=O)NC1=O]

To a stirred solution of 1-(3-(trifluoromethyl) phenyl) propan-1-one (commercially available) (45.0 g, 223.0 mmol) in a mixture of solvents ethanol/water (1:1; 1000 mL) was added ammonium carbonate (107.0 g, 1110.0 mmol) followed by potassium cyanide (17.10 g, 263.0 mmol) and the mixture was stirred at 60° C. for 16 h. The reaction mixture was poured into ice-cold water (1500 mL) and it was stirred for 30 min. The solid that formed was filtered off and dried to afford 5-ethyl-5-(3-(trifluoromethyl) phenyl) imidazolidine-2, 4-dione (55.0 g) as an off-white solid, which was used in the next step without further purification.

$^1$H NMR (400 MHz, DMSO-d$_6$: D$_2$O) δ 7.78 (d, 1H, J=7.68 Hz), 7.75 (s, 1H), 7.68 (d, 1H, J=7.84 Hz), 7.63 (t, 1H, J=7.76 Hz), 2.08 (q, 1H, J=7.20 Hz), 1.90 (q, 1H, J=7.32 Hz), 0.78 (t, 3H, J=7.24 Hz);
MS: m/z 271.1 (M−1).

Example 25, Step 2: Preparation of 2-amino-2-(3-(trifluoromethyl)phenyl) butanoic acid

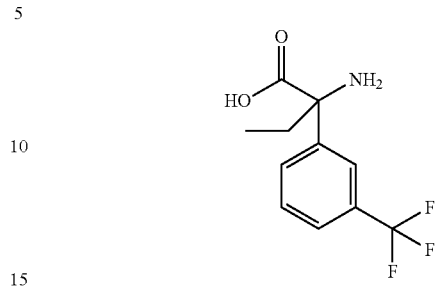

5-ethyl-5-(3-(trifluoromethyl)phenyl)imidazolidine-2,4-dione (from Example 25, Step 1) (55.0 g, 202.0 mmol) was dissolved in 10% aqueous sodium hydroxide solution (350 mL) and the mixture was refluxed for 48 h. The reaction mixture was neutralized (adjusted pH=7) with 6.0 N HCl (200 mL) and the solid that formed was filtered and dried to afford 2-amino-2-(3-(trifluoromethyl) phenyl) butanoic acid (31.0 g) as a white solid, which was used in the next step without further purification.

$^1$H NMR (400 MHz, DMSO-d$_6$: D$_2$O) δ 7.86 (s, 1H), 7.80 (d, 1H, J=7.60 Hz), 7.62 (d, 1H, J=7.60 Hz), 7.57 (t, 1H, J=7.60 Hz), 2.14-2.08 (m, 2H), 0.81 (t, 3H, J=7.60 Hz);
MS: m/z 248.2 (M+1).

Example 25, Step 3: Preparation of 2-amino-2-(3-(trifluoromethyl) phenyl) butan-1-ol

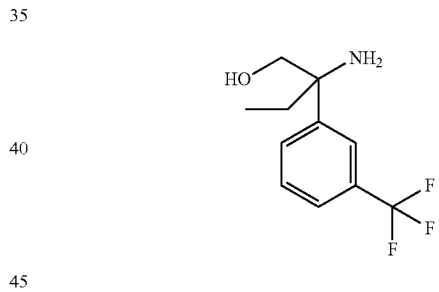

To a solution of 2-amino-2-(3-(trifluoromethyl) phenyl) butanoic acid (from Example 25, Step 2) (40.00 g, 162.00 mmol) in dry tetrahydrofuran (1200 mL) was added 2M solution of lithium aluminumhydride in tetrahydrofuran (202.0 mL, 405.0 mmol) at 0° C. and the reaction mixture was slowly warmed to ambient temperature and stirred for 3 h. The reaction mixture was cooled to 0° C. and quenched with dropwise addition of ethyl acetate solution (120 mL) and stirred for 30 min. Then treated with saturated solution of ammonium chloride dropwise (150 mL) and stirred for 15 min at 0° C. The precipitate obtained was separated by filtration and the filtrate was concentrated under reduced pressure to afford a yellow gum (40.00 g). This was diluted with 10% sodium hydroxide solution (100 mL) and extracted with ethyl acetate (4×1000 mL). The combined organic layer was dried over anhydrous sodium sulphate, filtered and concentrated to afford 2-amino-2-(3-(trifluoromethyl)phenyl)butan-1-ol (18.50 g) as a yellow oil, which was used in the next step without further purification.

$^1$H NMR (400 MHz, DMSO-d$_6$) δ 7.85 (s, 1H), 7.75 (d, 1H, J=6.00 Hz), 7.53 (d, 2H, J=6.40 Hz), 4.76 (t, 1H, J=5.60

Hz), 3.54 (dd, 2H, J=10.20, 5.60 Hz), 1.84 (s, 2H), 1.75 (q, 1H, J=7.60 Hz), 1.62 (q, 1H, J=6.80 Hz), 0.61 (t, 3H, J=7.60 Hz);

MS: m/z 234.1 (M+1).

Example 25, Step 4: Preparation of tert-butyl N-{1-hydroxy-2-[3-(trifluoromethyl)phenyl]butan-2-yl}carbamate

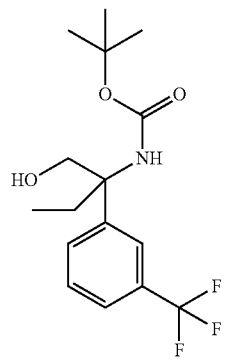 [SMILES: CCC(CO)(NC(=O)OC(C)(C)C)c1cccc(C(F)(F)F)c1]

To a suspension of 2-amino-2-(3-(trifluoromethyl)phenyl) butan-1-ol (from Example 25, Step 3) (18.50 g, 51.60 mmol) in a mixture of solvents dichloromethane:1, 4-dioxane (4:1; 500 mL) was added di-tert-butyl dicarbonate (13.50 mL, d: 0.950 g/cm³, 61.90 mmol) dropwise at 0° C. and the mixture was stirred at ambient temperature for 48 h. The reaction mixture was diluted with water (200 mL) and extracted with ethyl acetate (4×1000 mL). The combined organic layer was dried over sodium sulphate, filtered and concentrated to afford a yellow gum (18.00 g). This was purified by chromatography on a Grace instrument using 220 g pre-packed flash cartridge filled with normal phase silica gel 60 Å, 40-63 μm and the product eluted with 25-30% ethyl acetate in hexane to afford tert-butyl N-{1-hydroxy-2-[3-(trifluoromethyl)phenyl]butan-2-yl}carbamate (11.50 g) as a colourless gum.

$^1$H NMR (400 MHz, DMSO-$d_6$: $D_2O$) δ 7.58 (s, 1H), 7.56 (d, 2H, J=2.16 Hz), 7.53 (t, 1H, J=6.32 Hz), 3.61 (t, 2H, J=12.40 Hz), 1.97 (q, 2H, J=7.64 Hz), 1.46 (s, 9H), 0.61 (t, 3H, J=7.60 Hz);

MS: m/z 234.2 [(M+1)-Boc].

Example 25, Step 5: Preparation of 2-{[(tert-butoxy)carbonyl]amino}-2-[3-(trifluoromethyl)phenyl] butyl 2,2-dimethylpropanoate

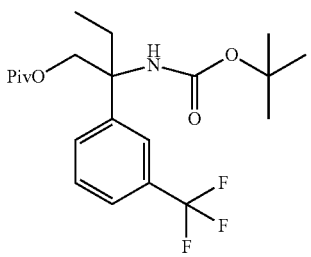

To a solution of tert-butyl N-{1-hydroxy-2-[3-(trifluoromethyl)phenyl]butan-2-yl}carbamate (from Example 25, Step 4) (11.50 g, 34.50 mmol) in dry dichloromethane (300 mL) under a nitrogen atmosphere was added triethylamine (31.30 mL, d=0.726 g/cm³, 224.0 mmol) followed by pivaloyl chloride (12.70 mL, d=0.985 g/cm³, 103.00 mmol) at 0° C., dropwise and the reaction mixture was stirred at ambient temperature for 48 h. The reaction mixture was quenched with ice cold water (100 mL) and extracted with dichloromethane (4×500 mL). The combined organic layer was dried over sodium sulphate, filtered and concentrated to afford a brown gum (15.00 g). This was purified by chromatography on a Grace instrument using 120 g pre-packed flash cartridge filled with normal phase silica gel 60 Å, 40-63 μm and the product eluted with 15-20% ethyl acetate in hexane to afford 2-{[(tert-butoxy)carbonyl]amino}-2-[3-(trifluoromethyl)phenyl]butyl 2,2-di methylpropanoate (10.0 g) as a colourless gum.

$^1$H NMR (400 MHz, DMSO-$d_6$: $D_2O$) δ 7.61 (s, 1H), 7.59 (d, 2H, J=7.52 Hz), 7.58 (t, 1H, J=7.00 Hz), 4.38 (q, 2H, J=14.40 Hz), 1.95 (q, 2H, J=7.28 Hz), 1.39 (s, 9H), 1.11 (s, 9H), 1.09 (t, 3H, J=6.08 Hz);

MS: m/z 318.2 [(M+1)-Boc].

Example 25, Step 6: Preparation of 2-amino-2-[3-(trifluoromethyl)phenyl]butyl 2,2-dimethylpropanoate hydrochloride

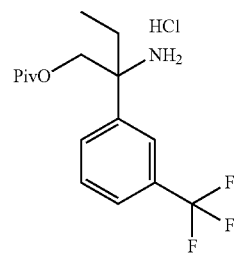

To a solution of 2-{[(tert-butoxy)carbonyl]amino}-2-[3-(trifluoromethyl)phenyl]butyl 2,2-dimethylpropanoate (from Example 25, Step 5) (10.00 g, 24.00 mmol) in dry dichloromethane (300 mL) under a nitrogen atmosphere was added 4M HCl in dioxane solution (15.00 mL, 59.90 mmol) dropwise at 0° C. The reaction mixture was stirred at ambient temperature for 16 h, then concentrated and the residue was triturated with hexane (3×250 mL). The supernatant layer was decanted and the solid was dried to afford 2-amino-2-[3-(trifluoromethyl)phenyl]butyl 2,2-dimethylpropanoate hydrochloride (8.50 g) as a colourless gum, which was used in the next step without further purification.

$^1$H NMR (400 MHz, DMSO-$d_6$: $D_2O$) δ 7.74 (s, 1H), 7.68 (d, 2H, J=13.60 Hz), 7.56 (t, 1H, J=8.84 Hz), 4.56 (d, 1H, J=12.08 Hz), 4.22 (d, 1H, J=12.12 Hz), 2.17-1.97 (m, 2H), 1.02 (s, 9H), 0.78 (t, 3H, J=7.36 Hz);

MS: m/z 318.2 [(M+1)-HCl].

Example 25, Step 7: Preparation of 2-isothiocyanato-2-[3-(trifluoromethyl)phenyl]butyl 2,2-dimethylpropanoate

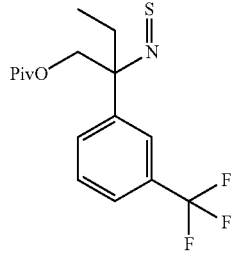

To a solution of 2-amino-2-[3-(trifluoromethyl)phenyl] butyl 2,2-dimethylpropanoate hydrochloride (from Example 25, Step 6) (8.50 g, 24.00 mmol) in dry dichloromethane (300 mL) was added 10% aqueous sodium bicarbonate solution (300 mL) at 0° C. After 30 min, thiophosgene (11.00 mL, d=1.5 g/cm$^3$, 144.0 mmol) was added and the mixture was stirred at the same temperature for 1 h. The reaction mixture was extracted with dichloromethane (3×500 mL) and the combined organic layer was dried over anhydrous sodium sulphate, filtered, and concentrated to afford a yellow liquid (9.00 g). This was purified by chromatography on a Grace instrument using 60.0 g pre-packed flash cartridge filled with normal phase silica gel 60 Å, 40-63 µm and the product was eluted with 5-10% ethyl acetate in hexane to afford 2-isothiocyanato-2-[3-(trifluoromethyl)phenyl]butyl 2,2-dimethylpropanoate (6.50 g) as a yellow liquid $^1$H NMR (400 MHz, DMSO-d$_6$) δ 7.62 (s, 1H), 7.59 (d, 2H, J=7.16 Hz), 7.56 (t, 1H, J=7.76 Hz), 4.39 (d, 2H, J=4.04 Hz), 2.21 (q, 1H, J=7.20 Hz), 2.07 (q, 1H, J=6.96 Hz), 1.16 (s, 9H), 0.91 (t, 3H, J=7.12 Hz).

Example 25, Step 8: Preparation of 2-[({2-amino-3-[(2-imino-2,3-dihydro-1,3-oxazol-3-yl)methyl]phenyl}carbamothioyl)amino]-2-[3-(trifluoromethyl)phenyl]butyl 2,2-dimethylpropanoate and 2-[({2-amino-6-[(2-imino-2,3-dihydro-1,3-oxazol-3-yl)methyl]phenyl}carbamothioyl)amino]-2-[3-(trifluoromethyl)phenyl]butyl 2,2-dimethylpropanoate (Mixture of Regioisomers)

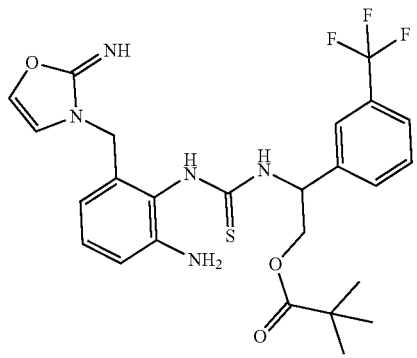

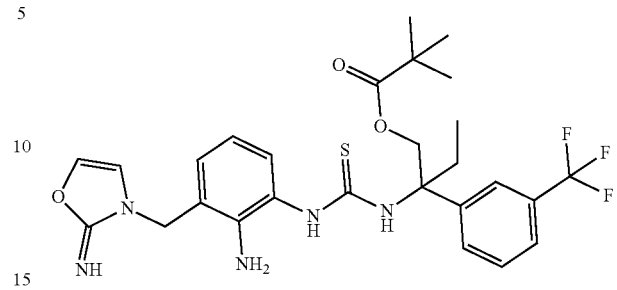

To a solution of 3-[(2-imino-2,3-dihydro-1,3-oxazol-3-yl)methyl]benzene-1,2-diamine (Example 1, step 5)) (0.300 g, 1.47 mmol) in a mixture of solvents dichloromethane:methanol (1:1; 8 mL) was added [2-isothiocyanato-2-[3-(trifluoromethyl)phenyl]butyl] 2,2-dimethylpropanoate (from Example 25, Step 7) (0.317 g, 0.880 mmol) and stirred at ambient temperature for 72 h. The reaction mixture was concentrated at 30° C. in a water bath to afford 2-[({2-amino-3-[(2-imino-2,3-dihydro-1,3-oxazol-3-yl)methyl]phenyl}carbamothioyl)amino]-2-[3-(trifluoromethyl)phenyl]butyl 2,2-dimethylpropanoate and 2-[({2-amino-6-[(2-imino-2,3-dihydro-1,3-oxazol-3-yl)methyl]phenyl}carbamothioyl)amino]-2-[3-(trifluoromethyl)phenyl]butyl 2,2-dimethylpropanoate (as a mixture of non-separable regioisomers) (0.600 g) as a brown gum, which was used in the next step without purification.

MS: m/z 564.4 (M+1).

Example 25, Step 9: Preparation of 2-({4-[(2-imino-2,3-dihydro-1,3-oxazol-3-yl)methyl]-1H-1,3-benzodiazol-2-yl}amino)-2-[3-(trifluoromethyl)phenyl]butyl 2,2-dimethylpropanoate

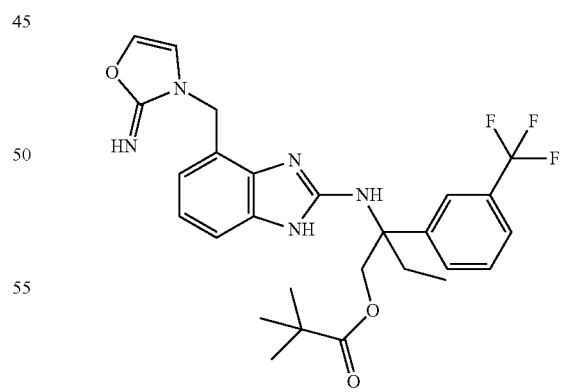

To a solution of 2-[({2-amino-3-[(2-imino-2,3-dihydro-1,3-oxazol-3-yl)methyl]phenyl}carbamothioyl)amino]-2-[3-(trifluoromethyl)phenyl]butyl 2,2-dimethylpropanoate and 2-[({2-amino-6-[(2-imino-2,3-dihydro-1,3-oxazol-3-yl)methyl]phenyl}carbamothioyl)amino]-2-[3-(trifluoromethyl)phenyl]butyl 2,2-dimethylpropanoate (as a mixture of non-separable regioisomers) (Example 25, Step 8) (0.600 g, 1.06 mmol) in methanol (8 mL) was added iodoacetic acid (0.297 g, 1.60 mmol) and the mixture was refluxed for 1.5 h. The reaction mixture was concentrated at 30° C. to remove the solvent methanol to afford a brown gum (0.700 g). This was purified by preparative HPLC (TFA:Acetonitrile) to afford 2-({4-[(2-imino-2,3-dihydro-1,3-oxazol-3-yl)methyl]-1H-1,3-benzodiazol-2-yl}amino)-2-[3-(trifluoromethyl)phenyl]butyl 2,2-dimethylpropanoate, isolated as the trifluoroacetate salt, (0.090 g) as a brown gum.

$^1$H NMR (400 MHz, AcOH-d$_4$) δ 7.82 (d, J=6.44 Hz, 2H), 7.74 (d, J=7.60 Hz, 1H), 7.66 (t, J=7.84 Hz, 1H), 7.58 (s, 1H), 7.32-7.30 (m, 3H), 7.23 (s, 1H), 5.40 (s, 2H), 4.94 (d, J=11.84 Hz, 1H), 4.76 (d, J=11.92 Hz, 1H), 2.35 (q, J=7.08 Hz, 2H), 1.15 (s, 9H), 0.92 (t, J=7.40 Hz, 3H);

MS: m/z 530.2/531.2 (M+1).

Example 25: Preparation 2-({4-[(2-imino-2,3-dihydro-1,3-oxazol-3-yl)methyl]-1H-1,3-benzodiazol-2-yl}amino)-2-[3-(trifluoromethyl)phenyl]butan-1-ol

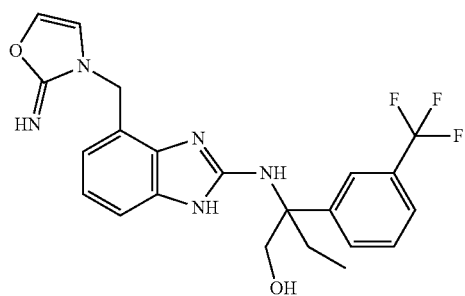 [SMILES: CCC(CO)(Nc1nc2c(Cn3ccoc3=N)cccc2[nH]1)c1cccc(C(F)(F)F)c1]

To a solution of 2-({4-[(2-imino-2,3-dihydro-1,3-oxazol-3-yl)methyl]-1H-1,3-benzodiazol-2-yl}amino)-2-[3-(trifluoromethyl)phenyl]butyl 2,2-dimethylpropanoate; trifluoroacetic acid (Example 25, Step 9) (0.080 g, 0.124 mmol) in methanol (10 mL) was added 0.5 N sodium hydroxide in methanol (0.990 mL, 0.497 mmol) dropwise and the mixture was stirred at ambient temperature for 3 h. The reaction mixture was quenched with 1.5 N hydrochloride solution (1 mL) and concentrated under reduced pressure at 30° C. to afford a brown gum (0.070 g). This was purified by preparative HPLC using 0.1% TFA in acetonitrile:water to afford 2-({4-[(2-imino-2,3-dihydro-1,3-oxazol-3-yl)methyl]-1H-1,3-benzodiazol-2-yl}amino)-2-[3-(trifluoromethyl)phenyl]butan-1-ol, isolated as the trifluoroacetate salt, (0.020 g) as a brown gum.

1H NMR (400 MHz, AcOH-d$_4$) δ 7.82 (s, 1H), 7.77 (d, J=8.00 Hz, 1H), 7.69 (d, J=8.00 Hz, 1H), 7.61 (t, J=8.00 Hz, 1H), 7.56 (d, J=1.60 Hz, 1H), 7.38 (dd, J=6.80, 2.00 Hz, 1H), 7.31-7.26 (m, 2H), 7.20 (d, J=1.60 Hz, 1H), 5.40 (q, J=16.00 Hz, 2H), 4.69 (d, J=12.40 Hz, 1H), 4.29 (d, J=12.40 Hz, 1H), 2.07 (q, J=7.32 Hz, 2H), 0.86 (t, J=7.20 Hz, 3H);

MS: m/z 446.1/447.1 [(M+1)].

Example 26: Preparation of 3-({4-[(2-imino-2,3-dihydro-1,3-oxazol-3-yl)methyl]-1H-1,3-benzodiazol-2-yl}amino)-3-[3-(trifluoromethyl)phenyl]butan-1-ol

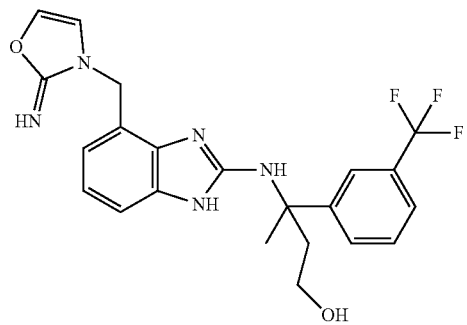 [SMILES: CC(CCO)(Nc1nc2c(Cn3ccoc3=N)cccc2[nH]1)c1cccc(C(F)(F)F)c1]

Example 26, Step 1: Preparation of (E)-2-methyl-N-(1-(3-(trifluoromethyl)phenyl) ethylidene)propane-2-sulfinamide

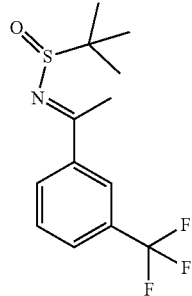 [SMILES: C/C(=N\S(=O)C(C)(C)C)c1cccc(C(F)(F)F)c1]

To a solution of 1-(3-(trifluoromethyl)phenyl)ethan-1-one (commercially available) (125.0 g, 664.0 mmol) under a nitrogen atmosphere in dry tetrahydrofuran (1500 mL) was added 2-methyl propane-2-sulfinamide (80.52 g, 664.00 mmol) followed by titanium (IV) ethoxide (278.60 mL, d=1.008 gm/mL, 1328.0 mmol) and the mixture was heated to 70° C. for 17 h. The reaction mixture was diluted with brine solution (200 mL), filtered and the filtrate was evaporated to afford a yellowish gum (200.0 g). This was purified by gravity column chromatography using silica gel 60-120 mesh) and the product was eluted with 10% ethyl acetate in hexane to afford of (E)-2-methyl-N-(1-(3-(trifluoromethyl)phenyl)ethylidene) propane-2-sulfinamide (150.0 g) as a yellowish gum.

$^1$H NMR (400 MHz, CD$_3$OD) δ 8.25 (s, 1H), 8.23 (d, J=7.60 Hz, 1H), 7.88 (d, J=7.60 Hz, 1H), 7.72 (t, J=8.00 Hz, 1H), 2.84 (s, 3H), 1.35 (s, 9H);

MS: m/z 292.3 (M+1).

Example 26, Step 2: Preparation of methyl 3-((tert-butylsulfinyl)amino)-3-(3-(trifluoromethyl)phenyl)butanoate

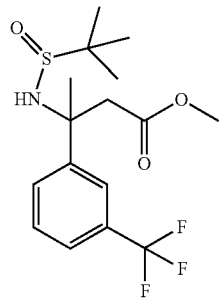 [SMILES: COC(=O)CC(C)(NS(=O)C(C)(C)C)c1cccc(C(F)(F)F)c1]

To a suspension of zinc dust (269.3 g, 4.120 gm atom) in dry tetrahydrofuran (750 mL) was added copper (I) chloride (51.0 g, 515.0 mmol) and the mixture was stirred at 60° C. After 30 min, a solution of methyl 2-bromoacetate (122.0 mL, d=1.616 gm/mL, 1287.0 mmol) in dry tetrahydrofuran (500 mL) was added dropwise and it was stirred for 30 min at same temperature. A solution of (E)-2-methyl-N-(1-(3-(trifluoromethyl)phenyl)ethylidene) propane-2-sulfinamide (from Example 26, Step 1) (150.0 g, 515.0 mmol) in dry tetrahydrofuran (500 mL) was added dropwise at 0-5° C. and stirred at same temperature for 1 h. The reaction mixture was quenched with saturated ammonium chloride solution (200 mL) and the solid that formed was filtered and the filtrate was extracted with ethyl acetate (3×1000 mL). The combined organic extracts were dried over anhydrous sodium sulphate, filtered and evaporated to afford a brownish gum (250.0 g). This was purified by gravity column chromatography over 60-120 silica gel and the product was eluted with 70-75% ethyl acetate in hexane to afford methyl 3-((tert-butylsulfinyl)amino)-3-(3-(trifluoromethyl)phenyl)butanoate (135.0 g) as a yellowish gum.

$^1$H NMR (400 MHz, AcOH-d$_4$) δ 7.81 (d, J=7.6 Hz, 1H), 7.74 (d, J=8.00 Hz, 1H), 7.62 (d, J=7.60 Hz, 1H), 7.56 (t, J=8.00 Hz, 1H), 3.62 (s, 3H), 3.20 (q, J=16.40 Hz, 2H), 1.87 (s, 3H), 1.35 (s, 9H);

MS: m/z 366.2 (M+1).

Example 26, Step 3: Preparation of N-(4-hydroxy-2-(3-(trifluoromethyl)phenyl)butan-2-yl)-2-methylpropane-2-sulfinamide

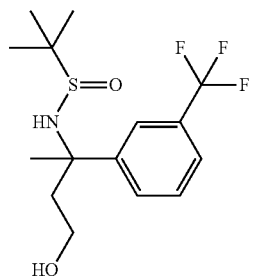 [SMILES: CC(CCO)(NS(=O)C(C)(C)C)c1cccc(C(F)(F)F)c1]

To a stirred solution of methyl 3-((tert-butylsulfinyl)amino)-3-(3-(trifluoromethyl)-phenyl)butanoate (from Example 26, Step 2) (20.00 g, 54.70 mmol) under a nitrogen atmosphere in dry tetrahydrofuran (300 mL) was added a 2M solution of lithium aluminium hydride in tetrahydrofuran (53.00 mL, 82.10 mmol) at 0° C. and the reaction mixture was stirred at the same temperature for 2 h. The reaction mixture was quenched with ethyl acetate (250 mL) followed by 10% aqueous ammonium chloride solution (200 mL) at 0° C. and the organic layer was separated and further extracted with ethyl acetate (4×750 mL). The combined organic layers were dried over sodium sulphate, filtered and concentrated to afford N-(4-hydroxy-2-(3-(trifluoromethyl)-phenyl)butan-2-yl)-2-methylpropane-2-sulfinamide (10.00 g) as a yellow oil, which was used in the next step without further purification.

$^1$H NMR (400 MHz, DMSO-d$_6$) δ 7.77 (s, 1H), 7.75 (d, J=7.60 Hz, 1H), 7.61 (t, J=7.60 Hz, 1H), 7.57 (d, J=7.60 Hz, 1H), 5.80 (s, 1H), 4.81 (t, J=4.80 Hz, 1H), 3.49 (q, J=4.80 Hz, 1H), 3.31 (q, J=4.00 Hz, 1H), 2.11 (q, J=7.20 Hz, 1H), 1.89 (q, J=6.00 Hz, 1H), 1.74 (s, 3H), 1.13 (s, 9H);

MS: m/z 338.2 (M+1).

Example 26, Step 4: Preparation of 3-[(2-methylpropane-2-sulfinyl)amino]-3-[3-(trifluoromethyl)phenyl]butyl 2,2-dimethylpropanoate

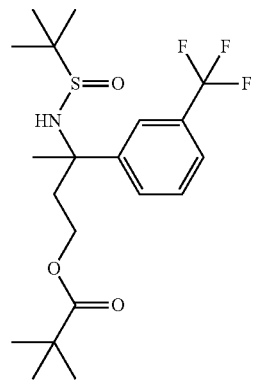 [SMILES: CC(C)(C)C(=O)OCCC(C)(NS(=O)C(C)(C)C)c1cccc(C(F)(F)F)c1]

To a suspension of N-(4-hydroxy-2-(3-(trifluoromethyl)phenyl)butan-2-yl)-2-methylpropane-2-sulfinamide (from Example 26, Step 3) (13.00 g, 38.50 mmol) under a nitrogen atmosphere in dry tetrahydrofuran (300 mL) was added sodium hydride (1.77 g, 77.10 mmol) at 0° C. and stirred at the same temperature for 30 min. Pivaloyl chloride (7.10 mL, d=0.985 g/cm$^3$, 57.80 mmol) was added and the reaction mixture was stirred at 0° C. for 3 h. The reaction mixture was quenched with ethyl acetate (200 mL) followed by 10% aqueous ammonium chloride solution (150 mL) at 0° C. and the organic layer was separated and further extracted with ethyl acetate (4×500 mL). The combined organic layers were dried over sodium sulphate, filtered and concentrated to afford a yellow liquid (17.0 g). This was purified by chromatography on a Grace instrument using 220.00 g pre-packed flash cartridge filled with normal phase silica gel 60 Å, 40-63 μm and the product was eluted with 35% ethyl acetate in hexane to afford 3-[(2-methylpropane-2-sulfinyl)amino]-3-[3-(trifluoromethyl)-phenyl]butyl 2,2-dimethylpropanoate (15.0 g) as a yellow oil.

$^1$H NMR (400 MHz, DMSO-d$_6$) δ 7.78 (s, 1H), 7.76 (d, J=7.60 Hz, 1H), 7.59 (t, J=7.32 Hz, 1H), 7.56 (d, J=7.60 Hz,

1H), 5.51 (s, 1H), 3.91 (t, J=8.80 Hz, 2H), 2.27 (t, J=8.40 Hz, 2H), 1.71 (s, 3H), 1.13 (s, 9H), 1.01 (s, 9H);
MS: m/z 422.1 (M+1).

Example 26, Step 5: Preparation of 3-amino-3-[3-(trifluoromethyl)phenyl]butyl 2,2-dimethylpropanoate hydrochloride

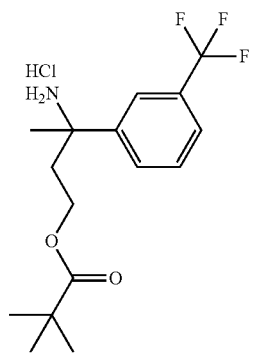 [SMILES: CC(C)(C)C(=O)OCCC(C)(N)c1cccc(C(F)(F)F)c1 ; Cl]

To a stirred solution of 3-[(2-methylpropane-2-sulfinyl)amino]-3-[3-(trifluoromethyl)phenyl]butyl 2,2-dimethylpropanoate (from Example 26, Step 4) (15.00 g, 35.60 mmol) in dichloromethane (200 mL) was added 4M HCl in dioxane (4.50 mL, 178.0 mmol) at 0° C. and the mixture was stirred at ambient temperature for 12 h. The reaction mixture was concentrated to afford 3-amino-3-[3-(trifluoromethyl)phenyl]butyl 2,2-dimethylpropanoate hydrochloride (12.0 g) as a yellow gum, which was used in the next step without further purification.
¹H NMR (400 MHz, DMSO-d₆) δ 8.90 (bs, 3H), 7.95 (s, 1H), 7.91 (d, J=7.60 Hz, 1H), 7.78 (d, J=8.00 Hz, 1H), 7.72 (t, J=8.00 Hz, 1H), 3.97-3.88 (m, 2H), 2.39 (t, J=6.80 Hz, 2H), 1.76 (s, 3H), 0.097 (s, 9H);
MS: m/z 318.2 [(M+1)-HCl].

Example 26, Step 6: Preparation of 3-isothiocyanato-3-[3-(trifluoromethyl)phenyl]butyl 2,2-dimethylpropanoate

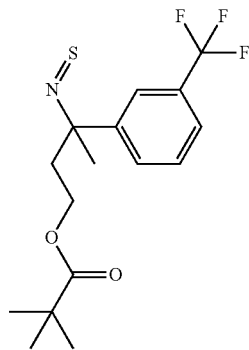 [SMILES: CC(C)(C)C(=O)OCCC(C)(N=S)c1cccc(C(F)(F)F)c1]

To a stirred solution of 3-amino-3-[3-(trifluoromethyl)phenyl]butyl 2,2-dimethylpropanoate hydrochloride (from Example 26, Step 5) (12.00 g, 33.90 mmol) in a biphasic mixture of dichloromethane (50 mL) and 10% aqueous sodium bicarbonate solution (50 mL) was added thiophosgene (3.90 mL, d=1.50 g/cm³, 50.90 mmol) at 0° C. and the mixture was stirred for 30 min. The organic layer was separated and further extracted with dichloromethane (2×250 mL). The combined organic extracts were dried over sodium sulphate, filtered and concentrated to afford 3-isothiocyanato-3-[3-(trifluoromethyl)phenyl]butyl 2,2-dimethylpropanoate (7.50 g) as a yellow oil, which was used in the next step without further purification.
¹H NMR (400 MHz, DMSO-d₆) δ 7.81 (s, 1H), 7.78 (s, 1H), 7.72 (t, J=7.20 Hz, 1H), 7.67 (d, J=8.80 Hz, 1H), 3.95 (t, J=7.60 Hz, 2H), 2.51 (d, J=8.80 Hz, 1H), 2.44 (d, J=8.40 Hz, 1H), 1.87 (s, 3H), 1.01 (s, 9H).

Example 26, Step 7: Preparation of 3-[({2-amino-3-[(2-imino-2,3-dihydro-1,3-oxazol-3-yl)methyl]phenyl}carbamothioyl)amino]-3-[3-(trifluoromethyl)-phenyl]butyl 2,2-dimethylpropanoate and 3-[({2-amino-6-[(2-imino-2,3-dihydro-1,3-oxazol-3-yl)methyl]phenyl}carbamothioyl)amino]-3-[3-(trifluoromethyl)-phenyl]butyl 2,2-dimethylpropanoate (Mixture of Regioisomers)

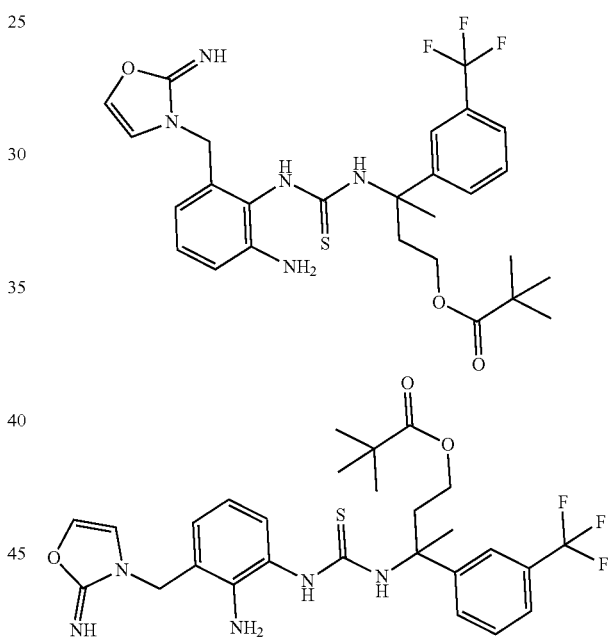

To a stirred solution of [3-isothiocyanato-3-[3-(trifluoromethyl)phenyl]butyl] 2,2-dimethyl propanoate (from Example 26, Step 6) (0.400 g, 1.11 mmol) in dichloromethane (10 mL) was added 3-[(2-imino-2,3-dihydro-1,3-oxazol-3-yl)methyl]benzene-1,2-diamine (from Example 1, Step 5) (0.273 g, 1.34 mmol) and the reaction mixture was stirred at ambient temperature for 48 h. The reaction mixture was concentrated to afford 3-[({2-amino-3-[(2-imino-2,3-dihydro-1,3-oxazol-3-yl)methyl]phenyl}carbamothioyl)amino]-3-[3-(trifluoromethyl)phenyl]butyl 2,2-dimethylpropanoate and 3-[({2-amino-6-[(2-imino-2,3-dihydro-1,3-oxazol-3-yl)methyl]phenyl}carbamothioyl)amino]-3-[3-(trifluoromethyl)phenyl]butyl 2,2-dimethylpropanoate (as a mixture of non-separable regioisomers) (0.600 g) as a brown gum, which was used in the next step without further purification.
MS: m/z 564.3 (M+1).

Example 26, Step 8: Preparation of 3-({4-[(2-imino-2,3-dihydro-1,3-oxazol-3-yl)methyl]-1H-1,3-benzodiazol-2-yl}amino)-3-[3-(trifluoromethyl)phenyl]butyl 2,2-dimethylpropanoate

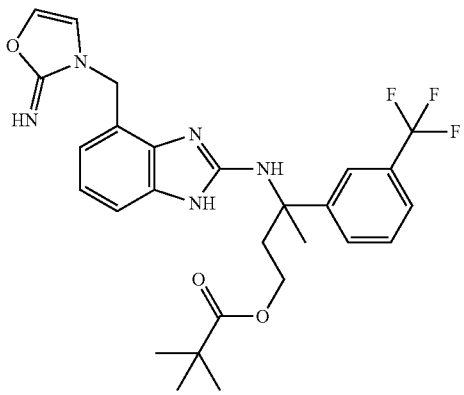 [SMILES: CC(C)(C)C(=O)OCCC(C)(Nc1nc2c(Cn3ccoc3=N)cccc2[nH]1)c1cccc(C(F)(F)F)c1]

To a solution of 3-[({2-amino-3-[(2-imino-2,3-dihydro-1,3-oxazol-3-yl)methyl]phenyl}carbamothioyl)amino]-3-[3-(trifluoromethyl)phenyl]butyl 2,2-dimethylpropanoate and 3-[({2-amino-6-[(2-imino-2,3-dihydro-1,3-oxazol-3-yl)methyl]phenyl}carbamothioyl)amino]-3-[3-(trifluoromethyl)phenyl]butyl 2,2-dimethylpropanoate (as a mixture of non-separable regioisomers) (from Example 26, Step 7) (0.600 g, 1.06 mmol) in methanol (20 mL) was added iodoacetic acid (0.198 g, 1.06 mmol) and the reaction mixture was stirred at ambient temperature for 3 h. The reaction mixture was concentrated to afford a brown gum (0.400 g), which was purified by preparative HPLC using a TFA method to afford 3-({4-[(2-imino-2,3-dihydro-1,3-oxazol-3-yl)methyl]-1H-1,3-benzodiazol-2-yl}amino)-3-[3-(trifluoromethyl)phenyl]butyl 2,2-dimethylpropanoate, isolated as the trifluoroacetate salt, (0.300 g) as a brown gum.

$^1$H NMR (400 MHz, AcOH-d$_4$) δ 7.91 (s, 1H), 7.85 (d, J=9.20 Hz, 1H), 7.70 (d, J=7.60 Hz, 1H), 7.62 (t, J=7.60 Hz, 1H), 7.59 (d, J=1.60 Hz, 1H), 7.34 (t, J=4.80 Hz, 1H), 7.29 (d, J=4.80 Hz, 2H), 7.25 (d, J=1.60 Hz, 1H), 5.44 (d, J=14.00 Hz, 2H), 4.27-4.10 (m, 2H), 2.63-2.53 (m, 2H), 2.02 (s, 3H), 1.11 (s, 9H);

MS: m/z 530.6 (M+1).

Example 26: Preparation 3-({4-[(2-imino-2,3-dihydro-1,3-oxazol-3-yl)methyl]-1H-1,3-benzodiazol-2-yl}amino)-3-[3-(trifluoromethyl)phenyl]butan-1-ol

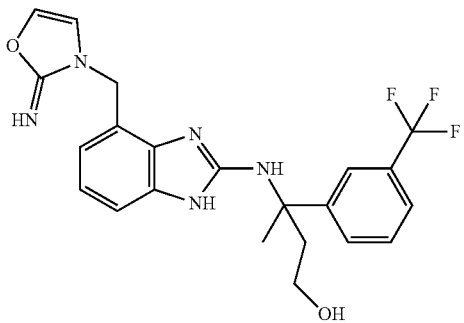 [SMILES: CC(CCO)(Nc1nc2c(Cn3ccoc3=N)cccc2[nH]1)c1cccc(C(F)(F)F)c1]

To a solution of 3-({4-[(2-imino-2,3-dihydro-1,3-oxazol-3-yl)methyl]-1H-1,3-benzodiazol-2-yl}amino)-3-[3-(trifluoromethyl)phenyl]butyl 2,2-dimethylpropanoate; trifluoroacetic acid (from Example 26, Step 8) (0.300 g, 0.466 mmol) in methanol (5 mL) was added a solution of 0.5 M sodium hydroxide in methanol (4.66 mL, 2.33 mmol) at 0° C. dropwise and the mixture was stirred at 28° C. for 4 h. The reaction mixture was quenched with 1.5N aqueous HCl solution (10 mL) and it was concentrated at 25° C. to afford a brown gum (0.100 g). This was purified by preparative HPLC in TFA method to afford 3-({4-[(2-imino-2,3-dihydro-1,3-oxazol-3-yl)methyl]-1H-1,3-benzodiazol-2-yl}amino)-3-[3-(trifluoromethyl)phenyl]butan-1-ol, isolated as the trifluoroacetate salt, (0.040 g) as a white solid.

$^1$H NMR (400 MHz, AcOH-d$_4$) δ 7.91 (s, 1H), 7.88 (dd, J=8.80, 17.80 Hz, 1H), 7.68 (dd, J=10.00, 17.20 Hz, 1H), 7.62 (t, J=7.60 Hz, 1H), 7.47-7.39 (m, 1H), 7.27 (d, J=1.60 Hz, 1H), 7.24 (t, J=7.20 Hz, 1H), 6.56 (dd, J=2.80 Hz, 1H), 6.50 (dd, J=0.80, 3.00 Hz, 1H), 4.88 (d, J=14.80 Hz, 2H), 3.88-3.80 (m, 2H), 2.51-2.41 (m, 2H), 2.04 (s, 3H);

MS: m/z 446.2 (M+1).

Example 27: Preparation of 2-({4-[(2-imino-2,3-dihydro-1,3-oxazol-3-yl)methyl]-1H-1,3-benzodiazol-2-yl}amino)-2-[3-(trifluoromethoxy)phenyl]propan-1-ol

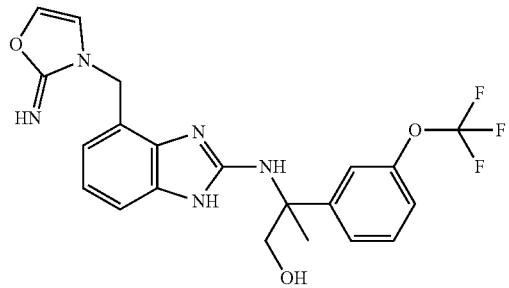 [SMILES: CC(CO)(Nc1nc2c(Cn3ccoc3=N)cccc2[nH]1)c1cccc(OC(F)(F)F)c1]

Example 27, Step 1: Preparation of 5-methyl-5-(3-(trifluoromethoxy)phenyl) imidazolidine-2, 4-dione

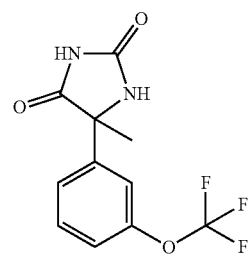 [SMILES: CC1(c2cccc(OC(F)(F)F)c2)NC(=O)NC1=O]

To a stirred solution of 1-(3-(trifluoromethoxy)phenyl)ethan-1-one (commercially available) (45.0 g, 220.0 mmol) in a mixture of solvents ethanol/water (1:1; 1000 mL) was added ammonium carbonate (106.0 g, 1100.0 mmol) followed by potassium cyanide (17.20 g, 265.0 mmol) and the mixture was stirred at 60° C. for 16 h. The reaction mixture was poured into ice-cold water (1500 mL) and stirred for 30 min. The solid that formed was filtered off and dried to afford 5-methyl-5-(3-(trifluoromethoxy) phenyl)imidazolidine-2,4-dione (56.0 g) as an off-white solid, which was used in the next step without further purification.

$^1$H NMR (400 MHz, DMSO-d$_6$) δ 10.88 (bs, 1H), 8.67 (s, 1H), 7.56 (t, 1H, J=8.00 Hz), 7.53 (d, 1H, J=7.60 Hz), 7.42 (s, 1H), 7.35 (d, 1H, J=6.80 Hz), 1.66 (s, 3H);

MS: m/z 273.1 (M−1).

Example 27, Step 2: Preparation of 2-amino-2-(3-(trifluoromethoxy)phenyl)propanoic acid

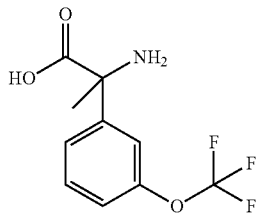 [SMILES: CC(N)(C(=O)O)c1cccc(OC(F)(F)F)c1]

5-methyl-5-(3-(trifluoromethoxy)phenyl)imidazolidine-2,4-dione (from Example 27, Step 1) (60.0 g, 219.0 mmol) was taken up into 10% aqueous sodium hydroxide solution (600 mL) and the mixture was stirred at 120° C. for 5 days. The reaction mixture was neutralized (adjusted pH=7) with 6.0 N HCl (300 mL) and the solid that formed was filtered and dried to afford 2-amino-2-(3-(trifluoromethoxy)-phenyl) propanoic acid (51.0 g) as a white solid, which was used in the next step without further purification.

$^1$H NMR (400 MHz, DMSO-d$_6$) δ 8.07 (bs, 3H), 7.52 (t, 1H, J=8.00 Hz), 7.51 (s, 1H), 7.47 (d, 1H, J=7.64 Hz), 7.28 (d, 1H, J=8.00 Hz), 1.64 (s, 3H);

MS: m/z 250.1 (M+1).

Example 27, Step 3: Preparation of 2-amino-2-(3-(trifluoromethoxy)-phenyl)propan-1-ol

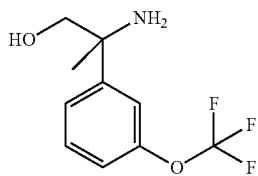 [SMILES: CC(N)(CO)c1cccc(OC(F)(F)F)c1]

To a solution of 2-amino-2-(3-(trifluoromethoxy)phenyl) propanoic acid (from Example 27, Step 2) (40.00 g, 161.00 mmol) in dry tetrahydrofuran (1000 mL) was added 2M solution of lithium aluminum hydride in tetrahydrofuran (120.00 mL, 241.0 mmol) at 0° C. and the reaction mixture was slowly warmed to ambient temperature and stirred for 3 h. The reaction mixture was cooled to 0° C. and quenched with dropwise addition of ethyl acetate solution (120 mL) and stirred for 30 min. Then treated with saturated solution of ammonium chloride added dropwise (150 mL) and stirred for 15 min at 0° C. The precipitate obtained was separated by filtration and the filtrate was concentrated under reduced pressure to afford a yellow gum (38.0 g). This was diluted with 10% sodium hydroxide solution (100 mL) and extracted with ethyl acetate (4×1000 mL). The combined organic layer was dried over anhydrous sodium sulphate, filtered and concentrated to afford 2-amino-2-(3-(trifluoromethoxy)phenyl) propan-1-ol (23.0 g) as a yellow oil, which was used in the next step without further purification.

$^1$H NMR (400 MHz, DMSO-d$_6$: D$_2$O) δ 7.47 (d, 1H, J=7.84 Hz), 7.44 (s, 1H), 7.41 (t, 1H, J=9.00 Hz), 7.15 (d, 1H, J=7.80 Hz), 3.41 (q, 2H, J=10.48 Hz), 1.33 (s, 3H);

MS: m/z 236.1 (M+1).

Example 27, Step 4: Preparation of tert-butyl N-{1-hydroxy-2-[3-(trifluoromethoxy)phenyl]propan-2-yl}carbamate

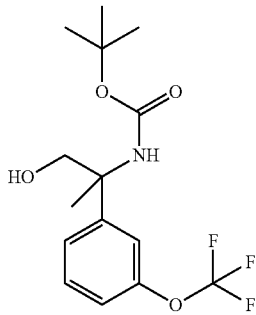 [SMILES: CC(C)(C)OC(=O)NC(C)(CO)c1cccc(OC(F)(F)F)c1]

To a suspension of 2-amino-2-(3-(trifluoromethoxy)phenyl)propan-1-ol (from Example 27, Step 3) (38.0 g, 162.0 mmol) in a mixture of solvents dichloromethane:1, 4-dioxane (4:1; 500 mL) was added di-tert-butyl dicarbonate (44.50 mL, d: 0.950 g/cm$^3$, 194.00 mmol) dropwise at 0° C. and the mixture was stirred at ambient temperature for 72 h. The reaction mixture was diluted with water (200 mL) and extracted with ethyl acetate (4×1000 mL). The combined organic layer was dried over sodium sulphate, filtered and concentrated to afford a yellow gum (55.0 g). This was purified by chromatography on a Grace instrument using 220.0 g pre-packed flash cartridge filled with normal phase silica gel 60 Å, 40-63 μm and the product was eluted with 30-40% ethyl acetate in hexane to afford tert-butyl N-{1-hydroxy-2-[3-(trifluoromethoxy)phenyl]propan-2-yl}carbamate (36.0 g) as a colourless gum.

$^1$H NMR (400 MHz, DMSO-d$_6$) δ 7.44 (d, 1H, J=7.40 Hz), 7.40 (s, 1H), 7.32 (d, 1H, J 11.20 Hz), 7.20 (t, 1H, J=9.60 Hz), 6.85 (bs, 1H), 4.96 (t, 1H, J=7.20 Hz), 4.03 (q, 2H, J=9.60 Hz), 1.56 (s, 3H), 1.37 (s, 9H);

MS: m/z 336.2 (M+1).

Example 27, Step 5: Preparation of 2-{[(tert-butoxy)carbonyl]amino}-2-[3-(trifluoromethoxy)phenyl]propyl 2,2-dimethylpropanoate

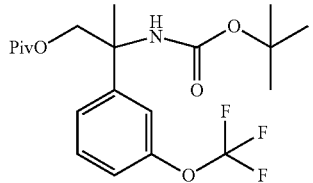

To a solution of tert-butyl N-{1-hydroxy-2-[3-(trifluoromethoxy)phenyl]propan-2-yl}carbamate (from Example 27, Step 4) (25.00 g, 74.60 mmol) in dry dichloromethane (500 mL) under a nitrogen atmosphere was added triethylamine (41.54 mL, d=0.726 g/cm³, 298.0 mmol) followed by pivaloyl chloride (18.24 mL, d=0.985 g/cm³, 149.00 mmol) at 0° C. dropwise and the reaction mixture was stirred at ambient temperature for 48 h. The reaction mixture was quenched with ice cold water (150 mL) and extracted with dichloromethane (4×750 mL). The combined organic layer was dried over sodium sulphate, filtered and concentrated to afford a brown gum (32.0 g). This was purified by chromatography on a Grace instrument using 120.0 g pre-packed flash cartridge filled with normal phase silica gel 60 Å, 40-63 μm and the product was eluted with 15-20% ethyl acetate in hexane to afford 2-{[(tert-butoxy)carbonyl]amino}-2-[3-(trifluoromethoxy)-phenyl]propyl 2,2-dimethylpropanoate (20.0 g) as a yellowish liquid.

¹H NMR (400 MHz, DMSO-d₆: D₂O) δ 7.47 (t, 1H, J=10.80 Hz), 7.37 (d, 1H, J=10.80 Hz), 7.27 (s, 1H), 7.23 (d, 1H, J=10.40 Hz), 4.26 (q, 2H, J=14.00 Hz), 1.55 (s, 3H), 1.40 (s, 9H), 1.11 (s, 9H);

MS: m/z 320.2 [(M+1)-Boc].

Example 27, Step 6: Preparation of 2-amino-2-[3-(trifluoromethoxy)-phenyl]propyl 2,2-dimethylpropanoate hydrochloride

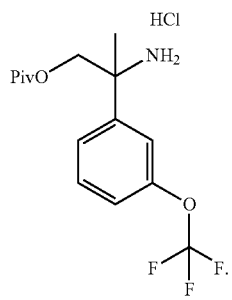

To a solution of 2-{[(tert-butoxy)carbonyl]amino}-2-[3-(trifluoromethoxy)phenyl]propyl 2,2-dimethylpropanoate (from Example 27, Step 5) (32.00 g, 76.30 mmol) in dry dichloromethane (400 mL) under a nitrogen atmosphere, was added 4M HCl in dioxane solution (95.40 mL, 381.00 mmol) dropwise at 0° C. The reaction mixture was stirred at ambient temperature for 16 h and then concentrated and the residue was triturated with hexane (3×250 mL). The supernatant layer was decanted and the solid was dried to afford 2-amino-2-[3-(trifluoromethoxy)phenyl]propyl 2,2-dimethylpropanoate hydrochloride (20.0 g) as a yellowish gum, which was used in the next step without further purification.

¹H NMR (400 MHz, DMSO-d₆) δ 8.98 (s, 3H), 7.61 (t, 1H, J=7.48 Hz), 7.57 (d, 2H, J=7.50 Hz), 7.43 (s, 1H), 4.46 (d, 1H, J=11.60 Hz), 4.28 (d, 1H, J=12.12 Hz), 1.70 (s, 3H), 1.04 (s, 9H);

MS: m/z 320.1 [(M+1)-HCl].

Example 27, Step 7: Preparation of 2-isothiocyanato-2-[3-(trifluoromethoxy)-phenyl]propyl 2,2-dimethylpropanoate

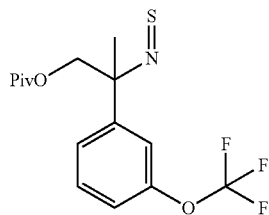

To a solution of 2-amino-2-[3-(trifluoromethoxy)phenyl]propyl 2,2-dimethylpropanoate hydrochloride (from Example 27, Step 6) (3.80 g, 12.00 mmol) in dry dichloromethane (50 mL) was added 10% aqueous sodium bicarbonate solution (50 mL) at 0° C. After 30 min, thiophosgene (1.82 mL, d=1.5 g/cm³, 24.00 mmol) was added and allowed to stir at same temperature for 1 h. The reaction mixture was extracted with dichloromethane (3×200 mL) and the combined organic layer was dried over anhydrous sodium sulphate, filtered, and concentrated to afford a yellow liquid (4.30 g). This was purified by chromatography on a Grace instrument using 60.0 g pre-packed flash cartridge filled with normal phase silica gel 60 Å, 40-63 μm and the product was eluted with 8-10% ethyl acetate in hexane to afford 2-isothiocyanato-2-[3-(trifluoromethoxy)phenyl]propyl 2,2-dimethylpropanoate (2.00 g) as a colorless liquid.

¹H NMR (400 MHz, DMSO-d₆) δ 7.59 (d, 1H, J=7.90 Hz), 7.56 (t, 1H, J=4.60 Hz), 7.47 (s, 1H), 7.38 (d, 1H, J=7.70 Hz), 4.47 (q, 2H, J=11.32 Hz), 1.79 (s, 3H), 1.05 (s, 9H).

Example 27, Step 8: Preparation of 2-[({2-amino-3-[(2-imino-2,3-dihydro-1,3-oxazol-3-yl)methyl]phenyl}carbamothioyl)amino]-2-[3-(trifluoromethoxy)phenyl]propyl 2,2-dimethylpropanoate and 2-[({2-amino-6-[(2-imino-2,3-dihydro-1,3-oxazol-3-yl)methyl]phenyl}carbamothioyl)amino]-2-[3-(trifluoromethoxy)phenyl]propyl 2,2-dimethylpropanoate (Mixture of Regioisomers)

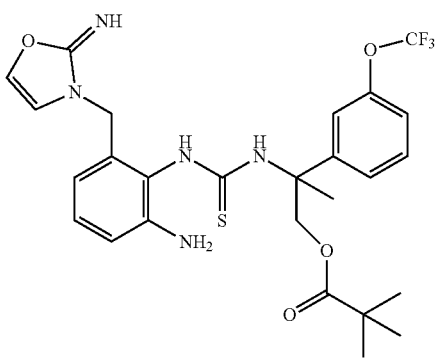

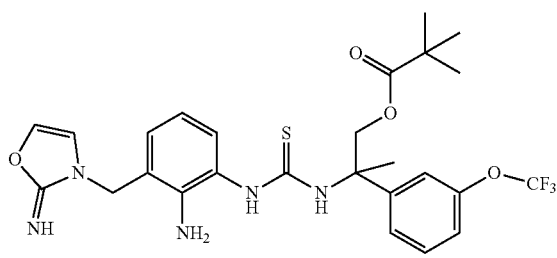

To a solution of 3-[(2-imino-2,3-dihydro-1,3-oxazol-3-yl)methyl]benzene-1,2-diamine (from Example 1, Step 5) (2.20 g, 1.08 mmol) in a mixture of solvents dichloromethane:methanol (4:1; 10 mL) was added [2-isothiocyanato-2-[3-(trifluoromethoxy)phenyl]propyl]2,2-dimethylpropanoate (from Example 27, Step 7) (3.89 g, 1.08 mmol) and the mixture was stirred at ambient temperature for 48 h. The reaction mixture was concentrated at 30° C. in a water bath to afford 2-[({2-amino-3-[(2-imino-2,3-dihydro-1,3-oxazol-3-yl)methyl]phenyl}carbamothioyl)amino)-2-[3-(trifluoromethoxy)phenyl]propyl 2,2-dimethylpropanoate and 2-[({2-amino-6-[(2-imino-2,3-dihydro-1,3-oxazol-3-yl)methyl]phenyl}carbamothioyl)amino)-2-[3-(trifluoromethoxy)phenyl]propyl 2,2-dimethylpropanoate (as a mixture of non-separable regioisomers) (6.00 g) as a brown gum, which was used in the next step without further purification.

MS: m/z 566.0 (M+1).

Example 27, Step 9: Preparation of 2-({4-[(2-imino-2,3-dihydro-1,3-oxazol-3-yl)methyl]-1H-1,3-benzodiazol-2-yl}amino)-2-[3-(trifluoromethoxy)phenyl]-propyl 2,2-dimethylpropanoate

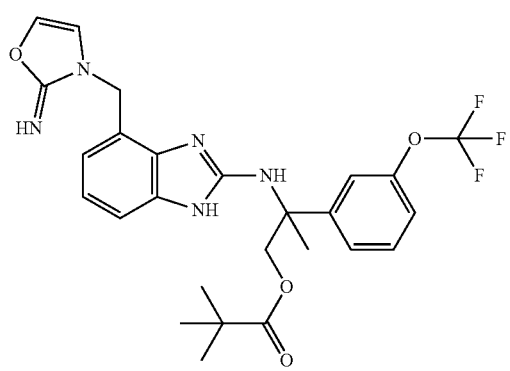 [SMILES: CC(C)(C)C(=O)OCC(C)(Nc1nc2c(Cn3ccoc3=N)cccc2[nH]1)c1cccc(OC(F)(F)F)c1]

To a solution of 2-[({2-amino-3-[(2-imino-2,3-dihydro-1,3-oxazol-3-yl)methyl]phenyl}carbamothioyl)amino)-2-[3-(trifluoromethoxy)phenyl]propyl 2,2-dimethylpropanoate and 2-[({2-amino-6-[(2-imino-2,3-dihydro-1,3-oxazol-3-yl)methyl]phenyl}carbamothioyl)amino)-2-[3-(trifluoromethoxy)phenyl]propyl 2,2-dimethylpropanoate (as a mixture of non-separable regioisomers) (from Example 27, Step 8) (6.00 g, 1.06 mmol) in methanol (50 mL) was added iodoacetic acid (2.96 g, 15.90 mmol) and the mixture was stirred at ambient temperature for 2 h. The reaction mixture was concentrated to remove the solvent methanol at 30° C. to afford 2-({4-[(2-imino-2,3-dihydro-1,3-oxazol-3-yl)methyl]-1H-1,3-benzodiazol-2-yl}amino)-2-[3-(trifluoromethoxy)phenyl]propyl 2,2-dimethylpropanoate as a brown gum (5.50 g), which was used in the next step without further purification.

MS: m/z 532.2 [(M+1)].

Example 27: Preparation of 2-({4-[(2-imino-2,3-dihydro-1,3-oxazol-3-yl)methyl]-1H-1,3-benzodiazol-2-yl}amino)-2-[3-(trifluoromethoxy)phenyl]propan-1-ol

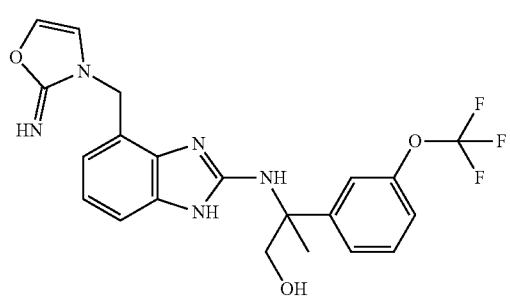 [SMILES: CC(CO)(Nc1nc2c(Cn3ccoc3=N)cccc2[nH]1)c1cccc(OC(F)(F)F)c1]

To a solution of 2-({4-[(2-imino-2,3-dihydro-1,3-oxazol-3-yl)methyl]-1H-1,3-benzodiazol-2-yl}amino)-2-[3-(trifluoromethoxy)phenyl]propyl 2,2-dimethylpropanoate (from Example 27, Step 9) (4.0 g, 7.53 mmol) in methanol (50 mL) was added 0.5 M sodium hydroxide in methanol (45.2 mL, 22.6 mmol) dropwise and the mixture was stirred at ambient temperature for 30 min. The reaction mixture was quenched with 1.5 N aqueous HCl solution (10 mL) at 0° C. and the reaction mixture was concentrated at 28° C. to afford a brown gum (0.520 g). This was purified by preparative HPLC to afford 2-({4-[(2-imino-2,3-dihydro-1,3-oxazol-3-yl)methyl]-1H-1,3-benzodiazol-2-yl}amino)-2-[3-(trifluoromethoxy)phenyl]propan-1-ol, isolated as the trifluoroacetate salt, (2.2 g) as a yellow gum.

$^1$H NMR (400 MHz, AcOH-$d_4$) δ 7.57-7.50 (m, 3H), 7.45 (s, 1H), 7.41 (dd, J=2.40, 6.80 Hz, 1H), 7.30 (d, J=6.40 Hz, 3H), 7.21 (d, J=1.60 Hz, 1H), 5.41 (d, J=4.80 Hz, 2H), 4.39 (d, J=12.00 Hz, 1H), 4.11 (d, J=12.00 Hz, 1H), 1.79 (s, 3H); MS: m/z 448.1 [(M+1)].

The above product was resolved into its two enantiomers by Chiral SFC using the method: Column: (R, R)-Whelk-01; Flow rate: 3.0 mL/min; Co-Solvent: 30%; Co-solvent Name: 0.5% isopropyl amine in isopropyl alcohol; injected Volume: 3.0 µL; outlet pressure: 100 bar; Temperature: 35° C. to obtain the two enantiomers 27a and 27b.

Example 27a: (+)-2-({4-[(2-imino-2,3-dihydro-1,3-oxazol-3-yl)methyl]-1H-1,3-benzodiazol-2-yl}amino)-2-[3-(trifluoromethoxy)phenyl]propan-1-ol The (+) enantiomer was the first compound to elute off the column.

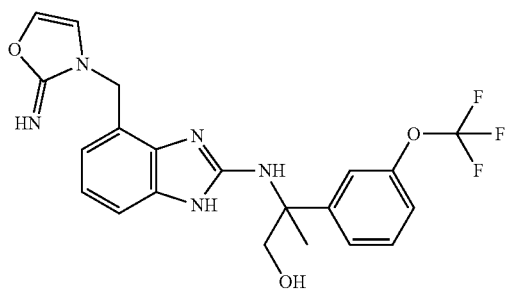 [SMILES: CC(CO)(Nc1nc2c(Cn3ccoc3=N)cccc2[nH]1)c1cccc(OC(F)(F)F)c1]

$^1$H NMR (400 MHz, AcOH-d$_4$) δ 7.56-7.52 (m, 3H), 7.45 (s, 1H), 7.41 (d, J=8.00 Hz, 1H), 7.30-7.27 (m, 3H), 7.20 (d, J=1.60 Hz, 1H), 5.41 (d, J=6.40 Hz, 2H), 4.39 (d, J=12.40 Hz, 1H), 4.11 (d, J=12.00 Hz, 1H), 1.78 (s, 3H);

MS: m/z 448.2 (M+1);

[α]$_D^4$ (+) 9.20 (MeOH, c=1.0).

Example 27b: (+2-({4-[(2-imino-2,3-dihydro-1,3-oxazol-3-yl)methyl]-1H-1,3-benzodiazol-2-yl}amino)-2-[3-(trifluoromethoxy)phenyl]propan-1-ol The (−) enantiomer was the second compound to elute off the column.

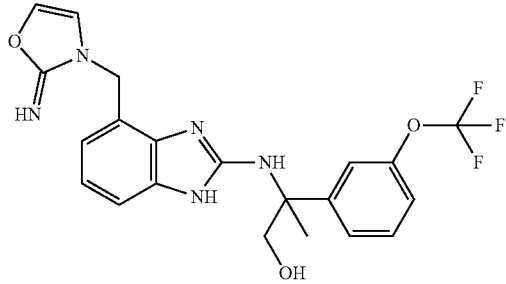 [SMILES: CC(CO)(Nc1nc2c(Cn3ccoc3=N)cccc2[nH]1)c1cccc(OC(F)(F)F)c1]

$^1$H NMR (400 MHz, AcOH-d$_4$) δ 7.57-7.49 (m, 3H), 7.45 (s, 1H), 7.41 (d, J=8.40 Hz, 1H), 7.30-7.24 (m, 3H), 7.20 (d, J=1.20 Hz, 1H), 5.41 (d, J=6.40 Hz, 2H), 4.39 (d, J=12.00 Hz, 1H), 4.11 (d, J=12.00 Hz, 1H), 1.78 (s, 3H);

MS: m/z 448.0 (M+1);

[α]$_D^{25.5}$ (−) 8.6 (MeOH, c=1.0).

Example 28: Preparation 2-({4-[(2-imino-4,5-dimethyl-2,3-dihydro-1,3-oxazol-3-yl)methyl]-1H-1,3-benzodiazol-2-yl}amino)-2-[3-(trifluoromethyl)phenyl]-propan-1-ol

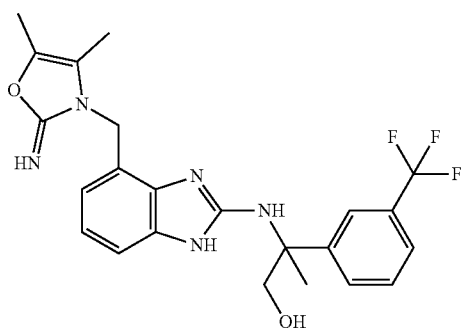 [SMILES: Cc1oc(=N)n(Cc2cccc3[nH]c(NC(C)(CO)c4cccc(C(F)(F)F)c4)nc23)c1C]

Starting with commercially available 4,5-dimethyloxazol-2-amine and then using [2-isothiocyanato-2-[3-(trifluoromethyl)phenyl]propyl] 2,2-dimethylpropanoate (from Example 18, Step 7) the titled compound was made by the method described for Example 18 and isolated as the trifluoroacetate salt.

$^1$H NMR (400 MHz, AcOH-d$_4$) δ 7.87 (s, 1H), 7.84 (d, J=8.00 Hz, 1H), 7.69 (d, J=8.00 Hz, 1H), 7.61 (t, J=8.00 Hz, 1H), 7.34 (d, J=8.00 Hz, 1H), 7.24 (t, J=8.00 Hz, 1H), 6.87 (d, J=7.60 Hz, 1H), 5.41 (s, 2H), 4.42 (d, J=12.00 Hz, 1H), 4.14 (d, J=12.00 Hz, 1H), 2.28 (d, J=0.80 Hz, 3H), 2.01 (d, J=0.80 Hz, 3H), 1.82 (s, 3H);

MS: m/z 460 (M+1).

Example 29: Preparation of 2-({4-[(2-imino-4-methyl-2,3-dihydro-1,3-oxazol-3-yl)methyl]-1H-1,3-benzodiazol-2-yl}amino)-2-[3-(trifluoromethoxy)phenyl]propan-1-ol

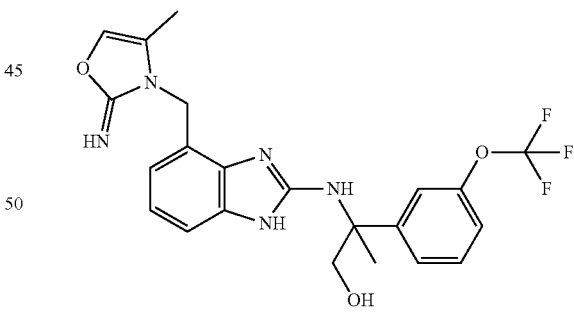

Starting with 3-[(2-imino-4-methyl-2,3-dihydro-1,3-oxazol-3-yl)methyl]benzene-1,2-diamine (from Example 5, Step 2) and [2-isothiocyanato-2-[3-(trifluoromethoxy)phenyl]propyl]2,2-dimethylpropanoate (from Example 27, Step 7) the titled compound was prepared by the method described for Example 27 and isolated as the trifluoroacetate salt.

$^1$H NMR (400 MHz, AcOH-d$_4$) δ 7.59-7.50 (m, 2H), 7.44 (d, J=1.56 Hz, 2H), 7.37 (d, J=8.00 Hz, 1H), 7.31-7.24 (m, 2H), 6.88 (d, J=7.84 Hz, 1H), 5.47 (s, 2H), 4.39 (d, J=12.04 Hz, 1H), 4.12 (d, J=12.12 Hz, 1H), 2.02 (s, 3H), 1.80 (s, 3H);

MS: m/z 462.2 (M+1).

Example 30: Preparation of 2-({4-[(2-imino-5-methyl-2,3-dihydro-1,3-oxazol-3-yl)methyl]-1H-1,3-benzodiazol-2-yl}amino)-2-[3-(trifluoromethoxy)phenyl]-propan-1-ol

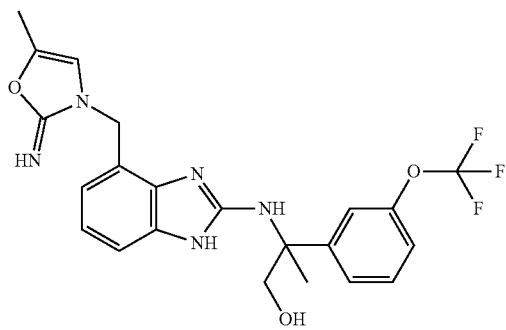 [SMILES: Cc1cn(Cc2cccc3[nH]c(NC(C)(CO)c4cccc(OC(F)(F)F)c4)nc23)c(=N)o1]

Example 30, Step 1: Preparation of 2-[({2-amino-3-[(2-imino-5-methyl-2,3-dihydro-1,3-oxazol-3-yl)methyl]phenyl}carbamothioyl)amino]-2-[3-(trifluoromethoxy)phenyl]propyl 2,2-dimethylpropanoate and 2-[({2-amino-6-[(2-imino-5-methyl-2,3-dihydro-1,3-oxazol-3-yl)methyl]phenyl}carbamothioyl)-amino]-2-[3-(trifluoromethoxy)phenyl]propyl 2,2-dimethylpropanoate (Mixture of Regioisomers)

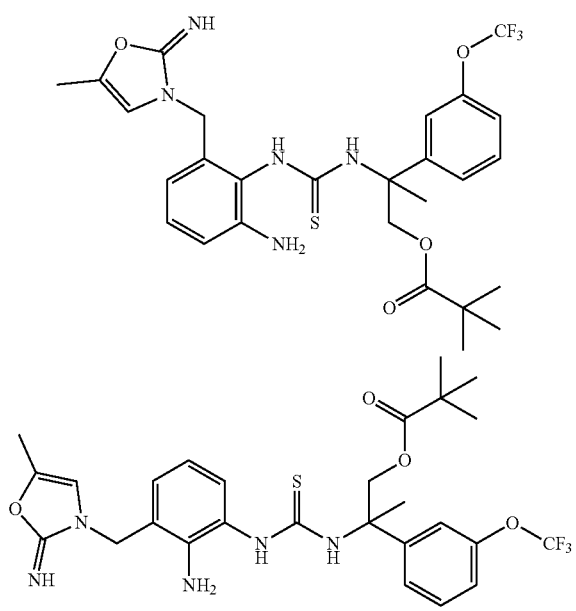

To a solution of 3-[(2-imino-5-methyl-2,3-dihydro-1,3-oxazol-3-yl)methyl]benzene-1,2-diamine (Example 24, Step 2) (0.280 g, 1.28 mmol) in a mixture of solvents dichloromethane:methanol (2:1; 9 mL) was added [2-isothiocyanato-2-[3-(trifluoromethoxy)phenyl]propyl]2,2-dimethylpropanoate (from Example 27, Step 7) (0.300 g, 0.830 mmol) and stirred at ambient temperature for 48 h. The reaction mixture was concentrated at 30° C. in a water bath to afford 2-[({2-amino-3-[(2-imino-5-methyl-2,3-dihydro-1, 3-oxazol-3-yl)methyl]phenyl}carbamothioyl)amino]-2-[3-(trifluoromethoxy)phenyl]propyl 2,2-dimethylpropanoate and 2-[({2-amino-6-[(2-imino-5-methyl-2,3-dihydro-1,3-oxazol-3-yl)methyl]phenyl}carbamothioyl)amino]-2-[3-(trifluoromethoxy)phenyl]propyl 2,2-dimethylpropanoate (as a mixture of non-separable regioisomers) (0.580 g) as a brown gum, which was used in the next step without purification.

MS: m/z 580.4 (M+1).

Example 30, Step 2: Preparation of 2-({4-[(2-imino-5-methyl-2,3-dihydro-1,3-oxazol-3-yl)methyl]-1H-1,3-benzodiazol-2-yl}amino)-2-[3-(trifluoromethoxy)-phenyl]propyl 2,2-dimethylpropanoate

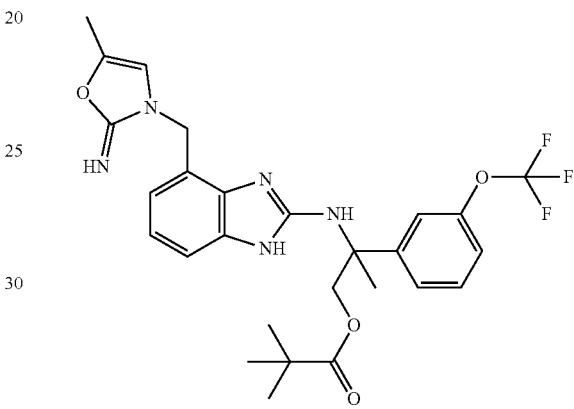

To a solution of 2-[({2-amino-3-[(2-imino-5-methyl-2,3-dihydro-1,3-oxazol-3-yl)methyl]phenyl}carbamothioyl)amino]-2-[3-(trifluoromethoxy)phenyl]propyl 2,2-dimethylpropanoate and 2-[({2-amino-6-[(2-imino-5-methyl-2,3-dihydro-1,3-oxazol-3-yl)methyl]phenyl}carbamothioyl)amino]-2-[3-(trifluoromethoxy)phenyl]propyl 2,2-dimethylpropanoate (as a mixture of non-separable regioisomers) (Example 30, Step 1) (0.550 g, 0.949 mmol) in methanol (8 mL) was added iodoacetic acid (0.265 g, 1.42 mmol) and the mixture was refluxed for 1.5 h. The reaction mixture was concentrated at 30° C. to remove the solvent methanol to afford a brown gum (0.600 g), which was purified by preparative HPLC (TFA:Acetonitrile) to afford 2-({4-[(2-imino-5-methyl-2,3-dihydro-1,3-oxazol-3-yl)methyl]-1H-1,3-benzodiazol-2-yl}amino)-2-[3-(trifluoromethoxy)phenyl]propyl 2,2-dimethylpropanoate, isolated as the trifluoroacetate salt, (0.200 g) as a brown gum.

$^1$H-NMR (400 MHz, AcOH-$d_4$): δ 7.58-7.53 (m, 2H), 7.48 (s, 1H), 7.37-7.29 (m, 4H), 6.86 (d, J=1.20 Hz, 1H), 5.34 (s, 2H), 4.61 (d, J=11.60 Hz, 1H), 4.50 (d, J=11.60 Hz, 1H), 2.26 (s, 3H), 2.01 (s, 3H), 1.17 (s, 9H);

MS: m/z 546.1 (M+1).

The above product was resolved into it two enantiomers by Chiral SFC using the method: Chiralcel OX-H, Mobile Phase: 0.5% isopropyl amine in isopropyl alcohol; co-solvent 40% $CO_2$; Flow rate: 4 ml/min, pressure: 100 bar; Temperature: 35° C. to obtain the two enantiomers 30-2a and 30-2b.

Example 30-2a: Preparation of 2-({4-[(2-imino-5-methyl-2,3-dihydro-1,3-oxazol-3-yl)methyl]-1H-1,3-benzodiazol-2-yl}amino)-2-[3-(trifluoromethoxy)-phenyl]propyl 2,2-dimethylpropanoate (Enantiomer A)

Enantiomer A was the first compound to elute off the column, isolated as the trifluoroacetate salt.

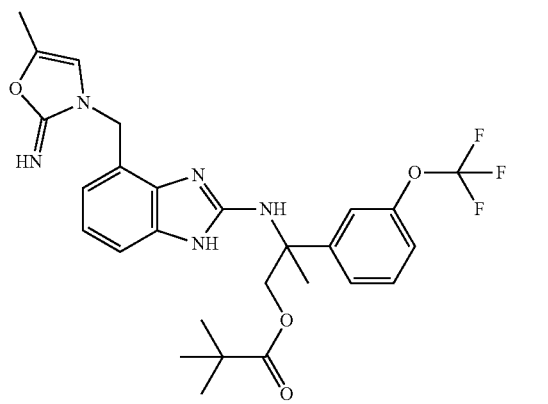 [SMILES: Cc1cn(Cc2cccc3[nH]c(NC(C)(COC(=O)C(C)(C)C)c4cccc(OC(F)(F)F)c4)nc23)c(=N)o1]

¹H-NMR (400 MHz, AcOH-d₄): δ 7.58-7.53 (m, 2H), 7.48 (s, 1H), 7.37-7.29 (m, 4H), 6.86 (d, J=1.20 Hz, 1H), 5.34 (s, 2H), 4.61 (d, J=11.60 Hz, 1H), 4.50 (d, J=11.60 Hz, 1H), 2.26 (s, 3H), 2.01 (s, 3H), 1.17 (s, 9H);

MS: m/z 546.1 (M+1).

Example 30-2b: Preparation of 2-({4-[(2-imino-5-methyl-2,3-dihydro-1,3-oxazol-3-yl)methyl]-1H-1,3-benzodiazol-2-yl}amino)-2-[3-(trifluoromethoxy)phenyl]-propyl 2,2-dimethylpropanoate (Enantiomer B)

Enantiomer B was the second compound to elute off the column, isolated as the trifluoroacetate salt.

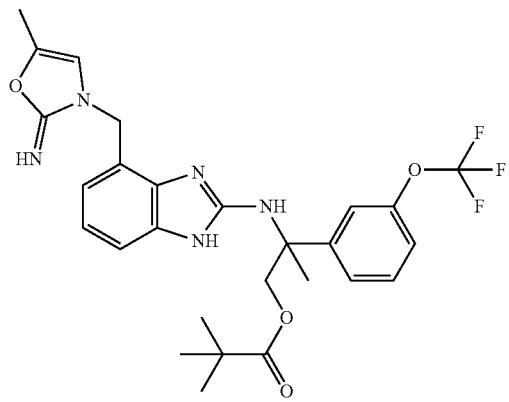 [SMILES: Cc1cn(Cc2cccc3[nH]c(NC(C)(COC(=O)C(C)(C)C)c4cccc(OC(F)(F)F)c4)nc23)c(=N)o1]

¹H-NMR (400 MHz, AcOH-d₄): δ 7.58-7.53 (m, 2H), 7.48 (s, 1H), 7.37-7.29 (m, 4H), 6.86 (d, J=1.20 Hz, 1H), 5.34 (s, 2H), 4.61 (d, J=11.60 Hz, 1H), 4.50 (d, J=11.60 Hz, 1H), 2.26 (s, 3H), 2.01 (s, 3H), 1.17 (s, 9H);

MS: m/z 546.1 (M+1).

Example 30: Preparation of 2-({4-[(2-imino-5-methyl-2,3-dihydro-1,3-oxazol-3-yl)methyl]-1H-1,3-benzodiazol-2-yl}amino)-2-[3-(trifluoromethoxy) phenyl]-propan-1-ol

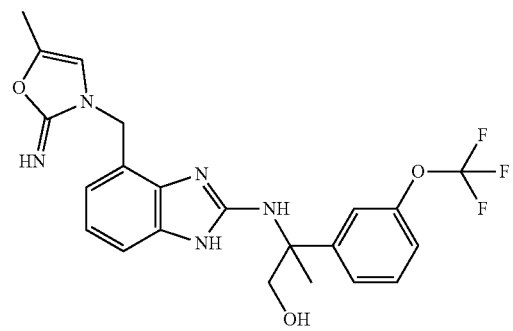 [SMILES: Cc1cn(Cc2cccc3[nH]c(NC(C)(CO)c4cccc(OC(F)(F)F)c4)nc23)c(=N)o1]

To a solution of 2-({4-[(2-imino-5-methyl-2,3-dihydro-1,3-oxazol-3-yl)methyl]-1H-1,3-benzodiazol-2-yl}amino)-2-[3-(trifluoromethoxy)phenyl]propyl 2,2-dimethylpropanoate; trifluoroacetic acid (from Example 30, Step 2) (0.200 g, 0.303 mmol) in methanol (20 mL) was added 0.5 N sodium hydroxide in methanol (6.0 ml, 3.03 mmol) dropwise and the mixture was stirred at ambient temperature for 5 h. The reaction mixture was quenched with 1.5 N hydrochloride solution (3 mL) and concentrated under reduced pressure at 30° C. to afford a brown gum (0.170 g). This was purified by preparative HPLC using 0.1% TFA in acetonitrile:water to afford 2-({4-[(2-imino-5-methyl-2,3-dihydro-1,3-oxazol-3-yl)methyl]-1H-1,3-benzodiazol-2-yl}amino)-2-[3-(trifluoromethoxy)phenyl]propan-1-ol, isolated as the trifluoroacetate salt, (0.080 g) as a brown gum.

¹H NMR (400 MHz, AcOH-d₄) δ 7.58-7.50 (m, 2H), 7.45 (s, 1H), 7.41 (dd, J=2.52, 6.56 Hz, 1H), 7.32-7.27 (m, 3H), 6.82 (d, J=1.40 Hz, 1H), 5.33 (d, J=3.76 Hz, 2H), 4.39 (d, J=12.08 Hz, 1H), 4.11 (d, J=12.12 Hz, 1H), 2.25 (s, 3H), 1.79 (s, 3H);

MS: m/z 462.3 (M+1).

Example 30a: Preparation of (−)-2-({4-[(2-imino-5-methyl-2,3-dihydro-1,3-oxazol-3-yl)methyl]-1H-1,3-benzodiazol-2-yl}amino)-2-[3-(trifluoromethoxy)-phenyl]propan-1-ol

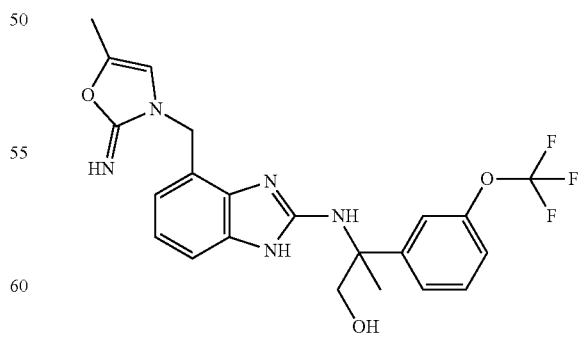

To a solution of 2-({4-[(2-imino-5-methyl-2,3-dihydro-1,3-oxazol-3-yl)methyl]-1H-1,3-benzodiazol-2-yl}amino)-2-[3-(trifluoromethoxy)phenyl]propyl 2,2-dimethylpropanoate (Example 30-2a, Enantiomer A) (0.480 g, 0.728 mmol)

in methanol (48 mL) was added 0.5 N sodium hydroxide in methanol (7.28 ml, 3.64 mmol) dropwise and the mixture was stirred at ambient temperature for 5 h. The reaction mixture was quenched with 1.5 N hydrochloride solution (4 mL) and concentrated under reduced pressure at 30° C. to afford a brown gum (0.410 g). This was purified by preparative HPLC using 0.1% TFA in acetonitrile:water to afford (−)-2-({4-[(2-imino-5-methyl-2,3-dihydro-1,3-oxazol-3-yl)methyl]-1H-1,3-benzodiazol-2-yl}amino)-2-[3-(trifluoromethoxy)phenyl]propan-1-ol, isolated as the trifluoroacetate salt, (0.165 g) as a brown gum.

$^1$H NMR (400 MHz, AcOH-d$_4$) δ 7.58-7.50 (m, 2H), 7.45 (s, 1H), 7.41 (dd, J=2.52, 6.56 Hz, 1H), 7.32-7.27 (m, 3H), 6.82 (d, J=1.40 Hz, 1H), 5.33 (d, J=3.76 Hz, 2H), 4.39 (d, J=12.08 Hz, 1H), 4.11 (d, J=12.12 Hz, 1H), 2.25 (s, 3H), 1.79 (s, 3H);

MS: m/z 462.4 (M+1);

SOR: [α]$_D^{24.9}$ (−) 9.20, (MeOH, c=0.5).

Example 30b: Preparation of (+)-2-({4-[(2-imino-5-methyl-2,3-dihydro-1,3-oxazol-3-yl)methyl]-1H-1,3-benzodiazol-2-yl}amino)-2-[3-(trifluoromethoxy)phenyl]propan-1-ol

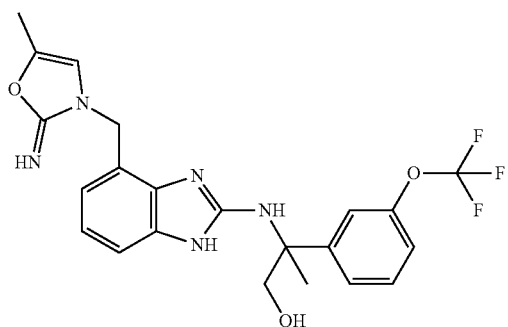 [SMILES: Cc1cn(Cc2cccc3[nH]c(NC(C)(CO)c4cccc(OC(F)(F)F)c4)nc23)c(=N)o1]

To a solution of 2-({4-[(2-imino-5-methyl-2,3-dihydro-1,3-oxazol-3-yl)methyl]-1H-1,3-benzodiazol-2-yl}amino)-2-[3-(trifluoromethoxy)phenyl]propyl 2,2-dimethylpropanoate (Example 30-2b, Enantiomer B) (0.550 g, 0.834 mmol) in methanol (55 mL) was added 0.5 N sodium hydroxide in methanol (8.34 ml, 4.17 mmol) dropwise and the mixture was stirred at ambient temperature for 5 h. The reaction mixture was quenched with 1.5 N hydrochloride solution (4 mL) and concentrated under reduced pressure at 30° C. to afford a brown gum (0.48 g). This was purified by preparative HPLC using 0.1% TFA in acetonitrile:water to afford (+)-2-({4-[(2-imino-5-methyl-2,3-dihydro-1,3-oxazol-3-yl)methyl]-1H-1,3-benzodiazol-2-yl}amino)-2-[3-(trifluoromethoxy)phenyl]propan-1-ol, isolated as the trifluoroacetate salt, (0.150 g) as a brown gum.

$^1$H NMR (400 MHz, AcOH-d$_4$) δ 7.58-7.50 (m, 2H), 7.45 (s, 1H), 7.41 (dd, J=2.52, 6.56 Hz, 1H), 7.32-7.27 (m, 3H), 6.82 (d, J=1.40 Hz, 1H), 5.33 (d, J=3.76 Hz, 2H), 4.39 (d, J=12.08 Hz, 1H), 4.11 (d, J=12.12 Hz, 1H), 2.25 (s, 3H), 1.79 (s, 3H);

MS: m/z 462.3 (M+1);

SOR: [α]$_D^{24.9}$ (+) 7.20, (MeOH, c=0.5).

Example 31: Preparation of 2-(3-chloro-4-fluorophenyl)-2-[(4-{1-[(1,3-oxazol-2-yl)amino]ethyl}-1H-1,3-benzodiazol-2-yl)amino]propan-1-ol

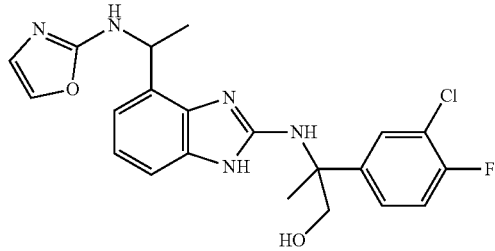 [SMILES: CC(Nc1ncco1)c1cccc2[nH]c(NC(C)(CO)c3ccc(F)c(Cl)c3)nc12]

Example 31, Step 1: Preparation of N-methoxy-N-methyl-2,1,3-benzothiadiazole-4-carboxamide

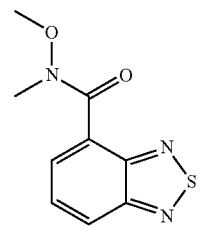

To a solution of 2,1,3-benzothiadiazole-4-carboxylic acid (6 g, 33.3 mmol) and N,O-dimethyl hydroxylamine hydrochloride (8.12 g, 83.2 mmol) in tetrahydrofuran (75 mL) was added triethylamine (18.6 ml, 133 mmol) and propylphosphonic anhydride (50% in EtOAc) (63.6 g, 200 mmol) and the reaction mixture was stirred at ambient temperature for 20 h. The reaction mixture was washed with water (250 mL) and extracted with ethyl acetate (3×100 mL), and the combined organic layer was washed with brine solution (100 mL), dried over sodium sulphate, filtered and concentrated to afford the crude product (13 g) as a brown solid. This was purified by column chromatography and eluted at 40% ethyl acetate in petroleum ether to afford N-methoxy-N-methyl-2,1,3-benzothiadiazole-4-carboxamide (7 g) as an off-white solid.

$^1$H NMR (400 MHz, DMSO-d$_6$) δ 8.21-8.17 (m, 1H), 7.79-7.77 (m, 2H), 3.50 (s, 3H), 3.33 (s, 3H);

MS: m/z 224.1 (M+1).

Example 31, Step 2: Preparation of 1-(2,1,3-benzothiadiazol-4-yl)ethan-1-one

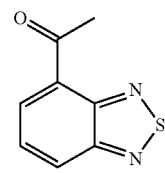

A solution of N-methoxy-N-methyl-2,1,3-benzothiadiazole-4-carboxamide (from Example 31, Step 1) (4 g, 17.9 mmol) in tetrahydrofuran:diethyl ether (1:1, 80 mL), was cooled to 0° C., and methyl magnesium bromide (2M in THF) (53.7 mL, 107 mmol) was added dropwise and the reaction mixture was stirred at ambient temperature for 16 h. The reaction mixture was quenched with aqueous ammonium chloride solution (100 mL), extracted with ethyl acetate (3×50 mL), and the combined organic layer was washed with brine solution (100 mL), dried over sodium sulphate, filtered and concentrated to afford the crude product (5.2 g) as a brown gum. This was purified by silica gel column chromatography and eluted with 10% ethyl acetate in petroleum ether to afford 1-(2,1,3-benzothiadiazol-4-yl)ethan-1-one (1.2 g) as a pale yellow solid.

$^1$H NMR (400 MHz, DMSO-$d_6$) δ 8.31-8.25 (m, 2H), 7.76-7.72 (m, 1H), 3.07 (s, 3H);

MS: m/z 179.0 (M+1).

Example 31, Step 3: Preparation of N-[1-(2,1,3-benzothiadiazol-4-yl)ethyl]-1,3-oxazol-2-amine

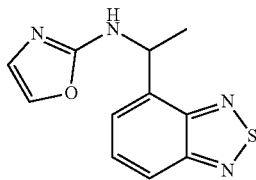 [SMILES: CC(Nc1ncco1)c1cccc2nsnc12]

To a solution of 1-(2,1,3-benzothiadiazol-4-34)ethan-1-one (from Example 31, Step 2) (1.2 g, 6.73 mmol) and 1,3-oxazol-2-amine (2.26 g, 26.9 mmol) in ethanol (40 mL), cooled to 0° C., was added titanium(IV) isopropoxide (34.1 mL, 114 mmol) and the reaction mixture was stirred at ambient temperature for 20 h. Then reaction mixture was cooled to 0° C., and sodium borohydride (0.764 g, 20.2 mmol) was added portion-wise and the reaction mixture was stirred at ambient temperature for 20 h. The reaction mixture was quenched with ice-water (75 mL), filtered through a Celite bed and washed with ethyl acetate. The filtrate was concentrated, then diluted with water (100 mL), and extracted with ethyl acetate (3×50 mL) and the combined organic layer was washed with brine solution (50 mL) and dried over sodium sulphate, filtered and concentrated to afford the crude product (1.3 g) as a brown gum. This was purified by silica gel column chromatography eluted with 30% ethyl acetate in petroleum ether to afford N-[1-(2,1,3-benzothiadiazol-4-yl)ethyl]-1,3-oxazol-2-amine (0.320 g) as a pale yellow solid.

$^1$H NMR (400 MHz, DMSO-$d_6$) δ 7.98-7.95 (m, 2H), 7.70 (t, J=6.80 Hz, 1H), 7.61 (d, J=7.20 Hz, 1H), 7.40 (d, J=0.80 Hz, 1H), 6.65 (d, J=0.80 Hz, 1H), 5.56-5.49 (m, 1H), 1.58 (d, J=6.80 Hz, 3H);

MS: m/z 247.1 (M+1).

Example 31, Step 4: Preparation of 3-{1-[(1,3-oxazol-2-yl)amino]ethyl}benzene-1,2-diamine

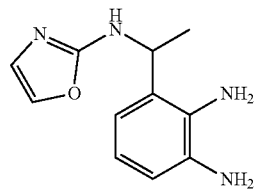 [SMILES: CC(Nc1ncco1)c1cccc(N)c1N]

To a solution of N-[1-(2,1,3-benzothiadiazol-4-yl)ethyl]-1,3-oxazol-2-amine (from Example 31, Step 3) (0.400 g, 1.62 mmol) in methanol (30 mL) was added Raney nickel (1.82 g, 300% wt/wt) and the reaction mixture was hydrogenated at 1.5 kg/cm$^2$ at ambient temperature for 16 h. The reaction mixture was filtered through a Celite bed and the filtrate was concentrated to afford the product (0.295 g) as a brown liquid, which was used in the next step without further purification.

MS: m/z 219.2 (M+1).

Example 31, Step 5: Preparation of 2-{[(2-amino-3-{1-[(1,3-oxazol-2-yl)amino]ethyl}-phenyl)carbamothioyl]amino}-2-(3-chloro-4-fluorophenyl)propyl 2,2-dimethyl-propanoate and 2-{[(2-amino-6-{1-[(1,3-oxazol-2-yl)amino]ethyl}phenyl)carbamothioyl]-amino}-2-(3-chloro-4-fluorophenyl)propyl 2,2-dimethylpropanoate

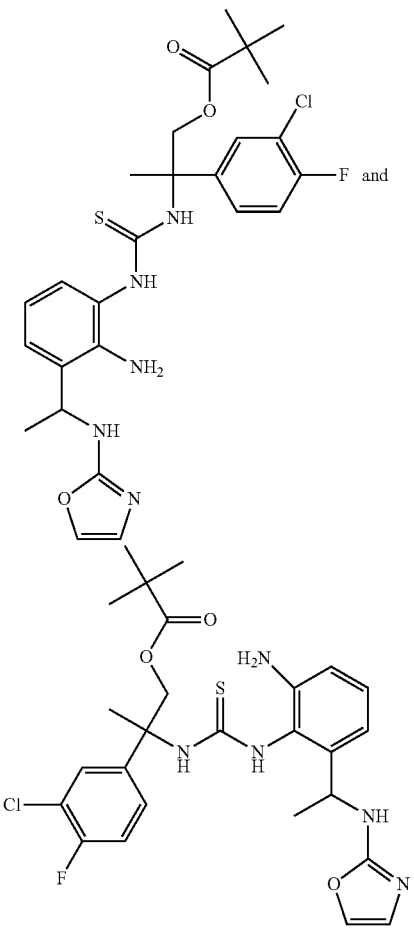

To a solution of 3-(1-(1,3-oxazol-2-ylamino)ethyl)benzene-1,2-diamine (from Example 31, Step 4) (0.295 g, 1.35 mmol) in a mixture of solvents dichloromethane:methanol (1:1, 8 mL) was added [2-(3-chloro-4-fluoro-phenyl)-2-isothiocyanato-propyl] 2,2-dimethylpropanoate (from Example 8, Step 7) (0.446 g, 1.35 mmol) and the mixture was stirred at ambient temperature for 16 h. The reaction mixture was concentrated to afford the crude product (0.700 g) as a brown gum, which was used in the next step without further purification.

MS: m/z 548.1 (M+1).

Example 31, Step 6: Preparation of 2-(3-chloro-4-fluorophenyl)-2-[(4-{1-[(1,3-oxazol-2-yl)amino]ethyl}-1H-1,3-benzodiazol-2-yl)amino]propyl 2,2-dimethylpropanoate

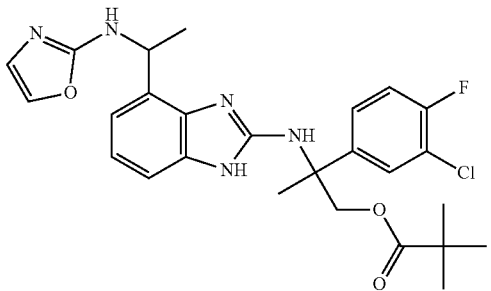 [SMILES: CC(Nc1ncco1)c1cccc2[nH]c(NC(C)(COC(=O)C(C)(C)C)c3ccc(F)c(Cl)c3)nc12]

To a solution of 2-{[(2-amino-3-{1-[(1,3-oxazol-2-yl)amino]ethyl}phenyl)carbamothioyl]-amino}-2-(3-chloro-4-fluorophenyl)propyl 2,2-di methylpropanoate and 2-{[(2-amino-6-{1-[(1,3-oxazol-2-yl)amino]ethyl}-phenyl)carbamothioyl]amino}-2-(3-chloro-4-fluorophenyl)-propyl 2,2-dimethylpropanoate (mixture of regio isomers) (from Example 31, Step 5) (0.700 g, 1.28 mmol) in methanol (10 mL) was added iodoacetic acid (0.237 g, 1.28 mmol) and the reaction mixture was stirred at ambient temperature for 5 h. The reaction mixture was concentrated and diluted with ice-cold water (50 mL). The aqueous layer was extracted with dichloromethane (3×50 mL). The combined organic layer was washed with saturated sodium bicarbonate solution (50 mL) followed by brine solution (50 mL), dried over sodium sulphate, filtered and concentrated to afford the crude product (0.530 g) as a brown gum. This was purified by preparative HPLC (0.1% TFA in Acetonitrile:water) to afford 2-(3-chloro-4-fluorophenyl)-2-[(4-{1-[(1,3-oxazol-2-yl)amino]ethyl}-1H-1,3-benzodiazol-2-yl)amino]-propyl 2,2-dimethylpropanoate (0.340 g) as a brown gum.

$^1$H NMR (400 MHz, DMSO-d$_6$) δ 12.18 (bs, 1H), 10.18 (bs, 1H), 8.48 (bs, 1H), 7.80-7.78 (m, 1H), 7.50-7.42 (m, 3H), 7.19-7.16 (m, 3H), 6.86 (d, J=6.00 Hz, 1H), 5.11 (t, J=4.00 Hz, 1H), 4.52-4.37 (m, 2H), 1.87 (d, J=6.80 Hz, 3H), 1.48 (d, J=9.20 Hz, 3H), 1.06 (s, 9H);

MS: m/z 514.1 (M+1).

Example 31, Step 7: Preparation of 2-(3-chloro-4-fluorophenyl)-2-[(4-{1-[(1,3-oxazol-2-yl)amino]ethyl}-1H-1,3-benzodiazol-2-yl)amino]propan-1-ol

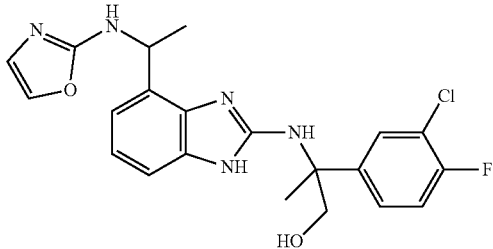 [SMILES: CC(Nc1ncco1)c1cccc2[nH]c(NC(C)(CO)c3ccc(F)c(Cl)c3)nc12]

To a solution of 2-(3-chloro-4-fluorophenyl)-2-[(4-{1-[(1,3-oxazol-2-yl)amino]ethyl}-1H-1,3-benzodiazol-2-yl) amino]propyl 2,2-dimethylpropanoate (from Example 31, Step 6) (0.240 g, 0.46 mmol) in methanol (5 mL) was added 0.5N sodium hydroxide in methanol (3.7 mL, 1.87 mmol) and the reaction mixture was stirred at ambient temperature for 1 h. The reaction mixture was concentrated, and the residue diluted with water (10 mL). The aqueous layer was extracted with dichloromethane (3×15 mL), and the combined organic layer was washed with water (10 mL) followed by brine solution (10 mL), dried over sodium sulphate, filtered and concentrated to afford the crude product (0.180 g). This was purified by preparative HPLC purification (Method: 0.1% TFA in acetonitrile:Water) to afford 2-(3-chloro-4-fluorophenyl)-2-[(4-{1-[(1,3-oxazol-2-yl)amino]ethyl}-1H-1,3-benzodiazol-2-yl)amino]propan-1-ol (0.060 g) as an off-white solid.

$^1$H NMR (400 MHz, DMSO-d$_6$: D$_2$O) δ 7.58-7.41 (m, 1H), 7.41-7.30 (m, 3H), 7.28-6.94 (m, 1H), 6.87-6.79 (m, 2H), 6.77-6.65 (m, 1H), 4.94-4.89 (m, 1H), 3.83-3.48 (m, 2H), 1.69 (d, J=4.40 Hz, 3H), 1.49 (d, J=6.80 Hz, 1H), 1.28 (dd, J=6.80, 21.20 Hz, 2H);

MS: m/z 430.2 (M+1).

Example 32: Preparation of 2-(3-chloro-4-fluorophenyl)-2-({4-[(2-imino-2,3-dihydro-1,3-thiazol-3-yl)methyl]-1H-1,3-benzodiazol-2-yl}amino)propan-1-ol

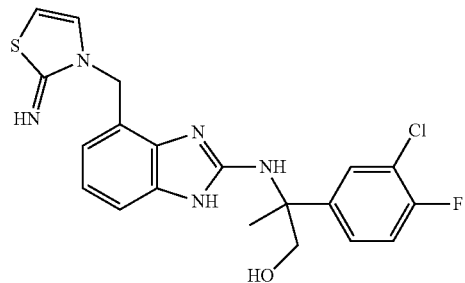 [SMILES: CC(CO)(Nc1nc2c(Cn3ccsc3=N)cccc2[nH]1)c1ccc(F)c(Cl)c1]

Example 32, Step 1: Preparation of 3-[(2,1,3-benzothiadiazol-4-yl)methyl]-2,3-dihydro-1,3-thiazol-2-imine hydrobromide

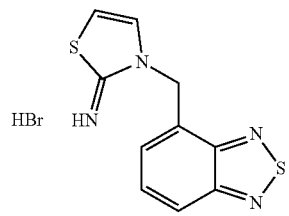 [SMILES: Br ; N=c1sccn1Cc1cccc2nsnc12]

To a solution of 4-(bromomethyl)-2,1,3-benzothiadiazole (from Example 1, Step 3) (12.0 g, 52.4 mmol) in acetonitrile (120 mL) was added 1,3-thiazol-2-amine (commercially available) (10.50 g, 105.0 mmol) and the mixture was stirred at 60° C. for 16 h. The solid formed in the reaction mixture was filtered and dried to afford the crude product (13 g) as a brown solid. This was stirred with water (6×50 mL) and the solid was filtered and dried under high vacuum at 40° C. to afford 3-[(2,1,3-benzothiadiazol-4-yl)methyl]-2,3-dihydro-1,3-thiazol-2-imine hydrobromide (9.0 g) as an off-white solid.

¹H NMR (400 MHz, DMSO-d₆) δ 9.75 (s, 2H), 8.12 (t, J=0.40 Hz, 1H), 7.76 (q, J=6.80 Hz, 1H), 7.49-7.43 (m, 2H), 7.10 (d, J=4.80 Hz, 1H), 5.81 (s, 2H);

MS: m/z 249.1 [(M+1)-HBr].

Example 32, Step 2: Preparation of 3-[(2-imino-2,3-dihydro-1,3-thiazol-3-yl)methyl]-benzene-1,2-diamine

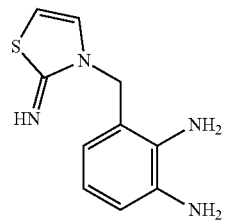 [SMILES: N=c1sccn1Cc1cccc(N)c1N]

To a de-gassed solution of 3-[(2,1,3-benzothiadiazol-4-yl)methyl]-2,3-dihydro-1,3-thiazol-2-imine hydrobromide (from Example 32, Step 1) (2.5 g, 10.1 mmol) in dry methanol (450 mL) was added Raney nickel (7.5 g, 300% w/w, pre-washed five times with dry methanol) and the resultant reaction mixture was stirred under a hydrogen atmosphere under pressure (approx. 1.5 kg/cm²) at ambient temperature for 24 h. The reaction mixture was filtered through a Celite bed and the bed was washed with methanol (250 mL). The combined filtrates were concentrated at 20° C. to afford 3-[(2-imino-2,3-dihydro-1,3-thiazol-3-yl)methyl]benzene-1,2-diamine (2.0 g) as a grey gum, which was used in the next step without further purification.

¹H NMR (400 MHz, DMSO-d₆) δ 6.84 (s, 1H), 6.56-6.41 (m, 4H), 4.79 (s, 2H);

MS: m/z 221.1 (M+1).

Example 32, Step 3: Preparation of 2-[({2-amino-3-[(2-imino-2,3-dihydro-1,3-thiazol-yl)methyl]phenyl}carbamothioyl)-amino]-2-(3-chloro-4-fluorophenyl)propyl 2,2-dimethylpropanoate and 2-[({2-amino-6-[(2-imino-2,3-dihydro-1,3-thiazol-3-yl)methyl]phenyl}carbamothioyl)amino]-2-(3-chloro-4-fluorophenyl)propyl 2,2-dimethylpropanoate (Mixture of Regioisomers)

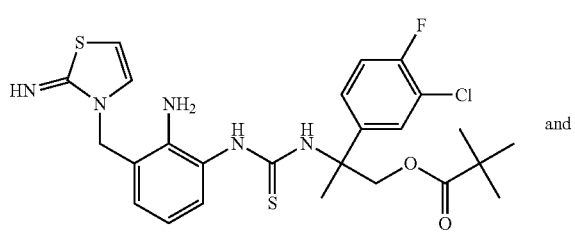
and

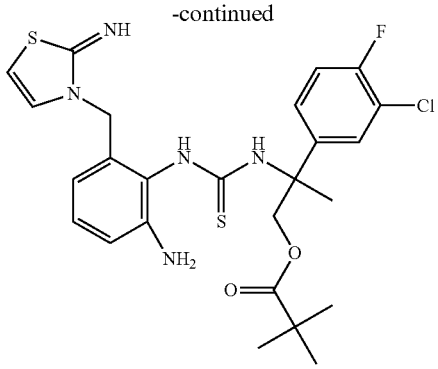

To a solution of 3-[(2-imino-2,3-dihydro-1,3-thiazol-3-yl)methyl]benzene-1,2-diamine (from Example 32, Step 2) (4 g, 18.157 mmol) in a mixture of solvents dichloromethane:methanol (1:1, 80 mL) was added [2-(3-chloro-4-fluorophenyl)-2-isothiocyanato-propyl] 2,2-dimethylpropanoate (from Example 8, Step 7) (3.0 g, 9.15 mmol) and the mixture was stirred at room temperature for 72 h. The reaction mixture was concentrated at 30° C. in a water bath to afford 2-[({2-amino-3-[(2-imino-2,3-dihydro-1,3-thiazol-3-yl)methyl]phenyl}carbamothioyl)amino]-2-(3-chloro-4-fluorophenyl)propyl 2,2-dimethylpropanoate and 2-[({2-amino-6-[(2-imino-2,3-dihydro-1,3-thiazol-3-yl)methyl]phenyl}carbamothioyl)amino]-2-(3-chloro-4-fluorophenyl)propyl 2,2-dimethylpropanoate (mixture of regioisomers) (7.00 g) as a yellow gum, which was used in the next step without further purification.

MS: m/z 550.1 (M+1).

Example 32, Step 4: Preparation of 2-(3-chloro-4-fluorophenyl)-2-({4-[(2-imino-2,3-dihydro-1,3-thiazol-3-yl)methyl]-1H-1,3-benzodiazol-2-yl}amino)propyl 2,2-dimethylpropanoate

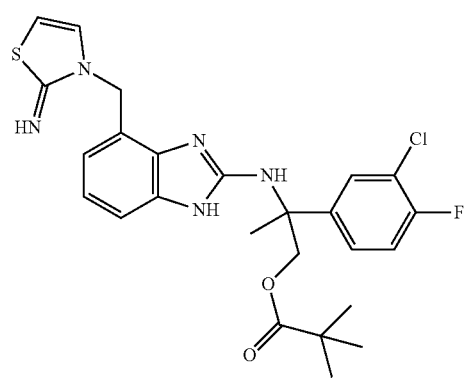 [SMILES: CC(C)(C)C(=O)OCC(C)(Nc1nc2c(Cn3ccsc3=N)cccc2[nH]1)c1ccc(F)c(Cl)c1]

To a solution of 2-[{2-amino-3-[(2-imino-2,3-dihydro-1,3-thiazol-3-yl)methyl]phenyl}carbamothioyl)amino]-2-(3-chloro-4-fluorophenyl)propyl 2,2-dimethylpropanoate and 2-[({2-amino-6-[(2-imino-2,3-dihydro-1,3-thiazol-3-yl)methyl]phenyl}carbamothioyl)amino]-2-(3-chloro-4-fluorophenyl)propyl 2,2-dimethylpropanoate (mixture of regioisomers) (from Example 32, step 3) (7.00 g, 12.70 mmol) in methanol (110 mL) was added iodoacetic acid (3.55 g, 19.10 mmol) and the mixture was refluxed for 1 h. The reaction mixture was concentrated to remove the solvent methanol at 30° C. to afford the crude product (8.0 g) as a reddish gum.

This was purified by preparative HPLC (0.1% TFA in acetonitrile:water) to afford 2-(3-chloro-4-fluorophenyl)-2-({4-[(2-imino-2,3-dihydro-1,3-thiazol-3-yl)methyl]-1H-1,3-benzodiazol-2-yl}amino)propyl 2,2-dimethylpropanoate, isolated as the trifluoroacetate salt (2.5 g), as a brown gum.

$^1$H NMR (400 MHz, DMSO-d$_6$: D$_2$O) δ 7.67 (q, J=2.00 Hz, 1H), 7.39-7.49 (m, 2H), 7.32 (d, J=8.00 Hz, 1H), 7.19 (q, J=8.40 Hz, 2H), 6.98 (d, J=4.80 Hz, 1H), 6.87 (d, J=7.60 Hz, 1H), 5.36 (s, 2H), 4.41 (q, J=11.20 Hz, 2H), 1.84 (s, 3H), 1.05 (s, 9H);

MS: m/z 516.1 [(M+1)].

Example 32, Step 5: Preparation of 2-(3-chloro-4-fluorophenyl)-2-({4-[(2-imino-2,3-dihydro-1,3-thiazol-3-yl)methyl]-1H-1,3-benzodiazol-2-yl}amino)propan-1-ol

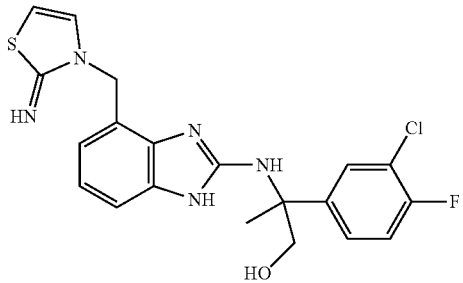 [SMILES: CC(CO)(Nc1nc2c(Cn3ccsc3=N)cccc2[nH]1)c1ccc(F)c(Cl)c1]

To a solution of 2-(3-chloro-4-fluorophenyl)-2-({4-[(2-imino-2,3-dihydro-1,3-thiazol-3-yl)methyl]-1H-1,3-benzodiazol-2-yl}amino)propyl 2,2-dimethylpropanoate; trifluoroacetic acid (from Example 32, step 4) (1.6 g, 2.54 mmol) in 1,4-dioxane:water (2:1, 90 mL) was added 4.0M HCl in dioxane (3.81 mL, 15.20 mmol) dropwise and the mixture was heated at 80° C. for 48 h. The reaction mixture was concentrated under reduced pressure at 30° C. to afford the crude product (1.2 g) as a brown gum. This was purified by preparative HPLC (Method: 0.1% TFA in acetonitrile:Water) to afford 2-(3-chloro-4-fluorophenyl)-2-({4-[(2-imino-2,3-dihydro-1,3-thiazol-3-yl)methyl]-1H-1,3-benzodiazol-2-yl}amino)propan-1-ol, isolated as the trifluoracetic acid salt (0.9 g) as a brown gum.

$^1$H NMR (400 MHz, DMSO-d$_6$: D$_2$O) δ 7.59 (t, J=2.00 Hz, 1H), 7.39-7.33 (m, 3H), 7.23-7.18 (m, 2H), 7.00 (d, J=4.40 Hz, 1H), 6.84 (d, J=7.60 Hz, 1H), 5.37 (s, 2H), 3.72 (q, J=11.20 Hz, 2H), 1.74 (s, 3H);

MS: m/z 432.0 [(M+1)].

The above product was separated into its two enantiomers by Chiral SFC using the method: Column: Chiralpak OX-H; Mobile Phase: 0.5% isopropyl amine in isopropyl alcohol; co-solvent 50% CO$_2$; Flow rate: 5 mL/min, pressure: 100 bar; Temperature: 35° C. to obtain the two enantiomers 32a and 32b.

Example 32a: (−)-2-(3-chloro-4-fluorophenyl)-2-({4-[(2-imino-2,3-dihydro-1,3-thiazol-3-yl)methyl]-1H-1,3-benzodiazol-2-yl}amino)propan-1-ol The (−) enantiomer was the first compound to elute-off the column, isolated as the hydrochloride salt.

$^1$H NMR (400 MHz, DMSO-d$_6$: D$_2$O) δ 7.54 (d, J=6.80 Hz, 1H), 7.30-7.21 (m, 2H), 7.22 (t, J=4.40 Hz, 2H), 7.02-6.95 (m, 2H), 6.83 (d, J=4.00 Hz, 1H), 5.15 (q, J=14.80 Hz, 2H), 3.66 (q, J=10.80 Hz, 2H), 1.72 (s, 3H);

MS: m/z 432.1 [(M+1)-HCl];
SOR: [α]$_D$$^{23.3}$ (−) 22.40, (MeOH, c=0.5).

Example 32b: (+)-2-(3-chloro-4-fluorophenyl)-2-({4-[(2-imino-2,3-dihydro-1,3-thiazol-3-yl)methyl]-1H-1,3-benzodiazol-2-yl}amino)propan-1-ol The (+) enantiomer was the second compound to elute-off the column, isolated as the hydrochloride salt.

$^1$H NMR (400 MHz, DMSO-d$_6$: D$_2$O) δ 7.61 (d, J=5.60 Hz, 1H), 7.42-7.36 (m, 2H), 7.30 (d, J=7.60 Hz, 1H), 7.24 (d, J=4.40 Hz, 1H), 7.10 (bs, 1H), 6.94-6.92 (m, 2H), 5.29 (bs, 2H) 3.71 (q, J=11.20 Hz, 2H), 1.72 (s, 3H);

MS: m/z 432.1 [(M+1)-HCl];
SOR: [α]$_D$$^{23.4}$ (+) 22.80, (MeOH, c=0.5).

Example 33: Preparation 1-[(2-{[2-(3-chloro-4-fluorophenyl)-1-hydroxypropan-2-yl]amino}-1H-1,3-benzodiazol-4-yl)methyl]-2,3-dihydro-1H-imidazol-2-one

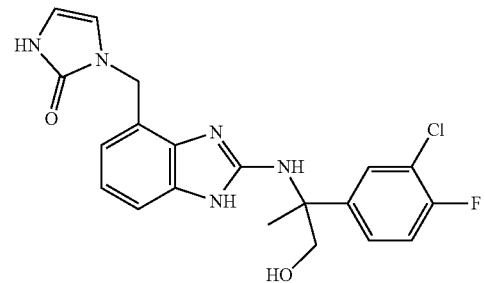 [SMILES: CC(CO)(Nc1nc2c(Cn3cc[nH]c3=O)cccc2[nH]1)c1ccc(F)c(Cl)c1]

Example 33, Step 1: Preparation of 1-[(2,1,3-benzothiadiazol-4-yl)methyl]-2,3-dihydro-1H-imidazol-2-one

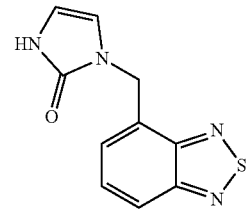 [SMILES: O=c1[nH]ccn1Cc1cccc2nsnc12]

To a solution of 2,3-dihydro-1H-imidazol-2-one (commercially available) (2.0 g, 23.80 mmol) in DMSO (200 mL) was added 60% sodium hydride (0.911 g, 23.8 mmol) at 0° C. and it was stirred for 30 mins. 4-(Bromomethyl)-2,1,3-benzothiadiazole (from Example 1, Step 3) (4.36 g, 19.0 mmol) was added at 0° C. and the mixture was stirred at ambient temperature for 3 h. The reaction mixture was quenched with ice-cold water and extracted with ethyl acetate. The organic layer was dried over sodium sulphate, filtered and concentrated to afford a brown gum. A solid formed which was filtered and dried to afford the crude product (1.2 g) as a brown solid, which was purified by silica gel column chromatography using 10% methanol in DCM as an eluent to afford 1-[(2,1,3-benzothiadiazol-4-yl)methyl]-2,3-dihydro-1H-imidazol-2-one (0.4 g) as an off-white solid.

$^1$H NMR (400 MHz, DMSO-$d_6$) δ 10.09 (s, 1H), 8.03 (d, J=8.00 Hz, 1H), 7.70 (q, J=6.80 Hz, 1H), 7.27 (q, J=1.20 Hz, 1H), 6.54 (q, J=2.00 Hz, 1H), 6.42 (t, J=2.80 Hz, 1H), 5.19 (s, 2H);

MS: m/z 232.9 (M+1).

Example 33, Step 2: Preparation of 1-[(2,3-diaminophenyl)methyl]-2,3-dihydro-1H-imidazol-2-one

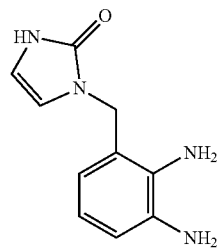 [SMILES: Nc1cccc(Cn2cc[nH]c2=O)c1N]

To a de-gassed solution of 1-[(2,1,3-benzothiadiazol-4-yl)methyl]-2,3-dihydro-1H-imidazol-2-one (from Example 33, step 1) (0.6 g, 2.58 mmol) in dry methanol (43 mL) was added Raney nickel (1.8 g, 300% w/w, pre-washed five times with dry methanol) and the resultant reaction mixture was stirred under a hydrogen atmosphere under pressure (Approx. 1.5 kg/cm$^2$) at ambient temperature for 24 h. The reaction mixture was filtered over a Celite bed, and the bed was washed with methanol (150 mL). The combined filtrates were concentrated at 20° C. to afford 1-[(2,3-diaminophenyl)methyl]-2,3-dihydro-1H-imidazol-2-one (0.22 g) as a brown gum, which was used in the next step without further purification.

MS: m/z 205.1 (M+1).

Example 33, Step 3: Preparation of 2-[({2-amino-3-[(2-oxo-2,3-dihydro-1H-imidazol-1-yl)methyl]phenyl}carbamothioyl)amino]-2-(3-chloro-4-fluorophenyl)propyl 2,2-dimethylpropanoate and 2-[({2-amino-6-[(2-oxo-2,3-dihydro-1H-imidazol-1-yl)methyl]phenyl}carbamothioyl)amino]-2-(3-chloro-4-fluorophenyl)propyl 2,2-dimethylpropanoate (Mixture of Regioisomers)

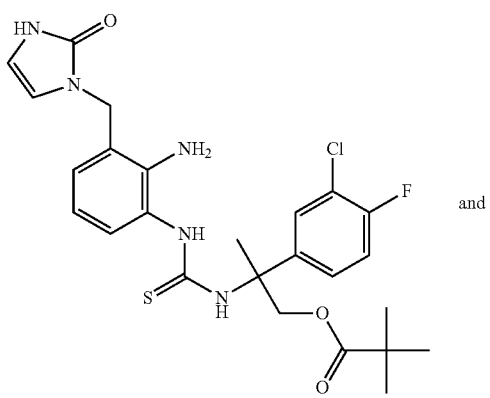

and

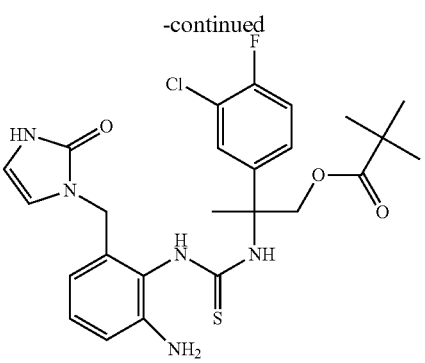

To a solution of 1-[(2,3-diaminophenyl)methyl]-2,3-dihydro-1H-imidazol-2-one (from Example 33, step 2) (0.22 g, 1.08 mmol) in acetonitrile (5 mL) was added [2-(3-chloro-4-fluoro-phenyl)-2-isothiocyanato-propyl] 2,2-dimethylpropanoate (from Example 8, Step 7) (0.42 g, 1.29 mmol) and it was stirred at room temperature for 48 h. The reaction mixture was concentrated at 30° C. to afford 2-[({2-amino-3-[(2-oxo-2,3-dihydro-1H-imidazol-1-yl)methyl]phenyl}carbamothioyl)amino]-2-(3-chloro-4-fluorophenyl)propyl 2,2-dimethyl-propanoate and 2-[({2-amino-6-[(2-oxo-2,3-dihydro-1H-imidazol-1-yl)methyl]phenyl}-carbamothioyl)amino]-2-(3-chloro-4-fluorophenyl)propyl 2,2-dimethylpropanoate (mixture of regioisomers) (0.35 g) as a colourless gum, which was used in the next step without further purification.

MS: m/z 534.2 (M+1).

Example 33, Step 4: Preparation of 2-(3-chloro-4-fluorophenyl)-2-({4-[(2-oxo-2,3-dihydro-1H-imidazol-1-yl)methyl]-1H-1,3-benzodiazol-2-yl}amino)propyl 2,2-dimethyl-propanoate

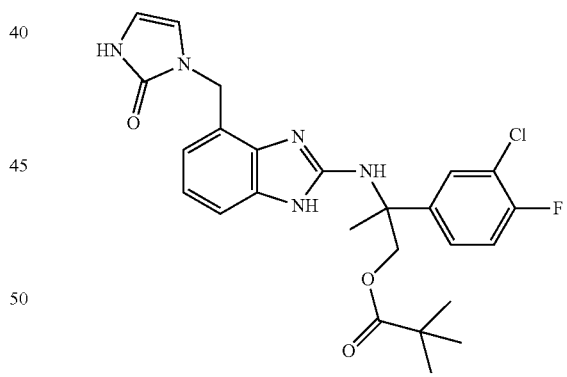

To a solution of 2-[({2-amino-3-[(2-oxo-2,3-dihydro-1H-imidazol-1-yl)methyl]phenyl}carbamothioyl)amino]-2-(3-chloro-4-fluorophenyl)propyl 2,2-dimethyl-propanoate and 2-[({2-amino-6-[(2-oxo-2,3-dihydro-1H-imidazol-1-yl)methyl]phenyl}-carbamothioyl)amino]-2-(3-chloro-4-fluorophenyl)propyl 2,2-dimethylpropanoate (mixture of regioisomers) (from Example 33, step 3) (0.35 g) in methanol (10 mL) was added iodoacetic acid (0.183 g, 0.983 mmol) and the mixture was refluxed for 2 h. The reaction mixture was concentrated to remove the solvent methanol at 30° C. to afford the crude product, which was purified by preparative HPLC (0.1% TFA in acetonitrile:Water) to afford 2-(3-chloro-4-fluorophenyl)-2-({4-[(2-oxo-2,3-dihydro-1H-imidazol-1-yl)methyl]-1H-1,3-benzodiazol-2-yl}amino)propyl 2,2-dimethylpropanoate, isolated as the trifluoroacetate salt, (0.07 g) as a yellow solid.

MS: m/z 500.1 (M+1).

Example 33, Step 5: Preparation of 1-[(2-{[2-(3-chloro-4-fluorophenyl)-1-hydroxypropan-2-yl]amino}-1H-1,3-benzodiazol-4-yl)methyl]-2,3-dihydro-1H-imidazol-2-one

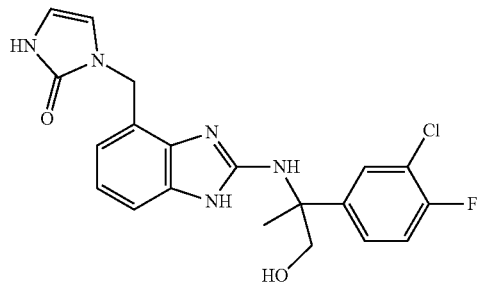 [SMILES: CC(CO)(Nc1nc2c(Cn3cc[nH]c3=O)cccc2[nH]1)c1ccc(F)c(Cl)c1]

To a solution of 2-(3-chloro-4-fluorophenyl)-2-({4-[(2-oxo-2,3-dihydro-1H-imidazol-1-yl)methyl]-1H-1,3-benzodiazol-2-yl}amino)propyl 2,2-dimethylpropanoate; trifluoroacetic acid, (from Example 33, step 4) (0.07 g, 0.140 mmol) in methanol (5 mL) was added 0.5 N sodium hydroxide in methanol (2.8 mL, 1.40 mmol) dropwise and the mixture was stirred at ambient temperature for 1 h. The reaction mixture was concentrated to afford a brown gum which was purified by preparative HPLC (0.1% FA in acetonitrile:water) to afford 1-[(2-{[2-(3-chloro-4-fluorophenyl)-1-hydroxypropan-2-yl]amino}-1H-1,3-benzodiazol-4-yl)methyl]-2,3-dihydro-1H-imidazol-2-one (0.025 g) as a colourless gum.

$^1$H NMR (400 MHz, AcOH-d$_4$) δ 7.67 (dd, J=2.40, 6.80 Hz, 1H), 7.53-7.49 (m, 1H), 7.42 (d, J=7.60 Hz, 1H), 7.24-7.20 (m, 3H), 6.50 (s, 2H), 5.00-4.89 (m, 2H), 4.20 (d, J=12.00 Hz, 1H), 4.01 (d, J=12.00 Hz, 1H), 1.84 (s, 3H);

MS: m/z 416.1 (M+1).

Example 34: Preparation of 1-[(2-{[2-(3-chloro-4-fluorophenyl)-1-hydroxypropan-2-yl]amino}-1H-1,3-benzodiazol-4-yl)methyl]imidazolidin-2-one

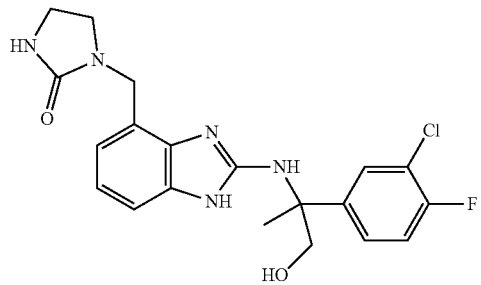 [SMILES: CC(CO)(Nc1nc2c(CN3CCNC3=O)cccc2[nH]1)c1ccc(F)c(Cl)c1]

Starting with imidazolidin-2-one (commercially available) (1.0 g, 11.615 mmol) in place of 2,3-dihydro-1H-imidazol-2-one, the method described for Example 33 was used to prepare 1-[(2-{[2-(3-chloro-4-fluorophenyl)-1-hydroxypropan-2-yl]amino}-1H-1,3-benzodiazol-4-yl)methyl]imidazolidin-2-one, (0.100 g) isolated as a white solid.

$^1$H NMR (400 MHz, DMSO-d$_6$: D$_2$O) δ 7.50 (d, J=6.80 Hz, 1H), 7.36 (s, 1H), 7.27 (t, J=8.80 Hz, 1H), 7.08 (d, J=7.20 Hz, 1H), 7.01 (d, J=7.60 Hz, 1H), 6.87 (d, J=7.60 Hz, 1H), 4.31 (s, 1H), 4.20 (s, 1H), 3.65 (d, J=10.80 Hz, 2H), 2.99 (t, J=7.20 Hz, 4H), 1.64 (s, 3H);

MS: m/z 418.0 (M+1).

Example 35: Preparation of 1-[(2-{[2-(3-chloro-4-fluorophenyl)-1-hydroxypropan-2-yl]amino}-1H-1,3-benzodiazol-4-yl)methyl]-3-methylimidazolidin-2-one

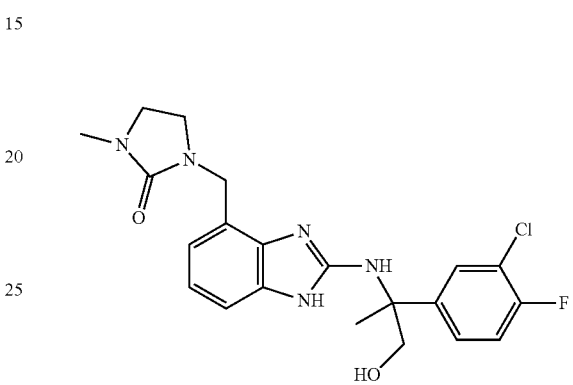

Starting with 1-methylimidazolidin-2-one (Commercially available) (1.0 g, 9.988 mmol) in place of 2,3-dihydro-1H-imidazol-2-one, the method described for Example 33 was used to prepare 1-[(2-{[2-(3-chloro-4-fluorophenyl)-1-hydroxypropan-2-yl]amino}-1H-1,3-benzodiazol-4-yl)methyl]-3-methylimidazolidin-2-one, (0.150 g) isolated as an off-solid.

$^1$H NMR (400 MHz, DMSO-d$_6$: D$_2$O) δ 7.63 (t, J=2.00 Hz, 1H), 7.40-7.38 (m, 3H), 7.22-7.14 (m, 2H), 4.35 (d, J=10.40 Hz, 2H), 3.72 (t, J=6.40 Hz, 2H), 3.24-3.16 (m, 4H), 2.66 (d, J=12.40 Hz, 3H), 1.75 (s, 3H);

MS: m/z 432.0 (M+1).

Example 36: Preparation 3-[(2-{[2-(3-chloro-4-fluorophenyl)-1-hydroxypropan-2-yl]amino}-1H-1,3-benzodiazol-4-yl)methyl]-1,3-thiazolidin-2-one

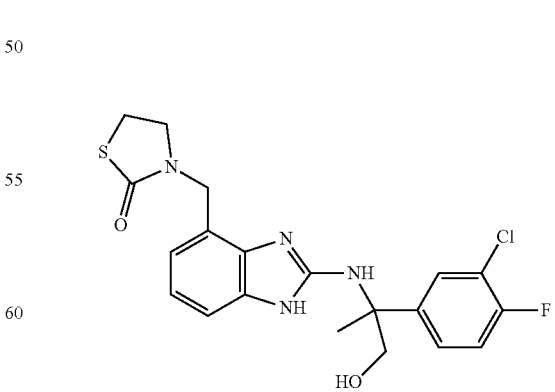

Starting with 1,3-thiazolidin-2-one (commercially available) (0.5 g, 4.85 mmol) in place of 2,3-dihydro-1H-imidazol-2-one, the method described for Example 33 was used to prepare 3-[(2-{[2-(3-chloro-4-fluorophenyl)-1-hydroxypropan-2-yl]amino}-1H-1,3-benzodiazol-4-yl)-methyl]-1,3-thiazolidin-2-one (0.2 g) isolated as a colourless gum.

$^1$H NMR (400 MHz, AcOH-d$_4$) δ 7.67 (dd, J=2.40, 6.80 Hz, 1H), 7.66-7.47 (m, 2H), 7.29-0.22 (m, 2H), 7.18 (d, J=6.80 Hz, 1H), 4.67 (d, J=15.20 Hz, 1H), 4.50 (d, J=15.20 Hz, 1H), 4.27 (d, J=12.00 Hz, 1H), 4.03 (d, J=12.00 Hz, 1H), 3.64-3.55 (m, 2H), 3.31-3.18 (m, 2H), 1.81 (s, 3H);

MS: m/z 435.0 [(M+1)-TFA].

Example 37: Preparation of 1-[(2-{[2-(3-chloro-4-fluorophenyl)-1-hydroxypropan-2-yl]amino}-1H-1,3-benzodiazol-4-yl)methyl]pyrrolidin-2-one

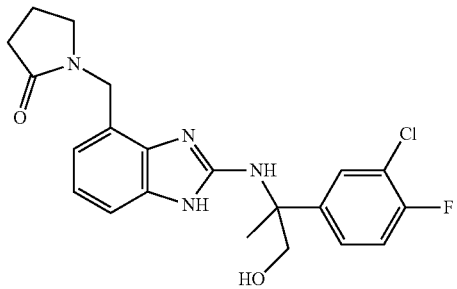 [SMILES: CC(CO)(Nc1nc2c(CN3CCCC3=O)cccc2[nH]1)c1ccc(F)c(Cl)c1]

Starting with pyrrolidine-2-one (Commercially available) (1.0 g, 11.750 mmol) in place of 2,3-dihydro-1H-imidazol-2-one, the method described for Example 33 was used to prepare 1-[(2-{[2-(3-chloro-4-fluorophenyl)-1-hydroxypropan-2-yl]amino}-1H-1,3-benzodiazol-4-yl)-methyl]pyrrolidin-2-one (0.130 g), isolated as the trifluoroacetate salt, as an off-white solid.

$^1$H NMR (400 MHz, DMSO-d$_6$: D$_2$O) δ 7.63-7.61 (m, 1H), 7.41-7.37 (m, 2H), 7.35-7.30 (m, 1H), 7.23-7.14 (m, 2H), 4.45 (q, J=14.80 Hz, 2H), 3.71 (t, J=11.60 Hz, 2H), 3.27 (t, J=7.20 Hz, 2H), 2.26-2.21 (m, 2H), 1.92 (s, 2H), 1.80 (s, 3H);

MS: m/z 417.1 (M+1).

Example 38: Preparation of 2-(3-chloro-4-fluorophenyl)-2-[(4-{[(1,3-oxazol-2-yl)amino]-methyl}-1H-1,3-benzodiazol-2-yl)amino]propan-1-ol

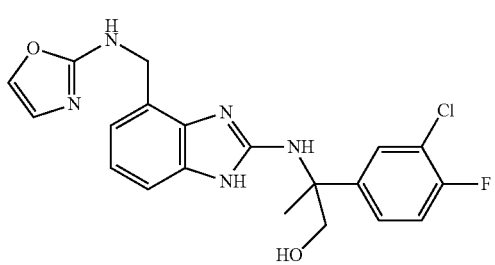 [SMILES: CC(CO)(Nc1nc2c(CNc3ncco3)cccc2[nH]1)c1ccc(F)c(Cl)c1]

Example 38, Step 1: Preparation of N-[(2,1,3-benzothiadiazol-4-yl)methyl]-1,3-oxazol-2-amine

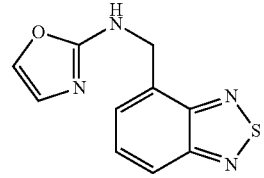 [SMILES: c1cc(CNc2ncco2)c2nsnc2c1]

To a solution of 2,1,3-benzothiadiazole-4-carbaldehyde (from Example 9, step 2) (0.8 g, 4.87 mmol) and 1,3-oxazol-2-amine (Commercially available) (0.819 g, 9.75 mmol) in ethanol (50 mL), cooled to 0° C., was added titanium(IV) isopropoxide (17.4 ml, 58.5 mmol) and the reaction mixture was stirred at ambient temperature for 20 h. The reaction mixture was cooled to 0° C., and sodium borohydride (0.368 g, 9.75 mmol) was added portion wise, and the reaction mixture was stirred at ambient temperature for 20 h. The reaction mixture was quenched with ice-cold water (50 mL) and filtered through a Celite bed and washed with ethyl acetate (50 mL). The filtrate was concentrated, and the crude mixture was diluted with water (50 mL), extracted with ethyl acetate (2×50 mL). The combined organic layer was washed with brine solution (50 mL), dried over sodium sulphate, filtered and concentrated to afford the crude product (1.1 g) as a brown gum. This was purified by silica gel column chromatography and eluted with 38% ethyl acetate in petroleum ether to afford N-[(2,1,3-benzothiadiazol-4-yl)methyl]-1,3-oxazol-2-amine (0.450 g) as an off white solid.

$^1$H NMR (400 MHz, DMSO-d$_6$) 7.99 (d, J=8.80 Hz, 1H), 7.86 (m, 1H), 7.70 (t, J=6.80 Hz, 1H), 7.60-7.58 (m, 1H), 7.45 (d, J=0.80 Hz, 1H), 6.75 (d, J=0.40 Hz, 1H), 4.88 (d, J=2.00 Hz, 2H);

MS: m/z 233.1 (M+1).

Example 38, Step 2: Preparation of 3-{[(1,3-oxazol-2-yl)amino]methyl}benzene-1,2-diamine

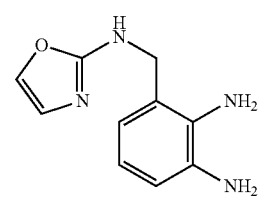 [SMILES: Nc1cccc(CNc2ncco2)c1N]

To a de-gassed solution of N-[(2,1,3-benzothiadiazol-4-yl)methyl]-1,3-oxazol-2-amine (from Example 38, step 1) (0.400 g, 1.72 mmol) in methanol (40 mL) was added Raney nickel (1.5 g, 300% w/w, pre-washed five times with dry methanol) and the resultant reaction mixture was stirred under hydrogen pressure (approx. 1.5 kg/cm$^2$) at ambient temperature for 16 h. The reaction mixture was filtered through Celite and the filtrate was concentrated under high vacuum to afford 3-{[(1,3-oxazol-2-yl)amino]methyl}benzene-1,2-diamine (0.285 g) as a brown liquid, which was used in the next step without further purification.

MS: m/z 205.2 (M+1).

Example 38, Step 3: Preparation of 2-{[(2-amino-3-{[(1,3-oxazol-2-yl)amino]methyl}-phenyl)carbamothioyl]amino}-2-(3-chloro-4-fluorophenyl)propyl 2,2-dimethylpropanoate and 2-{[(2-amino-6-{[(1,3-oxazol-2-yl)amino]methyl}phenyl)-carbamothioyl]amino}-2-(3-chloro-4-fluorophenyl)propyl 2,2-dimethylpropanoate (Mixture of Regioisomers)

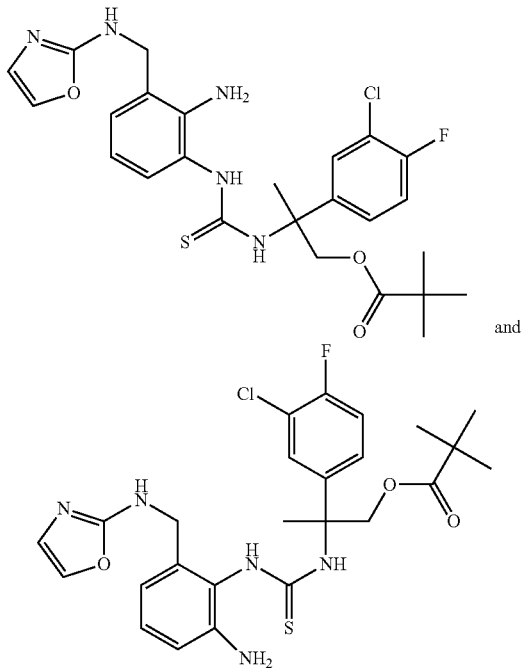

To a solution of 3-{[(1,3-oxazol-2-yl)amino]methyl}benzene-1,2-diamine (from Example 38, step 2) (0.275 g, 1.25 mmol) in a mixture of solvents dichloromethane:methanol (1:1, 8 mL) was added 2-(3-chloro-4-fluorophenyl)-2-isothiocyanatopropyl 2,2-dimethylpropanoate (from Example 8, Step 7) (0.453 g, 1.37 mmol) and the mixture was stirred at ambient temperature for 40 h. The reaction mixture was concentrated to afford the crude product (0.620 g) as a brown gum, which was used in the next step without further any purification.
MS: m/z 534.1 (M+1).

Example 38, Step 4: Preparation of 2-(3-chloro-4-fluorophenyl)-2-[(4-{[(1,3-oxazol-2-yl)amino]methyl}-1H-1,3-benzodiazol-2-yl)amino]propyl 2,2-dimethylpropanoate

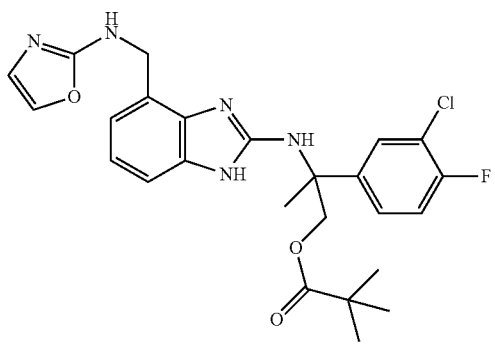 [SMILES: CC(C)(C)C(=O)OCC(C)(Nc1nc2c(CNc3ncco3)cccc2[nH]1)c1ccc(F)c(Cl)c1]

To a solution of 2-{[(2-amino-3-{[(1,3-oxazol-2-yl)amino]methyl}phenyl)-carbamothioyl]-amino}-2-(3-chloro-4-fluorophenyl)propyl 2,2-dimethylpropanoate and 2-{[(2-amino-6-{[(1,3-oxazol-2-yl)amino]methyl}phenyl)carbamothioyl]amino}-2-(3-chloro-4-fluorophenyl)propyl 2,2-dimethylpropanoate (mixture of regioisomers) (from Example 38, Step 3) (0.620 g, 1.16 mmol) in methanol (15 mL) was added iodoacetic acid (0.259 g, 1.39 mmol) and the reaction mixture was stirred at ambient temperature for 5 h. The reaction mixture was concentrated and diluted with ice-cold water (50 mL). The aqueous layer was extracted with dichloromethane (3×50 mL). The combined organic layer was washed with saturated sodium bicarbonate solution (50 mL), followed by brine solution (50 mL), dried over sodium sulphate, filtered and concentrated to afford the crude product (0.260 g) as a brown gum. This was purified by preparative HPLC (0.1% TFA in acetonitrile:water) to afford 2-(3-chloro-4-fluorophenyl)-2-[(4-{[(1,3-oxazol-2-yl) amino]methyl}-1H-1,3-benzodiazol-2-yl)amino]propyl 2,2-dimethylpropanoate (0.125 g) as a brown solid.
$^1$H NMR (400 MHz, DMSO-$d_6$) δ 11.93 (s, 1H), 8.51 (s, 2H), 7.71-7.62 (m, 2H), 7.47-7.23 (m, 3H), 7.01-6.96 (m, 1H), 6.80-6.72 (m, 2H), 4.54-4.45 (m, 4H), 1.82 (s, 3H), 1.06 (s, 9H);
MS: m/z 500.2 (M+1).

Example 38: Preparation of 2-(3-chloro-4-fluorophenyl)-2-[(4-{[(1,3-oxazol-2-yl)amino]methyl}-1H-1,3-benzodiazol-2-yl)amino]propan-1-ol

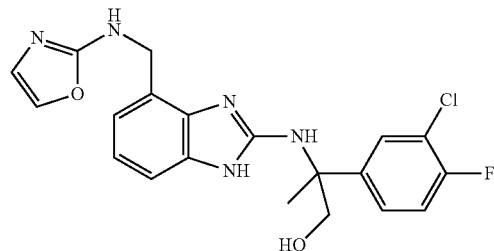 [SMILES: CC(CO)(Nc1nc2c(CNc3ncco3)cccc2[nH]1)c1ccc(F)c(Cl)c1]

To a solution of 2-(3-chloro-4-fluorophenyl)-2-[(4-{[(1,3-oxazol-2-yl)amino]methyl}-1H-1,3-benzodiazol-2-yl)amino]propyl 2,2-dimethylpropanoate (from Example 38, Step 4) (0.085 g, 0.17 mmol) in methanol (5 mL) was added 0.5N sodium hydroxide in methanol (0.68 ml, 0.34 mmol) and the reaction mixture was stirred at ambient temperature for 1 h. The reaction mixture was concentrated, and the residue was diluted with water (10 mL). The aqueous layer was extracted with dichloromethane (3×15 mL). The combined organic layer was washed with water (10 mL), followed by brine solution (10 mL), dried over sodium sulphate, filtered and concentrated to afford the crude product (120 mg) as a brown gum. This was purified by preparative HPLC purification (Method: 10 mmol ammonium acetate in water:acetonitrile) to afford 2-(3-chloro-4-fluorophenyl)-2-[(4-{[(1,3-oxazol-2-yl)amino]methyl}-1H-1,3-benzodiazol-2-yl)amino]propan-1-ol (0.028 g) as an off-white solid.
$^1$H NMR (400 MHz, CD$_3$OD) δ 7.61-7.58 (m, 1H), 7.46-7.42 (m, 1H), 7.29 (m, 1H), 7.19 (t, J=8.80 Hz, 1H), 7.13-7.11 (m, 1H), 6.97-6.95 (m, 2H), 6.78 (s, 1H), 4.60 (s, 2H), 3.95 (d, J=11.60 Hz, 1H), 3.81 (d, J=11.60 Hz, 1H), 1.31 (s, 3H);
MS: m/z 416.1 (M+1).

Example 39: Preparation of 2-(4-chloro-3-fluorophenyl)-2-({4-[(2-imino-2,3-dihydro-1,3-oxazol-3-yl)methyl]-1H-1,3-benzodiazol-2-yl}amino)propan-1-ol

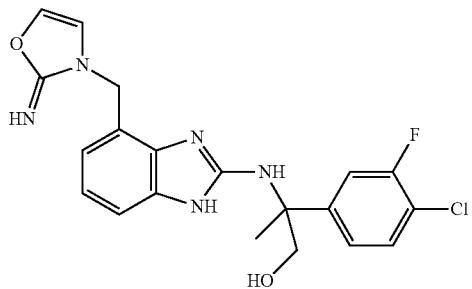 [SMILES: CC(CO)(Nc1nc2c(Cn3ccoc3=N)cccc2[nH]1)c1ccc(Cl)c(F)c1]

The commercially available 1-(4-chloro-3-fluorophenyl)ethan-1-one and 3-[(2-imino-2,3-dihydro-1,3-oxazol-3-yl)methyl]benzene-1,2-diamine (from Example 1, step 5) were used, following the method described for Example 18, to afford the required product which was isolated as its two enantiomers.

Example 39a: 2-(4-chloro-3-fluorophenyl)-2-({4-[(2-imino-2,3-dihydro-1,3-oxazol-3-yl)methyl]-1H-1,3-benzodiazol-2-yl}amino)propan-1-ol (Enantiomer a)

$^1$H NMR (400 MHz, DMSO-$d_6$: $D_2O$): δ 7.77 (d, J=10.40 Hz, 1H), 7.57 (t, J=8.00 Hz, 1H), 7.46 (d, J=10.80 Hz, 1H), 7.37-7.21 (m, 3H), 7.18 (d, J=7.60 Hz, 1H), 7.10 (t, J=5.60 Hz, 1H), 5.27 (d, J=10.80 Hz, 2H), 3.59 (m, 2H), 1.76 (s, 3H);
MS: m/z 416.0 [(M+1)-HCl].

Example 39b: 2-(4-chloro-3-fluorophenyl)-2-({4-[(2-imino-2,3-dihydro-1,3-oxazol-3-yl)methyl]-1H-1,3-benzodiazol-2-yl}amino)propan-1-ol (Enantiomer b)

$^1$H NMR (400 MHz, DMSO-$d_6$: $D_2O$) δ 7.76 (s, 1H), 7.56 (t, J=8.00 Hz, 1H), 7.45 (dd, J=2.00, 11.20 Hz, 1H), 7.35 (d, J=8.00 Hz, 1H), 7.23 (m, 3H), 7.09 (d, J=7.60 Hz, 1H), 5.26 (s, 2H), 3.69 (m, 2H), 1.75 (s, 3H);
MS: m/z 416.1 [(M+1)-HCl].

Example 40: Preparation of 2-(4-chloro-3-fluorophenyl)-2-[(4-{[(1,3-oxazol-2-yl)amino]-methyl}-1H-1,3-benzodiazol-2-yl)amino]propan-1-ol

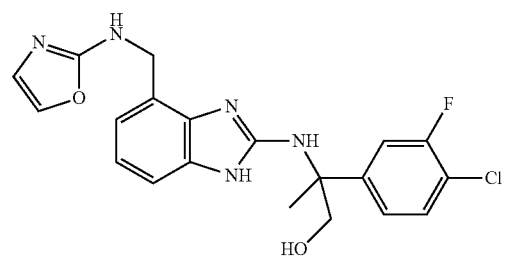 [SMILES: CC(CO)(Nc1nc2c(CNc3ncco3)cccc2[nH]1)c1ccc(Cl)c(F)c1]

Example 40, Step 1: Preparation of 2-{[(2-amino-3-{[(1,3-oxazol-2-yl)amino]methyl}phenyl)carbamothioyl]amino}-2-(4-chloro-3-fluorophenyl)propyl 2,2-dimethylpropanoate and 2-{[(2-amino-6-{[(1,3-oxazol-2-yl)amino]methyl}phenyl)-carbamothioyl]amino}-2-(4-chloro-3-fluorophenyl)propyl 2,2-dimethylpropanoate (Mixture of Regioisomers)

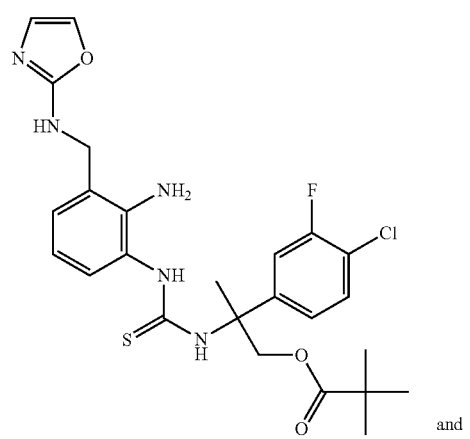

and

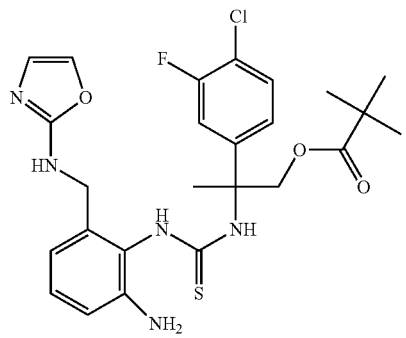

To a solution of 3-{[(1,3-oxazol-2-yl)amino]methyl}benzene-1,2-diamine (from Example 38, Step 2) (1.2 g, 4.94 mmol) in a mixture of solvents dichloromethane:methanol (1:1, 24 mL) was added 2-(4-chloro-3-fluorophenyl)-2-isothiocyanatopropyl 2,2-dimethylpropanoate (1.63 g, 4.94 mmol), (made from commercially available 1-(4-chloro-3-fluorophenyl)ethan-1-one, by the method described for Example 3, Steps 1 to 7). The reaction mixture was stirred at room temperature for 24 h and then concentrated at 30° C. in a water bath to afford 2-{[(2-amino-3-{[(1,3-oxazol-2-yl)amino]methyl}phenyl)carbamothioyl]amino}-2-(4-chloro-3-fluorophenyl)propyl 2,2-dimethylpropanoate and 2-{[(2-amino-6-{[(1,3-oxazol-2-yl)amino]methyl}phenyl)carbamothioyl]amino}-2-(4-chloro-3-fluorophenyl)propyl 2,2-dimethylpropanoate (mixture of regioisomers) (2.80 g) as a yellow gum, which was used in the next step without further purification.

MS: m/z 534.0 (M+1).

Example 40, Step 2: Preparation of 2-(4-chloro-3-fluorophenyl)-2-[(4-{[(1,3-oxazol-2-yl)amino]methyl}-1H-1,3-benzodiazol-2-yl)amino]propyl 2,2-dimethylpropanoate

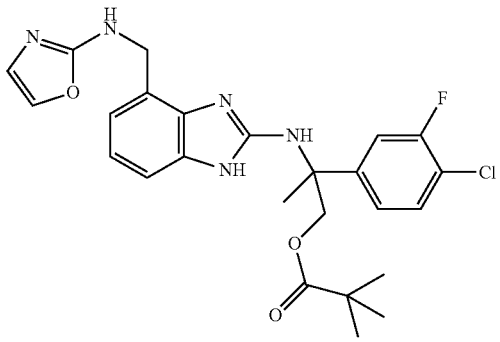 [SMILES: CC(C)(C)C(=O)OCC(C)(Nc1nc2c(CNc3ncco3)cccc2[nH]1)c1ccc(Cl)c(F)c1]

To a solution of 2-{[(2-amino-3-{[(1,3-oxazol-2-yl)amino]methyl}phenyl)-carbamothioyl]amino}-2-(4-chloro-3-fluorophenyl)propyl 2,2-dimethylpropanoate and 2-{[(2-amino-6-{[(1,3-oxazol-2-yl)amino]methyl}phenyl)carbamothioyl]amino}-2-(4-chloro-3-fluorophenyl)propyl 2,2-dimethylpropanoate (mixture of regioisomers) (from Example 40, step 1) (2.80 g, 5.24 mmol) in methanol (30 mL) was added iodoacetic acid (0.975 g, 5.24 mmol) and the mixture was stirred at ambient temperature for 1 h. The reaction mixture was concentrated to remove the solvent methanol at 30° C. to afford the crude product, which was dissolved in DCM and washed with 10% NaHCO$_3$ solution, followed by brine solution. The organic layer was dried over sodium sulphate and concentrated to afford the product (2.1 g) as a brown gum. This was purified by preparative HPLC (Method: 10 mmol ammonium acetate in water:acetonitrile) to afford 2-(4-chloro-3-fluorophenyl)-2-[(4-{[(1,3-oxazol-2-yl)amino]-methyl}-1H-1,3-benzodiazol-2-yl)amino]propyl 2,2-dimethylpropanoate (1.3 g) as a white solid.

$^1$H NMR (400 MHz, DMSO-d$_6$: D$_2$O) δ 7.54-7.35 (m, 4H), 7.01 (t, J=5.60 Hz, 1H), 6.82-6.71 (m, 3H), 4.54-4.44 (m, 4H), 1.81 (s, 3H), 1.05 (s, 9H);

MS: m/z 500.1 (M+1).

The product from Step 2 was separated into the two enantiomers by Chiral SFC using the method: Column: Chiralpak OX-H; Mobile Phase: 0.5% isopropyl amine in isopropyl alcohol; co-solvent 40% CO$_2$; Flow rate: 5 mL/min, pressure: 100 bar; Temperature: 35° C. to obtain the two enantiomers 40a and 40b.

Example 40, Step 3a: (+)-2-(4-chloro-3-fluorophenyl)-2-[(4-{[(1,3-oxazol-2-yl)amino]-methyl}-1H-1,3-benzodiazol-2-yl)amino]propyl 2,2-dimethylpropanoate The (+) enantiomer was the first compound to elute-off the column.

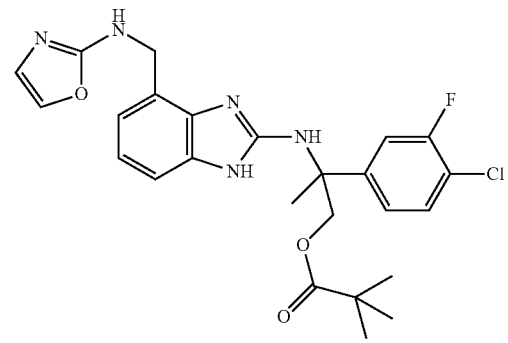 [SMILES: CC(C)(C)C(=O)OCC(C)(Nc1nc2c(CNc3ncco3)cccc2[nH]1)c1ccc(Cl)c(F)c1]

$^1$H NMR (AcOH-d$_4$) δ 7.55-7.47 (m, 2H), 7.42-7.40 (m, 2H), 7.29 (dd, J=1.60, 6.80 Hz, 1H), 7.25-7.19 (m, 2H), 7.16 (d, J=1.60 Hz, 1H), 4.80 (s, 2H), 4.58 (d, J=11.60 Hz, 1H), 4.49 (d, J=11.60 Hz, 1H), 1.95 (s, 3H), 1.18 (s, 9H);

MS: m/z 500.2 (M+1);

SOR: [α]$_D^{23.5}$ (+) 12.80, (MeOH, c=0.5).

Example 40, Step 3b: (−)-2-(4-chloro-3-fluorophenyl)-2-[(4-{[(1,3-oxazol-2-yl)amino]methyl}-1H-1,3-benzodiazol-2-yl)amino]propyl 2,2-dimethylpropanoate The (−) enantiomer was the second compound to elute-off the column.

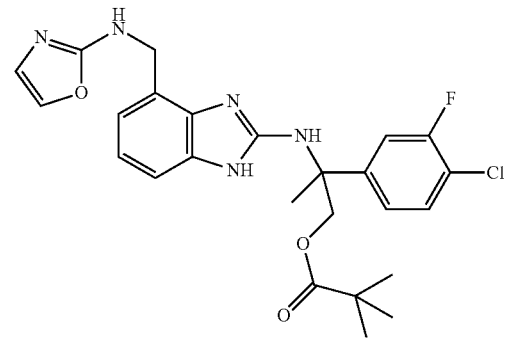 [SMILES: CC(C)(C)C(=O)OCC(C)(Nc1nc2c(CNc3ncco3)cccc2[nH]1)c1ccc(Cl)c(F)c1]

$^1$H NMR (400 MHz, AcOH-d$_4$) δ 7.53-7.47 (m, 2H), 7.43-7.40 (m, 2H), 7.30 (dd, J=1.60, 6.80 Hz, 1H), 7.25-0.21 (m, 2H), 7.17 (d, J=1.60 Hz, 1H), 4.81 (s, 2H), 4.53 (m, 2H), 1.96 (s, 3H), 1.21 (s, 9H);

MS: m/z 500.1 (M+1);

SOR: [α]r) 23.2 (−) 11.60, (MeOH, c=0.5).

Example 40a: Preparation of (−)-2-(4-chloro-3-fluorophenyl)-2-[(4-{[(1,3-oxazol-2-yl)amino]methyl}-1H-1,3-benzodiazol-2-yl)amino]propan-1-ol

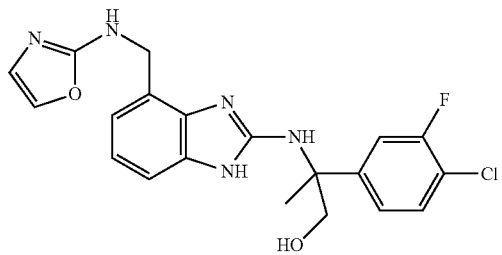 [SMILES: CC(CO)(Nc1nc2c(CNc3ncco3)cccc2[nH]1)c1ccc(Cl)c(F)c1]

To a stirred solution of (+)-2-(4-chloro-3-fluorophenyl)-2-[(4-{[(1,3-oxazol-2-yl)amino]methyl}-1H-1,3-benzodiazol-2-yl)amino]propyl 2,2-dimethylpropanoate (from Example 40, step 3a) (0.5 g, 1.00 mmol) in methanol (50.0 mL) was added 0.5 N sodium hydroxide in methanol solution (8 mL, 4.00 mmol) and the reaction mixture was stirred at ambient temperature for 1 h. The reaction mixture was concentrated, and the residue diluted with water (5 mL). The aqueous layer was extracted with DCM (3×75 mL), and the combined organic layer was washed with brine solution (10 mL), dried over sodium sulphate, filtered and concentrated to afford the crude product (0.36 g) as an off-white solid. This had purified by preparative HPLC (Method: 10 mmol ammonium acetate in water:acetonitrile) to afford (−)-2-(4-chloro-3-fluorophenyl)-2-[(4-{[(1,3-oxazol-2-yl)amino]methyl}-1H-1,3-benzodiazol-2-yl)amino]propan-1-ol (0.22 g) as a white solid.

$^1$H NMR (400 MHz, AcOH-d$_4$) δ 7.50-7.40 (m, 3H), 5.60 (dd, J=28.02, 14.08 Hz, 1H), 7.30-7.21 (m, 3H), 7.15 (d, J=1.20 Hz, 1H), 4.78 (s, 2H), 4.30 (d, J=12.00 Hz, 1H), 4.08 (d, J=12.00 Hz, 1H), 1.76 (s, 3H);

MS: m/z 416.1 (M+1);

SOR: [α]$_D^{23.4}$ (−) 5.60, (MeOH, c=0.5).

Example 40b: Preparation of (+)-2-(4-chloro-3-fluorophenyl)-2-[(4-{[(1,3-oxazol-2-yl)amino]methyl}-1H-1,3-benzodiazol-2-yl)amino]propan-1-ol

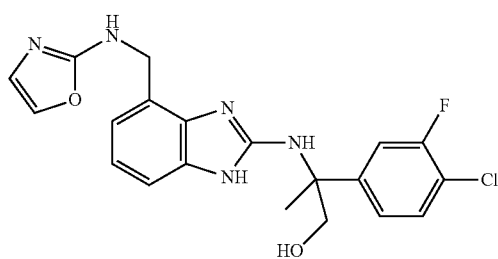 [SMILES: CC(CO)(Nc1nc2c(CNc3ncco3)cccc2[nH]1)c1ccc(Cl)c(F)c1]

To a stirred solution of (+2-(4-chloro-3-fluorophenyl)-2-[(4-{[(1,3-oxazol-2-yl)amino]methyl}-1H-1,3-benzodiazol-2-yl)amino]propyl 2,2-dimethylpropanoate (from Example 40, step 3b) (0.45 g, 0.900 mmol) in methanol (45.0 mL) was added 0.5 N sodium hydroxide in methanol solution (7.20 mL, 3.600 mmol) and the reaction mixture was stirred at ambient temperature for 1 h. The reaction mixture was concentrated and the residue diluted with water (5 mL). The aqueous layer was extracted with DCM (3×75 mL), and the combined organic layer was washed with brine solution (10 mL), dried over sodium sulphate, filtered and concentrated to afford the crude product (0.33 g) as an off-white solid. This was purified by preparative HPLC (Method: 10 mmol ammonium acetate in water:acetonitrile) to afford (+)-2-(4-chloro-3-fluorophenyl)-2-[(4-{[(1,3-oxazol-2-yl)amino]methyl}-1H-1,3-benzodiazol-2-yl)amino]propan-1-ol (0.14 g) as a white solid.

$^1$H NMR (400 MHz, AcOH-d$_4$) δ 7.49-7.40 (m, 3H), 7.36 (d, J=8.40 Hz, 1H), 7.30-7.21 (m, 3H), 7.15 (s, 1H), 4.79 (s, 2H), 4.30 (d, J=12.00 Hz, 1H), 4.08 (d, J=12.00 Hz, 1H), 1.76 (s, 3H);

MS: m/z 416.1 (M+1);

SOR: [α]$_D^{23.2}$ (+) 4.80, (MeOH, c=0.5).

Example 41: Preparation of 2-(3-chloro-2-fluorophenyl)-2-({4-[(2-imino-2,3-dihydro-1,3-oxazol-3-yl)methyl]-1H-1,3-benzodiazol-2-yl}amino)propan-1-ol

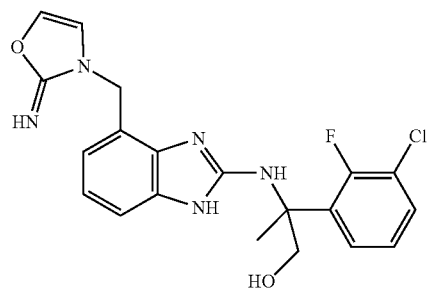 [SMILES: CC(CO)(Nc1nc2c(Cn3ccoc3=N)cccc2[nH]1)c1cccc(Cl)c1F]

The commercially available 1-(3-chloro-2-fluorophenyl)ethan-1-one and 3-[(2-imino-2,3-dihydro-1,3-oxazol-3-yl)methyl]benzene-1,2-diamine (from Example 1, step 5) were used, following the method described for Example 18, to afford the required product which was isolated as its two enantiomers.

Example 41a: (−)-2-(3-chloro-2-fluorophenyl)-2-({4-[(2-imino-2,3-dihydro-1,3-oxazol-3-yl)methyl]-1H-1,3-benzodiazol-2-yl}amino)propan-1-ol Isolated as its hydrochloride salt as an off-white solid.

$^1$H NMR (400 MHz, AcOH-d$_4$) δ 7.54-7.41 (m, 4H), 7.33-7.18 (m, 4H), 5.68-5.57 (m, 2H), 4.51 (d, J=12.40 Hz, 1H), 4.17 (d, J=12.00 Hz, 1H), 1.89 (s, 3H);

MS: m/z 416.0 (M+1);

[α]$_D^{23.0}$ (−) 1.60 (MeOH, c=0.5).

Example 41b: (+)-2-(3-chloro-2-fluorophenyl)-2-({4-[(2-imino-2,3-dihydro-1,3-oxazol-3-yl)methyl]-1H-1,3-benzodiazol-2-yl}amino)propan-1-ol Isolated as the hydrochloride salt as an off-white solid.

$^1$H NMR (400 MHz, AcOH-d$_4$) δ 7.57 (d, J=1.60 Hz, 1H), 7.48-7.44 (m, 3H), 7.32-7.27 (m, 2H), 7.22-7.17 (m, 2H), 5.41 (d, J=5.20 Hz, 2H), 4.52 (d, J=12.40 Hz, 1H), 4.15 (d, J=12.00 Hz, 1H), 1.83 (s, 3H);

MS: m/z 416.0 (M+1);

[α]$_D^{22.5}$ (+) 6.0 (MeOH, c=0.5).

Example 42: Preparation of 2-(3-chloro-2-fluorophenyl)-2-[(4-{[(1,3-oxazol-2-yl)amino]methyl}-1H-1,3-benzodiazol-2-yl)amino]propan-1-ol

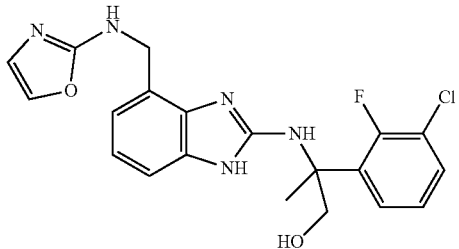 [SMILES: CC(CO)(Nc1nc2c(CNc3ncco3)cccc2[nH]1)c1cccc(Cl)c1F]

3-{[(1,3-Oxazol-2-yl)amino]methyl}benzene-1,2-diamine (from Example 38, Step 2) and 2-(3-chloro-2-fluorophenyl)-2-isothiocyanatopropyl-2,2-dimethylpropanoate, (made from commercially available 1-(3-chloro-2-fluorophenyl)ethan-1-one by the method described for Example 3, Steps 1 to 7) were used, following the method described for Example 40, to afford the required product, which was separated into its two enantiomers.

Example 42a: (+)-2-(3-chloro-2-fluorophenyl)-2-[(4-{[(1,3-oxazol-2-yl)amino]methyl}-1H-1,3-benzodiazol-2-yl)amino]propan-1-ol Isolated as an off-white solid.
$^1$H NMR (400 MHz, AcOH-d$_4$) δ 7.48-7.46 (m, 2H), 7.37-7.34 (m, 2H), 7.28-7.21 (m, 2H), 7.17-7.13 (m, 2H), 4.78 (t, J=16.00 Hz, 2H), 4.52 (d, J=13.20 Hz, 1H), 4.17 (d, J=12.40 Hz, 1H), 1.81 (s, 3H);
MS: m/z 416.0 (M+1);
$[α]_D^{23.7}$ (+) 39.6 (MeOH, c=0.5).

Example 42b: (+)-2-(3-chloro-2-fluorophenyl)-2-[(4-{[(1,3-oxazol-2-yl)amino]methyl}-1H-1,3-benzodiazol-2-yl)amino]propan-1-ol Isolated as an off-white solid.
$^1$H NMR (400 MHz, AcOH-d$_4$) δ 7.48-7.44 (m, 2H), 7.36-7.34 (m, 2H), 7.28-7.21 (m, 2H), 7.17-7.13 (m, 2H), 4.78 (t, J=16.00 Hz, 2H), 4.52 (d, J=13.20 Hz, 1H), 4.17 (d, J=12.80 Hz, 1H), 1.81 (s, 3H);
MS: m/z 416.1 (M+1);
$[α]_D^{23.6}$ (−) 37.6 (MeOH, c=0.5).

Example 43: Preparation of 2-(3-chloro-2-fluorophenyl)-2-[(4-{[(1,2-oxazol-3-yl)amino]methyl}-1H-1,3-benzodiazol-2-yl)amino]propan-1-ol

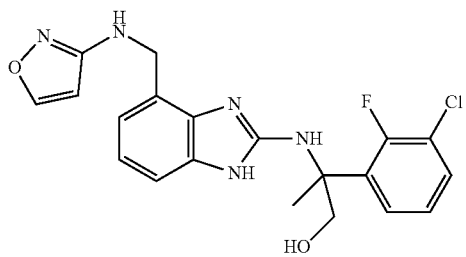 [SMILES: CC(CO)(Nc1nc2c(CNc3ccon3)cccc2[nH]1)c1cccc(Cl)c1F]

Example 43, Step 1: Preparation of (2,1,3-benzothiadiazol-4-yl)methanol

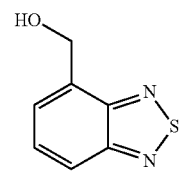

To a solution of 4-(bromomethyl)-2,1,3-benzothiadiazole (from Example 1, Step 3) (50 g, 218 mmol) in 1,4-Dioxane:water (1:1, 1000 mL) was added potassium carbonate (151 g, 1091 mmol) and the reaction mixture was stirred at 100° C. for 20 h. The reaction mass was cooled to ambient temperature, washed with water (500 mL) and extracted with ethyl acetate (3×300 mL). The combined organic layer was washed with brine solution (300 mL), dried over sodium sulphate, filtered and concentrated to afford the crude product (36 g) as a brown gum. This was purified by silica gel column chromatography and eluted with 25% ethyl acetate in petroleum ether to afford (2,1,3-benzothiadiazol-4-yl)methanol (27 g) as an off-white solid.
$^1$H NMR (400 MHz, DMSO-d$_6$) δ 7.98-7.96 (m, 1H), 7.75-7.68 (m, 2H), 5.51 (t, J=4.00 Hz, 1H), 5.03 (d, J=5.60 Hz, 2H);

Example 43, Step 2: Preparation of 2,1,3-benzothiadiazole-4-carbaldehyde

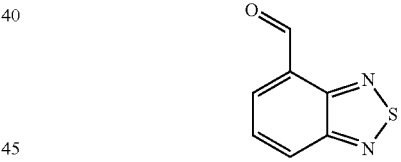

To a solution of (2,1,3-benzothiadiazol-4-yl)methanol (from Example 43, step 1) (10 g, 60.2 mmol) in dichloromethane (400 mL), cooled to 0° C., Dess-Martin periodinane (51 g, 120 mmol) was added portionwise and the reaction mixture was stirred at ambient temperature for 1 h. The reaction was quenched with aqueous sodium bicarbonate solution (300 mL), filtered through a Celite bed and washed with dichloromethane. The filtrate separated into an aqueous and organic layer. The organic layer was washed with brine solution (150 mL), dried over sodium sulphate, filtered and concentrated to afford the crude product (12 g) as a yellow solid. This was purified by silica gel column chromatography and eluted with 30% ethyl acetate in petroleum ether to afford 2,1,3-benzothiadiazole-4-carbaldehyde (8.0 g) as an off-white solid.
$^1$H NMR (400 MHz, DMSO-d$_6$) δ 10.64 (s, 1H), 8.47 (dd, J=1.20, 8.80 Hz, 1H), 8.31 (dd, J=1.20, 7.00 Hz, 1H), 7.98-7.94 (m, 1H);
MS: m/z 165.1 (M+1).

Example 43, Step 3: Preparation of N-[(2,1,3-benzothiadiazol-4-yl)methyl]-1,2-oxazol-3-amine

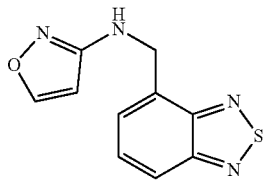 [SMILES: c1cc(CNc2ccon2)c2nsnc2c1]

To a solution of 2,1,3-benzothiadiazole-4-carbaldehyde (from Example 43, step 2) (4 g, 24.4 mmol) and 1,2-oxazol-3-amine (commercial, 4.1 g, 48.7 mmol) in ethanol (250 mL), cooled to 0° C., titanium(IV)isopropoxide (87 ml, 292 mmol) was added and the reaction mixture was then stirred at ambient temperature for 20 h. The reaction mixture was cooled to 0° C. and sodium borohydride (0.922 g, 24.4 mmol) was added portion wise. The reaction mixture was stirred at ambient temperature for 20 h, then quenched with ice water (100 mL), filtered through a Celite bed which was washed with ethyl acetate. The filtrate was concentrated, and the crude product was diluted with water (100 mL), extracted with ethyl acetate (2×100 mL) and the combined organic layer was washed with brine solution (50 mL), dried over sodium sulphate, filtered and concentrated to afford the crude product (6.5 g) as a brown gum. It was purified by silica gel column chromatography and eluted with 42% ethyl acetate in petroleum ether to afford N-[(2,1,3-benzothiadiazol-4-yl)methyl]-1,2-oxazol-3-amine (3.5 g) as a pale yellow solid.

$^1$H NMR (400 MHz, DMSO-$d_6$) δ 8.40 (d, J=2.00 Hz, 1H), 7.98 (d, J=8.80 Hz, 1H), 7.72-7.68 (m, 1H), 7.61-7.59 (m, 1H), 6.86 (t, J=6.00 Hz, 1H), 6.06 (d, J=1.60 Hz, 1H), 4.80 (d, J=6.00 Hz, 2H);
MS: m/z 233.1 (M+1).

Example 43, Step 4: Preparation of 3-{[(1,2-oxazol-3-yl)amino]methyl}benzene-1,2-diamine

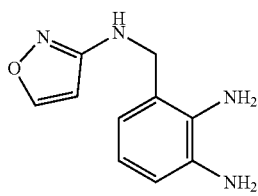 [SMILES: Nc1cccc(CNc2ccon2)c1N]

To a solution of N-[(2,1,3-benzothiadiazol-4-yl)methyl]-1,2-oxazol-3-amine (from Example 43, step 3) (2 g, 8.61 mmol) in acetic acid:water (1:1, 40 mL) was added zinc powder (2.82 g, 43.1 mmol) and the reaction mixture was stirred at room temperature for 20 h. The reaction mixture was washed with water (100 mL), extracted with ethyl acetate (2×100 mL) and the combined organic layer was washed with brine solution (50 mL). The organic layer was dried over sodium sulphate, filtered and concentrated to afford 3-{[(1,2-oxazol-3-yl)amino]-methyl}benzene-1,2-diamine as a brown gum (1.6 g), which was used in the next step without further purification.
MS: m/z 205.2 (M+1).

Example 43: Preparation of 2-(3-chloro-2-fluorophenyl)-2-[(4-{[(1,2-oxazol-3-yl)amino]methyl}-1H-1,3-benzodiazol-2-yl)amino]propan-1-ol

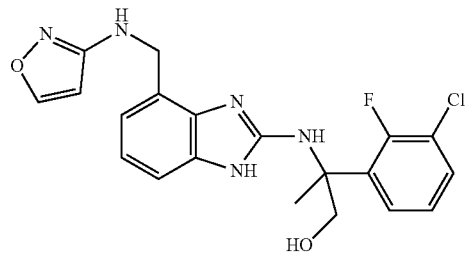 [SMILES: CC(CO)(Nc1nc2c(CNc3ccon3)cccc2[nH]1)c1cccc(Cl)c1F]

3-{[(1,2-oxazol-3-yl)amino]methyl}benzene-1,2-diamine (from Example 43, Step 4) and 2-(3-chloro-2-fluorophenyl)-2-isothiocyanatopropyl 2,2-dimethylpropanoate (made from commercially available 1-(3-chloro-2-fluorophenyl)ethan-1-one, by the method described for Example 3, Steps 1 to 7) were used, following the method described for Example 40, to afford the required product, which was separated into its two enantiomers.

Example 43a: (+2-(3-Chloro-2-fluorophenyl)-2-[(4-{[(1,2-oxazol-3-yl)amino]methyl}-1H-1,3-benzodiazol-2-yl)amino]propan-1-ol Isolated as a white solid.
$^1$H NMR (400 MHz, AcOH-$d_4$) δ 8.13 (d, J=1.60 Hz, 1H), 7.47-7.42 (m, 2H), 7.36-7.34 (m, 1H), 7.22-7.21 (m, 2H), 7.11 (t, J=8.00 Hz, 1H), 5.95 (d, J=2.00 Hz, 1H), 4.56 (s, 2H), 4.46 (d, J=12.80 Hz, 1H), 4.14 (d, J=12.40 Hz, 1H), 1.82 (s, 3H);
MS: m/z 416.1 (M+1);
$[α]_D^{23.7}$ (−) 39.84 (MeOH, c=0.5).

Example 43b: (+)-2-(3-Chloro-2-fluorophenyl)-2-[(4-{[(1,2-oxazol-3-yl)amino]methyl}-1H-1,3-benzodiazol-2-yl)amino]propan-1-ol Isolated as a white solid.
$^1$H NMR (400 MHz, AcOH-$d_4$) δ 8.13 (d, J=2.00 Hz, 1H), 7.46-7.42 (m, 2H), 7.36-7.33 (m, 1H), 7.23-7.19 (m, 2H), 7.11 (t, J=8.00 Hz, 1H), 5.95 (d, J=1.60 Hz, 1H), 4.56 (s, 2H), 4.46 (d, J=12.80 Hz, 1H), 4.14 (d, J=12.40 Hz, 1H), 1.82 (s, 3H);
MS: m/z 416.0 (M+1);
$[α]_D^{23.4}$ (+) 37.68 (MeOH, c=0.5).

Example 44: Preparation of 2-(4-chloro-3-fluorophenyl)-2-[(4-{[(1,2-oxazol-3-yl)amino]methyl}-1H-1,3-benzodiazol-2-yl)amino]propan-1-ol

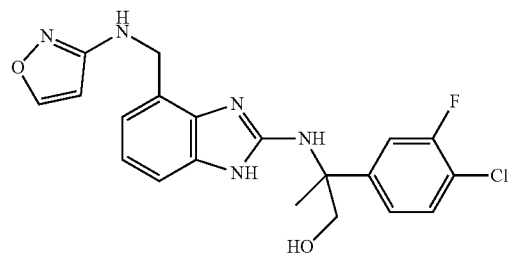 [SMILES: CC(CO)(Nc1nc2c(CNc3ccon3)cccc2[nH]1)c1ccc(Cl)c(F)c1]

3-{[(1,2-Oxazol-3-yl)amino]methyl}benzene-1,2-diamine (from Example 43, Step 4) and 2-(4-chloro-3-fluorophenyl)-2-isothiocyanatopropyl 2,2-dimethylpropanoate (made from commercially available 1-(4-chloro-3-fluorophenyl)ethan-1-one, by the method described for Example 3, Steps 1 to 7) were used, following the method described for Example 40, to afford the required product, which was separated into its two enantiomers.

Example 44a: (+2-(4-chloro-3-fluorophenyl)-2-[(4-{[(1,2-oxazol-3-yl)amino]methyl}-1H-1,3-benzodiazol-2-yl)amino]propan-1-ol Isolated as a white solid.
$^1$H NMR (400 MHz, AcOH-d$_4$): δ 8.16 (d, J=1.60 Hz, 1H), 7.48-7.43 (m, 2H), 7.37-7.34 (m, 1H), 7.31-7.28 (m, 1H), 7.22-7.18 (m, 2H), 5.97 (d, J=1.60 Hz, 1H), 4.55 (s, 2H), 4.24 (d, J=12.00 Hz, 1H), 4.05 (d, J=11.60 Hz, 1H), 1.77 (s, 3H);
MS: m/z 416.1 (M+1);
SOR: $[α]_D^{23.7}$ (−) 4.00, (MeOH, c=0.5).

Example 44b: (+)-2-(4-chloro-3-fluorophenyl)-2-[(4-{[(1,2-oxazol-3-yl)amino]methyl}-1H-1,3-benzodiazol-2-yl)amino]propan-1-ol Isolated as a white solid.
$^1$H NMR (400 MHz, AcOH-d$_4$): δ 8.16 (d, J=1.60 Hz, 1H), 7.48-7.43 (m, 2H), 7.35 (dd, J=2.00, 8.60 Hz, 1H), 7.32-7.30 (m, 1H), 7.22-7.19 (m, 2H), 5.97 (d, J=1.60 Hz, 1H), 4.55 (s, 2H), 4.24 (d, J=12.00 Hz, 1H), 4.05 (d, J=12.00 Hz, 1H), 1.77 (s, 3H);
MS: m/z 416.1 (M+1);
SOR: $[α]_D^{23.7}$ (+) 3.20, (MeOH, c=0.5).

Example 45: Preparation of 2-(3-chloro-5-fluorophenyl)-2-({4-[(2-imino-2,3-dihydro-1,3-oxazol-3-yl)methyl]4H-1,3-benzodiazol-2-yl}amino)propan-1-ol

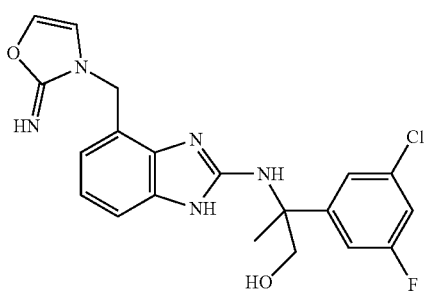 [SMILES: CC(CO)(Nc1nc2c(Cn3ccoc3=N)cccc2[nH]1)c1cc(F)cc(Cl)c1]

The commercially available 1-(3-chloro-5-fluorophenyl)ethan-1-one and 3-[(2-imino-2,3-dihydro-1,3-oxazol-3-yl)methyl]benzene-1,2-diamine (from Example 1, step 5) were used, following the method described for Example 18 to afford the required product, which was isolated as its two enantiomers.

Example 45a: (+2-(3-chloro-5-fluorophenyl)-2-({4-[(2-imino-2,3-dihydro-1,3-oxazol-3-yl)methyl]-1H-1,3-benzodiazol-2-yl}amino)propan-1-ol Isolated as the hydrochloride salt, as an off-white solid.
$^1$H NMR (400 MHz, DMSO-d$_6$) δ 10.01 (s, 2H), 7.85 (s, 1H), 7.38 (t, J=6.40 Hz, 5H), 7.28 (d, J=10.00 Hz, 1H), 7.16 (d, J=6.40 Hz, 2H), 5.39 (s, 2H), 3.78-3.71 (m, 2H), 1.81 (s, 3H);
MS: m/z 416.1 (M+1);
$[α]_D^{23.2}$ (−) 8.0 (MeOH, c=0.5).

Example 45b: (+)-2-(3-chloro-5-fluorophenyl)-2-({4-[(2-imino-2,3-dihydro-1,3-oxazol-3-yl)methyl]-1H-1,3-benzodiazol-2-yl}amino)propan-1-ol Isolated as the hydrochloride salt, as an off-white solid.
$^1$H NMR (400 MHz, DMSO-d$_6$) δ 10.01 (s, 2H), 7.85 (s, 1H), 7.48-7.37 (m, 4H), 7.30-7.15 (m, 4H), 5.40 (s, 2H), 3.78-3.68 (m, 2H), 1.78 (d, J=18.80 Hz, 3H);
MS: m/z 416.1 (M+1);
$[α]_D^{23.1}$ (+) 7.6 (MeOH, c=0.5).

Example 46: Preparation of 2-(3-chloro-5-fluorophenyl)-2-[(4-{[(1,2-oxazol-3-yl)amino]methyl}-1H-1,3-benzodiazol-2-yl)amino]propan-1-ol

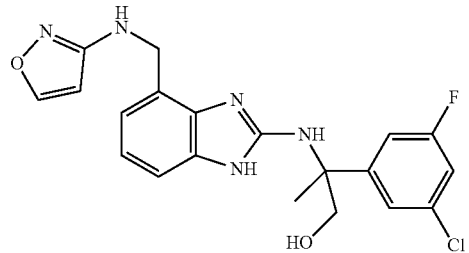 [SMILES: CC(CO)(Nc1nc2c(CNc3ccon3)cccc2[nH]1)c1cc(F)cc(Cl)c1]

3-{[(1,2-Oxazol-3-yl)amino]methyl}benzene-1,2-diamine (from Example 43, Step 4) and 2-(3-chloro-5-fluorophenyl)-2-isothiocyanatopropyl 2,2-dimethylpropanoate (made from commercially available 1-(3-chloro-5-fluorophenyl)ethan-1-one, by the method described for Example 3, Steps 1 to 7) were used, following the method described for Example 40, to afford the required product, which was separated into its two enantiomers.

Example 46a: (−)-2-(3-chloro-5-fluorophenyl)-2-[(4-{[(1,2-oxazol-3-yl)amino]methyl}-1H-1,3-benzodiazol-2-yl)amino]propan-1-ol Isolated as a white solid.
$^1$H NMR (400 MHz, AcOH-d$_4$) δ 8.17 (d, J=2.00 Hz, 1H), 7.42 (d, J=1.20 Hz, 1H), 7.32-7.27 (m, 2H), 7.23-7.15 (m, 2H), 7.14-7.13 (m, 1H), 5.98 (d, J=2.00 Hz, 1H), 4.56 (s, 2H), 4.25 (d, J=20.00 Hz, 1H), 4.06 (d, J=12.00 Hz, 1H), 1.78 (s, 3H);
MS: m/z 416.2 (M+1);
$[α]_D^{23.2}$ (−) 9.20 (MeOH, c=0.5).

Example 46b: (+)-2-(3-chloro-5-fluorophenyl)-2-[(4-{[(1,2-oxazol-3-yl)amino]methyl}-1H-1,3-benzodiazol-2-yl)amino]propan-1-ol Isolated as a white solid.
$^1$H NMR (400 MHz, AcOH-d$_4$) δ 8.17 (d, J=1.60 Hz, 1H), 7.42 (d, J=1.20 Hz, 1H), 7.32-7.27 (m, 2H), 7.23-7.15 (m, 2H), 7.14-7.13 (m, 1H), 5.98 (d, J=2.00 Hz, 1H), 4.56 (s, 2H), 4.26 (d, J=11.60 Hz, 1H), 4.06 (d, J=12.00 Hz, 1H), 1.78 (s, 3H);

MS: m/z 416.2 (M+1);

$[\alpha]_D^{23.6}$ (+) 3.60 (MeOH, c=0.5).

Example 47: Preparation of 2-(5-chloro-2-fluorophenyl)-2-({4-[(2-imino-2,3-dihydro-1,3-oxazol-3-yl)methyl]-1H-1,3-benzodiazol-2-yl}amino)propan-1-ol

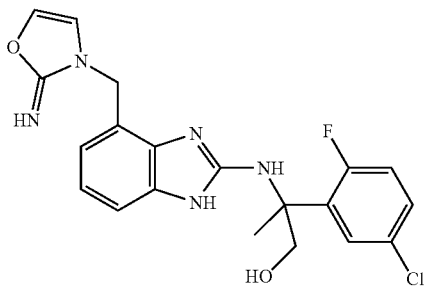 [SMILES: CC(CO)(Nc1nc2c(Cn3ccoc3=N)cccc2[nH]1)c1cc(Cl)ccc1F]

The commercially available 1-(5-chloro-2-fluorophenyl)ethan-1-one and 3-[(2-imino-2,3-dihydro-1,3-oxazol-3-yl)methyl]benzene-1,2-diamine (from Example 1, step 5) were used, following the method described for Example 18 to afford the required product, which was isolated as its two enantiomers.

Example 47a: (+2-(5-chloro-2-fluorophenyl)-2-({4-[(2-imino-2,3-dihydro-1,3-oxazol-3-yl)methyl]-1H-1,3-benzodiazol-2-yl}amino)propan-1-ol Isolated as the hydrochloride salt (0.210 g), as an off-white solid.

$^1$H NMR (400 MHz, AcOH-d$_4$) δ 7.57 (d, J=6.80 Hz, 3H), 7.40-7.26 (m, 4H), 7.13 (t, J=9.20 Hz, 1H), 5.69-5.58 (m, 2H), 4.47 (d, J=11.20 Hz, 1H), 4.15 (d, J=11.20 Hz, 1H), 1.88 (s, 3H);

MS: m/z 416.0 (M+1);

$[\alpha]_D^{22.8}$ (−) 20.0 (MeOH, c=0.5).

Example 47b: (+)-2-(5-chloro-2-fluorophenyl)-2-({4-[(2-imino-2,3-dihydro-1,3-oxazol-3-yl)methyl]-1H-1,3-benzodiazol-2-yl}amino)propan-1-ol Isolated as the hydrochloride salt (0.195 g), as an off-white solid.

$^1$H NMR (400 MHz, AcOH-d$_4$) δ 7.59-7.54 (m, 3H), 7.41-7.31 (m, 4H), 7.16-7.11 (m, 1H), 5.69-5.57 (m, 2H), 4.48 (d, J=12.00 Hz, 1H), 4.15 (d, J=12.40 Hz, 1H), 1.88 (s, 3H);

MS: m/z 416.1 (M+1);

$[\alpha]_D^{22.8}$ (+) 10.0 (MeOH, c=0.5).

Example 48: Preparation of 2-(5-chloro-2-fluorophenyl)-2-[(4-{[(1,3-oxazol-2-yl)amino]methyl}-1H-1,3-benzodiazol-2-yl)amino]propan-1-ol

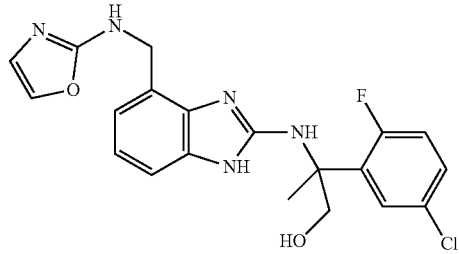 [SMILES: CC(CO)(Nc1nc2c(CNc3ncco3)cccc2[nH]1)c1cc(Cl)ccc1F]

3-{[(1,3-Oxazol-2-yl)amino]methyl}benzene-1,2-diamine (from Example 38, Step 2) and 2-(5-chloro-2-fluorophenyl)-2-isothiocyanatopropyl 2,2-dimethylpropanoate, (made from commercially available 1-(5-chloro-2-fluorophenyl)ethan-1-one, by the method described for Example 3, Steps 1 to 7) were used, following the method described for Example 40, to afford the required product, which was separated into its two enantiomers.

Example 48a: (+)-2-(5-chloro-2-fluorophenyl)-2-[(4-{[(1,3-oxazol-2-yl)amino]methyl}-1H-1,3-benzodiazol-2-yl)amino]propan-1-ol Isolated as a pale yellow solid.

$^1$H NMR (400 MHz, AcOH-d$_4$) δ 7.57-7.54 (m, 1H), 7.39-7.36 (m, 2H), 7.33 (d, J=7.60 Hz, 1H), 7.27 (d, J=6.80 Hz, 1H), 7.22 (t, J=8.00 Hz, 1H), 7.15-7.10 (m, 2H), 4.79 (d, J=1.2 Hz, 2H), 4.49 (d, J=12.00 Hz, 1H), 4.15 (d, J=12.00 Hz, 1H), 1.80 (s, 3H);

MS: m/z 416.0 (M+1);

$[\alpha]_D^{22.8}$ (+) 14.0 (MeOH, c=0.5).

Example 48b: (−)-2-(5-chloro-2-fluorophenyl)-2-[(4-{[(1,3-oxazol-2-yl)amino]methyl}-1H-1,3-benzodiazol-2-yl)amino]propan-1-ol Isolated as a pale-yellow solid.

$^1$H NMR (400 MHz, AcOH-d$_4$) δ 7.57-7.54 (m, 1H), 7.39-7.36 (m, 3H), 7.28-7.20 (m, 2H), 7.15-7.10 (m, 2H), 4.79 (d, J=0.80 Hz, 2H), 4.48 (d, J=12.40 Hz, 1H), 4.15 (d, J=12.00 Hz, 1H), 1.80 (s, 3H);

MS: m/z 416.0 (M+1);

$[\alpha]_D^{22.3}$ (−) 14.0 (MeOH, c=0.5).

Example 49: Preparation of 2-(5-chloro-2-fluorophenyl)-2-[(4-{[(1,2-oxazol-3-yl)amino]methyl}-1H-1,3-benzodiazol-2-yl)amino]propan-1-ol

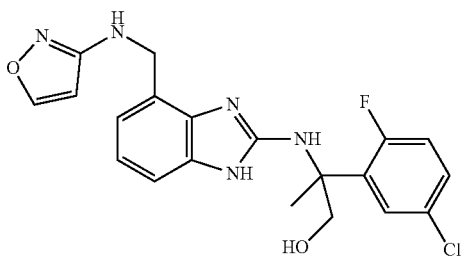 [SMILES: CC(CO)(Nc1nc2c(CNc3ccon3)cccc2[nH]1)c1cc(Cl)ccc1F]

3-{[(1,2-Oxazol-3-yl)amino]methyl}benzene-1,2-diamine (from Example 43, Step 4) and 2-(5-chloro-2-fluorophenyl)-2-isothiocyanatopropyl 2,2-dimethylpropanoate (made from commercially available 1-(5-chloro-2-fluorophenyl)ethan-1-one, by the method described for Example 3, Steps 1 to 7) were used, following the method described for Example 40, to afford the required product, which was separated into its two enantiomers.

Example 49a: (+)-2-(5-chloro-2-fluorophenyl)-2-[(4-{[(1,2-oxazol-3-yl)amino]methyl}-1H-1,3-benzodiazol-2-yl)amino]propan-1-ol Isolated as an off-white solid.
$^1$H NMR (400 MHz, AcOH-$d_4$) δ 8.14 (d, J=1.60 Hz, 1H), 7.56-7.53 (m, 1H), 7.38-7.32 (m, 2H), 7.23-7.18 (m, 2H), 7.14-7.09 (m, 1H), 5.97 (d, J=2.00 Hz, 1H), 4.56 (d, J=1.20 Hz, 2H), 4.43 (d, J=12.40 Hz, 1H), 4.12 (d, J=12.00 Hz, 1H), 1.81 (s, 3H);
MS: m/z 416.1 (M+1);
$[α]_D^{23.4}$ (+) 12.40 (MeOH, c=0.5).

Example 49b: (+2-(5-chloro-2-fluorophenyl)-2-[(4-{[(1,2-oxazol-3-yl)amino]methyl}-1H-1,3-benzodiazol-2-yl)amino]propan-1-ol Isolated as an off-white solid.
$^1$H NMR (400 MHz, AcOH-$d_4$) δ 8.14 (d, J=2.00 Hz, 1H), 7.56-7.53 (m, 1H), 7.38-7.32 (m, 2H), 7.23-7.18 (m, 2H), 7.14-7.09 (m, 1H), 5.97 (d, J=1.60 Hz, 1H), 4.57 (s, 2H), 4.43 (d, J=12.00 Hz, 1H), 4.12 (d, J=12.00 Hz, 1H), 1.82 (s, 3H);
MS: m/z 416.1 (M+1);
$[α]_D^{23.2}$ (−) 12.0 (MeOH, c=0.5).

We claim:
1. A compound of formula (I)

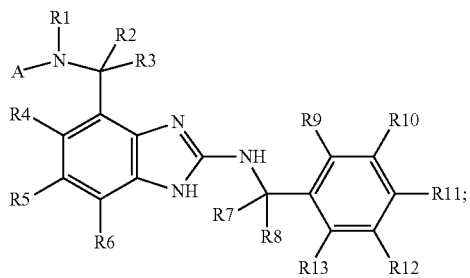

Wherein
A is a 5 or 6-membered aromatic heterocycle comprising at least one nitrogen atom and optionally 1 sulphur atom and optionally 1 oxygen atom, optionally substituted with at least one group selected from halogen, $C_{1-6}$ alkyl, $C_{1-6}$ alkyl substituted with at least one halogen, $C_{1-6}$ alkoxy, $C_{1-6}$ alkoxy substituted with at least one halogen, $C_{1-6}$ alkylthio, and cyano;
R1 is selected from hydrogen and $C_{1-6}$ alkyl;
or A and R1 taken together with the nitrogen atom to which they are linked form a 5-6 membered aromatic or non-aromatic heterocycle containing 1-2 nitrogen atoms, and optionally 1 oxygen atom, and optionally 1 sulphur atom, optionally substituted with a group selected from halogen, $C_{1-6}$ alkyl, $C_{1-6}$ alkyl substituted with a halogen, $C_{1-6}$ alkoxy, $C_{1-6}$ alkoxy substituted with a halogen, $C_{1-6}$ alkylthio, =NH, =O, —OH, and cyano;
R2-R3 are independently a group selected from hydrogen and $C_{1-6}$ alkyl;
or R2 and R3 taken together with the carbon atom to which they are linked form a $C_{3-4}$ cycloalkyl;
R4-R6 are independently a group selected from hydrogen, halogen, and $C_{1-4}$ alkyl;
R7-R8 are independently a group selected from hydrogen, $C_{1-4}$ alkyl, $C_{1-4}$ alkyl substituted with one OH, $C_{1-4}$ alkyl substituted with one $OC_{1-3}$ alkyl, $C_{1-4}$ alkyl substituted with at least one halogen,
or R7 and R8 taken together with the carbon atom to which they are linked form a $C_{3-4}$ cycloalkyl;
R9-R13 are independently a group selected from hydrogen, halogen, $C_{1-6}$ alkyl substituted with at least one halogen, $C_{1-6}$ alkoxy, $C_{1-6}$ alkoxy substituted with at least one halogen, $C_{1-6}$ alkylthio, and cyano; or
a pharmaceutically acceptable salt thereof.

2. The compound of claim 1 or a pharmaceutically acceptable salt thereof, wherein A is a 5-membered aromatic heterocycle containing 1-3 nitrogen atoms and optionally 1 oxygen atom, optionally substituted with a group selected from halogen, $C_{1-6}$ alkyl, $C_{1-6}$ alkyl substituted with at least one halogen, $C_{1-6}$ alkoxy, $C_{1-6}$ alkoxy substituted with at least one halogen, $C_{1-6}$ alkylthio, and cyano.

3. The compound of claim 1 or a pharmaceutically acceptable salt thereof, wherein A is a 6-membered aromatic heterocycle containing 1-3 nitrogen atoms, optionally substituted with at least one group selected from halogen, $C_{1-6}$ alkyl, $C_{1-6}$ alkyl substituted with at least one halogen, $C_{1-6}$ alkoxy, $C_{1-6}$ alkoxy substituted with at least one halogen, $C_{1-6}$ alkylthio, and cyano.

4. The compound of claim 2 or a pharmaceutically acceptable salt thereof, wherein A is selected from an imidazolyl, a pyrazolyl, an oxazolyl, an isoxazolyl, an oxadiazolyl, and a pyrimidinyl, optionally substituted with at least one group selected from halogen, $C_{1-6}$ alkyl, $C_{1-6}$ alkyl substituted with at least one halogen, $C_{1-6}$ alkoxy, $C_{1-6}$ alkoxy substituted with at least one halogen, $C_{1-6}$ alkylthio, and cyano.

5. The compound of claim 1 or a pharmaceutically acceptable salt thereof, wherein R1 is selected from hydrogen (H) and methyl.

6. The compound of claim 1 or a pharmaceutically acceptable salt thereof, wherein R1 is H.

7. The compound of claim 1 or a pharmaceutically acceptable salt thereof, wherein A and R1 taken together with the nitrogen atom to which they are linked form a 5 membered non-aromatic heterocycle containing 1-2 nitrogen atom and 1 oxygen atom substituted with one, two or three groups selected from methyl and =NH.

8. The compound of claim 1 or a pharmaceutically acceptable salt thereof, wherein R2-R3 are independently a group selected from H and $C_{1-3}$ alkyl.

9. The compound of claim 1 or a pharmaceutically acceptable salt thereof, wherein R2-R3 are both H.

10. The compound of claim 1 or a pharmaceutically acceptable salt thereof, wherein R2 and R3 taken together with the carbon atom to which they are linked form a cyclopropyl.

11. The compound of claim 1 or a pharmaceutically acceptable salt thereof, wherein R4-R6 are independently a group selected from H, F, Cl, and methyl.

12. The compound of claim 1 or a pharmaceutically acceptable salt thereof, wherein R7 is a group selected from H and $C_{1-3}$ alkyl.

13. The compound of claim 1 or a pharmaceutically acceptable salt thereof, wherein R8 is a group selected from $C_{1-4}$ alkyl, $C_{1-4}$ alkyl substituted with one OH, and $C_{1-4}$ alkyl substituted with one $OC_{1-3}$ alkyl.

14. The compound of claim 1 or a pharmaceutically acceptable salt thereof, wherein R7 and R8 taken together with the carbon atom to which they are linked form a cyclopropyl.

15. The compound of claim 1 or a pharmaceutically acceptable salt thereof, wherein R9-R13 are independently a group selected from H, halogen, $C_{1-6}$ alkyl substituted with at least one halogen, and $C_{1-6}$ alkoxy substituted with at least one halogen.

16. The compound of claim 1 or a pharmaceutically acceptable salt thereof, wherein R9, R12 and R13 are all H, and R1-R11 are independently a group selected from H, halogen, $C_{1-6}$ alkyl substituted with at least one halogen, and $C_{1-6}$ alkoxy substituted with at least one halogen; provided that R10 and R11 are not both H.

17. The compound of claim 1 or a pharmaceutically acceptable salt thereof, wherein each of R9, R10, R11 and R12 is a group selected from H and halogen and R13 is H.

18. The compound of claim 1 selected from the group consisting of:
- N-[1-(3-chlorophenyl)cyclopropyl]-4-[(2-imino-2,3-dihydro-1,3-oxazol-3-yl)methyl]-1H-1,3-benzodiazol-2-amine;
- N-[2-(3-chlorophenyl)propan-2-yl]-4-[(2-imino-2,3-dihydro-1,3-oxazol-3-yl)methyl]-1H-1,3-benzodiazol-2-amine;
- 2-(3-chlorophenyl)-2-({4-[(2-imino-2,3-dihydro-1,3-oxazol-3-yl)methyl]-1H-1,3-benzodiazol-2-yl}amino)propan-1-ol;
- (−)-2-(3-chlorophenyl)-2-({4-[(2-imino-2,3-dihydro-1,3-oxazol-3-yl)methyl]-1H-1,3-benzodiazol-2-yl}amino)propan-1-ol;
- (+)-2-(3-chlorophenyl)-2-({4-[(2-imino-2,3-dihydro-1,3-oxazol-3-yl)methyl]-1H-1,3-benzodiazol-2-yl}amino)propan-1-ol;
- 4-[(2-imino-2,3-dihydro-1,3-oxazol-3-yl)methyl]-N-{1-[3-(trifluoromethyl)phenyl]ethyl}-1H-1,3-benzodiazol-2-amine;
- 2-(3-chlorophenyl)-2-({4-[(2-imino-4-methyl-2,3-dihydro-1,3-oxazol-3-yl)methyl]-1H-1,3-benzodiazol-2-yl}amino)propan-1-ol;
- N-[2-(3-chlorophenyl)-1-methoxypropan-2-yl]-4-[(2-imino-2,3-dihydro-1,3-oxazol-3-yl)methyl]-1H-1,3-benzodiazol-2-amine;
- 4-[(2-imino-2,3-dihydro-1,3-oxazol-3-yl)methyl]-N-{2-[3-(trifluoromethyl)phenyl]propan-2-yl}-1H-1,3-benzodiazol-2-amine;
- 2-(3-chloro-4-fluorophenyl)-2-({4-[(2-imino-2,3-dihydro-1,3-oxazol-3-yl)methyl]-1H-1,3-benzodiazol-2-yl}amino)propan-1-ol;
- (−)-2-(3-chloro-4-fluorophenyl)-2-({4-[(2-imino-2,3-dihydro-1,3-oxazol-3-yl)methyl]-1H-1,3-benzodiazol-2-yl}amino)propan-1-ol;
- (+)-2-(3-chloro-4-fluorophenyl)-2-({4-[(2-imino-2,3-dihydro-1,3-oxazol-3-yl)methyl]-1H-1,3-benzodiazol-2-yl}amino)propan-1-ol;
- 2-(3-chloro-4-fluorophenyl)-2-[(4-{[(1,2-oxazol-3-yl)amino]methyl}-1H-1,3-benzodiazol-2-yl)amino]propan-1-ol;
- N-[2-(3-chlorophenyl)-1-methoxypropan-2-yl]-4-[(2-imino-4-methyl-2,3-dihydro-1,3-oxazol-3-yl)methyl]-1H-1,3-benzodiazol-2-amine;
- 2-(3-chloro-4-fluorophenyl)-2-[(4-{[(pyrimidin-4-yl)amino]methyl}-1H-1,3-benzodiazol-2-yl)amino]propan-1-ol;
- 2-(3-chloro-4-fluorophenyl)-2-[(4-{[(5-methyl-1,2-oxazol-3-yl)amino]methyl}-1H-1,3-benzodiazol-2-yl)amino]propan-1-ol;
- (−)-2-(3-chloro-4-fluorophenyl)-2-((4-(((5-methylisoxazol-3-yl)amino)methyl)-1H-benzo[d]imidazol-2-yl)amino)propan-1-ol;
- (+)-2-(3-chloro-4-fluorophenyl)-2-((4-(((5-methylisoxazol-3-yl)amino)methyl)-1H-benzo[d]imidazol-2-yl)amino)propan-1-ol;
- 2-(3-chloro-4-fluorophenyl)-2-({4-[(2-imino-4-methyl-2,3-dihydro-1,3-oxazol-3-yl)methyl]-1H-1,3-benzodiazol-2-yl}amino)propan-1-ol;
- (−)-2-(3-chloro-4-fluorophenyl)-2-({4-[(2-imino-4-methyl-2,3-dihydro-1,3-oxazol-3-yl)methyl]-1H-1,3-benzodiazol-2-yl}amino)propan-1-ol;
- (+)-2-(3-chloro-4-fluorophenyl)-2-({4-[(2-imino-4-methyl-2,3-dihydro-1,3-oxazol-3-yl)methyl]-1H-1,3-benzodiazol-2-yl}amino)propan-1-ol;
- N-[2-(3-chloro-4-fluorophenyl)-1-methoxypropan-2-yl]-4-[(2-imino-2,3-dihydro-1,3-oxazol-3-yl)methyl]-1H-1,3-benzodiazol-2-amine;
- 2-(3-chloro-4-fluorophenyl)-2-[(4-{[(5-methyl-1,2,4-oxadiazol-3-yl)amino]methyl}-1H-1,3-benzodiazol-2-yl)amino]propan-1-ol;
- 2-(3-chloro-4-fluorophenyl)-2-((4-(((5-methyl-1,3,4-oxadiazol-2-yl) amino) methyl)-1H-benzo[d]imidazol-2-yl) amino) propan-1-ol;
- 2-(3-chloro-4-fluorophenyl)-2-[(4-{[(3-methyl-1,2,4-oxadiazol-5-yl)amino]methyl}-1H-1,3-benzodiazol-2-yl)amino]propan-1-ol;
- 2-({4-[(2-imino-2,3-dihydro-1,3-oxazol-3-yl)methyl]-1H-1,3-benzodiazol-2-yl}amino)-2-[3-(trifluoromethyl)phenyl]propan-1-ol;
- (−)-2-({4-[(2-imino-2,3-dihydro-1,3-oxazol-3-yl)methyl]-1H-1,3-benzodiazol-2-yl}amino)-2-[3-(trifluoromethyl)-phenyl]propan-1-ol;
- (+)-2-({4-[(2-imino-2,3-dihydro-1,3-oxazol-3-yl)methyl]-1H-1,3-benzodiazol-2-yl}amino)-2-[3-(trifluoromethyl)-phenyl]propan-1-ol;
- 2-(3,4-dichlorophenyl)-2-({4-[(2-imino-2,3-dihydro-1,3-oxazol-3-yl)methyl]-1H-1,3-benzodiazol-2-yl}amino)propan-1-ol;
- (−)-2-(3,4-dichlorophenyl)-2-({4-[(2-imino-2,3-dihydro-1,3-oxazol-3-yl)methyl]-1H-1,3-benzodiazol-2-yl}amino)propan-1-ol;
- (+)-2-(3,4-dichlorophenyl)-2-({4-[(2-imino-2,3-dihydro-1,3-oxazol-3-yl)methyl]-1H-1,3-benzodiazol-2-yl}amino)propan-1-ol;
- 2-(3-chloro-4-fluorophenyl)-2-({4-[(2-imino-4,5-dimethyl-2,3-dihydro-1,3-oxazol-3-yl)methyl]-1H-1,3-benzodiazol-2-yl}amino)propan-1-ol;
- 2-((4-(((1-methyl-1H-pyrazol-5-yl)amino)methyl)-1H-benzo[d]imidazol-2-yl)amino)-2-(3-(trifluoromethyl) phenyl) propan-1-ol;
- 2-((4-(((1-methyl-1H-imidazol-2-yl)amino)methyl)-1H-benzo[d]imidazol-2-yl)amino)-2-(3-(trifluoromethyl) phenyl)propan-1-ol;
- 2-({4-[(2-imino-4-methyl-2,3-dihydro-1,3-oxazol-3-yl)methyl]-1H-1,3-benzodiazol-2-yl}amino)-2-[3-(trifluoromethyl)phenyl]-propan-1-ol;

(−)-2-({4-[(2-imino-4-methyl-2,3-dihydro-1,3-oxazol-3-yl)methyl]-1H-1,3-benzodiazol-2-yl}amino)-2-[3-(trifluoromethyl)phenyl]propan-1-ol;

(+)-2-({4-[(2-imino-4-methyl-2,3-dihydro-1,3-oxazol-3-yl)methyl]-1H-1,3-benzodiazol-2-yl}amino)-2-[3-(trifluoromethyl)phenyl]propan-1-ol;

2-({4-[(2-imino-5-methyl-2,3-dihydro-1,3-oxazol-3-yl)methyl]-1H-1,3-benzodiazol-2-yl}amino)-2-[3-(trifluoromethyl)phenyl]propan-1-ol;

(−)-2-({4-[(2-imino-5-methyl-2,3-dihydro-1,3-oxazol-3-yl)methyl]-1H-1,3-benzodiazol-2-yl}amino)-2-[3-(trifluoromethyl)-phenyl]propan-1-ol;

(+)-2-({4-[(2-imino-5-methyl-2,3-dihydro-1,3-oxazol-3-yl)methyl]-1H-1,3-benzodiazol-2-yl}amino)-2-[3-(trifluoromethyl)-phenyl]propan-1-ol;

2-({4-[(2-imino-2,3-dihydro-1,3-oxazol-3-yl)methyl]-1H-1,3-benzodiazol-2-yl}amino)-2-[3-(trifluoromethyl)phenyl]butan-1-ol;

3-({4-[(2-imino-2,3-dihydro-1,3-oxazol-3-yl)methyl]-1H-1,3-benzodiazol-2-yl}amino)-3-[3-(trifluoromethyl)phenyl]butan-1-ol;

2-({4-[(2-imino-2,3-dihydro-1,3-oxazol-3-yl)methyl]-1H-1,3-benzodiazol-2-yl}amino)-2-[3-(trifluoromethoxy)phenyl]propan-1-ol;

(+)-2-({4-[(2-imino-2,3-dihydro-1,3-oxazol-3-yl)methyl]-1H-1,3-benzodiazol-2-yl}amino)-2-[3-(trifluoromethoxy)phenyl]propan-1-ol;

(−)-2-({4-[(2-imino-2,3-dihydro-1,3-oxazol-3-yl)methyl]-1H-1,3-benzodiazol-2-yl}amino)-2-[3-(trifluoromethoxy)phenyl]propan-1-ol;

2-({4-[(2-imino-4,5-dimethyl-2,3-dihydro-1,3-oxazol-3-yl)methyl]-1H-1,3-benzodiazol-2-yl}amino)-2-[3-(trifluoromethyl)phenyl]-propan-1-ol;

2-({4-[(2-imino-4-methyl-2,3-dihydro-1,3-oxazol-3-yl)methyl]-1H-1,3-benzodiazol-2-yl}amino)-2-[3-(trifluoromethoxy)phenyl]propan-1-ol;

2-({4-[(2-imino-5-methyl-2,3-dihydro-1,3-oxazol-3-yl)methyl]-1H-1,3-benzodiazol-2-yl}amino)-2-[3-(trifluoromethoxy)phenyl]-propan-1-ol;

(−)-2-({4-[(2-imino-5-methyl-2,3-dihydro-1,3-oxazol-3-yl)methyl]-1H-1,3-benzodiazol-2-yl}amino)-2-[3-(trifluoromethoxy)-phenyl]propan-1-ol;

(+)-2-({4-[(2-imino-5-methyl-2,3-dihydro-1,3-oxazol-3-yl)methyl]-1H-1,3-benzodiazol-2-yl}amino)-2-[3-(trifluoromethoxy)-phenyl]propan-1-ol;

2-(3-chloro-4-fluorophenyl)-2-[(4-{1-[(1,3-oxazol-2-yl)amino]ethyl}-1H-1,3-benzodiazol-2-yl)amino]propan-1-ol;

2-(3-chloro-4-fluorophenyl)-2-({4-[(2-imino-2,3-dihydro-1,3-thiazol-3-yl)methyl]-1H-1,3-benzodiazol-2-yl}amino)propan-1-ol;

(−)-2-(3-chloro-4-fluorophenyl)-2-({4-[(2-imino-2,3-dihydro-1,3-thiazol-3-yl)methyl]-1H-1,3-benzodiazol-2-yl}amino)propan-1-ol;

(+)-2-(3-chloro-4-fluorophenyl)-2-({4-[(2-imino-2,3-dihydro-1,3-thiazol-3-yl)methyl]-1H-1,3-benzodiazol-2-yl}amino)propan-1-ol;

1-[(2-{[2-(3-chloro-4-fluorophenyl)-1-hydroxypropan-2-yl]amino}-1H-1,3-benzodiazol-4-yl)methyl]-2,3-dihydro-1H-imidazol-2-one;

1-[(2-{[2-(3-chloro-4-fluorophenyl)-1-hydroxypropan-2-yl]amino}-1H-1,3-benzodiazol-4-yl)methyl]imidazolidin-2-one;

1-[(2-{[2-(3-chloro-4-fluorophenyl)-1-hydroxypropan-2-yl]amino}-1H-1,3-benzodiazol-4-yl)methyl]-3-methylimidazolidin-2-one;

3-[(2-{[2-(3-chloro-4-fluorophenyl)-1-hydroxypropan-2-yl]amino}-1H-1,3-benzodiazol-4-yl)methyl]-1,3-thiazolidin-2-one;

1-[(2-{[2-(3-chloro-4-fluorophenyl)-1-hydroxypropan-2-yl]amino}-1H-1,3-benzodiazol-4-yl)methyl]pyrrolidin-2-one;

2-(3-chloro-4-fluorophenyl)-2-[(4-{[(1,3-oxazol-2-yl)amino]-methyl}-1H-1,3-benzodiazol-2-yl)amino]propan-1-ol;

2-(4-chloro-3-fluorophenyl)-2-({4-[(2-imino-2,3-dihydro-1,3-oxazol-3-yl)methyl]-1H-1,3-benzodiazol-2-yl}amino)propan-1-ol;

2-(4-chloro-3-fluorophenyl)-2-({4-[(2-imino-2,3-dihydro-1,3-oxazol-3-yl)methyl]-1H-1,3-benzodiazol-2-yl}amino)propan-1-ol (enantiomer a);

2-(4-chloro-3-fluorophenyl)-2-({4-[(2-imino-2,3-dihydro-1,3-oxazol-3-yl)methyl]-1H-1,3-benzodiazol-2-yl}amino)propan-1-ol (enantiomer b);

2-(4-chloro-3-fluorophenyl)-2-[(4-{[(1,3-oxazol-2-yl)amino]-methyl}-1H-1,3-benzodiazol-2-yl)amino]propan-1-ol;

(−)-2-(4-chloro-3-fluorophenyl)-2-[(4-{[(1,3-oxazol-2-yl)amino]methyl}-1H-1,3-benzodiazol-2-yl)amino]propan-1-ol;

(+)-2-(4-chloro-3-fluorophenyl)-2-[(4-{[(1,3-oxazol-2-yl)amino]methyl}-1H-1,3-benzodiazol-2-yl)amino]propan-1-ol;

2-(3-chloro-2-fluorophenyl)-2-({4-[(2-imino-2,3-dihydro-1,3-oxazol-3-yl)methyl]-1H-1,3-benzodiazol-2-yl}amino)propan-1-ol;

(−)-2-(3-chloro-2-fluorophenyl)-2-({4-[(2-imino-2,3-dihydro-1,3-oxazol-3-yl)methyl]-1H-1,3-benzodiazol-2-yl}amino)propan-1-ol;

(+)-2-(3-chloro-2-fluorophenyl)-2-({4-[(2-imino-2,3-dihydro-1,3-oxazol-3-yl)methyl]-1H-1,3-benzodiazol-2-yl}amino)propan-1-ol;

2-(3-chloro-2-fluorophenyl)-2-[(4-{[(1,3-oxazol-2-yl)amino]methyl}-1H-1,3-benzodiazol-2-yl)amino]propan-1-ol;

(+)-2-(3-chloro-2-fluorophenyl)-2-[(4-{[(1,3-oxazol-2-yl)amino]methyl}-1H-1,3-benzodiazol-2-yl)amino]propan-1-ol;

(−)-2-(3-chloro-2-fluorophenyl)-2-[(4-{[(1,3-oxazol-2-yl)amino]methyl}-1H-1,3-benzodiazol-2-yl)amino]propan-1-ol;

2-(3-chloro-2-fluorophenyl)-2-[(4-{[(1,2-oxazol-3-yl)amino]methyl}-1H-1,3-benzodiazol-2-yl)amino]propan-1-ol;

(−)-2-(3-Chloro-2-fluorophenyl)-2-[(4-{[(1,2-oxazol-3-yl)amino]methyl}-1H-1,3-benzodiazol-2-yl)amino]propan-1-ol;

(+)-2-(3-Chloro-2-fluorophenyl)-2-[(4-{[(1,2-oxazol-3-yl)amino]methyl}-1H-1,3-benzodiazol-2-yl)amino]propan-1-ol;

2-(4-chloro-3-fluorophenyl)-2-[(4-{[(1,2-oxazol-3-yl)amino]methyl}-1H-1,3-benzodiazol-2-yl)amino]propan-1-ol;

(−)-2-(4-chloro-3-fluorophenyl)-2-[(4-{[(1,2-oxazol-3-yl)amino]methyl}-1H-1,3-benzodiazol-2-yl)amino]propan-1-ol;

(+)-2-(4-chloro-3-fluorophenyl)-2-[(4-{[(1,2-oxazol-3-yl)amino]methyl}-1H-1,3-benzodiazol-2-yl)amino]propan-1-ol;

2-(3-chloro-5-fluorophenyl)-2-({4-[(2-imino-2,3-dihydro-1,3-oxazol-3-yl)methyl]-1H-1,3-benzodiazol-2-yl}amino)propan-1-ol;

(−)-2-(3-chloro-5-fluorophenyl)-2-({4-[(2-imino-2,3-di-hydro-1,3-oxazol-3-yl)methyl]-1H-1,3-benzodiazol-2-yl}amino)propan-1-ol;

(+)-2-(3-chloro-5-fluorophenyl)-2-({4-[(2-imino-2,3-di-hydro-1,3-oxazol-3-yl)methyl]-1H-1,3-benzodiazol-2-yl}amino)propan-1-ol;

2-(3-chloro-5-fluorophenyl)-2-[(4-{[(1,2-oxazol-3-yl)amino]methyl}-1H-1,3-benzodiazol-2-yl)amino]propan-1-ol;

(−)-2-(3-chloro-5-fluorophenyl)-2-[(4-{[(1,2-oxazol-3-yl)amino]methyl}-1H-1,3-benzodiazol-2-yl)amino]propan-1-ol;

(+)-2-(3-chloro-5-fluorophenyl)-2-[(4-{[(1,2-oxazol-3-yl)amino]methyl}-1H-1,3-benzodiazol-2-yl)amino]propan-1-ol;

2-(5-chloro-2-fluorophenyl)-2-({4-[(2-imino-2,3-di-hydro-1,3-oxazol-3-yl)methyl]-1H-1,3-benzodiazol-2-yl}amino)propan-1-ol;

(−)-2-(5-chloro-2-fluorophenyl)-2-({4-[(2-imino-2,3-di-hydro-1,3-oxazol-3-yl)methyl]-1H-1,3-benzodiazol-2-yl}amino)propan-1-ol;

(+)-2-(5-chloro-2-fluorophenyl)-2-({4-[(2-imino-2,3-di-hydro-1,3-oxazol-3-yl)methyl]-1H-1,3-benzodiazol-2-yl}amino)propan-1-ol;

2-(5-chloro-2-fluorophenyl)-2-[(4-{[(1,3-oxazol-2-yl)amino]methyl}-1H-1,3-benzodiazol-2-yl)amino]propan-1-ol;

(+)-2-(5-chloro-2-fluorophenyl)-2-[(4-{[(1,3-oxazol-2-yl)amino]methyl}-1H-1,3-benzodiazol-2-yl)amino]propan-1-ol;

(−)-2-(5-chloro-2-fluorophenyl)-2-[(4-{[(1,3-oxazol-2-yl)amino]methyl}-1H-1,3-benzodiazol-2-yl)amino]propan-1-ol;

2-(5-chloro-2-fluorophenyl)-2-[(4-{[(1,2-oxazol-3-yl)amino]methyl}-1H-1,3-benzodiazol-2-yl)amino]propan-1-ol;

(+)-2-(5-chloro-2-fluorophenyl)-2-[(4-{[(1,2-oxazol-3-yl)amino]methyl}-1H-1,3-benzodiazol-2-yl)amino]propan-1-ol; and (−)-2-(5-chloro-2-fluorophenyl)-2-[(4-{[(1,2-oxazol-3-yl)amino]methyl}-1H-1,3-benzodiazol-2-yl)amino]propan-1-ol; or a pharmaceutically acceptable salt thereof.

19. A pharmaceutical composition comprising the compound of claim 1, or a pharmaceutically acceptable salt thereof, and optionally a pharmaceutically acceptable additive.

20. A method for inhibiting SK3 channel in a mammal, wherein a therapeutically effective amount of at least one compound according to claim 1 or a pharmaceutically acceptable salt thereof is administered to a mammal in need of said treatment.

* * * * *